(12) United States Patent
Damude et al.

(10) Patent No.: US 10,053,702 B2
(45) Date of Patent: Aug. 21, 2018

(54) PLASTIDIC CARBONIC ANHYDRASE GENES FOR OIL AUGMENTATION IN SEEDS WITH INCREASED DGAT EXPRESSION

(71) Applicant: E I DU PONT DE NEMOURS AND COMPANY, Wilmington, DE (US)

(72) Inventors: Howard Glenn Damude, Hockessin, DE (US); Knut Meyer, Des Moines, IA (US); Kevin G. Ripp, Des Moines, IA (US); Kevin L. Stecca, Middletown, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 4 days.

(21) Appl. No.: 15/303,899

(22) PCT Filed: Apr. 22, 2015

(86) PCT No.: PCT/US2015/027008
§ 371 (c)(1),
(2) Date: Oct. 13, 2016

(87) PCT Pub. No.: WO2015/164457
PCT Pub. Date: Oct. 29, 2015

(65) Prior Publication Data
US 2017/0029836 A1   Feb. 2, 2017

Related U.S. Application Data

(60) Provisional application No. 61/982,485, filed on Apr. 22, 2014.

(51) Int. Cl.
| | | |
|---|---|---|
| C12N 15/82 | (2006.01) | |
| A23L 33/105 | (2016.01) | |
| A23L 2/52 | (2006.01) | |
| C07K 14/415 | (2006.01) | |
| C12N 9/10 | (2006.01) | |
| C12N 9/88 | (2006.01) | |

(52) U.S. Cl.
CPC ............ *C12N 15/8247* (2013.01); *A23L 2/52* (2013.01); *A23L 33/105* (2016.08); *C07K 14/415* (2013.01); *C12N 9/1029* (2013.01); *C12N 9/88* (2013.01); *C12N 15/8234* (2013.01); *C12Y 203/0102* (2013.01); *C12Y 402/01001* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,710,365 A | 1/1998 | Kerr et al. |
| 6,967,262 B2 | 11/2005 | Allen |
| 7,157,621 B2 | 1/2007 | Allen et al. |
| 7,294,756 B2 | 11/2007 | Stoop et al. |
| 7,294,759 B2 | 11/2007 | Allen et al. |
| 7,323,560 B2 | 1/2008 | Allen et al. |
| 7,476,778 B2 | 1/2009 | Stoop et al. |
| 7,524,945 B2 | 4/2009 | Cahoon et al. |
| 8,101,819 B2 | 1/2012 | Roesler et al. |
| 8,143,473 B2 | 3/2012 | Meyer et al. |
| 8,241,910 B2 | 8/2012 | Allen et al. |
| 8,399,736 B2 | 3/2013 | Meyer et al. |
| 8,404,926 B2 | 3/2013 | Meyer et al. |
| 8,455,714 B2 | 6/2013 | Roesler et al. |
| 8,497,362 B2 | 7/2013 | Cahoon et al. |
| 8,785,726 B2 | 7/2014 | Allen et al. |
| 8,927,809 B2 | 1/2015 | Meyer et al. |
| 8,937,217 B2 | 1/2015 | McGonigle |
| 8,993,840 B2 | 3/2015 | Allen et al. |
| 9,284,571 B2 | 3/2016 | Damude et al. |
| 9,347,066 B2 | 5/2016 | Meyer et al. |
| 9,574,204 B2 | 2/2017 | Meyer et al. |
| 9,574,207 B2 | 2/2017 | Meyer et al. |
| 9,617,556 B2 | 4/2017 | Meyer et al. |
| 2011/0091975 A1 | 4/2011 | McGonigle |
| 2013/0219565 A1 | 8/2013 | Damude et al. |
| 2013/0225799 A1 | 8/2013 | Roesler et al. |
| 2014/0352002 A1 | 11/2014 | Meyer et al. |
| 2015/0087069 A1 | 3/2015 | McGonigle |
| 2015/0089689 A1 | 3/2015 | Damude et al. |
| 2015/0101080 A1 | 4/2015 | Damude et al. |
| 2015/0143583 A1 | 5/2015 | Damude et al. |
| 2015/0218577 A1 | 8/2015 | Allen et al. |
| 2016/0186195 A1 | 6/2016 | Damude et al. |

FOREIGN PATENT DOCUMENTS

| | | |
|---|---|---|
| TW | 201224145 A1 | 6/2016 |
| WO | 2004/063333 A2 | 7/2004 |
| WO | 2006/009659 A2 | 1/2006 |
| WO | 2008/147935 A2 | 12/2008 |
| WO | 2009/124070 A1 | 10/2009 |
| WO | 2009/143397 A2 | 11/2009 |
| WO | 2010/114989 A1 | 10/2010 |
| WO | 2012/082731 A2 | 6/2012 |
| WO | 2012/125737 A2 | 9/2012 |
| WO | 2013/096562 A1 | 6/2013 |

OTHER PUBLICATIONS

DiMario et al, Molecular Plant, Jan. 2017, vol. 10, pp. 30-46.*
Chau V. Hoang et al., Biochemical and Molecular Inhibition of Plastidial Carbonic Anhydrase Reduces the Incorporation of Acetate into Lipids in Cotton Embryos and Tobacco Cell Suspensions and Leaves, Plant Physiology, Apr. 2002, pp. 1417-1427, vol. 128.

(Continued)

*Primary Examiner* — Eileen B O Hara

(57) ABSTRACT

Recombinant DNA constructs comprise plastidic carbonic anhydrase coding sequences operably linked to polynucleotides encoding DGAT or transcription factors such as ODP1. These constructs can be used to increase oil content in plants and seeds to levels that are not achieved with DGAT alone.

Methods of generating plants containing the constructs and for increasing oil content in the seeds of an oilseed plant are also disclosed.

20 Claims, 2 Drawing Sheets

(56) References Cited

OTHER PUBLICATIONS

Zhongsen Li et al., Stacking Multiple Transgenes at a Selected Genomic Site via Repeated Recombinase-Mediated DNA Cassette Exchanges, Plant Physiology, Aug. 18, 2010, pp. 622-631, vol. 154, No. 2.
Naira Quintana et al., Renewable energy from Cyanobacteria: energy production optimization by metabolic pathway engineering, Appl. Microbiol Biotechnol. 2011, pp. 471-490, vol. 91.
A. Tiwari et al., Carbonic anhydrase in relation to higher plants, Photosynthetica, 2005, pp. 1-11, vol. 43(1).
Harrie Van Erp et al., Multigene Engineering of Triacylglycerol Metabolism Boosts Seed Oil Content in *Arabidopsis*, Plant Physiology, May 2014, pp. 30-36, vol. 165.
Randall J. Weselake et al., Increasing the flow of carbon into seed oil, Biotechnology Advances, 2009, pp. 866-878, vol. 27, No. 6.
International Search Report—PCT/US2015/027008, dated Jul. 20, 2015.
Written Opinion—PCT/US2015/027008, dated Jul. 20, 2015.
A. Kinney, Enhancing Soybean Seeds for Industrial Applications, Mar. 8, 2013.
International Search Report PCT/US2014/048825, dated Jan. 9, 2015.

\* cited by examiner

Fig.1

| | | |
|---|---|---|
| SEQ ID NO 5.pro | MA--AT----PTHFS-...........VSHDPFSSTSLLNLQTQAIFGPNHSLKTTQLRIPASFI | 46 |
| SEQ ID NO 12.pro | MAGGSYEEAIAALTKLLSEKADLGG.........VAAAKIKQLTAELDT-........... | 40 |
| SEQ ID NO 17.pro | MVMPI----RSRISSLLCSKAPLMGSYIYDSCGLRFSAPTSSSITRHVPKIMDWWQMDR | 56 |

| | | |
|---|---|---|
| SEQ ID NO 5.pro | RRKATNLQVMASGKTPG-......LTQEANGVAIDRQNMTDVFDD----MKQRFLAFKKLK | 98 |
| SEQ ID NO 12.pro | .........ATANGSTPFNPDERIRTG-...............FAHFKNEK | 66 |
| SEQ ID NO 17.pro | CRAIASLPSIKEKQPESHSNRVRLGQEIKGLDEGNMAEIDSYQNLFGLMKQRFLSFKSQK | 116 |

| | | |
|---|---|---|
| SEQ ID NO 5.pro | YMDDFEHYKNLADAQAPKFLVIACADSRVCPSAVLGFQPGDAFTVRNIANLVPPYESGP- | 155 |
| SEQ ID NO 12.pro | YQKNPELYGELAKGQSPKFIMFACSDSRVCPSHILDFNPGEAFVRNIANWPPYDKTKY | 126 |
| SEQ ID NO 17.pro | VIKELEHFEALAEKQFPKFMIACADSRVCPSNILGFQPGEVFMIGFQPGEVFMRNIANLVPVMKNGP- | 175 |

| | | |
|---|---|---|
| SEQ ID NO 5.pro | TETKAALEFSVNTLNVENILVIGHSRCGGIQALMKMEDEGDS-RSFIHNWVVGKKAKES | 214 |
| SEQ ID NO 12.pro | SGTGAALEYAMLHLKVENIMVIGHSCCGGIKGLMSIPDDGTTASEFIEHMQICTPAKSK | 186 |
| SEQ ID NO 17.pro | SECNAALQFAVTTLQVENILVIGHSSQAGIEALMNMQEDAES-RNFIHKIWANGKLAKQR | 234 |

| | | |
|---|---|---|
| SEQ ID NO 5.pro | TKAVASNLHFDHQCQHCEKASINHSLERLLGYPMEEKVRQGSLSLHGGYYNFVDCTFEK | 274 |
| SEQ ID NO 12.pro | VKTEANTLEFSEQCTSCEKEAVNVSLGNLLTMRFVRDAMVKKTLALKGAHYNFVKGTFEL | 246 |
| SEQ ID NO 17.pro | TKAATAHLSFDQQCKFCEKESINQSLLNLLSYPMQDRVRKELLSLHGGYYNFISMCSFEK | 294 |

| | | |
|---|---|---|
| SEQ ID NO 5.pro | MTVDYAASRGKKEGSGIAVKDRSVWS........SVSV | 301 |
| SEQ ID NO 12.pro | MDLDLKISN-...........EEGSSYVWKEQEFWC | 259 |
| SEQ ID NO 17.pro | MTLDFKQCNV--EEGSSYVWKEQEFWC | 319 |

Fig.2

Percent Identity

|   | 1 | 2 | 3 |   |
|---|---|---|---|---|
| 1 |   | 38.2 | 45.5 | 1 SEQ ID NO 5.pro |
| 2 | 97.9 |   | 37.8 | 2 SEQ ID NO 12.pro |
| 3 | 84.9 | 99.2 |   | 3 SEQ ID NO 17.pro |
|   | 1 | 2 | 3 |   |

US 10,053,702 B2

PLASTIDIC CARBONIC ANHYDRASE GENES FOR OIL AUGMENTATION IN SEEDS WITH INCREASED DGAT EXPRESSION

CROSS REFERENCE TO RELATED APPLICATIONS

This application claims the benefit of U.S. Provisional Application No. 61/982,485, filed Apr. 22, 2014, the entire content of which is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "20150417_BB2339PCT_ST25_SeqLst.txt" created on Apr. 17, 2015 and having a size of 211 kilobytes and is filed concurrently with the specification. The sequence listing contained in this ASCII formatted document is part of the specification and is herein incorporated by reference in its entirety.

FIELD OF THE INVENTION

This invention is in the field of biotechnology, in particular, this pertains to increasing oil content of seeds that already have elevated oil content due to expression of DGAT genes.

BACKGROUND

Plant oil is a valuable renewable resource. Plant lipids have a variety of industrial and nutritional uses and are central to plant membrane function and climatic adaptation. Besides the nutritional uses, vegetable oils are gaining increasing interest as substitutes for petroleum-derived materials in fuels, lubricants, and specialty chemicals, especially as crude oil supplies decline. Oilseeds provide a unique platform for the production of high-value fatty acids that can replace non-sustainable petroleum products. (Cahoon et al. (2007) *Curr. Opin. Plant Biol.* 10:236-244). Methods to increase the content and to improve and alter the composition of plant oils are therefore desired.

Triacylglycerol (TAG) is the primary component of vegetable oil in plants; it is used by the seed as a stored form of energy to be used during seed germination. There are limitations to using conventional plant breeding to alter fatty acid composition and content. Molecular and cellular biology techniques offer the potential for overcoming some of the limitations of the conventional breeding approach. Some of the particularly useful technologies are seed-specific expression of foreign genes in transgenic plants (Goldberg et al. (1989) *Cell* 56:149-160), and the use of antisense RNA to inhibit plant target genes in a dominant and tissue-specific manner (van der Krol et al. (1988) *Gene* 72:45-50]. Other advances include the transfer of foreign genes into elite commercial varieties of commercial oilseed crops, such as soybean (Chee et al. (1989) *Plant Physiol.* 91:1212-1218; Christou et al. (1989) *Proc. Natl. Acad. Sci. U.S.A.* 86:7500-7504; Hinchee et al. (1988) *Bio/Technology* 6:915-922; EPO publication 0 301 749 A2], rapeseed (De Block et al. (1989) *Plant Physiol.* 91:694-701), and sunflower (Everett et al. (1987) *Bio/Technology* 5:1201-1204), and the use of genes as restriction fragment length polymorphism (RFLP) markers in a breeding program, which makes introgression of recessive traits into elite lines rapid and less expensive (Tanksley et al. (1989) *Bio/Technology* 7:257-264). However, application of each of these technologies requires identification and isolation of commercially-important genes.

Carbonic anhydrase (CA, EC 4.2.1.1) is a zinc-containing metalloenzyme that catalyzes the reverse hydration of $CO_2$ to $HCO_3^-$. The widespread abundance of CA isoforms in plants, animal, and microorganisms suggest that this enzyme has many diverse roles in biological processes (Chau et al. Plant Phys. 2002:128, 1417-1427).

SUMMARY

The present invention relates to the use of plastidic carbonic anhydrase to further increase oil content in seeds that already show increased oil contents due to expression of DGAT and/or ODP1 genes. It is being shown that plastidic carbonic anhydrase genes show increased expression in developing seeds of transgenic plants with increased seed oil content due to expression of the AP2 domain transcription factor, such as but not limited to ZM-ODP1 or due to the expression DGAT. Co-expression in soybean somatic embryos of genes from GM-CA and GM-CA2 or one gene for *Arabidopsis* (Ath-BCA5) with YL-DGAT2, increases oil content to levels that are not achieved with YL-DGAT2 alone.

In one embodiment, a recombinant DNA construct comprising at least one first heterologous polynucleotide encoding a plastidic carbonic anhydrase polypeptide, wherein said polynucleotide is operably linked to at least one regulatory sequence and at least one second heterologous polynucleotide encoding a DGAT polypeptide operably linked to at least one regulatory sequence, wherein expression of said recombinant DNA construct in a transgenic soybean seed results in an increased oil content in a transgenic soybean seed, when compared to a control seed that expresses said second polypeptide but does not express said first polypeptide. The second heterologous polynucleotide may encode an ODP1, a Lec1 or FUSCA3 polypeptide. Furthermore, the recombinant construct may further comprise a third polynucleotide comprising a construct downregulating galactinol synthase activity, wherein the first heterologous polynucleotide, the second heterologous polynucleotide and the galactinol synthase construct can be in the same construct or in separate constructs.

In one embodiment, the recombinant construct may further comprise a third polynucleotide comprising a construct downregulating PGM activity.

In another embodiment, the invention comprises regulatory sequences comprising at least two different seed-specific promoters, wherein one of said promoters is operably linked to the first heterologous polynucleotide and the other promoter is linked to the second heterologous polynucleotide of the invention. Said seed-specific promoters are selected from the group consisting of the alpha prime subunit of beta conglycinin promoter, soybean sucrose synthase promoter, *Medicago trunculata* sucrose synthase promoter, Kunitz trypsin inhibitor 3, annexin promoter, Gly1 promoter, beta subunit of beta conglycinin promoter, P34/Gly Bd m 30K promoter, albumin promoter, Leg A1 promoter and Leg A2 promoter.

In another embodiment of the present invention the increase in oil content is at least 5% expressing the recombinant constructs of the invention.

In yet another embodiment the recombinant DNA constructs of the invention comprise a carbonic anhydrase polypeptide comprising an amino acid sequence with at least 80%, 85%, 90%, 95% or 100% sequence identity to SEQ ID NOs: 5, 12 or 17.

In another embodiment, a recombinant DNA construct as described herein, wherein the recombinant DNA construct further comprises a seed-specific promoter operably linked to a second heterologous polynucleotide encoding a DGAT polypeptide. The second heterologous polynucleotide may encode a DGAT1 polypeptide. The DGAT1 polypeptide may comprise an amino acid sequence with at least 80%, 85%, 90%, 95% or 100% sequence identity to SEQ ID NO: 32. The second heterologous polynucleotide may encode a DGAT2 polypeptide. The DGAT2 polypeptide may comprise an amino acid sequence with at least 80%, 85%, 90%, 95% or 100% sequence identity to SEQ ID NO: 34.

In another embodiment, a recombinant DNA construct as described herein, wherein the recombinant DNA construct further comprises a seed-specific promoter operably linked to a second heterologous polynucleotide encoding an ODP1 polypeptide comprising an amino acid sequence with at least 80%, 85%, 90%, 95% or 100% identity to SEQ ID NO: 26 or 38.

In another embodiment, the ODP1 polypeptide is an allele of SEQ ID NO: 26 or 38

In another embodiment, the ODP1 polypeptide comprises two APETALA2 (AP2) domains.

ODP1 sequences have also been disclosed in PCT Publication Number WO2010114989, U.S. Pat. No. 7,157,621, and US20100242138, each of which are incorporated herein by reference.

In another embodiment, a recombinant DNA construct as described herein, wherein the recombinant DNA construct further comprises a seed-specific promoter operably linked to a second heterologous polynucleotide encoding an FUSCA3 polypeptide comprising an amino acid sequence with at least 80%, 85%, 90%, 95% or 100% identity to SEQ ID NO: 28 or 30.

In yet another embodiment, a recombinant DNA construct as described herein, wherein the recombinant DNA construct further comprises a seed-specific promoter operably linked to a second heterologous polynucleotide encoding a Lec1 polypeptide comprising an amino acid sequence with at least 80%, 85%, 90%, 95% or 100% identity to SEQ ID NO: 36.

Plants and seeds comprising the recombinant DNA construct of the invention are also embodiments of the invention. The plants and seeds can be soybean plants or soybean seeds. Cells, plants and seeds can further comprise any agronomic or quality improving trait or both. The seeds of the invention may further comprise seed treatments, such as but not limited to a herbicide, an insecticide or a fungicide Plants and seeds of the invention may comprise compositions effective against biotic or abiotic stresses and may be formulated as a spray, a powder, a granule, or a seed treatment.

Furthermore, the recombinant constructs of the invention may be combined with at least one recombinant construct that when expressed in a plant or seed is effective in enhancing the response to abiotic or biotic stresses in the plants or seeds of the invention.

In one embodiment a method for controlling plant diseases caused by fungal plant pathogens comprising applying to the plant of the invention or portion thereof, or to the plant seed of the invention, a fungicidally effective amount of a fugicidal compound.

One embodiment of the invention is a method of increasing oil content of a soybean seed, the method comprising the steps of:
(a) crossing the following:
(i) a first transgenic soybean plant comprising a first recombinant DNA construct comprising a first seed-specific promoter linked to at least one polynucleotide encoding a plastidic carbonic anhydrase; with
(ii) a second transgenic soybean plant comprising a second recombinant DNA construct comprising a second seed-specific promoter operably linked to a second heterologous polynucleotide encoding at least one DGAT polypeptide; and
(b) selecting a third transgenic plant from the cross of step (a), wherein seed of the third transgenic plant comprises the first and the second recombinant DNA constructs and wherein co-expression of said first polypeptide and said second polypeptide in said transgenic soybean seed results in an increased oil content in the transgenic soybean seed, when compared to a control soybean seed comprising only one, but not both, of the first and the second recombinant DNA constructs. The percent oil content of the transgenic soybean seed may be at least 3%, 4%, 5%, 6%, 7%, 8%, 9%, 10%, 11%, 12%, 13%, 14% or 15%. The methods of the invention may further comprise a step of crossing with an additional transgenic plant comprising a recombinant construct that is, when expressed in a plant or seed, effective in enhancing the response of plants and seeds of the invention to biotic and abiotic stresses.

The second recombinant construct may comprise at least one ODP1, FUSCA3 or Lec1 polypeptide. The DGAT polypeptide may be a DGAT1 or DGAT2 polypeptide.

In some embodiments, the percent increase in oil content is at least 3%, 4%, 5%, 6%, 7%, 8%, 9%, 10%, 11%, 12%, 13%, 14% or 15%.

An additional embodiment of the invention comprises a method of increasing oil content of a soybean seed, the method comprising the steps of introducing into a regenerable soybean cell the recombinant DNA constructs of the invention; regenerating a transgenic plant from the regenerable soybean cell of (a) wherein the transgenic plant comprises the recombinant DNA construct; and selecting a transgenic plant, or a transgenic progeny plant, wherein seed of the transgenic plant or the transgenic progeny plant comprises the recombinant construct and exhibits increased seed oil content, when compared to a control soybean seed not comprising the DNA recombinant construct.

Further embodiments include transgenic plants and seed obtained by the methods of the invention.

Products and or/by products obtained from the transgenic seed obtained by the methods of the invention are also included. Products and by/products include but are not limited to oil, protein isolate, a protein concentrate, meal, full fat flour, milk powder, defatted flour, milk, textured proteins, textured flours, textured concentrates and textured isolates.

Additional embodiments include food, beverages, and animal feed incorporating any of the products of the invention.

Progeny obtained from the transgenic seed of the invention is also included.

Another embodiment include sucrose synthase promoters from soybean and *Medicago truncatula*. Further embodiments include plastidic carbonic anhydrase from soybean and *Arabidopsis*.

In another embodiment, a plant or a seed comprising any of the recombinant DNA constructs described above. The plant and the seed may be an oilseed plant and seed. The plant or seed may be a soybean plant or seed.

In another embodiment, a method of increasing oil content of a soybean seed, the method comprising the steps of: (a) introducing into a regenerable soybean cell any one of the recombinant DNA constructs described herein; (b) regenerating a transgenic plant from the regenerable soybean cell of (a) wherein the transgenic plant comprises the recombinant DNA construct; and (c) selecting a transgenic plant of step (b), or a transgenic progeny plant from the transgenic plant of step (b), wherein seed of the transgenic plant or the transgenic progeny plant comprises the recombinant construct and exhibits increased seed oil content, when compared to a control soybean seed not comprising the DNA recombinant construct. The percent oil content of the transgenic soybean seed may be at least 3%, 4%, 5%, 6%, 7%, 8%, 9%, 10%, 11%, 12%, 13%, 14%, or 15%.

In another embodiment, a transgenic plant obtained by any of the methods described herein, and transgenic seed of said transgenic plant.

In another embodiment, a vector, cell, plant, plant tissue or seed comprising any of the recombinant DNA constructs described herein.

BRIEF DESCRIPTION OF THE DRAWINGS AND SEQUENCE LISTING

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 1 shows an alignment of the amino acid sequences of the plastidic carbonic anhydrases from *Arabidopsis* clone atgr1c.pk095.a9 (SEQ ID NO:5), soybean clone Glyma08g39510 (SEQ ID NO:12) and soybean clone Glyma02g37710 (SEQ ID NO:17).

FIG. 2 shows the percent identity of the sequences in the alignment of FIG. 1.

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NO:1 is the sequence of the construct PHP43186.
SEQ ID NO:2 is the sequence of the construct PHP43186A.
SEQ ID NO:3 is the full-length sequence of cDNA clone atgr1c.pk095.a9.
SEQ ID NO:4 is the CDS (coding sequence) of SEQ ID NO:3.
SEQ ID NO:5 is the amino acid sequence encoded by SEQ ID NO:4.
SEQ ID NO:6 and 7 are the sequences of the oligonucleotides oBCA5-1 and oBCA5-2, respectively.
SEQ ID NO:8 is the sequence of the construct pKR2559.
SEQ ID NO:9 is the CDS (coding sequence) for Glyma08g39510.
SEQ ID NO:10 and 11 are the sequences of the oligonucleotides SA542 and SA539, respectively.
SEQ ID NO:12 is the amino acid sequence of the soybean carbonic anhydrase (GM-CA).
SEQ ID NO:13 is the sequence of the construct pKR2495.
SEQ ID NO:14 is the CDS (coding sequence) of Glyma02g37710.
SEQ ID NO:15 and 16 are the sequences of the oligonucleotides oCA2-1 and oCA2-2, respectively.
SEQ ID NO:17 is the amino acid sequence of the soybean carbonic anhydrase (GM-CA2).
SEQ ID NO:18 is the sequence of the construct pKR2537.
SEQ ID NO:19 is the sequence of the construct pKR1256.
SEQ ID NO:20 is the sequence of the construct pKR2609.
SEQ ID NO:21 is the sequence of the construct pKR2749.
SEQ ID NO:22 is the sequence of the construct pKR2748.
SEQ ID NO:23 is the sequence of the hairpin construct GAS123hp-2.
SEQ ID NO:24 is the sequence of the construct PHP70086.
SEQ ID NO:25 is the CDS of GmODP1.
SEQ ID NO:26 is the amino acid sequence of GmODP1.
SEQ ID NO:27 is the full nucleotide sequence of GmFusca3-2.
SEQ ID NO:28 is the amino acid sequence of GmFusca3-2.
SEQ ID NO:29 is the full nucleotide sequence of GmFusca3-1.
SEQ ID NO:30 is the amino acid sequence of GmFusca3-1.
SEQ ID NO:31 is the CDS of GmDGAT1.
SEQ ID NO:32 is the amino acid sequence of Gm DGAT1.
SEQ ID NO:33 is the CDS of YLDGAT2.
SEQ ID NO:34 is the amino acid sequence of YLDGAT2.
SEQ ID NO:35 is the CDS of ZmLec1.
SEQ ID NO:36 is the amino acid sequence of ZmLec1.
SEQ ID NO:37 is the CDS of ZmODP1.
SEQ ID NO:38 is the amino acid sequence of ZmODP1.
SEQ ID NO:39 is the sequence of the construct PHP29252
SEQ ID NO:40 is the sequence of the AscI fragment of PHP29252 (PHP19031A).

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

In the context of this disclosure, a number of terms and abbreviations are used. The following definitions are provided.

The term "percentage points" (pp) refers to the arithmetic difference of two percentages, e.g. [transgenic value (%)−control value (%)]=percentage points. For example, a transgenic seed may contain 20% by weight of a component and the corresponding control seed may contain 15% by weight of that component. The difference in the component between the control seed and the transgenic seed would be expressed as 5 percentage points.

The term "relative change", "percent change", "percent increase", or "percent decrease" refers to a change expressed as a fraction of the control value, e.g. {[transgenic value (%)–control value (%)]/control value (%)}×100%=percent change. For example, a transgenic seed may contain 20% by weight of a component and the corresponding control seed may contain 15% by weight of that component. The difference in the component of the transgenic from the control would be expressed as a 33.3% relative change, percent change or percent increase.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

The control is a seed, plant, plant part or product, comparable to the transgenic seed, plant, plant part or product which, unless specified to the contrary, lacks the transgenes or is obtained from material lacking the transgenes.

In some embodiments the control is a seed, plant, plant part, or product, comparable to the transgenic seed, plant, plant part, or product which, lacks the transgene or recombinant construct comprising the heterologous polynucleotide encoding the plastidic carbonic anhydrase polypeptide.

In some embodiment the control is a recombinant construct, comparable to the transgenic or recombinant construct, which lacks the polynucleotide encoding plastidic carbonic anhydrase polypeptide.

In some embodiments the control seed is a seed that expresses the second polypeptide; e.g. DGAT, ODP1 or Lec1 but does not express the first polypeptide; e.g. carbonic anhydrase. In certain embodiments, the control lacks constructs which downregulate specified activities, but which includes the DGAT, ODP1 or Lec1 encoding polynucleotide. In certain embodiments, the control lacks both the constructs downregulating specified activities and the DGAT, ODP1 or Lec1 encoding polynucleotide. In certain embodiments, the control is a non-transgenic, null segregant soybean plant, plant part or seed.

"Non-transgenic, null segregant soybean, control null segregant" refers to a control near isogenic plant, plant part or seed that lacks the transgene (unless otherwise stated), and/or a control parental plant used in the transformation process to obtain the transgenic event. Null segregants can be plants, plant parts or seed that do not contain the transgenic trait due to normal genetic segregation during propagation of the heterozygous transgenic plants.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Propagule" includes all products of meiosis and mitosis able to propagate a new plant, including but not limited to, seeds, spores and parts of a plant that serve as a means of vegetative reproduction, such as corms, tubers, offsets, or runners. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within their genome. Each heterologous polynucleotide may confer a different trait to the transgenic plant.

"Heterologous" with respect to sequence means a sequence that originates from a foreign species, or, if from the same species, is substantially modified from its native form in composition and/or genomic locus by deliberate human intervention.

"Progeny" comprises any subsequent generation of a plant.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "full complement" and "full-length complement" are used interchangeably herein, and refer to a complement of a given nucleotide sequence, wherein the complement and the nucleotide sequence consist of the same number of nucleotides and are 100% complementary.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector.

This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) Nature Biotechnol. 17:287-91).

"Tissue-specific promoter" and "tissue-preferred promoter" are used interchangeably to refer to a promoter that is expressed predominantly but not necessarily exclusively in one tissue or organ, but that may also be expressed in one specific cell. Examples of some seed-specific promoters are the alpha prime subunit of beta conglycinin promoter, soybean sucrose synthase promoter, *Medicago truncatula* sucrose synthase promoter, Kunitz trypsin inhibitor 3, annexin promoter, Gly1 promoter, beta subunit of beta conglycinin promoter, P34/Gly Bd m 30K promoter, albumin promoter, Leg A1 promoter and Leg A2 promoter.

"Developmentally regulated promoter" refers to a promoter whose activity is determined by developmental events.

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

A minimal or basal promoter is a polynucleotide molecule that is capable of recruiting and binding the basal transcription machinery. One example of basal transcription machinery in eukaryotic cells is the RNA polymerase II complex and its accessory proteins.

Plant RNA polymerase II promoters, like those of other higher eukaryotes, are comprised of several distinct "cis-acting transcriptional regulatory elements," or simply "cis-elements," each of which appears to confer a different aspect of the overall control of gene expression. Examples of such cis-acting elements include, but are not limited to, such as TATA box and CCAAT or AGGA box. The promoter can roughly be divided in two parts: a proximal part, referred to as the core, and a distal part. The proximal part is believed to be responsible for correctly assembling the RNA polymerase II complex at the right position and for directing a basal level of transcription, and is also referred to as "minimal promoter" or "basal promoter". The distal part of the promoter is believed to contain those elements that regulate the spatio-temporal expression. In addition to the proximal and distal parts, other regulatory regions have also been described, that contain enhancer and/or repressors elements The latter elements can be found from a few kilobase pairs upstream from the transcription start site, in the introns, or even at the 3' side of the genes they regulate (Rombauts, S. et al. (2003) *Plant Physiology* 132:1162-1176, Nikolov and Burley, (1997) *Proc Natl Acad Sci USA* 94: 15-22), Tjian and Maniatis (1994) *Cell* 77: 5-8; Fessele et al., 2002 *Trends Genet* 18: 60-63, Messing et al., (1983) *Genetic Engineering of Plants: an Agricultural Perspective*, Plenum Press, NY, pp 211-227).

When operably linked to a heterologous polynucleotide sequence, a promoter controls the transcription of the linked polynucleotide sequence.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987).

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on over-expression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Transcription factors are proteins that generally bind DNA in a sequence-specific manner and either activate or repress transcription initiation. At least three types of separate domains have been identified within transcription factors. One is necessary for sequence-specific DNA recognition, one for the activation/repression of transcriptional initiation, and one for the formation of protein-protein interactions (such as dimerization). Studies indicate that many plant transcription factors can be grouped into distinct classes based on their conserved DNA binding domains (Katagiri F and Chua N H, 1992, *Trends Genet.* 8:22-27; Menkens A E, Schindler U and Cashmore A R, 1995, *Trends in Biochem Sci.* 13:506-510; Martin C and Paz-Ares J, 1997, *Trends Genet.* 13:67-73). Each member of these families interacts and binds with distinct DNA sequence motifs that are often found in multiple gene promoters controlled by different regulatory signals.

Ovule Development Proteins (ODP) are transcription factors containing two AP2 domains. AP2 transcription factors (herein referred to interchangeably as "AP2 domain transcription factors", "AP2 proteins", "AP2/EREBP transcription factors", or "AP2 transcription factor proteins") such as ODP activate several genes in the oil or TAG biosynthetic pathway in the plant cell.

The term "ODP1" refers to an ovule development protein 1 that is involved with increasing oil content. ODP1 is a member of the APETALA2 (AP2) family of proteins that play a role in a variety of biological events including, but not limited to, oil content.

U.S. Patent Application No. 61/165,548 describes the use of an ODP1 gene for alteration of oil traits in plants. U.S. Pat. No. 7,579,529 describes an AP2 domain transcription factor and methods of its use. U.S. Pat. No. 7,157,621 discloses the use of ODP1 transcription factor for increasing oil content in plants. DuPont patent application WO 2010/114989 describes the use of an *Arabidopsis* Sus2 promoter to drive ODP1 (WRI1) expression in *Arabidopsis*.

The putative AP2/EREBP transcription factor WRINKLED1 (WRI1) is involved in the regulation of seed storage metabolism in *Arabidopsis* (Cernac and Benning (2004) *Plant J.* 40:575-585). Expression of the WRI1 cDNA under the control of the CaMV 35S promoter led to increased seed oil content. Oil-accumulating seedlings, however, showed aberrant development consistent with a prolonged embryonic state. Nucleic acid molecules encoding WRINKLED1-LIKE polypeptides and methods of use are also described in International Publication No. WO 2006/00732 A2.

The AP2/EREBP family of proteins is a plant-specific class of putative transcription factors that have been shown to regulate a wide-variety of developmental processes and are characterized by the presence of an AP2/ERF DNA binding domain. Specifically, AP2 (APETALA2) and EREBPs (ethylene-responsive element binding proteins) are the prototypic members of a family of transcription factors unique to plants, whose distinguishing characteristic is that they contain the so-called AP2 DNA-binding domain. DNA sequence analysis suggests that AP2 encodes a theoretical polypeptide of 432 aa, with a distinct 68 aa repeated motif termed the AP2 domain. This domain has been shown to be essential for AP2 functions and contains within the 68 aa motif an eighteen amino acid core region that is predicted to form an amphipathic α-helix (Jofuku et al., Plant Cell 6:1211-1225, 1994). AP2-like domain-containing transcription factors have been also been identified in both *Arabidopsis thaliana* (Okamuro et al., (1997) *Proc. Natl. Acad. Sci. USA* 94:7076-7081) and in tobacco with the identification of the ethylene responsive element binding proteins (EREBPs) (Ohme-Takagi and Shinshi, (1995) *Plant Cell* 7:2:173-182,).

HAP proteins constitute a large family of transcription factors first identified in yeast. They combine to form a heteromeric protein complex that activates transcription by binding to CCAAT boxes in eukaryotic promoters. The orthologous Hap proteins display a high degree of evolutionary conservation in their functional domains in all species studied to date (Li et al. (1992) *Nucleic Acids Res* 20:1087-1091).

Leafy cotyledon1 (Lec1 or Lec1/Hap3) is a transcription factor that is a key regulator of seed development in plants. Lec1 is a CCAAT-binding factor (CBF)-type transcription factor. The terms "leafy cotyledon 1", "Lec1", and "Hap3/Lec1" are used interchangeably herein. LEC1 polypeptide is homologous to the HAP3 subunit of the CBF class of eukaryotic transcriptional activators that includes NF-Y, CP1, and HAP2/3/4/5 (Lotan et al. (1998) *Cell*, Vol. 93, 1195-1205, June 26).

The leafy cotyledon1 (LEC1) gene controls many distinct aspects of embryogenesis. The lec1 mutation is pleiotropic, which suggest that LEC1 has several roles in late embryo development. For example, LEC1 is required for specific aspects of seed maturation, inhibiting premature germination and plays a role in the specification of embryonic organ identity. Finally, LEC1 appears to act only during embryo development.

U.S. Pat. No. 6,235,975 describes leafy cotyledon1 genes and their uses. A pending US patent application (U.S. application Ser. No. 11/899,370) relates to isolated nucleic acid fragments encoding Lec1 related transcription factors. U.S. Pat. No. 7,294,759, U.S. Pat. No. 7,157,621, U.S. Pat. No. 7,888,560, U.S. Pat. No. 6,825,397 describe the use of Lec1 genes for altering oil content in plants.

In *Arabidopsis*, Lec1 has been shown to regulate the expression of fatty acid biosynthetic genes and Lec1 has also been shown to be involved in embryo development (Mu et al., *Plant Physiology* (2008) 148: 1042-1054; Lotan et al. (1998) *Cell, Vol.* 93, 1195-1205, June 26; PCT publication number WO/1998037184 & U.S. Pat. Nos. 6,235,975, 6,320,102, 6,545,201; PCT publication no. WO/2001064022 & U.S. Pat. No. 6,781,035, Braybrook, S. A. and Harada, J. J. (2008) *Trends Plant Sci* 13(12): 1360-1385).

WO 99/67405 describes leafy cotyledon1 genes and their uses. A maize Lec1 homologue of the *Arabidopsis* embryogenesis controlling gene AtLEC1 has been shown to increase oil content and transformation efficiencies in plants. See, for example, WO 03001902 and U.S. Pat. No. 6,512, 165.

Other polypeptides that influence ovule and embryo development and stimulate cell growth, such as, Lec1, Kn1, WUSCHEL, Zwille and Ainteguneta (ANT) allow for increased transformation efficiencies when expressed in plants. See, for example, U.S. Application No. 2003/0135889, herein incorporated by reference. In fact, a maize Lec1 homologue of the *Arabidopsis* embryogenesis controlling gene AtLEC1, has been shown to increase oil content and transformation efficiencies in plants. See, for example, WO 03001902 and U.S. Pat. No. 6,512,165.

Lec1 homologs may be further identified by using conserved sequence motifs, such as the following amino acid sequence (given in single letter code, with "x" representing any amino acid) (U.S. application No. 60/301,913). Underlined amino acids in the following sequence are those that are conserved in Lec1 but not found in Lec1-related proteins:

(SEQ ID NO: 41)
REQDxx<u>M</u>PxANVxRIMRxxLPxxAKI<u>SDD</u>AKEx<u>IQ</u>ECVSEx<u>IS</u>FxTxEA<u>N</u>
x<u>R</u>Cxxxx<u>R</u>KTxxxE The terms "FUS3", "FUSCA3" are used interchangeably herein. FUSCA3 is a transcription factor with a conserved VP1/ABI3-like B3 domain which is of functional importance for the regulation of seed maturation in *Arabidopsis*

*thaliana*. It controls developmental timing in *Arabidopsis* through the hormones gibberellin and abscisic acid and is itself regulated by the Lec1 transcription factor (Luerssen et al. (1998) *Plant J* (1998) 15 (6): 7557; Stone et al. (2001) *Proc Natl Acad Sci* 98 (20): 11806-11811; Lee et al. (2003) *Proc Natl Acad Sci* 100 (4): 2152-2156, U.S. Pat. No. 7,511,190 and U.S. Pat. No. 7,446,241, PCT Publication No. WO1998021336, PCT Publication No. WO2008157226, Braybrook, S. A. and Harada, J. J. (2008) *Trends Plant Sci* 13(12): 1360-1385). U.S. Pat. No. 7,612,253 describes methods of modulating cytokinin related processes in a plant using B3 domain proteins with a number of fusca3 homologs.

"Diacylglycerol acyltransferase" or "DGAT" (also known as "acyl-CoA-diacylglycerol acyltransferase" or "diacylglycerol O-acyltransferase") (EC 2.3.1.20) is an integral membrane protein that catalyzes the final enzymatic step in the production of triacylglycerols in plants, fungi and mammals. This enzyme is responsible for transferring an acyl group from acyl-coenzyme-A to the sn-3 position of 1,2-diacylglycerol ("DAG") to form triacylglycerol ("TAG"). DGAT is associated with membrane and lipid body fractions in plants and fungi, particularly, in oilseeds where it contributes to the storage of carbon used as energy reserves. DGAT is known to regulate TAG structure and direct TAG synthesis. Furthermore, it is known that the DGAT reaction is specific for oil synthesis (Lardizabal et al., *J. Biol. Chem.* 276(42):38862-28869 (2001)).

Two different families of DGAT proteins have been identified. The first family of DGAT proteins ("DGAT1") is related to the acyl-coenzyme A: cholesterol acyltransferase ("ACAT") and has been described in U.S. Pat. Nos. 6,100,077 and 6,344,548. A second family of DGAT proteins ("DGAT2") is unrelated to the DGAT1 family and is described in PCT Patent Publication WO 2004/011671 published Feb. 5, 2004. Other references to DGAT genes and their use in plants include PCT Publication No. WO1998/055,631 and U.S. Pat. No. 6,822,141.

"DGAT" and "diacylglycerol acyltransferase" are used interchangeably herein and refer to any member, or combination, of the DGAT1 or DGAT2 family of proteins.

Plant and fungal DGAT genes have been described previously (U.S. Pat. Nos. 7,198,937 and 7,465,565, US Publication No. 20080295204, U.S. application Ser. Nos. 12/470,569 and 12/470,517).

"Carbonic anhydrase" (CA, EC 4.2.1.1.) is a zinc-containing metalloenzyme that catalyzes the reversible hydration of $CO_2$ to $HCO_3^-$. The widespread abundance of CA isoforms in plants, animals, and microorganisms suggest that this enzyme has many diverse roles in biological processes. In photosynthetic organisms, one generally accepted physiological role of CA is to provide sufficient levels of inorganic carbon as part of a $CO_2$-concentrating mechanism for improved photosynthetic efficiency. In *Chlamydomonas reinhardtii*, it has been suggested that chloroplastic CA (plastidial carbonic anhydrase) plays a role in photosynthetic carbon assimilation by converting accumulated pools of $HCO_3^-$ to $CO_2$, which is the substrate for Rubisco (Chau et al. Plant Physiol. (2002) 128: 1417-1427. The present invention relates to the use of plastidic carbonic anhydrase to further increase oil content in seeds that already show increased oil contents due to expression of DGAT and/or ODP1 genes. It is being shown that plastidic carbonic anhydrase genes show increased expression in developing seeds of transgenic plants with increased seed oil content due to expression of the AP2 domain trans-cription factor, such as but not limited to ZM-ODP1 or due to the expression DGAT. Co-expression in soybean somatic embryos of genes from GM-CA and GM-CA2 or one gene for *Arabidopsis* (Ath-BCA5) with YL-DGAT2, increases oil content to levels that are not achieved with YL-DGAT2 alone.

"Agronomic traits" as used herein include traits that enhance production and consistency of production of soybean grain. Pests that have devastating effects on the agronomics and economics of soybean production, affecting yield and quality of grain and seed, include, but are not limited to weeds, fungi, insects, nematodes, and viruses. Also included is the enhancement or neutrality in yield in response to biotic or abiotic stresses, cultivation, and tolerance to factors such as climate and soil. "Quality-improvement traits" or "quality improving trait" include, but are not limited to, higher oil, higher protein, modifications in essential amino acids and protein compositional changes, changes in oil composition, nutritional traits such as vitamins, and new industrial uses including biodiesel, bio-lubricants, and polymers.

Stacking Other Traits of Interest.

The recombinant construct(s) of the invention can be combined with any agronomic trait and/or quality-improvement trait.

In some embodiments the recombinant constructs of the invention disclosed herein are engineered into a molecular stack. Thus, the various host cells, plants, plant cells and seeds disclosed herein can further comprise one or more traits of interest, and in more specific embodiments, the host cell, plant, plant part or plant cell is stacked with any combination of polynucleotide sequences of interest in order to create plants with a desired combination of traits. The traits can be agronomic or quality traits as described herein or any combination thereof. As used herein, the term "stacked" includes having the multiple traits present in the same plant or organism of interest. In one non-limiting example, "stacked traits" comprise a molecular stack where the sequences are physically adjacent to each other. A trait, as used herein, refers to the phenotype derived from a particular sequence or groups of sequences. In one embodiment, the molecular stack comprises at least one recombinant DNA construct comprising at least one first heterologous polynucleotide encoding a plastidic carbonic anhydrase polypeptide, wherein said polynucleotide is operably linked to at least one regulatory sequence and at least one second heterologous polynucleotide encoding a DGAT polypeptide and at least one additional polynucleotide that confers tolerance to abiotic and biotic stresses. In another embodiment, the at least one additional polynucleotide confers tolerance to a fungicide, herbicide, or insecticide. The at least one second heterologous polynucleotide may encode an DGAT 1, DGAT2, ODP1, a Lec1 or FUSCA3 polypeptide or any other quality improving trait as described herein. Furthermore, the stack may further comprise a construct downregulating galactinol synthase activity.

In one embodiment the stack(s) of the invention may further comprise(s) a construct downregulating PGM activity.

Thus, in one embodiment, the host cells, plants, plant cells or plant part having the recombinant constructs of the invention disclosed herein is stacked with at least one other fungicide, herbicide, or insecticide sequence. Some examples of such fungicide, herbicide, or insecticide sequence are disclosed for example in WO02/36782, US Publication 2004/0082770 and WO 2005/012515, U.S. Pat. No. 7,462,481, U.S. Pat. No. 7,405,074.

In some embodiments, the molecular stacks may comprise other herbicide-tolerance traits to create a transgenic plant of the disclosure with further properties. Other traits for example include polynucleotides that confer on the plant the capacity to produce a higher level or glyphosate insensitive 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; WO 00/66747, WO2007064828, WO2006110586, WO2007146765, WO2008002964, US App. Pubs. 2009/0307802, 201/0197499, 2009/0209427, and U.S. Pat. Nos. 8,436,159 and 6,040,497.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest, such a galactinol synthase. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

In one embodiment, a recombinant DNA construct comprising at least one first heterologous polynucleotide encoding a plastidic carbonic anhydrase polypeptide, wherein said polynucleotide is operably linked to at least one regulatory sequence and at least one second heterologous polynucleotide encoding a DGAT polypeptide operably linked to at least one regulatory sequence, wherein expression of said recombinant DNA construct in a transgenic soybean seed results in an increased oil content in a transgenic soybean seed, when compared to a control seed that expresses said second polypeptide but does not express said first polypeptide. The second heterologous polynucleotide may encode an ODP1, a Lec1 or FUSCA3 polypeptide. Furthermore, the recombinant construct may further comprise a construct downregulating galactinol synthase activity, wherein the first heterologous polynucleotide, the second heterologous polynucleotide and the galactinol synthase construct can be in the same construct or in separate constructs.

In another embodiment, the invention comprises regulatory sequences comprising at least two different seed-specific promoters, wherein one of said promoters is operably linked to the first heterologous polynucleotide and the other promoter is linked to the second heterologous polynucleotide of the invention. Said seed-specific promoters are selected from the group consisting of the alpha prime subunit of beta conglycinin promoter, soybean sucrose synthase promoter, Medicago trunculata sucrose synthase promoter, Kunitz trypsin inhibitor 3, annexin promoter, Gly1 promoter, beta subunit of beta conglycinin promoter, P34/Gly Bd m 30K promoter, albumin promoter, Leg A1 promoter and Leg A2 promoter.

In another embodiment of the present invention the increase in oil content is at least 10% in seeds expressing the recombinant constructs of the invention.

In yet another embodiment the recombinant DNA constructs of the invention comprise a carbonic anhydrase polypeptide comprising an amino acid sequence with at least 80%, 85%, 90%. 95% or 100% sequence identity to SEQ ID NOs: 5, 12 or 17.

In another embodiment, a recombinant DNA construct as described herein, wherein the recombinant DNA construct further comprises a seed-specific promoter operably linked to a second heterologous polynucleotide encoding a DGAT polypeptide. The second heterologous polynucleotide may encode a DGAT1 polypeptide. The DGAT1 polypeptide may comprise an amino acid sequence with at least 80%, 85%, 90%, 95% or 100% sequence identity to SEQ ID NO: 32. The second heterologous polynucleotide may encode a DGAT2 polypeptide. The DGAT2 polypeptide may comprise an amino acid sequence with at least 80%, 85%, 90%, 95% or 100% sequence identity to SEQ ID NO: 34.

In another embodiment, a recombinant DNA construct as described herein, wherein the recombinant DNA construct further comprises a seed-specific promoter operably linked to a second heterologous polynucleotide encoding an ODP1 polypeptide comprising an amino acid sequence with at least 80%, 85%, 90%, 95% or 100% identity to SEQ ID NO: 26 or 38.

In another embodiment, the ODP1 polypeptide is an allele of SEQ ID NO: 26 or 38.

In another embodiment, the ODP1 polypeptide comprises two APETALA2 (AP2) domains.

ODP1 sequences have also been disclosed in PCT Publication Number WO2010114989, U.S. Pat. No. 7,157,621, and US20100242138, each of which are incorporated herein by reference.

In another embodiment, a recombinant DNA construct as described herein, wherein the recombinant DNA construct further comprises a seed-specific promoter operably linked to a second heterologous polynucleotide encoding an FUSCA3 polypeptide comprising an amino acid sequence with at least 80%, 85%, 90%, 95% or 100% identity to SEQ ID NO: 28 or 30.

In yet another embodiment, a recombinant DNA construct as described herein, wherein the recombinant DNA construct further comprises a seed-specific promoter operably linked to a second heterologous polynucleotide encoding a Lec1 polypeptide comprising an amino acid sequence with at least 80%, 85%, 90%, 95% or 100% identity to SEQ ID NO: 36.

Examples of polypeptides that may be used include those having an amino acid sequence of at least 50%, 51%, 52%, 53%, 54%, 55%, 58%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the polypeptides disclosed herein, based on the Clustal V method of alignment.

Plants and seeds comprising the recombinant DNA construct of the invention are also embodiments of the invention. The plants and seeds can be soybean plants or soybean seeds. The seeds of the invention can comprise seed treatments, such as but not limited to a herbicide, an insecticide or a fungicide.

An additional embodiment of the invention comprises a method of increasing oil content of a soybean seed, the method comprising the steps of introducing into a regenerable soybean cell the recombinant DNA constructs of the invention; regenerating a transgenic plant from the regenerable soybean cell of (a) wherein the transgenic plant comprises the recombinant DNA construct; and selecting a transgenic plant, or a transgenic progeny plant, wherein seed of the transgenic plant or the transgenic progeny plant comprises the recombinant construct and exhibits increased seed oil content, when compared to a control soybean seed not comprising the DNA recombinant construct.

Further embodiments include transgenic plants and seed obtained by the methods of the invention.

Products and or/by products obtained from the transgenic seed obtained by the methods of the invention are also included. Products and by/products include but are not limited to oil, protein isolate, a protein concentrate, meal, full fat flour, milk powder, defatted flour, milk, textured proteins, textured flours, textured concentrates and textured isolates.

Additional embodiments include food, beverages, and animal feed incorporating any of the products of the invention.

Progeny obtained from the transgenic seed of the invention is also included. Another embodiment include sucrose synthase promoters from soybean and *Medicago truncatula*. Further embodiments include plastidic carbonic anhydrase from soybean and *Arabidopsis*.

In another embodiment, a plant or a seed comprising any of the recombinant DNA constructs described above. The plant and the seed may be an oilseed plant and seed. The plant or seed may be a soybean plant or seed.

In another embodiment, a method of increasing oil content of a soybean seed, the method comprising the steps of: (a) introducing into a regenerable soybean cell any one of the recombinant DNA constructs described herein; (b) regenerating a transgenic plant from the regenerable soybean cell of (a) wherein the transgenic plant comprises the recombinant DNA construct; and (c) selecting a transgenic plant of step (b), or a transgenic progeny plant from the transgenic plant of step (b), wherein seed of the transgenic plant or the transgenic progeny plant comprises the recombinant construct and exhibits increased seed oil content, when compared to a control soybean seed not comprising the DNA recombinant construct. The percent oil content of the transgenic soybean seed may be at least 3%, 4%, 5%, 6%, 7%, 8%, 9%, 10%, 11%, 12%, 13%, 14%, or 15%.

In another embodiment, a transgenic plant obtained by any of the methods described herein, and transgenic seed of said transgenic plant.

In another embodiment, a vector, cell, plant, plant tissue or seed comprising any of the recombinant DNA constructs described herein.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palm itoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"Lipid bodies" refer to lipid droplets that usually are bounded by specific proteins and a monolayer of phospholipid. These organelles are sites where most organisms transport/store neutral lipids. Lipid bodies are thought to arise from microdomains of the endoplasmic reticulum that contain TAG-biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or TAG, respectively (or collectively, acylglycerols). A hydrolysis reaction must occur to release free fatty acids from acylglycerols.

The term "oil" refers to a lipid substance that is liquid at 25° C. and usually polyunsaturated. In contrast, the term "fat" refers to a lipid substance that is solid at 25° C. and usually saturated.

The terms "triacylglycerol", "oil" and "TAGs" are used interchangeably herein, and refer to neutral lipids composed of three fatty acyl residues esterified to a glycerol molecule (and such terms will be used interchangeably throughout the present disclosure herein). Such oils can contain long chain PUFAs (polyunsaturated fatty acids), as well as shorter saturated and unsaturated fatty acids and longer chain saturated fatty acids. Thus, "oil biosynthesis" generically refers to the synthesis of TAGs in the cell (PCT Publication Nos. WO2005063988, WO2007087492, WO2007101273 and WO2007103738, U.S. Pat. No. 7,812,216).

Oil and protein content in seeds can be determined using Near Infrared Spectroscopy by methods familiar to one skilled in the art (Agelet, et al. (2012) Journal of Agricultural and Food Chemistry, 60(34): 8314-8322). An apparatus and methods for NIR analysis of single seeds and multiple seeds has been described in U.S. Pat. No. 7,508,517, herein incorporated by reference. Additional methods for the analysis of seed composition are provided in U.S. Pat. No. 8,143,473, herein incorporated by reference.

*Medicago truncatula* is a small legume native to the Mediterranean region that is used in genomic research. This species has been used as a model organism for legume biology because it has a small diploid genome, is self-fertile, has a rapid generation time and prolific seed production, and is amenable to genetic transformation.

The term "sucrose synthase" (SUS) refers to an enzyme used in carbohydrate metabolism that catalyzes the reversible conversion of sucrose and uridine diphosphate (UDP) to UDP-glucose and fructose in vitro. The terms "Soybean sucrose synthase 2" and "GmSuS" are used interchangeably herein. The Soybean sucrose synthase gene is from genomic locus Glyma13g17420.

The term "germination" refers to the process by which a dormant seed begins to sprout and grow into a seedling.

"Normal germination", as used herein, refers to a germination rate for seed of a transgenic plant comprising the recombinant DNA construct that is within at least 85%, 86%, 87%, 88%, 89%, 90%, 91%, 92%, 93%, 94%, 95%, 96%, 97%, 98%, 99% or 100% of the observed germination rate, under the same conditions, for seed of a corresponding control plant that does not comprise the recombinant DNA construct.

In an embodiment of the present invention, the "cis-acting transcriptional regulatory elements" from the promoter sequence disclosed herein can be operably linked to "cis-acting transcriptional regulatory elements" from any heterologous promoter. Such a chimeric promoter molecule can be engineered to have desired regulatory properties. In an embodiment of this invention a fragment of the disclosed promoter sequence that can act either as a cis-regulatory sequence or a distal-regulatory sequence or as an enhancer sequence or a repressor sequence, may be combined with either a cis-regulatory or a distal regulatory or an enhancer sequence or a repressor sequence or any combination of any of these from a heterologous promoter sequence.

In a related embodiment, a cis-element of the disclosed promoter may confer a particular specificity such as conferring enhanced expression of operably linked polynucleotide molecules in certain tissues and therefore is also capable of regulating transcription of operably linked polynucleotide molecules.

Promoter fragments that comprise regulatory elements can be added, for example, fused to the 5' end of, or inserted within, another promoter having its own partial or complete regulatory sequences (Fluhr et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991; 1987; Aryan et al., Mol. Gen. Genet. 225:65-71, 1991).

Cis elements can be identified by a number of techniques, including deletion analysis, i.e., deleting one or more nucleotides from the 5' end or internal to a promoter; DNA binding protein analysis using DNase I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, *Methods in Plant Biochemistry and Molecular Biology*, Dashek, ed., CRC Press, 1997, pp. 397-422; and *Methods in Plant Molecular Biology*, Maliga et al., eds., Cold Spring Harbor Press, 1995, pp. 233-300).

Cis elements can be obtained by chemical synthesis or by cloning from promoters that include such elements, and they can be synthesized with additional flanking sequences that contain useful restriction enzyme sites to facilitate subsequent manipulation. Promoter fragments may also comprise other regulatory elements such as enhancer domains, which may further be useful for constructing chimeric molecules.

Methods for construction of chimeric and variant promoters of the present invention include, but are not limited to, combining control elements of different promoters or duplicating portions or regions of a promoter (see for example, U.S. Pat. No. 4,990,607; U.S. Pat. No. 5,110,732; and U.S. Pat. No. 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In an embodiment of the present invention, the soy sucrose synthase promoter disclosed herein can be modified. Those skilled in the art can create promoters that have variations in the polynucleotide sequence. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

The present invention encompasses functional fragments and variants of the promoter sequence disclosed herein.

A "functional fragment" herein is defined as any subset of contiguous nucleotides of the promoter sequence disclosed herein, that can perform the same, or substantially similar function as the full length promoter sequence disclosed herein. A "functional fragment" with substantially similar function to the full length promoter disclosed herein refers to a functional fragment that retains largely the same level of activity as the full length promoter sequence and exhibits the same pattern of expression as the full length promoter sequence. A "functional fragment" of the promoter sequence disclosed herein exhibits constitutive expression.

A "variant", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof. Variant polynucleotides also encompass sequences derived from a mutagenic and recombinogenic procedure such as DNA shuffling. With such a procedure, one or more cis-elements for the promoter can be manipulated to create a new enhancer domain. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Substitutions, deletions, insertions or any combination thereof can be combined to produce a final construct.

For polynucleotides, naturally occurring variants can be identified with the use of well-known molecular biology techniques, such as, for example, with polymerase chain reaction (PCR) and hybridization techniques as outlined herein. Generally, variants of a particular polynucleotide of the invention will have at least about 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

A biologically active variant of a polynucleotide of the invention may differ from that sequence by as few as 1-15 nucleic acid residues, as few as 1-10, such as 6-10, as few as 10, 9, 8, 7, 6, 5, 4, 3, 2, or even 1 nucleic acid residue.

The promoter of the present invention may also be a promoter which comprises a nucleotide sequence hybridizable under stringent conditions with the complementary strand of the nucleotide sequence as described in PCT publication (PCT/US12/70828, incorporated herewith by reference).

Hybridization of such sequences may be carried out under stringent conditions. The terms "stringent conditions" and "stringent hybridization conditions" as used herein refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

Stringent conditions may also be achieved with the addition of destabilizing agents such as formamide.

It is also possible to use a commercially available hybridization kit which uses no radioactive substance as a probe. Specific examples include hybridization with an ECL direct labeling & detection system (commercially available from Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See also Sambrook.

In an embodiment of the current invention, isolated sequences that have seed-specific promoter activity and which hybridize under stringent conditions to the soybean sucrose synthase promoter sequence disclosed herein, or to fragments thereof, are encompassed by the present invention. Generally, stringent conditions are selected to be about 5° C. lower than the T$_m$ for the specific sequence at a defined ionic strength and pH. However, stringent conditions encompass temperatures in the range of about 1° C. to about 20° C. lower than the T$_m$, depending upon the desired degree of stringency as otherwise qualified herein.

It is well understood by those skilled in the art that different terminator sequences may be used for the constructs described in the current invention. Terminators include, but are not limited to, bean phaseolin 3' terminator (WO 2004/071467), *Glycine max* Myb2 3' (U.S. application Ser. No. 12/486,793), *Glycine max* kunitz trypsin inhibitor 3' (WO 2004/071467), *Glycine max* BD30 (also called P34) 3' (WO 2004/071467), *Pisum sativum* legumin A2 3' (WO 2004/071467), and *Glycine max* albumin 2S 3' (WO 2004/071467).

In addition, WO 2004/071467 and U.S. Pat. No. 7,129,089 describe the further linking together of individual promoter/gene/transcription terminator cassettes in unique combinations and orientations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination or orientations. In so doing, any combination and orientation of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, *CABIOS.* 5:151-153 (1989); Higgins, D. G. et al., *Comput Appl. Biosci.* 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit altered oil content or used in a breeding program to produce hybrid seed, which can be grown to produce plants that would exhibit such altered oil content.

The modified seed and grain of the invention can also be obtained by breeding with transgenic plants, by breeding between independent transgenic events, by breeding of plants with one or more alleles (including mutant alleles) of genes encoding the proteins of the invention. Breeding, including introgression of transgenic and mutant loci into elite breeding germplasm and adaptation (improvement) of breeding germplasm to the expression of transgenes and mutant alleles, can be facilitated by methods such as by marker assisted selected breeding.

Embodiments of the invention include:

In one embodiment, a recombinant DNA construct comprising at least one first heterologous polynucleotide encoding a plastidic carbonic anhydrase polypeptide, wherein said polynucleotide is operably linked to at least one regulatory sequence and at least one second heterologous polynucleotide encoding a DGAT polypeptide operably linked to at least one regulatory sequence, wherein expression of said recombinant DNA construct in a transgenic soybean seed results in an increased oil content in a transgenic soybean seed, when compared to a control seed that expresses said second polypeptide but does not express said first polypeptide. In one embodiment, a recombinant DNA construct wherein the second heterologous polynucleotide encodes an ODP1 polypeptide, a LeC1 polypeptide or a FUSCA3 polypeptide.

In another embodiment, a recombinant construct wherein the recombinant construct(s) of the invention further comprise a construct downregulating galactinol synthase activity. The recombinant constructs of the invention can be in the same construct or in separate constructs.

In yet another embodiment, a recombinant construct of the invention, wherein the regulatory sequence(s) comprise at least two different seed-specific promoters, wherein one of the promoters is operably linked to the first heterologous polynucleotide and the other promoter is linked to the second heterologous polynucleotide.

In a further embodiment, a recombinant construct of the invention wherein the regulatory sequence comprises at least two different seed-specific promoters, wherein one of the promoters is operably linked to the first heterologous polynucleotide and the other promoter is linked to the second heterologous polynucleotide and wherein the seed-specific promoters are selected from the group consisting of the alpha prime subunit of beta conglycinin promoter, soybean sucrose synthase promoter, *Medicago trunculata* sucrose synthase promoter, Kunitz trypsin inhibitor 3, annexin promoter, Gly1 promoter, beta subunit of beta conglycinin promoter, P34/Gly Bd m 30K promoter, albumin promoter, Leg A1 promoter and Leg A2 promoter.

One embodiment comprises an increase in oil content of at least 10%. In one embodiment, a recombinant DNA construct of the invention, wherein the carbonic anhydrase polypeptide comprises an amino acid sequence with at least 80%, 85%, 90%, 95% or 100% sequence identity to SEQ ID NO:5, 12 or 17.

In one embodiment, a recombinant DNA construct of the invention, wherein the second heterologous polynucleotide encodes a DGAT1 polypeptide.

In one embodiment, a recombinant DNA construct of the invention, wherein the DGAT1 polypeptide comprises an amino acid sequence with at least 80%, 90%, 95% or 100% sequence identity to SEQ ID NOs:32.

In one embodiment, a recombinant DNA construct of the invention, wherein the second heterologous polynucleotide encodes a DGAT2 polypeptide. In one embodiment, a recombinant DNA construct of the invention, wherein the DGAT2 polypeptide comprises an amino acid sequence with at least 80%, 90%, 95% or 100% sequence identity to SEQ ID NOs:34.

In one embodiment, a recombinant DNA construct of the invention, wherein the ODP1 polypeptide comprises an amino acid sequence with at least 80%, 85%, 90%, 95% or 100% sequence identity to SEQ ID NOs:26 or 38.

In one embodiment, a recombinant DNA construct of the invention, wherein the Lec1 polypeptide comprises an amino acid sequence with at least 80%, 85%, 90%, 95% or 100% sequence identity to SEQ ID NOs:36.

In one embodiment, a recombinant DNA construct of the invention, wherein the FUCSA3 polypeptide comprises an amino acid sequence with at least 80%, 85%, 90%, 95% or 100% sequence identity to SEQ ID NO:28 or 30.

Additional embodiments comprise plant or a seed comprising the recombinant DNA construct of the invention.

The plant or seed can be a soybean plant or soybean seed.

The seed(s) of the invention can further comprise a seed treatment.

The seed treatment can be a herbicide, an insecticide or a fungicide.

There are a large number of chemical compounds in use as herbicides including organic and inorganic molecules, such as but not limited to Phenoxycarboxylic acids (e.g. 2,4 D), Benzoates (e.g. pyrithiobac), Benzonitriles (e.g. Dichlobenil and some of the hydroxybenzonnitriles), Benzothiadiazoles (e.g. Bentazon), Triazines (e.g. chlortriazines and methylthiotriazines), Acetam ides (e.g. Acetochlor), Aliphatics (e.g. acrolein), Ureas and phenylureas (e.g. diuron sulphonylureas and monouron), Aromatic acids (e.g. Benzoic acid derivatives, dicamba, picloram), Carbamates and thiocarbamates (e.g. asulam desmedipham), Cineoles (e.g. cinmethylin), Cyclohexanediones (e.g. cycloxidim, sethoxydim, Dinitroanilines, Diphenyl ethers e.g. Acifluorfen), Imidazolidinones and imidazolinones (e.g. buthidazole, Imazaquin), Imines (e.g. CGA-248757), N-Phenylphthallmides (e.g. Flumiclorac), Nitriles (e.g. Bromoxynil, Dichlobenil), Organic arsenicals (e.g. cacodylic acid and monosodium methanearsonate), Oxadiazoles and oxydiazolidines (e.g. oxadiazon, methazole), Phenols (e.g. dinoseb), Phenylpyridazines (e.g. Pyridate), Phenyl Triazinones (e.g. Sulfentrazone), Phthalamates (e.g. Naptalam), Phosphonic acid derivatives (e.g. glyphosate), Pyrazollums (e.g. Difenzoquat), Pyridazinones and pyridinones (e.g. Norflurizon, Fluridone), Pyridines and related nitrogenous compounds (e.g. pyrichlor, thiazophyr, paraquat, diquat), Quinollinecarboxylic acids (e.g. Quinclorac), Tetrahydropyrimidinones, Triazinones (e.g. Metribuzin), Triazoles (e.g. Amitrole), Triazolopyrimidine sulfonanilides (e.g. Flumetsulam), Uracils, Sodium compounds, Heavy metal sulphate.

Low biological impact methods have been of emerging interest in reducing the widespread ecological impacts of chemicals of historic herbicide usage. Thus some research has focused upon formulations that avoid acute toxicity to organisms, especially non-target species. An example of such a herbicide is corn meal gluten, which has virtually no toxicity, but acts by inhibiting seed germination in certain plant species.

One embodiment comprises a method of increasing oil content of a soybean seed, the method comprising the steps of introducing into a regenerable soybean cell the recombinant DNA construct(s) of the invention, regenerating a transgenic plant from the regenerable soybean cell of (a) wherein the transgenic plant comprises the recombinant DNA construct; and selecting a transgenic plant, or a transgenic progeny plant from the transgenic plant, wherein seed of the transgenic plant or the transgenic progeny plant comprises the recombinant construct and exhibits increased seed oil content, when compared to a control soybean seed not comprising the DNA recombinant construct.

Plants are subject to multiple potential stresses, diseases, and pests, including abiotic stresses such as temperature stress, moisture stress, and nutrient stress, as well as biotic stresses caused by various microbial pathogens, parasites, attack by insects and other pests, and herbivoy. Agronomic experiments focus on a variety of factors relating to crop plants, including yield, diseases, cultivation, and sensitivity to factors such as climate and soil to enhance the plants response to abiotic and biotic stresses.

The present invention can be, in practice, combined with one or more stress response(s) including disease control traits in a plant to achieve desired traits for enhanced plant stress resistance. Combining traits that employ distinct modes-of-action can provide protected transgenic plants with superior durability over plants harboring a single control trait because of the reduced probability that resistance will develop in the field.

The response to biotic and abiotic stresses, and in particular to identifying elicitors of defense signaling in plants of the invention can be enhanced using methods known to those of skill in the art (see for example US 2014/0090103 A1, published Mar. 27, 2014.

In one embodiment compositions formulated for application to a plant or a part thereof can be applied to the plants of the invention. These compositions may be formulated as a spray, a powder, a granule, or a seed treatment. Another embodiment includes expressing a polypeptide as a transgene effective in enhancing the plants response to abiotic or biotic stresses in the plants of the invention.

Pesticides and insecticides that are useful in compositions in combination with the methods and compositions of the present invention, including as seed treatments and coatings as well as methods for using such compositions can be found, for example, in U.S. Pat. No. 6,551,962.

Although it is believed that the seed treatments can be applied to a transgenic seed in any physiological state, it may be preferred that the seed be in a sufficiently durable state that it incurs no damage during the treatment process. Typically, the seed would be a seed that had been harvested from the field; removed from the transgenic plant; and separated from any other non-seed plant material. The seed would preferably also be biologically stable to the extent that the treatment would cause no biological damage to the seed. Unless advised otherwise, it is believed that the treatment can be applied to the seed at any time between harvest of the seed and sowing of the seed. As used herein, the term "unsown seed" is meant to include seed at any period between the harvest of the seed and the sowing of the seed in the ground for the purpose of germination and growth of the plant. When it is said that unsown seed is "treated" with the pesticide, such treatment is not meant to include those practices in which the pesticide is applied to the soil, rather than to the seed.

The pesticide, or combination of pesticides, can be applied "neat", that is, without any diluting or additional components present. However, the pesticide is typically applied to the seeds in the form of a pesticide formulation. This formulation may contain one or more other desirable components including but not limited to liquid diluents, binders to serve as a matrix for the pesticide, fillers for protecting the seeds during stress conditions, and plasticizers to improve flexibility, adhesion and/or spreadability of the coating.

The subject pesticides can be applied to a seed as a component of a seed coating. Seed coating methods and compositions that are known in the art are useful when they are modified by the addition of one of the embodiments of the combination of pesticides of the present invention. Such coating methods and apparatus for their application are disclosed in, for example, U.S. Pat. Nos. 5,918,413, 5,891, 246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

The pesticides that are useful in the coating are those pesticides that are described herein. The amount of pesticide that is used for the treatment of the seed will vary depending upon the type of seed and the type of active ingredients, but the treatment will comprise contacting the seeds with an amount of the combination of pesticides that is pesticidally effective. When insects are the target pest, that amount will be an amount of the insecticide that is insecticidally effective. An insecticidally effective amount means that amount of insecticide that will kill insect pests in the larvae or pupal state of growth, or will consistently reduce or retard the amount of damage produced by insect pests.

In general, the amount of pesticide that is applied to the seed in the treatment will range from about 10 gm to about 2000 gm of the active ingredient of the pesticide per 100 kg of the weight of the seed. Preferably, the amount of pesticide will be within the range of about 50 gm to about 1000 gm active per 100 kg of seed, more preferably within the range of about 100 gm to about 600 gm active per 100 kg of seed, and even more preferably within the range of about 200 gm to about 500 gm of active per 100 kg of seed weight.

Alternatively, it has been found to be preferred that the amount of the pesticide be over about 60 gm of the active ingredient of the pesticide per 100 kg of the seed, and more preferably over about 80 gm per 100 kg of seed.

The pesticides that are used in the treatment must not inhibit germination of the seed and should be efficacious in protecting the seed and/or the plant during that time in the target insect's life cycle in which it causes injury to the seed or plant. In general, the coating will be efficacious for approximately 0 to 120 days after sowing. The pesticides of the subject invention can be applied to the seed in the form of a coating.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As referred to in this disclosure, the terms "fungal pathogen" and "fungal plant pathogen" include pathogens in the Basidiomycete, Ascomycete, Oomycete and Deuteromycete classes that are the causal agents of a broad spectrum of plant diseases of economic importance, affecting ornamental, turf, vegetable, field, cereal and fruit crops. In the context of this disclosure, "protecting a plant from disease" or "control of a plant disease" includes preventative action (interruption of the fungal cycle of infection, colonization, symptom development and spore production) and/or curative action (inhibition of colonization of plant host tissues).

As referred to in this disclosure, the term mode of action (MOA) is as defined broadly by the Fungicide Resistance Action Committee (FRAC), and is used to distinguish fungicide groups according to their biochemical mode of action in the biosynthetic pathways of plant pathogens. These FRAC-defined MOAs are (A) nucleic acid synthesis, (B) mitosis and cell division, (C) respiration, (D) amino acid and protein synthesis, (E) signal transduction, (F) lipid synthesis and membrane integrity, (G) sterol biosynthesis in membranes, (H) cell wall biosynthesis in membranes, (I) melanin synthesis in cell wall, (P) host plant defense induction, multi-site contact activity and unknown mode of action. Each MOA class consists of one or more groups based either on individual validated target sites of action, or in cases where the precise target site is unknown, based on cross resistance profiles within a group or in relation to other groups. Each of these groupings within a FRAC-defined MOA, whether the target site is known or unknown, is designated by a FRAC code. Additional information on target sites and FRAC codes can be found on the FRAC website.

As referred to in this disclosure, the term "cross resistance" refers to a phenomenon wherein a pathogen evolves resistance to one fungicide and in addition acquires resistance to others. These additional fungicides are typically, but not always, in the same chemical class or have the same target site of action, or can be detoxified by the same mechanism.

As referred to in this disclosure, the term "resistance factor" refers to the ratio of $ED_{50}$ values between resistant and sensitive isolates of a fungal pathogen, where $ED_{50}$ is the effective dose required to control 50% of the fungal pathogen. For additional information on fungicide resistance see K. J. Brent and Derek W. Hollomon, *Fungicide Resistance: The Assessment of Risk*, FRAC Monograph No. 2, $2^{nd}$ ed., 2007.

Preferably, fungicidal compounds are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant and seed cultivars which can be treated include those that are resistant against one or more biotic stresses (pests such as nematodes, insects, mites, fungi, etc.) or abiotic stresses (drought, cold temperature, soil salinity, etc.), or that contain other desirable characteristics. Plants and seeds can be genetically modified to exhibit traits of, for example, herbicide tolerance, insect-resistance, modified oil profiles or drought tolerance. Useful genetically modified plants and seeds containing single gene transformation events or combinations of transformation events are listed in Table 1A. Additional information for the genetic modifications listed in Table 1A can be obtained from the following the OECD, the aphis/USDA and gmoinfo databases.

Treatment of genetically modified plants and seeds with fungicidal compounds may result in super-additive or synergistic effects. For example, reduction in application rates, broadening of the activity spectrum, increased tolerance to biotic/abiotic stresses or enhanced storage stability may be greater than expected from just simple additive effects of the application of fungicidal compounds on genetically modified plants and seeds.

Fungicidal compounds are useful in seed treatments for protecting seeds from plant diseases. In the context of the present disclosure and claims, treating a seed means contacting the seed with a biologically effective amount of a fungicidal compound, which is typically formulated as a composition with the composition(s) of the invention. This seed treatment protects the seed from soil-borne disease pathogens and generally can also protect roots and other plant parts in contact with the soil of the seedling developing from the germinating seed. The seed treatment may also provide protection of foliage by translocation of the fungicide or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with herbicidal, fungicdal or insecticidal compounds can also increase vigor of plants growing from the seed.

Herbicidal, fungicidal or insecticidal compounds and their compositions, both alone and in combination with additional fungicides, nematicides and insecticides, are particularly

TABLE 1A

| Soybean | 260-05 (G94-1, G94-19, G168) | NA | Modified oil/fatty acid | gm-fad2-1 (silencing locus) |
|---|---|---|---|---|
| Soybean | A2704-12 | ACS-GM005-3 | Glufosinate tol. | pat |
| Soybean | A2704-21 | ACS-GM004-2 | Glufosinate tol. | pat |
| Soybean | A5547-127 | ACS-GM006-4 | Glufosinate tol. | pat |
| Soybean | A5547-35 | ACS-GM008-6 | Glufosinate tol. | pat |
| Soybean | CV127 | BPS-CV127-9 | Imidazolinone tol. | csr1-2 |
| Soybean | DAS68416-4 | DAS68416-4 | Glufosinate tol. | pat |
| Soybean | DP305423 | DP-305423-1 | Modified oil/fatty acid; ALS herbicide tol. | gm-fad2-1 (silencing locus); gm-hra |
| Soybean | DP356043 | DP-356043-5 | Modified oil/fatty acid; glyphosate tol. | gm-fad2-1 (silencing locus); gat4601 |
| Soybean | FG72 | MST-FG072-3 | Glyphosate & HPPD tol. | 2mepsps; hppdPF W336 |
| Soybean | GTS 40-3-2 (40-3-2) | MON-04032-6 | Glyphosate tol. | cp4 epsps (aroA:CP4) |
| Soybean | GU262 | ACS-GM003-1 | Glufosinate tol. | pat |
| Soybean | MON87701 | MON-87701-2 | Insect res. | cry1Ac |
| Soybean | MON87705 | MON-87705-6 | Modified oil/fatty acid; glyphosate tol. | fatb1-A (sense & antisense); fad2-1A (sense & antisense); cp4 epsps (aroA:CP4) |
| Soybean | MON87708 | MON-87708-9 | Dicamba & glyphosate tol. | dmo; cp4 epsps (aroA:CP4) |
| Soybean | MON87769 | MON-87769-7 | Modified oil/fatty acid; glyphosate tol. | Pj.D6D; Nc.Fad3; cp4 epsps (aroA:CP4) |
| Soybean | MON89788 | MON-89788-1 | Glyphosate tol. | cp4 epsps (aroA:CP4) |
| Soybean | W62 | ACS-GM002-9 | Glufosinate tol. | bar |
| Soybean | W98 | ACS-GM001-8 | Glufosinate tol. | bar |
| Soybean | MON87754 | MON-87754-1 | High oil | dgat2A |
| Soybean | DAS21606 | DAS-21606 | Aryloxyalkanoate & glufosinate tol. | Modified aad-12; pat |
| Soybean | DAS44406 | DAS-44406-6 | Aryloxyalkanoate, glyphosate & glufosinate tol. | Modified aad-12; 2mepsps; pat |
| Soybean | SYHT04R | SYN-0004R-8 | Mesotrione tol. | Modified avhppd | useful in seed treatment for crops including, but not limited to, maize or corn, soybeans, cotton, cereal (e.g., wheat, oats, barley, rye and rice), potatoes, vegetables and oilseed rape.

Furthermore, fungicidal compounds are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with fungicidal compounds can increase the period of time during which perishable edible plant parts (e.g, fruits, seeds, foliage, stems, bulbs, tubers) can be stored refrigerated or un-refrigerated after harvest, and remain edible and free from noticeable or harmful degradation or contamination by fungi or other microorganisms. Treatment of edible plant parts before or after harvest with fungicidal compounds can also decrease the formation of toxic metabolites of fungi or other microorganisms, for example, mycotoxins such as aflatoxins.

Plant disease control is ordinarily accomplished by applying an effective amount of a compound of this invention either pre- or post-infection, to the portion of the plant to be protected such as the roots, stems, foliage, fruits, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants. Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.001 g (more typically about 0.1 g) to about 10 g per kilogram of seed.

Fungicidal compounds can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising the compositions of the invention, a fungicidal compound (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures, one or more other biologically active compounds or agents can be formulated together, to form a premix, or one or more other biologically active compounds or agents can be formulated separately and the formulations combined together before application (e.g., in a spray tank) or, alternatively, applied in succession.

Fungicidal compounds and compositions thereof can be applied to plants genetically transformed, such as the pants of the invention, to express in addition to the recombinant constructs of the invention, proteins toxic to invertebrate pests (such as *Bacillus thuringiensis* delta-endotoxins). The effect of the exogenously applied fungicidal compounds may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

In certain instances, combinations of a fungicidal compound with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Also in certain instances, combinations of a fungicidal compound with other biologically active compounds or agents can result in a less-than-additive (i.e. safening) effect on organisms beneficial to the agronomic environment. For example, a fungicidal compound may safen a herbicide on crop plants or protect a beneficial insect species (e.g., insect predators, pollinators such as bees) from an insecticide.

Fungicides of note for formulation to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Insecticides or nematicides with which fungicidal compounds can be formulated to provide mixtures useful in seed treatment include but are not limited to abamectin, acetamiprid, acrinathrin, afidopyropen, am itraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyclaniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, fluensulfone, flufenoxuron, flufenoxystrobin, fufiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, momfluorothrin, nitenpyram, nithiazine, novaluron, oxamyl, pyflubumide, pymetrozine, pyrethrin, pyridaben, pyriminostrobin, pyridalyl, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

Compositions comprising fungicidal compounds useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM 1-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureociffium lilacinum*.

Seed treatments can also include one or more nematicidal agents of natural origin such as the elicitor protein called harpin which is isolated from certain bacterial plant pathogens such as Erwinia amylovora. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by rhizobia bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

In one embodiment a method for controlling plant diseases caused by fungal plant pathogens comprising applying to the plant of the invention or portion thereof, or to the plant seed of the invention, a fungicidally effective amount of a fungicidal compound as described herein.

Additional embodiments include transgenic plant(s) and seed(s) obtained by the methods of the invention. The transgenic plant(s) or seed(s) can be soybean plants or soybean seeds.

Product(s) and or/by product(s) obtained from the transgenic seed are also part of the invention. Product and/or by-product include oil, protein isolate, protein concentrate, meal, full fat flour, milk powder, defatted flour, milk, textured proteins, textured flours, textured concentrates and textured isolates.

Additional embodiments comprise a food, beverage, and animal feed which has incorporated therein the products and/or by-products of the invention.

Yet another embodiment includes progeny obtained from the transgenic plant or seed of the invention.

DGAT sequences have also been described in the following: US Publication Numbers US20080295204, US20090293152, US20090293151, US20090158460, US20090293150 and US20090291479; U.S. Pat. No. 7,273,746 and U.S. Pat. No. 7,267,976; and PCT Publication No. WO2011062748; each of which is incorporated herein by reference.

One embodiment of the invention is a method of increasing oil content of a soybean seed, the method comprising the steps of: (a) introducing into a regenerable soybean cell one or more recombinant DNA constructs as described herein; (b) regenerating a transgenic plant from the regenerable soybean cell of (a) wherein the transgenic plant comprises the recombinant DNA construct; and (c) selecting a transgenic plant of step (b), or a transgenic progeny plant from the transgenic plant of step (b), wherein seed of the transgenic plant or the transgenic progeny plant comprises the recombinant DNA construct and wherein expression of said one or more polypeptides in the transgenic soybean seed comprising said recombinant DNA construct results in an increased oil content in the transgenic soybean seed, when compared to a control soybean seed not comprising said one or more recombinant DNA constructs. The percent oil content of the transgenic soybean seed may be at least 3%, 4%, 5%, 6%, 7%, 8%, 9%, 10%, 11%, 12%, 13%, 14% or 15%.

One embodiment of the invention is a method of increasing oil content of a soybean seed, the method comprising the steps of:

(a) crossing the following:

(i) a first transgenic soybean plant comprising a first recombinant DNA construct comprising a first seed-specific promoter linked to at least one polynucleotide encoding a plastidic carbonic anhydrase; with (ii) a second transgenic soybean plant comprising a second recombinant DNA construct comprising a second seed-specific promoter operably linked to a second heterologous polynucleotide encoding at least one DGAT polypeptide; and (b) selecting a third transgenic plant from the cross of step (a), wherein seed of the third transgenic plant comprises the first and the second recombinant DNA constructs and wherein co-expression of said first polypeptide and said second polypeptide in said transgenic soybean seed results in an increased oil content in the transgenic soybean seed, when compared to a control soybean seed comprising only one, but not both, of the first and the second recombinant DNA constructs. The percent oil content of the transgenic soybean seed may be at least 3%, 4%, 5%, 6%, 7%, 8%, 9%, 10%, 11%, 12%, 13%, 14% or 15%.

The second recombinant construct may comprise at least one ODP1, FUSCA3 or Lec1 polypeptide. The DGAT polypeptide may be a DGAT1 or DGAT2 polypeptide.

In some embodiments, the percent change or percent increase in oil content is at least 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75% or 80% and less than about 200%, 150%, 100%, 90%, 75%, 60% or 50%.

In some embodiments, the percentage point increase in oil compared with a control seed is at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2., 2.3, 2.4, 2.5, 2.6, 2.7, 2.8, 2.9, 3.0, 3.1, 3.2, 3.3., 3.4, 3.5, 3.6, 3.7, 3.8, 3.9, 4.0, 4.1, 4.2, 4.3, 4.4, 4.5, 4.6, 4,7, 4.8, 4.9, or 5.0 percentage points and less than about 20, 15, 10, 5, or 4 percentage points.

In some embodiments, the percent change or percent increase in protein content is at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 150%, 200% and less than about 300%, 200%, 150%, 100%, 90%, 75%, 60% or 50%.

In yet another embodiment, the percentage point increase in protein content is at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2., 2.3, 2.4, 2.5, 2.6, 2.7, 2.8, 2.9, 3.0, 3.1, 3.2, 3.3., 3.4, 3.5, 3.6, 3.7, 3.8, 3.9, 4.0, 4.1, 4.2, 4.3, 4.4, 4.5, 4.6, 4,7, 4.8, 4.9, or 5.0 percentage points and less than about 20, 15,10, 5, or 4 percentage points.

In the above embodiments, the control seed comprising only one, but not both, of the first and the second recombinant DNA constructs may be either: (a) a control seed comprising the first recombinant DNA construct but not comprising the second recombinant DNA construct, or (b) a control seed comprising the second recombinant DNA construct but not comprising the first recombinant DNA construct.

Additional embodiments include a vector, cell, plant, or seed comprising one or more of the recombinant DNA constructs described in the present invention.

The invention also encompasses regenerated, mature and fertile transgenic plants comprising one or more of the recombinant DNA constructs described above, transgenic seeds produced therefrom, T1 and subsequent generations. The transgenic plant cells, tissues, plants, and seeds may comprise at least one recombinant DNA construct of interest.

In another embodiment, the plant or seed comprising the recombinant DNA construct described herein may be at least one selected from the group consisting of: a dicotyledonous plant or seed; a legume plant or seed; an oilseed plant or seed; and a soybean plant or seed.

In another embodiment, the transgenic soybean seeds of the invention may be processed to yield soy oil, soy products and/or soy by-products. The transgenic soybean seeds of the invention can be processed to yield soy oil, soy products and/or soy by-products.

"Soy products" can include, but are not limited to, those items listed in Table 1B.

TABLE 1B

| Soy Protein Products Derived from Soybean Seeds[a] |
|---|
| Whole Soybean Products |
| Roasted Soybeans<br>Baked Soybeans<br>Soy Sprouts<br>Soy Milk<br>Specialty Soy Foods/Ingredients |
| Soy Milk<br>Tofu<br>Tempeh |

TABLE 1B-continued

| Soy Protein Products Derived from Soybean Seeds[a] |
|---|
| Miso<br>Soy Sauce<br>Hydrolyzed Vegetable Protein<br>Whipping Protein<br>Processed Soy Protein Products |
| Full Fat and Defatted Flours<br>Soy Grits<br>Soy Hypocotyls<br>Soybean Meal<br>Soy Milk<br>Soy Protein Isolates<br>Soy Protein Concentrates<br>Textured Soy Proteins<br>Textured Flours and Concentrates<br>Textured Concentrates<br>Textured Isolates |

[a]See Soy Protein Products: Characteristics, Nutritional Aspects and Utilization (1987). Soy Protein Council.

"Processing" refers to any physical and chemical methods used to obtain the products listed in Table 1A and includes, but is not limited to, heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991-1992). Products referred to as being "high protein" or "low protein" are those as described by these Standard Specifications. "NSI" refers to the Nitrogen Solubility Index as defined by the American Oil Chemists' Society Method Ac4 41. "KOH Nitrogen Solubility" is an indicator of soybean meal quality and refers to the amount of nitrogen soluble in 0.036 M KOH under the conditions as described by Araba and Dale [(1990) *Poult. Sci.* 69:76-83]. "White" flakes refer to flaked, dehulled cotyledons that have been defatted and treated with controlled moist heat to have an NSI of about 85 to 90. This term can also refer to a flour with a similar NSI that has been ground to pass through a No. 100 U.S. Standard Screen size. "Cooked" refers to a soy protein product, typically a flour, with an NSI of about 20 to 60. "Toasted" refers to a soy protein product, typically a flour, with an NSI below 20. "Grits" refer to defatted, dehulled cotyledons having a U.S. Standard screen size of between No. 10 and 80. "Soy Protein Concentrates" refer to those products produced from dehulled, defatted soybeans by three basic processes: acid leaching (at about pH 4.5), extraction with alcohol (about 55-80%), and denaturing the protein with moist heat prior to extraction with water. Conditions typically used to prepare soy protein concentrates have been described by Pass [(1975) U.S. Pat. No. 3,897,574; Campbell et al., (1985) in New Protein Foods, ed. by Altschul and Wilcke, Academic Press, Vol. 5, Chapter 10, *Seed Storage Proteins*, pp 302-338]. "Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously [Atkinson (1970) U.S. Pat. No. 3,488,770, Horan (1985) In *New Protein Foods, ed. by Altschul and Wilcke, Academic*

Press, Vol. 1A, Chapter 8, pp 367-414]. Moreover, conditions used during extrusion processing of complex foodstuff mixtures that include soy protein products have been described previously [Rokey (1983) *Feed Manufacturing Technology III*, 222-237; McCulloch, U.S. Pat. No. 4,454, 804].

TABLE 1C

Generalized Steps for Soybean Oil and Byproduct Production

| Process Step | Process | Impurities Removed and/or By-Products Obtained |
| --- | --- | --- |
| #1 | soybean seed | |
| #2 | oil extraction | meal |
| #3 | Degumming | lecithin |
| #4 | alkali or physical refining | gums, free fatty acids, pigments |
| #5 | water washing | soap |
| #6 | Bleaching | color, soap, metal |
| #7 | (hydrogenation) | |
| #8 | (winterization) | stearine |
| #9 | Deodorization | free fatty acids, tocopherols, sterols, volatiles |
| #10 | oil products | |

More specifically, soybean seeds are cleaned, tempered, dehulled, and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production, and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel, and cocoa butter.

Plant and microbial oils containing PUFAs that have been refined and/or purified can be hydrogenated, thereby resulting in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, linoleic, and linolenic fatty acids, and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation, and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease. To protect and to enhance yield production and trait technologies, seed treatment options can provide additional crop plan flexibility and cost effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

In yet another embodiment the seeds of the invention may include seed treatments. Seed treatments that may be used on crop seed include, but are not limited to, one or more of abscisic acid, acibenzolar-S-methyl, avermectin, amitrol, azaconazole, azospirillum, azadirachtin, azoxystrobin, *bacillus* spp. (including one or more of cereus, firmus, megaterium, pumilis, sphaericus, subtilis and/or thuringiensis), *bradyrhizobium* spp. (including one or more of betae, canariense, elkanii, iriomotense, japonicum, liaonigense, pachyrhizi and/or yuanmingense), captan, carboxin, chitosan, clothianidin, copper, cyazypyr, difenoconazole, etidiazole, fipronil, fludioxonil, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofosmethyl, triadimenol, trichoderma, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

A cell of the invention can be part of an oilseed plant, such as, but not limited to, soybean, corn, canola, sunflower, flax, cotton, and safflower.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Identification of Carbonic Anhydrases from Soy and *Arabidopsis* Expression of YLDGAT2 in Soybean The *Yarrowia lipolytica* diacylglycerolacyltransferase 2 (YLDGAT2) was described in U.S. Pat. No. 7,901,928. Cloning of YLDGAT2 into soybean expression vectors under control of the strong, seed-specific soy beta-conglycinin promoter, followed by a phaseolin transcription terminator, was described in U.S. Pat. Nos. 8,153,859 and 8,399,736 (incorporated herewith by reference). Expression of these vectors in soybean or soybean somatic embryos was shown to lead to higher seed oil content.

Using methods described in U.S. Pat. Nos. 8,153,859 and 8,399,736 a new expression vector (PHP43186; SEQ ID NO: 1) was constructed which comprises the YLDGAT2 (nt 5498-7042) under control of the soy beta-conglycinin promoter (nt 4875-5491), followed by a phaseolin transcription terminator (7045-8210). In addition, PHP43186 comprises a soybean acetolactate synthase (als) gene coding region (nt 3392-1437) encoding a mutant ALS enzyme insensitive to sulfonylurea herbicides and having a P178A and W555L mutation in the encoded protein (GM-HRA), under control of the constitutive soy SAMS promoter region (nt 4767-3459) (U.S. Pat. No. 7,217,858) and followed by a soy ALS transcription terminator (nt 1436-786).

Other regulatory elements present on PHP43186 include an ORF stop with stop codons in all 6 frames (ORFSTOP-A, nt 657-672), a FLP recombinase recognition site FRT1 (nt 3407-3454) (U.S. Pat. No. 8,293,533) and a FLP recombinase recognition site FRT87 (nt 701-748) (U.S. Pat. No. 8,293,533). In addition, sequence 8257-624 is vector backbone containing the T7 promoter (sequence 9542-9445), the hygromycin phosphotransferase (hpt) gene coding region (sequence 9444-8404) and the T7 terminator (sequence 8403-8257).

PHP4318A (SEQ ID NO:2) was digested with AscI and the fragment containing YLDGAT2 (SEQ ID NO:33) under control of the soy beta-conglycinin promoter, was purified and used to transform soy as described in U.S. Pat. Nos. 8,153,859 and 8,399,736. Events from this experiment, called Oil57, were selected, plants were regenerated and seed harvested and analyzed for oil content by NMR analysis and fatty acid profile by GC exactly as described in U.S. Pat. Nos. 8,153,859 and 8,399,736.

In this way, a single copy event (called Oil57 6925.8.1.4) was identified having a typical oil increase from overexpression of YLDGAT2 under control of the soy beta-conglycinin promoter. The average percent oil content and average fatty acid profile (reported as wt. % of total fatty acids) for all null T1 seed and all transgenic T1 seed (greater than 18% oleic acid) from event Oil57 6925.8.1.4 is shown in Table 2. In addition, Table 2 shows the change in oil content and fatty acid profile (reported as Delta in Table 2; average value transgenic–average value null) as well as the percent increase or decrease (% Change; (average value transgenic–average value null)/average value null×100%).

TABLE 2

Oil content, protein content and fatty acid profile for null and transgenic T1 seed from event Oil57 6925.8.1.4.

|  | % oil | 16:0% | 18:0% | 18:1% | 18:2% | 18:3% |
|---|---|---|---|---|---|---|
| AFS 6925.8.1.4 Avg. Transgenic | 24.2 | 10.5 | 4.4 | 24.5 | 52.7 | 8.0 |
| AFS 6925.8.1.4 Avg. Null | 21.2 | 12.0 | 3.5 | 13.9 | 58.1 | 12.5 |
| Delta | 3.0 | −1.5 | 0.9 | 10.6 | −5.5 | −4.5 |
| % Change | 14% | −13% | 25% | 76% | −9% | −36% |

T1 seed from event Oil57 6925.8.1.4 was planted and zygosity of plants determined by construct-specific quantitative PCR (qPCR), as described previously in U.S. Pat. No. 8,293,533, issued Oct. 23, 2012.

Based on the qPCR results of T1 plants, T2 seed from homozygous and null T1 plants were planted and plants grown as described in U.S. Pat. No. 8,153,859, issued Apr. 10, 2012 and in U.S. Pat. No. 8,399,73, issued Mar. 19, 2013. Flowers from plants were tagged and developing seed was collected at 15 DAF (days after flowering), 30 DAF and 50 DAF. Seed harvested at each time point were immediately frozen in liquid nitrogen, were ground with a mortar and pestle and the powders were aliquoted into 5 individual reps.

In addition, T3 seed was collected from each plant used in the developmental study and analyzed for % Oil, % Protein, fatty acid profile (Wt. % of Total fatty acids) % Stachyose, % Sucrose, % Total Carbohydrate and % Moisture by single seed Near-Infrared Spectroscopy as described in below.

NIT Measurements, Data Analysis, and Model Development

NIR Spectra, from 850-1050 nm (2-nm step; 30-mm path length), for 400-500 g bulk samples of intact soybeans were acquired in transmission mode using a Foss Tecator AB model 1241 grain analyzer (Hoğanäs, Sweden) fitted with a standard instrument hopper and sample transport mechanism. Each batch was analyzed in duplicate using 10 sub-sample scans, which were saved as the average.

All data analysis was performed using the InfraSoft International (ISI) chemometrics software WinISI II v.1.50e (NIRSystems Inc., Silver Spring, Md., USA). Pre-treatment of the raw NIR (log 1/T) spectral data included multiplicative scatter correction and first derivative transformation over a 4-point (8-nm) gap using a 4-point smoothing function. Predictions of oil and protein content (corrected to a 13% moisture basis) were based on calibration models developed by USDA-FGIS\GIPSA. Calibration models for oleic and linolenic acid were proprietary and were developed in-house using Partial Least-Squares (PLS) regression (Williams and Norris, 1987) utilizing the transformed spectrum captured from material presenting a wide compositional diversity for these two components. The reference chemistry used for the calibrations was developed by gas chromatographic analysis of fatty acid methyl esters of oil extracts derived from the bean samples, after spectral capture. All calibration development work was performed using standardized PLS algorithms within the Win ISI II v.1.50e software. The optimum number of PLS factors was defined as that number of factors beyond which no further improvement in the Standard Error of Cross-Validation (SECV) was observed. Calculation of the SECV was handled automatically by the WinISI software. The SECV was obtained by sequentially removing subsets of samples from the calibration set, re-deriving the model and predicting the removed samples in an iterative manner. Six separate cross-validation tests provided the most reliable estimate of calibration accuracy obtainable from the sample set in question. The coefficient of determination ($R^2$), was used to describe the correlation between reference (observed) and NIR-predicted values for the calibration set. The Relative Predictive Determinant (RPD), defined as the ratio of the SD of the reference values to the SECV, was used as a normalized indicator for comparing NIR models where values >2.0 are generally recognized as sufficient for quantitative measurement (Chang et al., 2001).

% Oil plus % Protein (% Proil) was calculated by adding the individual measurements together.

Results for compositional analysis of T3 seed from event (T2 plants) Oil57 6925.8.1.4 are presented in Table 3. In addition, Table 3 shows the change in content for each species measured (reported as Delta in Table 3; average value transgenic−average value null) as well as the percent increase or decrease (% Change; (average value transgenic−average value null)/average value null×100%).

TABLE 3[1]

Compositional analysis and fatty acid profile of null and transgenic T3 seed from event Oil57 6925.8.1.4 as analyzed by ssNIR.

| Oil 57 | Fatty acid | | | | | oil | prot | proil | stach | suc | tcrb | ms |
|---|---|---|---|---|---|---|---|---|---|---|---|---|
|  | 16:0 | 18:0 | 18:1 | 18:2 | 18:3 | | | | | | | |
| Hz avg | 9.9 | 4.9 | 42.4 | 43.2 | 5.4 | 22.4 | 36.2 | 58.7 | 3.9 | 2.9 | 7.7 | 7.7 |
| Null avg | 10.9 | 4.2 | 24.6 | 53.9 | 8.5 | 19.5 | 31.7 | 51.2 | 4.6 | 4.1 | 9.6 | 7.0 |
| delta | −1.0 | 0.8 | 17.7 | −10.7 | −3.1 | 3.0 | 4.5 | 7.5 | −0.7 | −1.2 | −1.9 | 0.8 |

TABLE 3[1]-continued

Compositional analysis and fatty acid profile of null and transgenic T3 seed from event Oil57 6925.8.1.4 as analyzed by ssNIR.

| Oil 57 | Fatty acid | | | | | oil | prot | proil | stach | suc | tcrb | ms |
|---|---|---|---|---|---|---|---|---|---|---|---|---|
| | 16:0 | 18:0 | 18:1 | 18:2 | 18:3 | | | | | | | |
| % delta | −9 | 18 | 72 | 20 | 36 | 15 | 14 | 15 | −16 | −30 | −20 | 11 |

[1]For this table the following abreviations were used. Fatty acid relates the individual fatty acid to the sum of the five major fatty acids indicated.
16:0 = palmitic acid,
18:0 = stearic acid,
18:1 = oleic acid,
18:2 = linoleic acid,
18:3 = linolenic acid.
Prot = protein,
proil = protein + oil,
stach = stachyose,
suc = sucrose,
tcrb = total carbohydrate,
ms = moisture.
Hz = homozygous.
Avg = average.
All components are expressed in %.

RNA Quantification (RNA SEQ)

Total RNAs were isolated from ground frozen tissue with RNeasy (Qiagen Inc., Valencia, Calif.) according to manufacture protocols. Total RNAs were analyzed for quality and quantity with the Agilent Bioanalyzer RNA Nano kit (Agilent Technologies, Santa Clara, Calif.) and normalized to 1 ug input per sample.

Sequencing libraries were prepared according to Illlumina Inc. (San Diego, Calif.) TruSeq mRNA-Seq protocols. Messenger RNAs were isolated via attachment to oligo (dT) beads, fragmented and reverse transcribed into cDNA by random hexamer prime with Superscript II reverse transcriptase (Life Technologies, Carlsbad, Calif.). Resulting cDNAs were end repairs, 3 prime A-tailed, and ligated with Illumina indexed TruSeq adapters. Ligated cDNA fragments were PCR amplified with Illumina TruSeq primers, purified with AmpureXP Beads (Beckman Coulter Genomics, Danvers, Mass.), and checked for quality and quantity with the Agilent Bioanalyzer DNA 7500 kit.

Libraries were combined into twelve sample pools and pools were normalized to 2 nM. Each pool was denatured according to Illumina sequencing protocols, hybridized and clustered on one flowcell lane using the Illumina cBot. Single-end fifty base sequences and seven base index sequences were generated on the HiSeq 2000 according to Illumina protocols. Data was trimmed for quality with a minimum threshold of Q20 and resulting sequences were split by index identifier.

Sequences were aligned uniquely to the Glyma1 gene models v1.1 via the Bowtie algorithm. Resulting per sample alignments were counted and normalized to Relative Parts Per Ten Million reads (RPKtM) (Mortazavi et al 2008).

Table 4 shows that expression of Glyma02g37710 and Glyma08g39510 is significantly increased in developing seed expressing YLDGAT2, especially at 50 DAF. These 2 genes encode proteins with similarity to carbonic anhydrase enzymes with inferred localization in plastids.

TABLE 4

Expression analysis for null and transgenic homozygous seed expressing YLDGAT2 at 15, 30 and 50 DAF

| gene | construct | DAF[1] | expression (RPKtM)[1] | | ProbT[3] |
|---|---|---|---|---|---|
| | | | TG[2] | Null | |
| Glyma02g37710 | BC::YL_DGAT2 | 15 | 169.8 | 127.7 | 0.6 |
| | | 30 | 49.3 | 57.8 | 0.7 |
| | | 50 | 249.0 | 80.2 | 2.8E−02 |
| Glyma08g39510 | BC::YL_DGAT2 | 15 | 151.9 | 169.8 | 0.4 |
| | | 30 | 74.6 | 71.7 | 0.7 |
| | | 50 | 380.2 | 136.1 | 2.8E−02 |

[1]RPKtM = Relative Parts Per Ten Million
[1]DAF = days after flowering.
[2]TG = Transgenic
[3]ProbT = significance level Analysis of Silique Gene Expression in Transgenic Arabidopsis Events with Increased Seed Oil Content U.S. Pat. No. 8,404,926, describes transgenic Arabidopsis events with increased oil content due to seed-preferred expression of the maize ODP1 transcription factor. Specifically said patent describes one event (C00536) with seed specific (Soy betaconglycinin promoter-driven) overexpression of Zm-ODP1 and three events (36162, 36180 and 36181) in which expression of said gene is under control of the Arabidopsis SU52 promoter. Comparative analysis of gene expression in developing siliques in response to presence of the maize ODP1 transcription factor was performed as follows. Briefly, 24 transgenic plants were grown alongside 12 wild type (wt) plants in the same flats in a total of three biological replicates. Green siliques were harvested 21 days after planting in soil, pooled by genotype and total silique RNA was isolated. Hence two RNA samples were generated from every flat (biological rep). Additional flats planted from identical seed sources were allowed to grow to maturity and oil content of mature, dry seed was determined by NMR. There was at least a 1.2% point increase in seed oil content when transgenic plants expressing the maize ODP1 transcription factor were compared to null plants grown in the same flat. Total RNA was isolated and subjected to comparative transcriptome sequencing using a MiSeq Desktop Sequencer (Illumina, San Diego, Calif. USA) according to manufacturer's instructions.

Table 5 shows that expression of AT4G33580 is significantly increased in developing siliques of all events with seed preferred expression of ZM-ODP1. AT4G33580 encodes a gene encoding a protein with similarity to carbonic anhydrase enzymes with inferred localization in plastids.

TABLE 5

Gene expression of AT4G33580 in developing siliques of *Arabidopsis* plants

| construct | event | Expression (RPKtM) | | |
|---|---|---|---|---|
| | | TG | Null | Prob T |
| SUS2::ZM-ODP1 | 36180 | 52.9 | 30.8 | 6.5E−02 |
| | 36162 | 40.8 | 24.8 | 9.4E−03 |
| | 36181 | 67.6 | 29.4 | 3.9E−04 |
| BC::ZM-ODP1 | C00536 | 43.3 | 17.9 | 3.4E−02 |

Example 2

Cloning *Arabidopsis* and Soy Carbonic Anhydrases Into Soybean Expression Vectors and Co-Expression with Diacylglycerolacyltransferase (DGAT)

*Arabidopsis* Carbonic Anhydrase (At-BCA5):

A full-length-enriched *Arabidopsis thaliana* cDNA library, atgr1c, derived from root and shoot tissue was prepared, cDNA clones were sequenced and the sequences were analyzed by BLAST® (Basic Local Alignment Search Tool) program as described in U.S. Pat. No. 7,157,621.

The full-length sequence of cDNA clone atgr1c.pk095.a9, identified as a beta carbonic anhydrase 5 (AT4G33580) as described in Example 1, is set forth in SEQ ID NO: 3. The coding sequence from clone atgr1c.pk095.a9 is shown in SEQ ID NO: 4 and the encoded amino acid sequence is shown in SEQ ID NO:5.

DNA was prepared from an aliquot of clone atgr1c.pk095.a9 using the QIAprep Spin Miniprep Kit (Qiagen Inc., Valencia, Calif.) following the manufacturer's protocol. NotI restriction sites were added to the ends of At-BCA5 by PCR-amplification using oligonucleotides oBCA5-1 (SEQ ID NO: 6) and oBCA5-2 (SEQ ID NO: 7) with the PHUSION™ High-Fidelity DNA Polymerase (Cat. No. F553S, Finnzymes Oy, Finland), following the manufacturer's protocol. The sequence of the PCR product was identical to that expected from the sequence of atgr1c.pk095.19.

The *Yarrowia lipolytica* diacylglycerolacyltransferase 2 (YLDGAT2) was described in U.S. Pat. No. 7,901,928. The cloning of YLDGAT2 into soybean expression vectors under control of the strong, seed-specific beta-conglycinin promoter, where expression in soybean or soybean somatic embryos leads to higher oil was described in U.S. Pat. Nos. 8,153,859 and 8,399,736.

Using methods familiar to one skilled in the art, the NotI fragment containing At-BCA5 was cloned into a soybean expression vector containing the strong, seed specific soy albumin promoter (WO2000040710, published Jul. 13, 2000), and containing the YLDGAT2 under control of the soy beta-conglycinin promoter, to give pKR2559 (SEQ ID NO: 8).

Soy Carbonic Anhydrase (GM-CA):

A cDNA library, s2, derived from Soybean (*Glycine max* L.) seed, Stage was prepared, cDNA clones were sequenced and the sequences were analyzed by BLAST® (Basic Local Alignment Search Tool) program as described in U.S. Pat. No. 7,157,621.

A full length cDNA clone s2.15f08, identified as a chloroplastic-like carbonic anhydrase as described in Example 1, corresponds to Glyma08g39510. The predicted coding sequence for Glyma08g39510 is set forth in SEQ ID NO: 9. The gene from s2.15f08 was given the designation GM-CA.

DNA was prepared from an aliquot of s2.15f08 using the QIAprep Spin Miniprep Kit (Qiagen Inc., Valencia, Calif.) following the manufacturer's protocol. NotI restriction sites were added to the ends of GM-CA by PCR-amplification using oligonucleotides 5A542 (SEQ ID NO: 10) and 5A539 (SEQ ID NO: 11) with the "Platinum"-brand Taq DNA polymerase (Life Technologies), following the manufacturer's protocol.

The CDS from the resulting PCR product was sequenced and the sequence for GM-CA is identical to that of Glyma08g39510 (SEQ ID NO: 9) with the corresponding amino acid sequence set forth in SEQ ID NO: 12.

Using methods familiar to one skilled in the art, the NotI fragment containing GM-CA was cloned into a soybean expression vector containing the strong, seed specific soy albumin promoter, and containing the YLDGAT2 under control of the soy beta-conglycinin promoter, to give pKR2495 (SEQ ID NO: 13).

Soy Carbonic Anhydrase 2 (GM-CA2):

A cDNA library, sls1c, derived from Soybean (*Glycine max* L., S1990) leaf tissue was prepared, cDNA clones were sequenced and the sequences were analyzed by BLAST® (Basic Local Alignment Search Tool) program as described in U.S. Pat. No. 7,157,621.

A full length cDNA clone sls1c.pk008.a22, identified as a carbonic anhydrase as described in Example 1, corresponds to Glyma02g37710. The predicted coding sequence for Glyma02g37710 is set forth in SEQ ID NO: 14. The gene from sls1c.pk008.a22 was given the designation GM-CA2.

DNA was prepared from an aliquot of sls1c.pk008.a22 using the QIAprep Spin Miniprep Kit (Qiagen Inc., Valencia, Calif.) following the manufacturer's protocol. NotI restriction sites were added to the ends of GM-CA by PCR-amplification using oligonucleotides oCA2-1 (SEQ ID NO: 15) and oCA2-1 (SEQ ID NO: 16) the PHUSION™ High-Fidelity DNA Polymerase (Cat. No. F553S, Finnzymes Oy, Finland), following the manufacturer's protocol.

The CDS from the resulting PCR product was sequenced and the sequence for GM-CA2 is identical to that of Glyma02g37710 (SEQ ID NO: 14) with the corresponding amino acid sequence set forth in SEQ ID NO: 17.

Using methods familiar to one skilled in the art, the NotI fragment containing GM-CA2 was cloned into a soybean expression vector containing the strong, seed specific soy albumin promoter, with a soy albumin transcription terminator and containing the YLDGAT2 under control of the soy beta-conglycinin promoter, to give pKR2537 (SEQ ID NO: 18).

Example 3

Co-Expressing YLDGAT2 with At-BCA5, GM-CA or GM-CA2 in Soybean Somatic Embryos

Plasmid pKR1256 (SEQ ID NO:19) having YLDGAT2 under control of the strong, seed-specific beta-conglycinin promoter and having a hygromycin selectable marker for expression in soy somatic embryos was described in U.S. Pat. Nos. 8,153,859 and 8,399,736. In the following experiments, pKR1256 was used as a control to assess the concentration of oil produced in soy somatic embryos when YLDGAT2 alone was expressed.

DNA from plasmids pKR1256 (YLDGAT only, SEQ ID NO:19), pKR2559 (YLDGAT2+At-BCA5, SEQ ID NO:8), pKR2495 (YLDGAT2+GM-CA, SEQ ID NO:13) or pKR2537 (YLDGAT2+GM-CA2, SEQ ID NO:18) was prepared for particle bombardment into soybean embryogenic suspension culture and transformed exactly as described previously in WO 2008/147935, published Dec. 4, 2008. Soybean embryogenic suspension culture was initiated, grown, maintained and bombarded and events were selected and matured on SHaM media also exactly as described (WO 2008/147935, published Dec. 4, 2008).

Three separate experiments were carried out comparing soy somatic embryos transformed with pKR1256 or pKR2495, two experiments were carried out comparing soy somatic embryos transformed with pKR1256 or pKR2559 and one experiment was carried out comparing soy somatic embryos transformed with pKR1256 with pKR2537.

A summary of genes, plasmids and model system experiment ("MSE") numbers is shown in Table 6.

TABLE 6

Summary of Genes, Plasmids and Experiments

| Experiment(s) | Plasmid | Gene(s) | SEQ ID NO (Carbonic Anhydrase) | |
|---|---|---|---|---|
| | | | nt | aa |
| MSE 3439 | pKR1256 | YLDGAT2 | — | — |
| MSE 3442 | pKR2495 | YLDGAT2 + GM-CA | 9 | 12 |
| MSE 3544 | pKR1256 | YLDGAT2 | — | — |
| MSE 3546 | pKR2495 | YLDGAT2 + GM-CA | 9 | 12 |
| MSE 3547 | pKR2559 | YLDGAT2 + At-BCA5 | 4 | 5 |
| MSE 3628 | pKR1256 | YLDGAT2 | — | — |
| MSE 3631 | pKR2495 | YLDGAT2 + GM-CA | 9 | 12 |
| MSE 3630 | pKR2559 | YLDGAT2 + At-BCA5 | 4 | 5 |
| MSE 3634 | pKR1256 | YLDGAT2 | — | — |
| MSE 3637 | pKR2537 | YLDGAT2 + GM-CA2 | 14 | 17 |

Approximately 10-20 matured embryos from each of approximately 30 events per bombardment experiment were lyophilized, ground, oil content was measured by NMR and fatty acid profile was evaluated by FAME-GC analysis exactly as described in PCT Publication No. WO 2008/147935. The results for average oil content and average fatty acid profile for all events within an experiment (Avg.), as well as the average for the top 5 events having highest oil content (Top5 Avg.) for MSE 3439 and MSE 3442, are shown in Table 7.

In Table 7, results are sorted based on oil content from highest to lowest. In Table 2, oil content is reported as a percent of total dry weight (% Oil) and fatty acid content for each fatty acid [palmitic acid (16:0), stearic acid (18:0), oleic acid (18:1), linoleic acid (18:2) & alpha-linolenic acid (18:3)] is reported as a weight % of total fatty acids.

TABLE 7

Summary of Oil Content and Fatty Acid Profiles for Events expressing YLDGAT2 (MSE 3439) and YLDGAT2 with GM-CA (MSE 3442)

| Event | % oil | 16:0 | 18:0 | 18:1 | 18:2 | 18:3 |
|---|---|---|---|---|---|---|
| 3439-15 | 9.0 | 12.8 | 6.4 | 29.9 | 41.4 | 9.4 |
| 3439-10 | 8.5 | 13.1 | 5.2 | 33.5 | 39.4 | 8.8 |
| 3439-6 | 7.8 | 16.1 | 5.4 | 22.1 | 43.3 | 13.1 |
| 3439-20 | 7.5 | 13.8 | 3.8 | 30.6 | 40.5 | 11.3 |
| 3439-16 | 6.9 | 13.1 | 6.6 | 39.2 | 33.0 | 8.1 |
| 3439-22 | 6.7 | 13.3 | 5.6 | 31.6 | 39.5 | 10.0 |
| 3439-11 | 6.5 | 15.7 | 6.1 | 22.2 | 44.0 | 12.0 |
| 3439-25 | 6.1 | 15.5 | 4.5 | 24.9 | 41.7 | 13.4 |
| 3439-8 | 6.1 | 14.6 | 4.9 | 33.0 | 37.0 | 10.5 |
| 3439-13 | 5.8 | 16.0 | 4.9 | 27.8 | 39.7 | 11.5 |
| 3439-14 | 5.6 | 16.6 | 4.9 | 21.1 | 45.2 | 12.2 |
| 3439-7 | 5.5 | 16.4 | 5.7 | 19.9 | 44.7 | 13.3 |
| 3439-1 | 5.4 | 14.2 | 5.0 | 23.2 | 43.3 | 14.3 |
| 3439-12 | 5.2 | 17.1 | 4.8 | 20.7 | 44.6 | 12.8 |
| 3439-4 | 5.0 | 14.5 | 5.3 | 29.3 | 40.2 | 10.7 |
| 3439-27 | 4.4 | 15.6 | 4.3 | 24.5 | 41.6 | 14.1 |
| 3439-18 | 4.3 | 17.4 | 4.7 | 20.7 | 42.4 | 14.7 |
| 3439-26 | 4.2 | 15.6 | 5.2 | 21.7 | 41.5 | 15.9 |
| 3439-19 | 4.2 | 14.9 | 5.6 | 26.7 | 39.9 | 12.9 |
| 3439-23 | 4.0 | 16.5 | 5.0 | 27.7 | 38.2 | 12.5 |
| 3439-28 | 3.9 | 16.5 | 5.7 | 23.3 | 40.4 | 14.0 |
| 3439-2 | 3.8 | 17.5 | 4.6 | 19.7 | 42.8 | 15.3 |
| 3439-17 | 3.7 | 17.8 | 5.0 | 20.6 | 42.3 | 14.2 |
| 3439-21 | 3.7 | 17.1 | 4.4 | 19.9 | 42.7 | 16.0 |
| 3439-5 | 3.5 | 17.0 | 6.3 | 22.8 | 39.7 | 14.1 |
| 3439-24 | 3.2 | 16.0 | 4.9 | 24.0 | 41.1 | 14.0 |
| 3439-9 | 2.8 | 17.7 | 5.7 | 23.7 | 38.8 | 14.2 |
| 3439-3 | 2.0 | 17.9 | 5.4 | 20.7 | 39.3 | 16.7 |
| Avg. | 5.2 | 15.7 | 5.2 | 25.2 | 41.0 | 12.9 |
| Top5 Avg. | 8.0 | 13.8 | 5.5 | 31.1 | 39.5 | 10.1 |
| 3442-16 | 11.0 | 12.6 | 5.9 | 31.1 | 42.8 | 7.7 |
| 3442-14 | 10.0 | 14.3 | 5.0 | 24.8 | 45.7 | 10.3 |
| 3442-20 | 9.6 | 12.1 | 5.6 | 27.7 | 44.6 | 10.0 |
| 3442-18 | 8.7 | 12.5 | 6.3 | 33.6 | 38.7 | 8.9 |
| 3442-22 | 7.9 | 14.5 | 6.5 | 27.4 | 41.0 | 10.6 |
| 3442-24 | 7.7 | 14.0 | 6.1 | 26.4 | 42.4 | 11.1 |
| 3442-19 | 7.6 | 14.8 | 6.0 | 23.3 | 42.8 | 13.0 |
| 3442-3 | 7.5 | 14.4 | 6.4 | 24.9 | 41.8 | 12.5 |
| 3442-17 | 7.3 | 15.6 | 6.0 | 21.1 | 44.3 | 13.0 |
| 3442-7 | 7.3 | 15.6 | 7.4 | 26.5 | 39.1 | 11.4 |
| 3442-21 | 7.2 | 15.4 | 5.9 | 19.3 | 45.0 | 14.4 |
| 3442-2 | 7.1 | 15.8 | 5.5 | 17.8 | 46.6 | 14.2 |
| 3442-1 | 7.0 | 15.7 | 5.6 | 20.3 | 45.6 | 12.9 |
| 3442-25 | 6.9 | 16.1 | 6.8 | 21.6 | 42.6 | 12.9 |
| 3442-26 | 6.9 | 16.1 | 6.2 | 21.3 | 42.6 | 13.8 |
| 3442-4 | 6.4 | 15.4 | 6.4 | 24.5 | 40.0 | 13.7 |
| 3442-5 | 6.3 | 14.2 | 6.3 | 25.1 | 40.5 | 13.9 |
| 3442-28 | 6.3 | 15.1 | 5.9 | 23.7 | 40.7 | 14.5 |
| 3442-13 | 6.1 | 16.0 | 6.3 | 23.0 | 42.8 | 11.8 |
| 3442-23 | 5.9 | 14.7 | 6.1 | 23.3 | 41.9 | 14.1 |
| 3442-12 | 5.8 | 15.5 | 7.2 | 25.9 | 38.6 | 12.9 |
| 3442-27 | 5.6 | 16.4 | 5.7 | 18.3 | 43.6 | 16.1 |
| 3442-6 | 4.7 | 16.6 | 5.0 | 17.1 | 41.8 | 19.4 |
| 3442-11 | 4.3 | 16.4 | 5.3 | 17.0 | 44.0 | 17.2 |
| 3442-10 | 4.2 | 17.2 | 5.0 | 16.8 | 42.9 | 18.1 |
| 3442-9 | 4.0 | 17.4 | 5.5 | 14.9 | 43.7 | 18.6 |
| 3442-8 | 3.9 | 14.8 | 5.9 | 26.3 | 39.9 | 13.1 |
| 3442-15 | 3.2 | 16.9 | 5.9 | 19.0 | 40.7 | 17.5 |
| Avg. | 6.7 | 15.2 | 6.0 | 22.9 | 42.4 | 13.5 |
| Top5 Avg. | 9.4 | 13.2 | 5.8 | 28.9 | 42.6 | 9.5 |

A summary comparing the average oil content and average fatty acid profile for all events in each experiment is shown in Table 8. In Table 8, average oil content is reported as a percent of total dry weight (Avg. Oil) and average fatty acid content for each fatty acid [palmitic acid (16:0), stearic acid (18:0), oleic acid (18:1), linoleic acid (18:2) & alpha-linolenic acid (18:3)] is reported as a weight % of total fatty acids. Table 8 also shows the change in oil content (Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 8

Summary of Average Oil Content and Fatty
Acid Profiles for All Events Expressing YLDGAT2
(MSE 3439) or YLDGAT2 and GM-CA (MSE 3442)

| MSE | Vector (Gene) | Avg Oil | % Inc | 16:0 | 18:0 | 18:1 | 18:2 | 18:3 |
|---|---|---|---|---|---|---|---|---|
| 3439 | pKR1256 (n/a) | 5.2 | 0% | 15.7 | 5.2 | 25.2 | 41.0 | 12.9 |
| 3442 | pKR2495 (GM-CA) | 6.7 | 28% | 15.2 | 6.0 | 22.9 | 42.4 | 13.5 |

A summary comparing the average oil content and average fatty acid profile of the top 5 events having the highest oil content for each experiment is shown in Table 9. In Table 9, average oil for the 5 events having highest oil content is reported as a percent of total dry weight (Top5 Avg. Oil) and average fatty acid content for each fatty acid, palmitic acid (16:0), stearic acid (18:0), oleic acid (18:1), linoleic acid (18:2) & alpha-linolenic acid (18:3)] is reported as a weight % of total fatty acids. Table 9 also shows the change in oil content (Top5 Avg. % Inc.) as compared to the Control experiment where Avg. % Inc. is calculated as the Avg. Oil for that experiment minus the Avg. Oil for the control experiment divided by the Avg. Oil for the control experiment expressed as a percent.

TABLE 9

Summary of Average Oil Content and Fatty Acid Profiles for the
Top5 Events Having Highest Oil Contents and Expressing
YLDGAT2 (MSE 3439) or YLDGAT2 and GM-CA (MSE 3442)

| MSE | Vector (Gene) | Avg. Oil | Avg. % Inc | 16:0 | 18:0 | 18:1 | 18:2 | 18:3 |
|---|---|---|---|---|---|---|---|---|
| 3439 | pKR1256 (n/a) | 8.0 | 0% | 13.8 | 5.5 | 31.1 | 39.5 | 10.1 |
| 3442 | pKR2495 (GM-CA) | 9.4 | 18% | 13.2 | 5.8 | 28.9 | 42.6 | 9.5 |

Tables 7, 8 and 9 demonstrate that expression of GM-CA with YLDGAT2 lead to an increase in oil content in soy above that for YLDGAT2 alone.

The results for average oil content and average fatty acid profile for all events within an experiment (Avg.), as well as the average for the top 5 events having highest oil content (Top5 Avg.) for MSE 3544, MSE 3546 and MSE 3547, are shown in Table 10.

TABLE 10

Summary of Oil Content and Fatty Acid Profiles for
Events Expressing YLDGAT2 (MSE 3544) and YLDGAT2
with GM-CA (MSE 3546) or At-BCA5 (MSE 3547)

| Event | % oil | 16:0 | 18:0 | 18:1 | 18:2 | 18:3 |
|---|---|---|---|---|---|---|
| 3544-21 | 9.3 | 13.1 | 6.3 | 32.2 | 38.4 | 10.0 |
| 3544-26 | 8.9 | 13.6 | 5.8 | 31.2 | 39.2 | 10.2 |
| 3544-20 | 8.1 | 13.7 | 7.1 | 29.9 | 39.0 | 10.3 |
| 3544-15 | 7.8 | 16.1 | 5.7 | 21.2 | 43.3 | 13.7 |
| 3544-9 | 6.4 | 15.9 | 4.3 | 27.2 | 38.6 | 14.0 |
| 3544-18 | 6.4 | 15.8 | 4.6 | 26.4 | 39.3 | 14.0 |
| 3544-30 | 6.3 | 15.2 | 6.2 | 25.9 | 39.0 | 13.7 |
| 3544-16 | 6.0 | 16.6 | 5.4 | 20.3 | 42.6 | 15.1 |
| 3544-11 | 5.5 | 18.9 | 4.5 | 15.7 | 34.8 | 26.0 |
| 3544-19 | 5.5 | 15.9 | 4.5 | 25.9 | 39.2 | 14.5 |
| 3544-5 | 5.4 | 15.3 | 5.5 | 31.5 | 35.4 | 12.2 |
| 3544-25 | 5.3 | 15.7 | 4.8 | 25.7 | 38.9 | 15.0 |
| 3544-13 | 5.2 | 17.6 | 6.0 | 19.6 | 41.9 | 14.9 |
| 3544-28 | 5.2 | 16.8 | 5.5 | 22.1 | 39.7 | 15.9 |
| 3544-1 | 5.1 | 17.6 | 4.8 | 25.5 | 38.6 | 13.6 |
| 3544-2 | 5.1 | 17.0 | 6.2 | 23.6 | 38.8 | 14.4 |
| 3544-10 | 5.0 | 16.0 | 6.2 | 27.6 | 37.9 | 12.2 |
| 3544-6 | 4.9 | 17.0 | 7.2 | 26.7 | 36.6 | 12.4 |
| 3544-27 | 4.8 | 15.5 | 4.6 | 26.9 | 38.5 | 14.6 |
| 3544-12 | 4.6 | 19.5 | 5.6 | 16.2 | 34.8 | 23.9 |
| 3544-23 | 4.6 | 17.7 | 5.8 | 22.7 | 39.3 | 14.5 |
| 3544-17 | 4.5 | 16.2 | 4.8 | 28.9 | 36.5 | 13.7 |
| 3544-14 | 4.0 | 18.3 | 5.4 | 18.3 | 40.1 | 17.9 |
| 3544-24 | 3.9 | 17.3 | 6.0 | 21.2 | 40.7 | 14.8 |
| 3544-3 | 3.6 | 18.4 | 4.8 | 17.9 | 41.2 | 17.7 |
| 3544-22 | 3.2 | 19.5 | 4.5 | 17.9 | 40.7 | 17.4 |
| 3544-29 | 3.1 | 17.9 | 4.0 | 16.2 | 41.0 | 20.9 |
| 3544-4 | 3.0 | 18.5 | 4.7 | 19.1 | 40.2 | 17.5 |
| 3544-7 | 3.0 | 18.6 | 5.1 | 21.5 | 39.0 | 15.8 |
| 3544-8 | 2.9 | 18.4 | 4.5 | 16.2 | 39.9 | 21.1 |
| Avg. | 5.2 | 16.8 | 5.3 | 23.4 | 39.1 | 15.4 |
| Top5 Avg. | 8.1 | 14.5 | 5.8 | 28.3 | 39.7 | 11.6 |
| 3546-12 | 13.2 | 11.0 | 5.2 | 41.1 | 36.0 | 6.7 |
| 3546-6 | 13.1 | 12.8 | 4.8 | 29.1 | 44.1 | 9.1 |
| 3546-22 | 13.0 | 12.4 | 6.3 | 31.2 | 41.7 | 8.5 |
| 3546-10 | 12.6 | 12.9 | 4.3 | 28.3 | 44.9 | 9.6 |
| 3546-30 | 12.5 | 11.3 | 5.0 | 37.5 | 38.1 | 8.0 |
| 3546-13 | 12.2 | 12.7 | 5.9 | 28.4 | 43.8 | 9.2 |
| 3546-7 | 11.3 | 12.7 | 4.6 | 28.0 | 44.3 | 10.4 |
| 3546-5 | 10.8 | 12.4 | 6.1 | 34.5 | 39.1 | 7.9 |
| 3546-31 | 10.6 | 12.0 | 5.7 | 28.9 | 43.6 | 9.7 |
| 3546-23 | 10.0 | 13.5 | 5.7 | 29.5 | 40.9 | 10.3 |
| 3546-24 | 10.0 | 14.0 | 5.2 | 25.6 | 44.5 | 10.7 |
| 3546-16 | 9.8 | 12.8 | 4.7 | 24.2 | 46.1 | 12.1 |
| 3546-18 | 9.2 | 16.0 | 5.0 | 21.0 | 45.7 | 12.3 |
| 3546-15 | 9.2 | 11.9 | 6.7 | 39.9 | 34.1 | 7.5 |
| 3546-21 | 8.8 | 14.3 | 6.2 | 28.9 | 40.2 | 10.5 |
| 3546-2 | 8.7 | 14.5 | 5.0 | 26.5 | 44.1 | 9.9 |
| 3546-3 | 8.6 | 13.1 | 5.7 | 31.5 | 38.7 | 11.1 |
| 3546-4 | 8.4 | 13.0 | 6.8 | 35.4 | 35.8 | 9.0 |
| 3546-25 | 8.0 | 14.7 | 5.5 | 24.6 | 43.1 | 12.1 |
| 3546-17 | 7.7 | 14.0 | 6.4 | 30.9 | 37.9 | 10.9 |
| 3546-29 | 7.6 | 15.5 | 6.0 | 21.5 | 43.4 | 13.6 |
| 3546-9 | 7.6 | 15.5 | 7.1 | 23.7 | 40.4 | 13.3 |
| 3546-26 | 7.5 | 13.4 | 4.0 | 31.5 | 38.5 | 12.5 |
| 3546-8 | 7.4 | 13.2 | 6.1 | 28.8 | 39.7 | 12.2 |
| 3546-19 | 7.4 | 14.6 | 5.7 | 28.3 | 38.1 | 13.3 |
| 3546-14 | 6.9 | 14.7 | 4.2 | 28.3 | 40.0 | 12.7 |
| 3546-1 | 6.5 | 16.5 | 5.5 | 25.4 | 40.2 | 12.4 |
| 3546-27 | 6.4 | 14.9 | 7.5 | 28.3 | 36.6 | 12.7 |
| 3546-11 | 5.8 | 15.7 | 7.3 | 27.9 | 37.1 | 12.0 |
| 3546-28 | 3.7 | 17.1 | 5.9 | 22.1 | 42.7 | 12.3 |
| 3546-20 | 2.1 | 18.2 | 6.2 | 21.9 | 37.5 | 16.1 |
| Avg. | 8.9 | 13.9 | 5.7 | 28.8 | 40.7 | 10.9 |
| Top5 Avg. | 12.9 | 12.1 | 5.1 | 33.4 | 41.0 | 8.4 |
| 3547-20 | 11.6 | 12.4 | 5.5 | 33.8 | 40.5 | 7.8 |
| 3547-14 | 10.8 | 13.3 | 5.5 | 30.6 | 42.2 | 8.4 |
| 3547-26 | 10.7 | 14.7 | 5.0 | 29.8 | 40.8 | 9.7 |
| 3547-15 | 10.5 | 12.4 | 5.2 | 33.3 | 39.3 | 9.7 |
| 3547-9 | 10.5 | 12.8 | 5.4 | 47.0 | 28.4 | 6.4 |
| 3547-12 | 10.3 | 13.2 | 5.7 | 33.7 | 38.7 | 8.7 |
| 3547-25 | 10.0 | 13.8 | 5.1 | 28.6 | 41.4 | 11.1 |
| 3547-13 | 10.0 | 12.4 | 4.9 | 35.7 | 37.1 | 9.9 |
| 3547-16 | 9.7 | 13.1 | 6.3 | 35.0 | 36.4 | 9.1 |
| 3547-27 | 9.1 | 15.1 | 4.4 | 16.3 | 48.9 | 15.3 |
| 3547-19 | 8.7 | 12.5 | 6.0 | 39.0 | 31.8 | 10.6 |
| 3547-3 | 8.7 | 12.3 | 5.3 | 40.0 | 33.7 | 8.7 |
| 3547-21 | 8.6 | 15.3 | 5.1 | 25.6 | 40.8 | 13.1 |
| 3547-7 | 8.3 | 13.1 | 5.2 | 35.3 | 35.8 | 10.6 |
| 3547-29 | 8.3 | 13.7 | 4.4 | 30.6 | 38.4 | 12.9 |
| 3547-18 | 8.2 | 14.7 | 5.1 | 28.1 | 41.4 | 10.7 |
| 3547-8 | 7.8 | 14.9 | 4.3 | 24.5 | 44.4 | 11.9 |
| 3547-11 | 7.7 | 14.6 | 5.7 | 34.9 | 34.6 | 10.3 |
| 3547-5 | 7.6 | 14.3 | 6.0 | 34.5 | 34.6 | 10.6 |
| 3547-22 | 7.3 | 16.0 | 5.4 | 28.4 | 39.3 | 10.9 |
| 3547-23 | 6.6 | 13.3 | 5.5 | 32.8 | 36.8 | 11.5 |
| 3547-17 | 6.3 | 16.5 | 6.5 | 28.0 | 38.3 | 10.7 |
| 3547-2 | 6.1 | 13.7 | 4.2 | 17.4 | 45.4 | 19.3 |

TABLE 10-continued

Summary of Oil Content and Fatty Acid Profiles for Events Expressing YLDGAT2 (MSE 3544) and YLDGAT2 with GM-CA (MSE 3546) or At-BCA5 (MSE 3547)

| Event | % oil | 16:0 | 18:0 | 18:1 | 18:2 | 18:3 |
|---|---|---|---|---|---|---|
| 3547-30 | 5.7 | 16.4 | 4.4 | 23.0 | 42.8 | 13.5 |
| 3547-24 | 5.4 | 15.5 | 4.7 | 28.0 | 38.8 | 12.9 |
| 3547-6 | 5.4 | 17.3 | 4.7 | 23.1 | 41.9 | 13.0 |
| 3547-28 | 5.3 | 16.6 | 4.5 | 25.7 | 40.2 | 12.9 |
| 3547-10 | 4.7 | 17.0 | 5.6 | 24.2 | 39.9 | 13.3 |
| 3547-1 | 4.5 | 17.3 | 4.1 | 17.3 | 42.6 | 18.7 |
| 3547-4 | 3.4 | 16.6 | 4.3 | 14.4 | 44.8 | 19.8 |
| Avg. | 7.9 | 14.5 | 5.1 | 29.3 | 39.3 | 11.7 |
| Top5 Avg. | 10.8 | 13.1 | 5.3 | 34.9 | 38.2 | 8.4 |

A summary comparing the average oil content and average fatty acid profile for all events in each experiment is shown in Table 11.

TABLE 11

Summary of Average Oil Content and Fatty Acid Profiles for All Events Expressing YLDGAT2 (MSE 3544) or YLDGAT2 and GM-CA (MSE 3546) or At-BCA5 (MSE 3547)

| MSE | Vector (Gene) | Avg Oil | % Inc | 16:0 | 18:0 | 18:1 | 18:2 | 18:3 |
|---|---|---|---|---|---|---|---|---|
| 3544 | pKR1256 (n/a) | 5.2 | 0% | 16.8 | 5.3 | 23.4 | 39.1 | 15.4 |
| 3546 | pKR2495 (GM-CA) | 8.9 | 71% | 13.9 | 5.7 | 28.8 | 40.7 | 10.9 |
| 3547 | pKR2559 (At-BCA5) | 7.9 | 52% | 14.5 | 5.1 | 29.3 | 39.3 | 11.7 |

A summary comparing the average oil content and average fatty acid profile of the top 5 events having the highest oil content for each experiment is shown in Table 12.

TABLE 12

Summary of Average Oil Content and Fatty Acid Profiles for the Top5 Events Having Highest Oil Contents and Expressing YLDGAT2 (MSE 3439) or YLDGAT2 and GM-CA (MSE 3442) or At-BCA5 (MSE 3547)

| MSE | Vector (Gene) | Avg. Oil | Avg. % Inc | 16:0 | 18:0 | 18:1 | 18:2 | 18:3 |
|---|---|---|---|---|---|---|---|---|
| 3544 | pKR1256 (n/a) | 8.1 | 0% | 14.5 | 5.8 | 28.3 | 39.7 | 11.6 |
| 3546 | pKR2495 (GM-CA) | 12.9 | 60% | 12.1 | 5.1 | 33.4 | 41.0 | 8.4 |
| 3547 | pKR2559 (At-BCA5) | 10.8 | 34% | 13.1 | 5.3 | 34.9 | 38.2 | 8.4 |

Tables 10, 11 and 12 demonstrate that expression of GM-CA with YLDGAT2 or At-BCA5 with YLDGAT2 lead to an increase in oil content in soy above that for YLDGAT2 alone.

The results for average oil content and average fatty acid profile for all events within an experiment (Avg.), as well as the average for the top 5 events having highest oil content (Top5 Avg.) for MSE 3628, MSE 3630 and MSE 3631, are shown in Table 13.

TABLE 13

Summary of Oil Content and Fatty Acid Profiles for Events Expressing YLDGAT2 (MSE 3628) and YLDGAT2 with GM-CA (MSE 3631) or At-BCA5 (MSE 3630)

| Event | % Oil | % 16:0 | % 18:0 | % 18:1 | % 18:2 | % 18:3 |
|---|---|---|---|---|---|---|
| MSE3628-28 | 9.6 | 12.7 | 4.8 | 33.8 | 38.2 | 10.4 |
| MSE3628-05 | 9.6 | 12.3 | 4.7 | 34.5 | 39.7 | 8.7 |
| MSE3628-08 | 9.2 | 13.1 | 4.7 | 36.5 | 36.8 | 8.9 |
| MSE3628-22 | 7.2 | 14.4 | 4.6 | 28.6 | 42.0 | 10.4 |
| MSE3628-01 | 7.1 | 14.0 | 4.4 | 25.4 | 41.2 | 15.0 |
| MSE3628-20 | 6.8 | 15.2 | 4.3 | 23.7 | 42.0 | 14.8 |
| MSE3628-02 | 6.7 | 15.3 | 4.9 | 27.6 | 41.2 | 11.0 |
| MSE3628-04 | 6.0 | 16.3 | 4.4 | 21.4 | 45.2 | 12.8 |
| MSE3628-11 | 5.7 | 15.8 | 4.1 | 24.6 | 43.1 | 12.4 |
| MSE3628-24 | 5.4 | 14.4 | 5.1 | 25.5 | 40.7 | 14.3 |
| MSE3628-10 | 5.4 | 16.8 | 4.9 | 22.1 | 42.8 | 13.5 |
| MSE3628-16 | 5.3 | 13.7 | 5.0 | 31.5 | 36.4 | 13.5 |
| MSE3628-13 | 5.3 | 15.6 | 4.4 | 28.4 | 39.3 | 12.3 |
| MSE3628-17 | 5.1 | 14.1 | 4.5 | 25.5 | 40.4 | 15.5 |
| MSE3628-12 | 4.9 | 17.1 | 4.7 | 25.7 | 39.7 | 12.7 |
| MSE3628-07 | 4.8 | 15.4 | 5.7 | 34.6 | 34.6 | 9.7 |
| MSE3628-15 | 4.7 | 14.0 | 5.6 | 32.3 | 36.8 | 11.3 |
| MSE3628-19 | 4.6 | 16.7 | 4.2 | 18.8 | 44.2 | 16.0 |
| MSE3628-27 | 4.6 | 16.3 | 4.3 | 20.0 | 43.8 | 15.6 |
| MSE3628-03 | 4.6 | 15.5 | 4.7 | 27.8 | 37.9 | 14.2 |
| MSE3628-25 | 4.4 | 16.0 | 3.8 | 17.9 | 44.7 | 17.6 |
| MSE3628-06 | 4.1 | 16.4 | 3.9 | 15.5 | 43.3 | 21.0 |
| MSE3628-21 | 3.7 | 18.6 | 5.3 | 17.9 | 39.6 | 18.7 |
| MSE3628-23 | 3.6 | 17.6 | 3.9 | 19.4 | 42.6 | 16.6 |
| MSE3628-18 | 3.6 | 16.4 | 4.3 | 15.1 | 43.4 | 20.8 |
| MSE3628-09 | 3.6 | 16.2 | 4.2 | 15.4 | 45.3 | 18.8 |
| MSE3628-29 | 3.4 | 15.0 | 5.3 | 20.3 | 40.5 | 19.0 |
| MSE3628-14 | 3.3 | 16.3 | 4.5 | 20.3 | 41.2 | 17.7 |
| MSE3628-30 | 2.5 | 17.3 | 4.3 | 17.4 | 40.7 | 20.3 |
| MSE3628-26 | 2.1 | 16.8 | 5.8 | 20.7 | 40.0 | 16.8 |
| Avg. | 5.2 | 15.5 | 4.6 | 24.3 | 40.9 | 14.7 |
| Top5 Avg. | 8.5 | 13.3 | 4.6 | 31.8 | 39.6 | 10.7 |
| MSE3630-22 | 13.0 | 11.7 | 5.8 | 36.1 | 37.7 | 8.6 |
| MSE3630-11 | 11.1 | 10.7 | 8.0 | 38.6 | 36.5 | 6.2 |
| MSE3630-24 | 11.0 | 11.4 | 6.4 | 44.4 | 32.0 | 5.7 |
| MSE3630-08 | 9.2 | 13.5 | 5.6 | 28.4 | 42.7 | 9.8 |
| MSE3630-09 | 8.7 | 13.0 | 7.9 | 34.3 | 35.4 | 9.4 |

TABLE 13-continued

Summary of Oil Content and Fatty Acid Profiles for Events Expressing YLDGAT2 (MSE 3628) and YLDGAT2 with GM-CA (MSE 3631) or At-BCA5 (MSE 3630)

| Event | % Oil | % 16:0 | % 18:0 | % 18:1 | % 18:2 | % 18:3 |
|---|---|---|---|---|---|---|
| MSE3630-06 | 8.2 | 13.8 | 6.5 | 29.0 | 40.9 | 9.7 |
| MSE3630-02 | 8.1 | 12.9 | 5.7 | 29.2 | 41.3 | 10.9 |
| MSE3630-25 | 7.3 | 13.9 | 4.7 | 27.8 | 40.2 | 13.5 |
| MSE3630-30 | 7.3 | 14.3 | 5.3 | 28.2 | 39.4 | 12.7 |
| MSE3630-17 | 7.1 | 13.2 | 7.1 | 32.1 | 38.2 | 9.4 |
| MSE3630-26 | 7.1 | 16.2 | 4.5 | 18.1 | 47.2 | 13.9 |
| MSE3630-15 | 6.8 | 16.8 | 4.2 | 16.1 | 49.4 | 13.6 |
| MSE3630-16 | 6.7 | 15.7 | 5.1 | 20.3 | 45.2 | 13.8 |
| MSE3630-19 | 6.5 | 15.1 | 5.3 | 29.4 | 38.7 | 11.4 |
| MSE3630-14 | 6.5 | 16.1 | 4.5 | 20.8 | 44.3 | 14.4 |
| MSE3630-23 | 6.0 | 15.4 | 5.4 | 31.4 | 37.3 | 10.5 |
| MSE3630-21 | 5.7 | 14.5 | 5.7 | 33.3 | 35.6 | 10.9 |
| MSE3630-13 | 5.7 | 14.8 | 5.1 | 27.9 | 40.1 | 12.2 |
| MSE3630-27 | 5.1 | 15.6 | 6.8 | 20.6 | 42.4 | 14.6 |
| MSE3630-18 | 5.0 | 15.0 | 5.5 | 19.5 | 46.5 | 13.5 |
| MSE3630-10 | 4.7 | 16.3 | 6.1 | 20.5 | 40.6 | 16.5 |
| MSE3630-01 | 4.7 | 15.5 | 3.8 | 20.9 | 42.1 | 17.7 |
| MSE3630-07 | 4.5 | 16.7 | 6.6 | 22.3 | 41.4 | 12.9 |
| MSE3630-20 | 3.3 | 18.3 | 4.6 | 14.6 | 44.5 | 18.0 |
| MSE3630-29 | 3.2 | 17.6 | 5.6 | 20.5 | 42.7 | 13.6 |
| MSE3630-03 | 3.0 | 17.6 | 6.0 | 17.8 | 41.4 | 17.2 |
| MSE3630-28 | 2.7 | 17.3 | 4.8 | 19.9 | 41.9 | 16.1 |
| MSE3630-04 | 2.6 | 16.7 | 6.9 | 24.7 | 36.1 | 15.6 |
| MSE3630-12 | 2.6 | 18.2 | 4.8 | 17.9 | 42.9 | 16.3 |
| MSE3630-05 | 2.0 | 15.4 | 4.2 | 14.4 | 39.9 | 26.2 |
| Avg. | 6.2 | 15.1 | 5.6 | 25.3 | 40.8 | 13.2 |
| Top5 Avg. | 10.6 | 12.1 | 6.8 | 36.4 | 36.8 | 7.9 |
| MSE3631-24 | 16.0 | 11.0 | 6.3 | 30.7 | 44.2 | 7.8 |
| MSE3631-15 | 15.7 | 9.8 | 6.3 | 44.6 | 33.0 | 6.3 |
| MSE3631-19 | 14.3 | 10.2 | 7.3 | 32.4 | 40.6 | 9.5 |
| MSE3631-29 | 14.1 | 12.1 | 5.5 | 30.1 | 43.0 | 9.2 |
| MSE3631-23 | 12.6 | 11.3 | 7.1 | 37.8 | 36.0 | 7.9 |
| MSE3631-02 | 10.8 | 12.1 | 7.5 | 33.9 | 36.5 | 9.9 |
| MSE3631-31 | 10.3 | 13.3 | 6.5 | 26.0 | 42.7 | 11.5 |
| MSE3631-08 | 9.3 | 13.7 | 5.8 | 27.4 | 42.4 | 10.8 |
| MSE3631-18 | 9.1 | 12.7 | 7.2 | 33.6 | 37.7 | 8.9 |
| MSE3631-21 | 9.0 | 14.1 | 5.6 | 20.5 | 46.8 | 13.1 |
| MSE3631-26 | 8.7 | 12.7 | 6.2 | 30.2 | 41.1 | 9.8 |
| MSE3631-14 | 8.4 | 12.9 | 7.3 | 32.7 | 38.0 | 9.1 |
| MSE3631-22 | 8.2 | 14.5 | 4.6 | 26.3 | 41.6 | 13.0 |
| MSE3631-30 | 7.6 | 13.8 | 9.2 | 32.7 | 32.2 | 12.0 |
| MSE3631-17 | 7.5 | 13.9 | 4.6 | 23.6 | 45.0 | 12.9 |
| MSE3631-01 | 7.4 | 14.7 | 4.2 | 25.7 | 42.3 | 13.1 |
| MSE3631-20 | 7.3 | 13.4 | 8.0 | 21.9 | 41.4 | 15.3 |
| MSE3631-13 | 6.9 | 16.3 | 6.8 | 23.8 | 40.0 | 13.2 |
| MSE3631-12 | 6.9 | 15.0 | 5.0 | 23.0 | 42.4 | 14.5 |
| MSE3631-28 | 6.6 | 13.7 | 6.6 | 22.3 | 41.5 | 16.0 |
| MSE3631-05 | 6.1 | 16.5 | 4.6 | 34.8 | 34.0 | 10.1 |
| MSE3631-25 | 6.0 | 16.3 | 6.0 | 17.1 | 45.0 | 15.7 |
| MSE3631-16 | 5.5 | 16.7 | 5.9 | 23.0 | 41.7 | 12.7 |
| MSE3631-06 | 5.1 | 16.7 | 6.3 | 21.5 | 40.6 | 14.9 |
| MSE3631-04 | 4.9 | 15.7 | 4.6 | 24.5 | 39.6 | 15.5 |
| MSE3631-27 | 4.6 | 15.0 | 4.6 | 21.0 | 44.5 | 14.9 |
| MSE3631-03 | 4.4 | 16.6 | 5.9 | 20.7 | 40.3 | 16.5 |
| MSE3631-10 | 4.3 | 16.9 | 6.4 | 24.0 | 37.5 | 15.2 |
| MSE3631-11 | 4.3 | 15.6 | 5.2 | 26.5 | 36.9 | 15.9 |
| MSE3631-09 | 4.3 | 17.8 | 5.1 | 19.6 | 40.1 | 17.4 |
| MSE3631-07 | 4.0 | 14.1 | 7.7 | 29.8 | 37.1 | 11.2 |
| Avg. | 8.1 | 14.2 | 6.1 | 27.2 | 40.2 | 12.4 |
| Top5 Avg. | 14.6 | 10.9 | 6.5 | 35.1 | 39.4 | 8.2 |

A summary comparing the average oil content and average fatty acid profile for all events in each experiment is shown in Table 14.

TABLE 14

Summary of Average Oil Content and Fatty Acid Profiles for All Events Expressing YLDGAT2 (MSE 3628) and YLDGAT2 with GM-CA (MSE 3631) or At BCA5 (MSE 3630)

| MSE | Vector (Gene) | % Inc | Avg Oil | 16:0 | 18:0 | 18:1 | 18:2 | 18:3 |
|---|---|---|---|---|---|---|---|---|
| 3628 | pKR1256 (n/a) | 0% | 15.5 | 4.6 | 24.3 | 40.9 | 14.7 | 0% |
| 3630 | pKR2559 (At-BCA5) | 18% | 15.1 | 5.6 | 25.3 | 40.8 | 13.2 | 18% |
| 3631 | pKR2495 (GM-CA) | 54% | 14.2 | 6.1 | 27.2 | 40.2 | 12.4 | 54% |

A summary comparing the average oil content and average fatty acid profile of the top 5 events having the highest oil content for each experiment is shown in Table 15.

TABLE 15

Summary of Average Oil Content and Fatty Acid Profiles for the Top5 Events Having Highest Oil Contents and Expressing YLDGAT2 (MSE 3628) and YLDGAT2 with GM-CA (MSE 3631) or At-BCA5 (MSE 3630)

| MSE | Vector (Gene) | Avg. Oil | Avg. % Inc | 16:0 | 18:0 | 18:1 | 18:2 | 18:3 |
|---|---|---|---|---|---|---|---|---|
| 3628 | pKR1256 (n/a) | 8.5 | 0% | 13.3 | 4.6 | 31.8 | 39.6 | 10.7 |
| 3630 | pKR2559 (At-BCA5) | 10.6 | 24% | 12.1 | 6.8 | 36.4 | 36.8 | 7.9 |
| 3631 | pKR2495 (GM-CA) | 14.6 | 71% | 10.9 | 6.5 | 35.1 | 39.4 | 8.2 |

Tables 13, 14 and 15 demonstrate that expression of GM-CA with YLDGAT2 or At-BCA5 with YLDGAT2 lead to an increase in oil content in soy above that for YLDGAT2 alone.

The results for average oil content and average fatty acid profile for all events within an experiment (Avg.), as well as the average for the top 5 events having highest oil content (Top5 Avg.) for MSE 3634 and MSE 3637, are shown in Table 16.

TABLE 16

Summary of Oil Content and Fatty Acid Profiles for Events Expressing YLDGAT2 (MSE 3634) and YLDGAT2 with GM-CA2 (MSE 3637)

| Event | % Oil | 16:0 | 18:0 | 18:1 | 18:2 | 18:3 |
|---|---|---|---|---|---|---|
| MSE3634-24 | 2.5 | 17.3 | 5.3 | 19.4 | 40.4 | 17.7 |
| MSE3634-08 | 3.7 | 16.6 | 4.9 | 21.7 | 41.2 | 15.6 |
| MSE3634-26 | 4.7 | 15.7 | 6.2 | 17.9 | 41.9 | 18.2 |
| MSE3634-17 | 4.8 | 16.6 | 5.9 | 20.9 | 42.8 | 13.8 |
| MSE3634-21 | 5.2 | 15.5 | 7.1 | 27.8 | 38.2 | 11.4 |
| MSE3634-19 | 5.8 | 13.4 | 8.0 | 27.0 | 41.0 | 10.6 |
| MSE3634-05 | 5.9 | 14.6 | 5.2 | 31.5 | 37.1 | 11.7 |
| MSE3634-31 | 6.0 | 15.0 | 7.3 | 26.2 | 39.0 | 12.4 |
| MSE3634-25 | 6.0 | 13.6 | 4.5 | 30.3 | 35.3 | 16.4 |
| MSE3634-07 | 6.0 | 17.8 | 4.7 | 23.1 | 40.2 | 14.2 |
| MSE3634-20 | 6.2 | 14.0 | 5.3 | 28.7 | 39.5 | 12.6 |
| MSE3634-18 | 6.5 | 14.9 | 6.8 | 30.1 | 36.9 | 11.3 |
| MSE3634-27 | 7.0 | 14.9 | 5.4 | 27.0 | 39.7 | 13.1 |
| MSE3634-04 | 7.6 | 13.7 | 4.6 | 33.0 | 37.3 | 11.5 |
| MSE3634-30 | 7.7 | 14.1 | 7.9 | 27.1 | 39.6 | 11.3 |
| MSE3634-09 | 7.8 | 15.0 | 4.6 | 27.6 | 40.3 | 12.5 |
| MSE3634-16 | 7.9 | 16.2 | 4.9 | 16.4 | 47.3 | 15.1 |
| MSE3634-15 | 7.9 | 13.0 | 6.8 | 34.1 | 36.5 | 9.7 |
| MSE3634-22 | 8.0 | 13.5 | 4.8 | 29.2 | 41.2 | 11.3 |
| MSE3634-02 | 8.3 | 14.6 | 6.1 | 26.5 | 42.4 | 10.2 |
| MSE3634-14 | 8.7 | 15.6 | 5.3 | 24.1 | 43.4 | 11.5 |
| MSE3634-10 | 8.8 | 13.1 | 6.3 | 32.2 | 38.9 | 9.5 |
| MSE3634-29 | 8.9 | 11.8 | 6.8 | 36.9 | 36.3 | 8.2 |
| MSE3634-23 | 8.9 | 16.1 | 4.9 | 17.7 | 49.5 | 11.8 |
| MSE3634-01 | 9.1 | 15.2 | 4.6 | 22.1 | 45.0 | 13.1 |
| MSE3634-13 | 9.3 | 13.3 | 6.5 | 29.0 | 40.4 | 10.7 |
| MSE3634-03 | 9.3 | 13.1 | 8.7 | 33.9 | 35.3 | 9.0 |
| MSE3634-12 | 9.4 | 12.7 | 7.3 | 33.7 | 37.1 | 9.3 |
| MSE3634-28 | 9.6 | 13.3 | 6.6 | 27.9 | 41.4 | 10.8 |
| MSE3634-06 | 10.7 | 12.7 | 6.5 | 34.4 | 38.4 | 8.0 |
| MSE3634-11 | 11.2 | 13.4 | 6.5 | 26.3 | 44.0 | 9.8 |
| Avg. | 7.4 | 14.5 | 6.0 | 27.2 | 40.2 | 12.0 |
| Top5 Avg. | 10.0 | 13.0 | 7.1 | 31.3 | 39.2 | 9.4 |
| MSE3637-19 | 5.6 | 14.7 | 4.7 | 30.5 | 39.0 | 11.2 |
| MSE3637-26 | 5.9 | 15.0 | 6.7 | 25.6 | 38.4 | 14.2 |
| MSE3637-18 | 6.3 | 14.3 | 4.1 | 28.2 | 40.3 | 13.0 |
| MSE3637-11 | 6.5 | 14.9 | 5.3 | 28.9 | 40.0 | 10.8 |
| MSE3637-03 | 6.6 | 14.3 | 5.1 | 20.0 | 46.4 | 14.3 |
| MSE3637-07 | 7.0 | 15.6 | 4.7 | 23.5 | 43.5 | 12.7 |
| MSE3637-06 | 7.4 | 14.9 | 6.2 | 22.5 | 43.4 | 13.0 |
| MSE3637-21 | 7.5 | 14.4 | 6.3 | 23.1 | 44.7 | 11.6 |
| MSE3637-27 | 8.0 | 13.0 | 5.0 | 31.9 | 37.2 | 12.9 |
| MSE3637-13 | 8.2 | 12.8 | 4.4 | 30.1 | 40.2 | 12.6 |
| MSE3637-25 | 8.3 | 14.2 | 6.4 | 22.5 | 43.4 | 13.5 |
| MSE3637-04 | 8.4 | 12.5 | 6.0 | 40.3 | 33.0 | 8.2 |
| MSE3637-29 | 8.7 | 11.9 | 7.1 | 34.9 | 35.8 | 10.4 |
| MSE3637-14 | 8.7 | 13.8 | 5.3 | 28.5 | 41.7 | 10.8 |
| MSE3637-08 | 9.1 | 12.4 | 6.6 | 37.3 | 34.8 | 8.9 |
| MSE3637-16 | 9.3 | 12.7 | 5.2 | 41.0 | 32.8 | 8.4 |
| MSE3637-02 | 9.4 | 13.0 | 4.8 | 31.9 | 38.6 | 11.6 |
| MSE3637-05 | 9.4 | 12.5 | 4.3 | 44.4 | 30.4 | 8.3 |
| MSE3637-12 | 9.9 | 11.7 | 6.8 | 39.4 | 34.3 | 7.8 |
| MSE3637-10 | 10.1 | 11.1 | 6.8 | 44.9 | 29.5 | 7.8 |
| MSE3637-23 | 10.4 | 11.5 | 6.0 | 39.5 | 34.4 | 8.5 |
| MSE3637-30 | 10.5 | 11.6 | 8.4 | 38.5 | 32.5 | 8.9 |
| MSE3637-28 | 10.8 | 11.2 | 4.8 | 33.8 | 39.8 | 10.3 |
| MSE3637-15 | 10.9 | 11.9 | 5.1 | 38.0 | 36.3 | 8.6 |
| MSE3637-01 | 11.1 | 11.9 | 5.6 | 38.2 | 36.8 | 7.5 |

TABLE 16-continued

Summary of Oil Content and Fatty Acid Profiles for Events
Expressing YLDGAT2 (MSE 3634) and
YLDGAT2 with GM-CA2 (MSE 3637)

| Event | % Oil | 16:0 | 18:0 | 18:1 | 18:2 | 18:3 |
|---|---|---|---|---|---|---|
| MSE3637-17 | 11.6 | 12.1 | 5.4 | 30.6 | 42.8 | 9.1 |
| MSE3637-09 | 11.6 | 11.9 | 4.6 | 37.6 | 38.0 | 7.9 |
| MSE3637-20 | 12.0 | 10.5 | 6.3 | 42.7 | 33.3 | 7.2 |
| MSE3637-22 | 12.7 | 11.1 | 8.0 | 41.6 | 32.2 | 7.2 |
| MSE3637-24 | 16.5 | 9.7 | 4.3 | 40.8 | 36.9 | 8.3 |
| Avg. | 9.3 | 12.8 | 5.7 | 33.7 | 37.7 | 10.2 |
| Top5 Avg. | 12.9 | 11.1 | 5.7 | 38.7 | 36.6 | 7.9 |

A summary comparing the average oil content and average fatty acid profile for all events in each experiment is shown in Table 17.

TABLE 17

Summary of Average Oil Content and Fatty Acid
Profiles for All Events Expressing YLDGAT2 (MSE 3634)
and YLDGAT2 with GM-CA2 (MSE 3637)

| MSE | Vector (Gene) | Avg Oil | % Inc | 16:0 | 18:0 | 18:1 | 18:2 | 18:3 |
|---|---|---|---|---|---|---|---|---|
| 3634 | pKR1256 (n/a) | 7.4 | 0% | 14.5 | 6.0 | 27.2 | 40.2 | 12.0 |
| 3637 | pKR2537 (GM-CA2) | 9.3 | 25% | 12.8 | 5.7 | 33.7 | 37.7 | 10.2 |

A summary comparing the average oil content and average fatty acid profile of the top 5 events having the highest oil content for each experiment is shown in Table 18.

TABLE 18

Summary of Average Oil Content and Fatty Acid Profiles
for the Top5 Events Having Highest Oil Contents
and Expressing YLDGAT2 (MSE 3634)
and YLDGAT2 with GM-CA2 (MSE 3637)

| MSE | Vector (Gene) | Avg. Oil | Avg. % Inc | 16:0 | 18:0 | 18:1 | 18:2 | 18:3 |
|---|---|---|---|---|---|---|---|---|
| 3634 | pKR1256 (n/a) | 10.0 | 0% | 13.0 | 7.1 | 31.3 | 39.2 | 9.4 |
| 3637 | pKR2537 (GM-CA2) | 12.9 | 28% | 11.1 | 5.7 | 38.7 | 36.6 | 7.9 |

Tables 16, 17 and 18 demonstrate that expression of GM-CA2 with YLDGAT2 leads to an increase in oil content in soy above that for YLDGAT2 alone.

Example 4

Cloning Arabidopsis and Soy Carbonic Anhydrases
Into Soybean Expression Vectors And
Co-Expression with Soy Ovule Development
Protein (GM-ODP1) or Maize Ovule Development
Protein (ZM-ODP1)

The cloning the corn (ZM-ODP1) and soy (GM-ODP1) ovule development protein (ODP) genes under control of the soy sucrose synthase promoter, where expression in soybean or soybean somatic embryos leads to higher oil, was described in PCT WO2013096562. Specifically, soybean expression pKR1971, comprising the GM-ODP1 under control of the soy sucrose synthase promoter, and pKR2114, comprising the ZM-ODP1 under control of the soy sucrose synthase promoter were described.

Using methods familiar to one skilled in the art, the NotI fragment containing GM-CA was cloned into a soybean expression vector containing the strong, seed specific soy albumin promoter (WO2000040710), with a soy albumin transcription terminator, to give pKR2609 (SEQ ID NO: 20).

Using methods familiar to one skilled in the art, a DNA fragment comprising the soy sucrose synthase promoter (as described in PCT/US12/70828) driving expression of GM-ODP1, with a legumin transcription terminator, was cloned into pKR2609, comprising the GM-CA under control of the soy albumin promoter, to give pKR2749 (SEQ ID NO: 21).

Similarly, a DNA fragment comprising the soy sucrose synthase promoter driving expression of ZM-ODP1, with a legumin transcription terminator, was cloned into pKR2609, comprising the GM-CA under control of the soy albumin promoter, to give pKR2748 (SEQ ID NO: 22).

DNA from plasmids pKR2609 (SEQ ID NO: 20), comprising the GM-CA alone, pKR1971, comprising the GM-ODP1 alone, pKR2114, comprising the ZM-ODP1 alone, pKR2749 (SEQ ID NO: 21), comprising the GM-ODP1 with the GM-CA, pKR2748 (SEQ ID NO: 22), comprising the ZM-ODP1 with the GM-CA and pKR278 (a plasmid containing no genes but having the hygromycin selectable marker as a negative control), was prepared for particle bombardment into soybean embryogenic suspension culture and transformed exactly as described previously in PCT Publication No. WO 2008/147935. Soybean embryogenic suspension culture was initiated, grown, maintained and bombarded and events were selected and matured on SHaM media also exactly as described in PCT Publication No. WO 2008/147935.

Example 5A

Co-Expressing YLDGAT2 with GM-CA and
Seed-Targeted Silencing of Galactinol Synthase
Genes in Soybeans Site-Specific Integration Donor Vector Stacking the Soy Beta-Conglycinin::YLDGAT2 with the Soy Abumin::GM-CA Overexpression Cassettes with the Galactinol Synthase Dilencing Cassette (PHP70086)

An RNAi hairpin construct comprising polynucleotide fragments of the galactinol synthase 1 (GAS1, described in Applicants' Assignee's U.S. Pat. No. 5,648,210; Issued Jul. 15, 1997), galactinol synthase 2 (GAS2; Applicants' Assignee's U.S. Pat. No. 6,967,262; Issued Nov. 22, 2005) and galactinol synthase 3 (GAS3; described in Applicants' Assignee's U.S. Pat. No. 7,294,756 B2; Issued Nov. 13, 2007) in the stem structure and loop structures was produced by standard PCR methods resulting in the Not1 fragment of SEQ ID NO: 23 (called Gas123hp-2).

The Gas123hp-2 was cloned into a cassette comprising the Kunitz soybean Trypsin Inhibitor (KTi) promoter (Jofuku et al., Plant Cell 1:1079 1093 (1989)) and the KTi 3' termination region, the isolation of which is described in U.S. Pat. No. 6,372,965, followed by the soy albumin transcription terminator, which was previously described in PCT Publication No. WO 2004/071467.

DNA fragments comprising the soy albumin promoter driving expression of the GM-CA with the soy albumin transcription terminator and the soy beta-conglycinin promoter driving expression of YLDGAT2 with the phaseolin transcription terminator were described herein.

The yeast FLP/FRT site specific recombination system has been shown to function in plants. Earlier, the system was utilized for excision of unwanted DNA. See, Lyznik et al. (1993) *Nucleic Acid Res.* 21:969-975. Subsequently, non-identical FRTs were used for the exchange, targeting, arrangement, insertion and control of expression of nucleotide sequences into the plant genome (PCT Publication No. WO1999025821; PCT Publication No. WO1999025840; PCT Publication No. WO1999025854; PCT Publication No. 1999025855; and PCT Publication No. WO2007011733; the contents of all are herein incorporated by reference).

Constructs and methods for FLP/FRT site specific recombination to achieve recombinase mediated cassette exchange (RMCE) for stacking gene cassettes in soy was previously described in U.S. Pat. No. 8,293,533 (the contents of which are herein incorporated by reference).

Using standard PCR and cloning methods by one skilled in the art, the following DNA elements were assembled to produce a 16111 bp basic donor construct PHP70086 (SEQ ID NO: 24).

Sequence 1903-1950 of PHP70086 (SEQ ID NO: 24) is a FLP recombinase recognition site FRT1 (described previously in U.S. Pat. No. 8,293,533). Sequence 1965-3920 is the soybean acetolactate synthase (als) gene coding region encoding a mutant ALS enzyme insensitive to sulfonylurea herbicides and having a P178S mutation in the encoded protein. Sequence 3937-4247 is the potato proteinase II inhibitor gene (PINII) terminator. Sequence 4283-4298 is a sequence of DNA comprising ORF stop codons in all 6 frames (ORFSTOP-A). Sequence 4301-5470 is the phaseolin transcription terminator. Sequence 5475-8817 is the soy beta-::YLDGAT2: phaseolin transcription terminator cassette. Sequence 8876-10953 is the soy albumin promoter:: GM-CA::soy albumin transcription terminator cassette. Sequence 10985-15265 is the soy Kunitz Trypsin inhibitor 3 (KTi3) promoter::Gas123hp-2::KTi3::albumin transcription terminator cassette. Sequence 15316-15332 is a sequence of DNA comprising ORF stop codons in all 6 frames (ORF-STOP-B). Sequence 15408-15455 is a FLP recombinase recognition site FRT87.

Sequence 15409-1902 is vector backbone (described previously in BB1626) containing the T7 promoter (sequence 601-696), the hygromycin phosphotransferase (hpt) gene coding region (sequence 697-1722) and the T7 terminator (sequence 1744-1876).

FLP Recombinase Expression Plasmid (PHP44664)

The construction of the 4860 bp FLP recombinase expression plasmid was described previously in U.S. Pat. No. 8,293,533.

Transformation into Soy SSI Target Events

Transgenic SSI target events were produced with the target DNA fragment QC288A as described previously in U.S. Pat. No. 8,293,533. One target event described in U.S. Pat. No. 8,293,533, 4729.5.1, also called the "A" line, was chosen to be re-transformed. Target line A contains a well characterized cassette from QC288A having frt1 and frt87 recombination sites with the constitutive SCP1 promoter upstream of the frt1 site.

Suspension cultures were initiated from developing embryos from homozygous plants of target line A using methods described previously in U.S. Pat. No. 8,293,533.

Target line A cultures were retransformed with the donor construct PHP70086 (SEQ ID NO: 24 and the FLP recombinase construct using intact plasm id at a 9:3 pg/bp/prep ratio with the biolistic bombardment transformation protocol described herein and using 90 ng/ml chlorsulfuron (DuPont, Wilmington, Del., USA) as the selection agent. The experiment name given for this transformation was Soil116.

Soil116 events created through RMCE bring the promoter-less als (P178S) coding region of donor construct PHP70086 (SEQ ID NO: 24) downstream of the scp1 promoter of QC288A in target line A for expression and thus chlorsulfuron resistance. The frt1 and frt87 sites from Target line A recombine with those in plasmid PHP70086 (SEQ ID NO: 24) in a successful recombination mediated cassette exchange (RMCE).

Example 5B

Analysis of Soybean Plants Co-Expressing YLDGAT2, GM-CA and Seed-Targeted Silencing of Galactinol Synthase Genes Site specific integration donor plasmid PHP50573, comprising YLDGAT2 under control of the strong, seed-preferred soy beta-conglycinin promoter and fad3 and galactinol synthase gene silencing cassettes, was previously described in PCT Publication No. WO2015/017510.

The creation and characterization of soybean Soil19 events created through Recombinase-Mediated Cassette Exchange (RMCE) using PHP50573 was also described in PCT Publication No. WO2015/017510.

T0 plants generated with donor construct PHP70086 (SEQ ID NO:24) were grown under greenhouse conditions. MatureT1 seeds were harvested and analyzed by near-infrared spectroscopy as described in Example 1. Transgenic T1 seeds of event SOY4139.11.3 were identified based on the increased oleic acid content associated with expression of YL_DGAT2 and named Soil 116.

T2 seeds of a transgenic line heterozygous for an event (AFS8377.1.2) generated with PHP50573 in the target site for site-specific insertion site that was also used in the SOIL116 experiment were analyzed in a similar fashion.

TABLE 19

|  | Oil | Protein | Pro + Oil |
| --- | --- | --- | --- |
| Soil 19 (AFS 8377.1.2) |  |  |  |
| TG | 22.39 | 44.07 | 66.46 |
| null | 19.13 | 43.25 | 62.38 |
| change % pts | 3.26 | 0.82 | 4.08 |
| Soil 116 (SOY 4139.11.3) |  |  |  |
| TG | 23.83 | 39.53 | 63.36 |
| null | 20.32 | 37.78 | 58.10 |
| change % pts | 3.51 | 1.75 | 5.26 |

Table 19 shows that there is a greater increase in oil in protein content in experiment SOIL 116 compared to SOIL 19 which demonstrates that expression of plastidic carbonic anhydrase adds to the increase of seed protein and oil content associated with expression of DGAT proteins.

Example 6

Amplification of Partial Plastidial Phosphoducmutase (pPGM):

A polynucleotide fragment encoding a part of pPGM (pPGM is described in Applicants' Assignee's U.S. Pat. No. 7,250,557; Issued Jul. 31, 2007; was amplified by standard PCR methods using Pfu Turbo DNA polymerase (Stratagene, La Jolla, Calif.) and the following primer sets. The DNA template for the PCR reaction was plasm id pTC103 (described in Applicants' Assignee's U.S. Pat. No. 7,250, 557; Issued Jul. 31, 2007.

The assembly of vector PHP29252 (SEQ ID NO: 39) is described in Applicants' U.S. Pat. No. 8,143,476, incorporated herewith by reference.

Soybean can be transformed (as described in U.S. Pat. No. 8,143,476) with a seed-specific expression Ascl fragment of PHP29252 (SEQ ID NO:40) containing the KTi promoter linked to the GAS1 GAS2 GAS3 PGM haripin by the method of particle gun bombardment (Klein, T. M. et al. (1987) Nature (London) 327:70-73; U.S. Pat. No. 4,945, 050).

We claim:

1. A recombinant DNA construct comprising a first regulatory sequence operably linked to a first heterologous polynucleotide encoding a plastidic carbonic anhydrase polypeptide and a second regulatory sequence operably linked to a second heterologous polynucleotide encoding a diacylglycerol acyltransferase (DGAT) polypeptide, wherein expression of the recombinant DNA construct in a transgenic soybean seed results in an increased oil content in the transgenic soybean seed, when compared to a control seed that expresses the second polypeptide but does not express the first polypeptide.

2. The recombinant construct of claim 1 wherein the second heterologous polynucleotide further encodes a polypeptide selected from the group consisting of: an Ovule Development Protein 1 (ODP1) polypeptide, a leafy cotyledon1 (Lec1) polypeptide and a transcription factor FUS3 (FUSCA3) polypeptide.

3. The recombinant construct of claim 2, wherein the second heterologous polynucleotide further encodes an ODP1 polypeptide comprising an amino acid sequence with at least 80% sequence identity to SEQ ID NO:26 or 38, a Lec1 polypeptide comprising an amino acid sequence with at least 80% sequence identity to SEQ ID NO:36, or a FUCSA3 polypeptide comprising an amino acid sequence with at least 80% sequence identity to SEQ ID NO:28 or 30.

4. The recombinant construct of claim 1, wherein said recombinant construct further comprises a third polynucleotide downregulating galactinol synthase activity.

5. The recombinant construct of claim 1, wherein the first regulatory sequence and the second regulatory sequence each comprise a different seed-specific promoter.

6. The recombinant construct of claim 1, wherein the percent increase in oil content is at least 5%.

7. The recombinant construct of claim 1, wherein the carbonic anhydrase polypeptide comprises an amino acid sequence with at least 80% sequence identity to SEQ ID NO:5, SEQ ID NO:12 or SEQ ID NO:17.

8. The recombinant construct of claim 1, wherein said DGAT polypeptide comprises an amino acid sequence with at least 80% sequence identity to SEQ ID NO:32 or to SEQ ID NO:34.

9. A soybean plant or a seed comprising the recombinant DNA construct of claim 1.

10. The seed of claim 9, further comprising a seed treatment.

11. The seed of claim 9, further comprising an agronomic trait.

12. A method of generating a soybean seed, having increased oil content, the method comprising the steps of:
 a. regenerating a transgenic plant comprising the recombinant construct of claim 1 from a regenerable soybean cell comprising the recombinant construct; and
 b. selecting the transgenic plant of step (a) or a transgenic progeny plant from the transgenic plant, wherein seed of the transgenic plant or the transgenic progeny plant comprises the recombinant construct and exhibits increased seed oil content, when compared to a control soybean seed expressing a comparable construct not comprising the first heterologous polynucleotide encoding the plastidic carbonic anhydrase polypeptide.

13. The recombinant construct of claim 1, wherein the carbonic anhydrase polypeptide comprises an amino acid sequence with at least 95% sequence identity to SEQ ID NO:5, SEQ ID NO:12 or SEQ ID NO:17.

14. A method of generating a soybean plant with seed having increased oil content, the method comprising the steps of:
 (a) crossing:
  (i) a first transgenic soybean plant comprising a first recombinant DNA construct comprising a first seed-specific promoter linked to at least one polynucleotide encoding a plastidic carbonic anhydrase; with
  (ii) a second transgenic soybean plant comprising a second recombinant DNA construct comprising a second seed-specific promoter operably linked to a second heterologous polynucleotide encoding at least one DGAT polypeptide; and
 (b) selecting a third transgenic plant from the cross of step (a), wherein seed of the third transgenic plant comprises the first and the second recombinant DNA constructs and wherein co-expression of said first polypeptide and said second polypeptide in said transgenic soybean seed results in an increased oil content in the transgenic soybean seed, when compared to a control soybean seed comprising the second recombinant construct, but not the first recombinant construct.

15. The method of claim 14, wherein the second recombinant construct comprises a polynucleotide encoding at least one ODP1, FUSCA3 or Lec1 polypeptide.

16. The method of claim 14, wherein the second recombinant construct comprises a construct downregulating phosphoglucomutase (PGM) activity.

17. The method of claim 14, wherein the DGAT polypeptide is a DGAT1 or DGAT2 polypeptide.

18. A transgenic soybean plant or seed obtained by the method of claim 14.

19. A product obtained from the transgenic seed of claim 18, wherein the product comprises at least one of the first and the second recombinant constructs.

20. A food or beverage comprising the product of claim 19.

* * * * *

SEQUENCE LISTING

```
<160> NUMBER OF SEQ ID NOS: 41

<210> SEQ ID NO 1
<211> LENGTH: 10146
<212> TYPE: DNA
<213> ORGANISM: artificial sequence
<220> FEATURE:
<223> OTHER INFORMATION: vector PHP43186

<400> SEQUENCE: 1
ctggtaacag gattagcaga gcgaggtatg taggcggtgc tacagagttc ttgaagtggt      60
ggcctaacta cggctacact agaagaacag tatttggtat ctgcgctctg ctgaagccag     120
ttaccttcgg aaaaagagtt ggtagctctt gatccggcaa acaaaccacc gctggtagcg     180
gtggtttttt tgtttgcaag cagcagatta cgcgcagaaa aaaaggatct caagaagatc     240
ctttgatctt ttctacgggg tctgacgctc agtggaacga aaactcacgt taagggattt     300
tggtcatgac attaacctat aaaaataggc gtatcacgag gccctttcgt ctcgcgcgtt     360
tcggtgatga cggtgaaaac ctctgacaca tgcagctccc ggagacggtc acagcttgtc     420
tgtaagcgga tgccgggagc agacaagccc gtcagggcgc gtcagcgggt gttggcgggt     480
gtcggggctg gcttaactat gcggcatcag agcagattgt actgagagtg caccatatgg     540
acatattgtc gttagaacgc ggctacaatt aatacataac cttatgtatc atacacatac     600
gatttaggtg acactataga acggcgcgcc ggtaccgggc cccccctcga gtggcgttag     660
ctgattaagt cagcatgcgc ggccggccgc aagctctagt gaagttccta tactttctgg     720
agaataggaa cttcggaata ggaacttcac cgggatcatc agctgggccg gcccagctga     780
tgggtctaga actagaaacg tgatgccact tgttattgaa gtcgattaca gcatctattc     840
tgttttacta tttataactt tgccatttct gacttttgaa aactatctct ggatttcggt     900
atcgctttgt gaagatcgag caaaagagac gttttgtgga cgcaatggtc caaatccgtt     960
ctacatgaac aaattggtca caatttccac taaaagtaaa taaatggcaa gttaaaaaag    1020
gaatatgcat tttactgatt gcctaggtga gctccaagag aagttgaatc tacacgtcta    1080
ccaaccgcta aaaaagaaa aacattgaat atgtaacctg attccattag cttttgactt    1140
cttcaacaga ttctctactt agatttctaa cagaaatatt attactagca catcattttc    1200
agtctcacta cagcaaaaaa tccaacggca caatacagac aacaggagat atcagactac    1260
agagatagat agatgctact gcatgtagta agttaaataa aaggaaaata aaatgtcttg    1320
ctaccaaaac tactacagac tatgatgctc accacaggcc aaatcctgca actaggacag    1380
cattatctta tatatattgt acaaaacaag catcaaggaa catttggtct aggcaatcag    1440
tacctcgttc taccatcacc ctcagttatc acatccttga aggatccatt actgggaatc    1500
atcggcaaca catgctcctg atgggcaca atgacatcaa gaaggtaggg gccaggggtg    1560
tccaacattc tctgaattgc cgctctaagc tcttccttct tcgtcactcg cgctgccggt    1620
atcccacaag catcagcaaa cttgagcatg tttgggaata tctcgctctc gctagacgga    1680
tctccaagat aggtgtgagc tctattggac ttgtagaacc tatcctccaa ctgaaccacc    1740
```

```
atacccaaat gctgattgtt caacaacaat atcttaactg ggagattctc cactcttata   1800
gtggccaact cctgaacatt catgatgaaa ctaccatccc catcaatgtc aaccacaaca   1860
gccccagggt tagcaacagc agcaccaata gccgcaggca atccaaaacc catggctcca   1920
agacccctg aggtcaacca ctgcctcggt ctcttgtact tgtaaaactg cgcagcccac    1980
atttgatgct gcccaacccc agtactaaca atagcatctc cattagtcaa ctcatcaaga   2040
acctcgatag catgctgcgg agaaatcgcg tcctggaatg tcttgtaacc caatggaaac   2100
ttgtgtttct gcacattaat ctcttctctc caacctccaa gatcaaactt accctccact   2160
cctttctcct ccaaaatcat attaattccc ttcaaggcca acttcaaatc cgcgcaaacc   2220
gacacgtgcg cctgcttgtt cttcccaatc tcggcagaat caatatcaat gtgaacaatc   2280
ttagccctac tagcaaaagc ctcaagcttc ccagtaacac ggtcatcaaa ccttacccca   2340
aaggcaagca acaaatcact attgtcaaca gcatagttag cataaacagt accatgcata   2400
cccagcatct gaagggaata ttcatcacca ataggaaaag ttccaagacc cattaaagtg   2460
ctagcaacgg gaataccagt gagttcaaca aagcgcctca attcagcact ggaattcaaa   2520
ctgccaccgc cgacgtagag aacgggcttt tgggcctcca tgatgagtct gacaatgtgt   2580
tccaattggg cctcggcggg gggcctgggc agcctggcga ggtaaccggg gaggttaacg   2640
ggctcgtccc aattaggcac ggcgagttgc tgctgaacgt ctttgggaat gtcgatgagg   2700
accgaccgg ggcggccgga ggtggcgacg aagaaagcct cggcgacgac gcggggggatg   2760
tcgtcgacgt cgaggatgag gtagttgtgc ttcgtgatgg atctgctcac ctccacgatc   2820
ggggtttctt ggaaggcgtc ggtgccgatc atccggcggg cgacctggcc ggtgatggcg   2880
acgactggga cgctgtccat taaagcgtcg gcgaggccgc tcacgaggtt ggtggcgccg   2940
gggccggagg tggcaatgca gacgccgggg aggccggagg aacgcgcgta gccttcggcg   3000
gcgaagacgc cgccctgctc gtggcgcggg agcacgttgc ggatggcggc ggagcgcgtg   3060
agcgcctggt ggatctccat cgacgcaccg ccggggtacg cgaacaccgt cgtcacgccc   3120
tgcctctcca gcgcctccac aaggatgtcc gcgcccttgc gaggttcgcc ggaggcgaac   3180
cgtgacacga agggctccgt ggtcggcgct tccttggtga agggcgccgc cgtgggggt    3240
ttggagatgg aacatttgat tttgagagcg tggttgggtt tggtgagggt ttgatgagag   3300
agagggaggg tggatctagt aatgcgtttg gggaaggtgg ggtgtgaaga ggaagaagag   3360
aatcgggtgg ttctggaagc ggtggccgcc attgtgttgt gtggtggaag ttcctatact   3420
ttctagagaa taggaacttc ggaataggaa cttctgttgt tatacttcaa aaactgcaca   3480
acaagcctag agttagtacc taaacagtaa atttacaaca gagagcaaag acacatgcaa   3540
aaatttcagc cataaaaaaa gttataatag aatttaaagc aaaagtttca ttttttaaac   3600
atatatacaa acaaactgga tttgaaggaa gggattaatt cccctgctca aagtttgaat   3660
tcctattgtg acctatactc gaataaaatt gaagcctaag gaatgtatga gaaacaagaa   3720
aacaaaacaa aactacagac aaacaagtac aattacaaaa ttcgctaaaa ttctgtaatc   3780
accaaacccc atctcagtca gcacaaggcc caaggtttat tttgaaataa aaaaaaagtg   3840
attttatttc tcataagcta aaagaaagaa aggcaattat gaaatgattt cgactagatc   3900
tgaaagtcaa acgcgtattc cgcagatatt aaagaaagag tagagtttca catggatcct   3960
agatggaccc agttgaggaa aaagcaaggc aaagcaaacc agaagtgcaa gatccgaaat   4020
tgaaccacgg aatctaggat ttggtagagg gagaagaaaa gtaccttgag aggtagaaga   4080
gaagagaaga gcagagagat atatgaacga gtgtgtcttg gtctcaactc tgaagcgata   4140
```

```
cgagtttaga ggggagcatt gagttccaat ttatagggaa accgggtggc aggggtgagt    4200
taatgacgga aaagccccta agtaacgaga ttggattgtg ggttagattc aaccgtttgc    4260
atccgcggct tagattgggg aagtcagagt gaatctcaac cgttgactga gttgaaaatt    4320
gaatgtagca accaattgag ccaacccag cctttgccct ttgattttga tttgtttgtt    4380
gcatactttt tatttgtctt ctggttctga ctctctttct ctcgtttcaa tgccaggttg    4440
cctactccca caccactcac aagaagattc tactgttagt attaaatatt ttttaatgta    4500
ttaaatgatg aatgcttttg taaacagaac aagactatgt ctaataagtg tcttgcaaca    4560
ttttttaaga aattaaaaaa aatatattta ttatcaaaat caaatgtatg aaaaatcatg    4620
aataatataa ttttatacat tttttaaaa aatcttttaa tttcttaatt aatatcttaa    4680
aaataatgat taatatttaa cccaaaataa ttagtatgat tggtaaggaa gatatccatg    4740
ttatgtttgg atgtgagttt gatctagagc aaagcttggg aagggcgaat tccagcacac    4800
tggcggccgt tactagtgtt tagcttacta gagtcgacct gcaggtcgac tcgtacccgg    4860
gggcgcgcgc gccaagcttt tgatccatgc ccttcatttg ccgcttatta attaatttgg    4920
taacagtccg tactaatcag ttacttatcc ttcccccatc ataattaatc ttggtagtct    4980
cgaatgccac aacactgact agtctcttgg atcataagaa aaagccaagg aacaaaagaa    5040
gacaaaacac aatgagagta tcctttgcat agcaatgtct aagttcataa aattcaaaca    5100
aaaacgcaat cacacacagt ggacatcact tatccactag ctgatcagga tcgccgcgtc    5160
aagaaaaaaa aactggaccc caaaagccat gcacaacaac acgtactcac aaaggtgtca    5220
atcgagcagc ccaaaacatt caccaactca acccatcatg agccctcaca tttgttgttt    5280
ctaacccaac ctcaaactcg tattctcttc cgccacctca tttttgttta tttcaacacc    5340
cgtcaaactg catgccaccc cgtggccaaa tgtccatgca tgttaacaag acctatgact    5400
ataaatagct gcaatctcgg cccaggtttt catcatcaag aaccagttca atatcctagt    5460
acaccgtatt aaagaattta agatatactg cggccgcatg actatcgact cacaatacta    5520
caagtcgcga gacaaaaacg acacggcacc caaaatcgcg ggaatccgat atgccccgct    5580
atcgacacca ttactcaacc gatgtgagac cttctctctg gtctggcaca ttttcagcat    5640
tcccactttc ctcacaattt tcatgctatg ctgcgcaatt ccactgctct ggccatttgt    5700
gattgcgtat gtagtgtacg ctgttaaaga cgactccccg tccaacggag gagtggtcaa    5760
gcgatactcg cctatttcaa gaaacttctt catctggaag ctctttggcc gctacttccc    5820
cataactctg cacaagacgg tggatctgga gcccacgcac acatactacc ctctggacgt    5880
ccaggagtat cacctgattg ctgagagata ctggccgcag aacaagtacc tccgagcaat    5940
catcaccacc atcgagtact ttctgcccgc cttcatgaaa cggtctcttt ctatcaacga    6000
gcaggagcag cctgccgagc gagatcctct cctgtctccc gtttctccca gctctccggg    6060
ttctcaacct gacaagtgga ttaaccacga cagcagatat agccgtggag aatcatctgg    6120
ctccaacggc cacgcctcgg gctccgaact taacggcaac ggcaacaacg gcaccactaa    6180
ccgacgacct ttgtcgtccg cctctgctgg ctccactgca tctgattcca cgcttcttaa    6240
cgggtccctc aactcctacg ccaaccagat cattggcgaa aacgaccac agctgtcgcc    6300 cacaaaactc aagcccactg gcagaaaata catcttcggc taccacccc acggcattat    6360 cggcatggga gcctttggtg gaattgccac cgagggagct ggatggtcca agctcttttcc    6420 gggcatccct gtttctctta tgactctcac caacaacttc cgagtgcctc tctacagaga    6480
gtacctcatg agtctgggag tcgcttctgt ctccaagaag tcctgcaagg ccctcctcaa    6540
```

```
gcgaaaccag tctatctgca ttgtcgttgg tggagcacag gaaagtcttc tggccagacc    6600
cggtgtcatg gacctggtgc tactcaagcg aaagggtttt gttcgacttg gtatggaggt    6660
cggaaatgtc gcccttgttc ccatcatggc ctttggtgag aacgacctct atgaccaggt    6720
tagcaacgac aagtcgtcca agctgtaccg attccagcag tttgtcaaga acttccttgg    6780
attcacccct cctttgatgc atgcccgagg cgtcttcaac tacgatgtcg gtcttgtccc    6840
ctacaggcga cccgtcaaca ttgtggttgg ttcccccatt gacttgcctt atctcccaca    6900
ccccaccgac gaagaagtgt ccgaatacca cgaccgatac atcgccgagc tgcagcgaat    6960
ctacaacgag cacaaggatg aatatttcat cgattggacc gaggagggca aaggagcccc    7020
agagttccga atgattgagt aagcggccgc aagtatgaac taaaatgcat gtaggtgtaa    7080
gagctcatgg agagcatgga atattgtatc cgaccatgta acagtataat aactgagctc    7140
catctcactt cttctatgaa taaacaaagg atgttatgat atattaacac tctatctatg    7200
caccttattg ttctatgata aatttcctct tattattata aatcatctga atcgtgacgg    7260
cttatggaat gcttcaaata gtacaaaaac aaatgtgtac tataagactt tctaaacaat    7320
tctaacctta gcattgtgaa cgagacataa gtgttaagaa gacataacaa ttataatgga    7380
agaagtttgt ctccatttat atattatata ttacccactt atgtattata ttaggatgtt    7440
aaggagacat aacaattata aagagagaag tttgtatcca tttatatatt atatactacc    7500
catttatata ttatacttat ccacttattt aatgtcttta taaggtttga tccatgatat    7560
ttctaatatt ttagttgata tgtatatgaa aaggtactat ttgaactctc ttactctgta    7620
taaaggttgg atcatcctta aagtgggtct atttaatttt attgcttctt acagataaaa    7680
aaaaaattat gagttggttt gataaaatat tgaaggattt aaaataataa taaataacat    7740
ataatatatg tatataaatt tattataata taacatttat ctataaaaaa gtaaatattg    7800
tcataaatct atacaatcgt ttagccttgc tggaacgaat ctcaattatt taaacgagag    7860
taaacatatt tgactttttg gttatttaac aaattattat ttaacactat atgaaatttt    7920
tttttttatc agcaaagaat aaaattaaat taagaaggac aatggtgtcc caatccttat    7980
acaaccaact tccacaagaa agtcaagtca gagacaacaa aaaacaagc aaaggaaatt    8040 ttttaatttg agttgtcttg tttgctgcat aatttatgca gtaaaacact acacataacc    8100
cttttagcag tagagcaatg gttgaccgtg tgcttagctt ctttttatttt atttttttat    8160 cagcaaagaa taaataaaat aaaatgagac acttcaggga tgtttcaaca agcttggatc    8220
cttaattaag tctagagtcg actgtttggg taccggcgcg cccgagcatc cggatatagt    8280
tcctcctttc agcaaaaaac ccctcaagac ccgtttagag gccccaaggg gttatgctag    8340
ttattgctca gcgtggcag cagccaactc agcttccttt cgggctttgt tagcagccgg    8400
atcgatccaa gctgtacctc actattcctt tgccctcgga cgagtgctgg ggcgtcggtt    8460
tccactatcg gcgagtactt ctacacagcc atcggtccag acggccgcgc ttctgcgggc    8520
gatttgtgta cgcccgacag tcccggctcc ggatcggacg attgcgtcgc atcgaccctg    8580
cgcccaagct gcatcatcga aattgccgtc aaccaagctc tgatagagtt ggtcaagacc    8640
aatgcggagc atatacgccc ggagccgcgg cgatcctgca agctccggat gcctccgctc    8700
gaagtagcgc gtctgctgct ccatacaagc caaccacggc ctccagaaga agatgttggc    8760
gacctcgtat tgggaatccc cgaacatcgc ctcgctccag tcaatgaccg ctgttatgcg    8820
gccattgtcc gtcaggacat tgttggagcc gaaatccgcg tgcacgaggt gccggacttc    8880
ggggcagtcc tcggcccaaa gcatcagctc atcgagagcc tgcgcgacgg acgcactgac    8940
```

```
ggtgtcgtcc atcacagttt gccagtgata cacatgggga tcagcaatcg cgcatatgaa    9000
atcacgccat gtagtgtatt gaccgattcc ttgcggtccg aatgggccga acccgctcgt    9060
ctggctaaga tcggccgcag cgatcgcatc catagcctcc gcgaccggct gcagaacagc    9120
gggcagttcg gtttcaggca ggtcttgcaa cgtgacaccc tgtgcacggc gggagatgca    9180
ataggtcagg ctctcgctga attccccaat gtcaagcact tccggaatcg ggagcgcggc    9240
cgatgcaaag tgccgataaa cataacgatc tttgtagaaa ccatcggcgc agctatttac    9300
ccgcaggaca tatccacgcc ctcctacatc gaagctgaaa gcacgagatt cttcgccctc    9360
cgagagctgc atcaggtcgg agacgctgtc gaacttttcg atcagaaact tctcgacaga    9420
cgtcgcggtg agttcaggct tttccatggg tatatctcct tcttaaagtt aaacaaaatt    9480
atttctagag ggaaaccgtt gtggtctccc tatagtgagt cgtattaatt tcgcgggatc    9540
gagatctgat caacctgcat taatgaatcg gccaacgcgc ggggagaggc ggtttgcgta    9600
ttgggcgctc ttccgcttcc tcgctcactg actcgctgcg ctcggtcgtt cggctgcggc    9660
gagcggtatc agctcactca aaggcggtaa tacggttatc cacagaatca ggggataacg    9720
caggaaagaa catgtgagca aaaggccagc aaaaggccag gaaccgtaaa aaggccgcgt    9780
tgctggcgtt tttccatagg ctccgccccc ctgacgagca tcacaaaaat cgacgctcaa    9840
gtcagaggtg gcgaaacccg acaggactat aaagatacca ggcgtttccc cctggaagct    9900
ccctcgtgcg ctctcctgtt ccgaccctgc cgcttaccgg atacctgtcc gcctttctcc    9960
cttcgggaag cgtggcgctt tctcatagct cacgctgtag gtatctcagt tcggtgtagg   10020
tcgttcgctc caagctgggc tgtgtgcacg aaccccccgt tcagcccgac cgctgcgcct   10080
tatccggtaa ctatcgtctt gagtccaacc cggtaagaca cgacttatcg ccactggcag   10140
cagcca                                                              10146

<210> SEQ ID NO 2
<211> LENGTH: 7632
<212> TYPE: DNA
<213> ORGANISM: artificial sequence
<220> FEATURE:
<223> OTHER INFORMATION: vector PHP43186A

<400> SEQUENCE: 2
cgcgccggta ccgggccccc cctcgagtgg cgttagctga ttaagtcagc atgcgcggcc      60
ggccgcaagc tctagtgaag ttcctatact ttctggagaa taggaacttc ggaataggaa     120
cttcaccggg atcatcagct gggccggccc agctgatggg tctagaacta gaaacgtgat     180
gccacttgtt attgaagtcg attacagcat ctattctgtt ttactattta aactttgcc      240 atttctgact tttgaaaact atctctggat ttcggtatcg ctttgtgaag atcgagcaaa     300
agagacgttt tgtggacgca atggtccaaa tccgttctac atgaacaaat tggtcacaat     360
ttccactaaa agtaaataaa tggcaagtta aaaaaggaat atgcatttta ctgattgcct     420
aggtgagctc caagagaagt tgaatctaca cgtctaccaa ccgctaaaaa agaaaaaaca     480
ttgaatatgt aacctgattc cattagcttt tgacttcttc aacagattct ctacttagat     540
ttctaacaga aatattatta ctagcacatc attttcagtc tcactacagc aaaaaatcca     600
acggcacaat acagacaaca ggagatatca gactacagag atagatagat gctactgcat     660
gtagtaagtt aaataaaagg aaaataaaat gtcttgctac caaaactact acagactatg     720
atgctcacca caggccaaat cctgcaacta ggacagcatt atcttatata tattgtacaa     780
```

```
aacaagcatc aaggaacatt tggtctaggc aatcagtacc tcgttctacc atcaccctca    840
gttatcacat ccttgaagga tccattactg ggaatcatcg gcaacacatg ctcctgatgg    900
ggcacaatga catcaagaag gtaggggcca ggggtgtcca acattctctg aattgccgct    960
ctaagctctt ccttcttcgt cactcgcgct gccggtatcc cacaagcatc agcaaacttg   1020
agcatgtttg ggaatatctc gctctcgcta gacggatctc caagataggt gtgagctcta   1080
ttggacttgt agaacctatc ctccaactga accaccatac ccaaatgctg attgttcaac   1140
aacaatatct taactgggag attctccact cttatagtgg ccaactcctg aacattcatg   1200
atgaaactac catccccatc aatgtcaacc acaacagccc cagggttagc aacagcagca   1260
ccaatagccg caggcaatcc aaaacccatg ctccaagac ccctgaggt caaccactgc    1320 ctcggtctct tgtacttgta aaactgcgca gcccacattt gatgctgccc aaccccagta   1380
ctaacaatag catctccatt agtcaactca tcaagaacct cgatagcatg ctgcggagaa   1440
atcgcgtcct ggaatgtctt gtaacccaat ggaaacttgt gtttctgcac attaatctct   1500
tctctccaac ctccaagatc aaacttaccc tccactcctt tctcctccaa aatcatatta   1560
attcccttca aggccaactt caaatccgcg caaaccgaca cgtgcgcctg cttgttcttc   1620
ccaatctcgg cagaatcaat atcaatgtga acaatcttag ccctactagc aaaagcctca   1680
agcttcccag taacacggtc atcaaaacctt accccaaagg caagcaacaa atcactattg   1740
tcaacagcat agttagcata aacagtacca tgcatacca gcatctgaag gaatattca   1800 tcaccaatag gaaaagttcc aagacccatt aaagtgctag caacgggaat accagtgagt   1860
tcaacaaagc gcctcaattc agcactggaa ttcaaactgc caccgccgac gtagagaacg   1920
ggcttttggg cctccatgat gagtctgaca atgtgttcca attgggcctc ggcggggggc   1980
ctgggcagcc tggcgaggta accggggagg ttaacgggct cgtcccaatt aggcacggcg   2040
agttgctgct gaacgtcttt gggaatgtcg atgaggaccg gaccggggcg gccggaggtg   2100
gcgacgaaga aagcctcggc gacgacgcgg gggatgtcgt cgacgtcgag gatgaggtag   2160
ttgtgcttcg tgatggatct gctcaccttcc acgatcgggg tttcttggaa ggcgtcggtg   2220
ccgatcatcc ggcgggcgac ctggccggtg atggcgacga ctgggacgct gtccattaaa   2280
gcgtcggcga ggccgctcac gaggttggtg gcgccggggc cggaggtggc aatgcagacg   2340
ccggggaggc cggaggaacg cgcgtagcct tcggcggcga agacgccgcc ctgctcgtgg   2400
cgcgggagca cgttgcggat ggcggcggag cgcgtgagcg cctggtggat ctccatcgac   2460
gcaccgccgg ggtacgcgaa caccgtcgtc acgccctgcc tctccagcgc ctccacaagg   2520
atgtccgcgc ccttgcgagg ttcgccggag gcgaaccgtg acacgaaggg ctccgtggtc   2580
ggcgcttcct tggtgaaggg cgccgccgtg ggggtttgg agatggaaca tttgattttg   2640
agagcgtggt tgggtttggt gagggtttga tgagagagag ggagggtgga tctagtaatg   2700
cgtttgggga aggtggggtg tgaagaggaa aagagaatc gggtggttct ggaagcggtg    2760
gccgccattg tgttgtgtgg tggaagttcc tatactttct agagaatagg aacttcggaa   2820
taggaacttc tgttgttata cttcaaaaac tgcacaacaa gcctagagtt agtacctaaa   2880
cagtaaattt acaacagaga gcaaagacac atgcaaaaat ttcagccata aaaaagtta   2940 taatagaatt taaagcaaaa gtttcatttt ttaaacatat atacaaacaa actgatttg    3000 aaggaaggga ttaattcccc tgctcaaagt ttgaattcct attgtgacct atactcgaat   3060
aaaattgaag cctaaggaat gtatgagaaa caagaaaaca aaacaaaact acagacaaac   3120
aagtacaatt acaaaattcg ctaaaattct gtaatcacca aaccccatct cagtcagcac   3180
```

```
aaggcccaag gtttattttg aaataaaaaa aaagtgattt tatttctcat aagctaaaag    3240
aaagaaaggc aattatgaaa tgatttcgac tagatctgaa agtcaaacgc gtattccgca    3300
gatattaaag aaagagtaga gtttcacatg gatcctagat ggacccagtt gaggaaaaag    3360
caaggcaaag caaccagaa gtgcaagatc cgaaattgaa ccacggaatc taggatttgg    3420
tagagggaga agaaaagtac cttgagaggt agaagagaag agaagagcag agagatatat    3480
gaacgagtgt gtcttggtct caactctgaa gcgatacgag tttagagggg agcattgagt    3540
tccaatttat agggaaaccg ggtggcaggg gtgagttaat gacggaaaag cccctaagta    3600
acgagattgg attgtgggtt agattcaacc gtttgcatcc gcggcttaga ttggggaagt    3660
cagagtgaat ctcaaccgtt gactgagttg aaaattgaat gtagcaacca attgagccaa    3720
ccccagcctt tgcccttttga ttttgatttg tttgttgcat actttttatt tgtcttctgg    3780
ttctgactct ctttctctcg tttcaatgcc aggttgccta ctcccacacc actcacaaga    3840
agattctact gttagtatta aatattttt aatgtattaa atgatgaatg cttttgtaaa    3900
cagaacaaga ctatgtctaa taagtgtctt gcaacatttt ttaagaaatt aaaaaaaata    3960
tatttattat caaaatcaaa tgtatgaaaa atcatgaata atataatttt atacattttt    4020
ttaaaaaatc ttttaatttc ttaattaata tcttaaaaat aatgattaat atttaaccca    4080
aaataattag tatgattggt aaggaagata tccatgttat gtttggatgt gagtttgatc    4140
tagagcaaag cttgggaagg gcgaattcca gcacactggc ggccgttact agtgtttagc    4200
ttactagagt cgacctgcag gtcgactcgt acccggggc gcgcgcgcca agcttttgat    4260
ccatgccctt catttgccgc ttattaatta atttggtaac agtccgtact aatcagttac    4320
ttatccttcc cccatcataa ttaatcttgg tagtctcgaa tgccacaaca ctgactagtc    4380
tcttggatca taagaaaaag ccaaggaaca aaagaagaca aaacacaatg agagtatcct    4440
ttgcatagca atgtctaagt tcataaaatt caaacaaaaa cgcaatcaca cacagtggac    4500
atcacttatc cactagctga tcaggatcgc cgcgtcaaga aaaaaaaact ggaccccaaa    4560
agccatgcac aacaacacgt actcacaaag gtgtcaatcg agcagcccaa acattcacc    4620 aactcaaccc atcatgagcc ctcacatttg ttgtttctaa cccaacctca aactcgtatt    4680
ctcttccgcc acctcatttt tgtttatttc aacacccgtc aaactgcatg ccaccccgtg    4740
gccaaatgtc catgcatgtt aacaagacct atgactataa atagctgcaa tctcggccca    4800
ggttttcatc atcaagaacc agttcaatat cctagtacac cgtattaaag aatttaagat    4860
atactgcggc cgcatgacta tcgactcaca atactcaag tcgcgagaca aaacgacac    4920 ggcacccaaa atcgcgggaa tccgatatgc cccgctatcg acaccattac tcaaccgatg    4980
tgagaccttc tctctggtct ggcacatttt cagcattccc actttcctca caattttcat    5040
gctatgctgc gcaattccac tgctctggcc atttgtgatt gcgtatgtag tgtacgctgt    5100
taaagacgac tccccgtcca acggaggagt ggtcaagcga tactcgccta tttcaagaaa    5160
cttcttcatc tggaagctct ttggccgcta cttccccata actctgcaca agacggtgga    5220
tctggagccc acgcacacat actaccctct ggacgtccag gagtatcacc tgattgctga    5280
gagatactgg ccgcagaaca agtacctccg agcaatcatc accaccatcg agtactttct    5340
gcccgccttc atgaaacggt ctctttctat caacgagcag gagcagcctg ccgagcgaga    5400
tcctctcctg tctcccgttt ctcccagctc tccgggttct caacctgaca gtggattaa    5460 ccacgacagc agatatagcc gtggagaatc atctggctcc aacggccacg cctcgggctc    5520
```

```
cgaacttaac ggcaacggca acaacggcac cactaaccga cgacctttgt cgtccgcctc    5580
tgctggctcc actgcatctg attccacgct tcttaacggg tccctcaact cctacgccaa    5640
ccagatcatt ggcgaaaacg acccacagct gtcgcccaca aaactcaagc ccactggcag    5700
aaaatacatc ttcggctacc accccacgg cattatcggc atgggagcct ttggtggaat     5760
tgccaccgag ggagctggat ggtccaagct cttccgggc atccctgttt ctcttatgac     5820
tctcaccaac aacttccgag tgcctctcta cagagagtac ctcatgagtc tgggagtcgc    5880
ttctgtctcc aagaagtcct gcaaggccct cctcaagcga aaccagtcta tctgcattgt    5940
cgttggtgga gcacaggaaa gtcttctggc cagacccggt gtcatggacc tggtgctact    6000
caagcgaaag ggttttgttc gacttggtat ggaggtcgga aatgtcgccc ttgttcccat    6060
catggccttt ggtgagaacg acctctatga ccaggttagc aacgacaagt cgtccaagct    6120
gtaccgattc cagcagtttg tcaagaactt ccttggattc acccttcctt tgatgcatgc    6180
ccgaggcgtc ttcaactacg atgtcggtct tgtcccctac aggcgacccg tcaacattgt    6240
ggttggttcc cccattgact tgccttatct cccacacccc accgacgaag aagtgtccga    6300
ataccacgac cgatacatcg ccgagctgca gcgaatctac aacgagcaca aggatgaata    6360
tttcatcgat tggaccgagg agggcaaagg agccccagag ttccgaatga ttgagtaagc    6420
ggccgcaagt atgaactaaa atgcatgtag gtgtaagagc tcatggagag catggaatat    6480
tgtatccgac catgtaacag tataataact gagctccatc tcacttcttc tatgaataaa    6540 caaggatgt tatgatatat taacactcta tctatgcacc ttattgttct atgataaatt     6600
tcctcttatt attataaatc atctgaatcg tgacggctta tggaatgctt caaatagtac    6660
aaaaacaaat gtgtactata agactttcta acaattcta accttagcat tgtgaacgag      6720
acataagtgt taagaagaca taacaattat aatggaagaa gtttgtctcc atttatatat    6780
tatatattac ccacttatgt attatattag gatgttaagg agacataaca attataaaga    6840
gagaagtttg tatccattta tatattat actacccatt tatatattat acttatccac       6900
ttatttaatg tctttataag gtttgatcca tgatatttct aatattttag ttgatatgta    6960
tatgaaaagg tactatttga actctcttac tctgtataaa ggttggatca tccttaaagt    7020
gggtctattt aattttattg cttcttacag ataaaaaaaa aattatgagt tggtttgata    7080
aaatattgaa ggatttaaaa taataataaa taacatataa tatatgtata taaatttatt    7140
ataatataac atttatctat aaaaagtaa atattgtcat aaatctatac aatcgtttag     7200
ccttgctgga acgaatctca attatttaaa cgagagtaaa catatttgac ttttggtta    7260 tttaacaaat tattatttaa cactatatga aattttttt tttatcagca aagaataaaa     7320
ttaaattaag aaggacaatg gtgtcccaat ccttatacaa ccaacttcca caagaaagtc     7380
aagtcagaga caacaaaaaa acaagcaaag gaaattttt aatttgagtt gtcttgtttg      7440
ctgcataatt tatgcagtaa aacactacac ataacccttt tagcagtaga gcaatggttg    7500
accgtgtgct tagcttcttt tattttattt tttatcagc aaagaataaa taaaataaaa      7560
tgagacactt cagggatgtt tcaacaagct tggatcctta attaagtcta gagtcgactg    7620
tttgggtacc gg                                                         7632
```

<210> SEQ ID NO 3
<211> LENGTH: 1209
<212> TYPE: DNA
<213> ORGANISM: Arabidopsis thaliana

<400> SEQUENCE: 3

```
attgatccag attcgaagta cccaacttta ctctctagac cttttcatg gcagccactc    60 ccacacactt ctctgtctcc catgatcctt tttcttccac gtctctcctt aatctccaaa   120
ctcaagcgat cttgggtccc aatcacagtt taaagacaac ccagttgaga attccagctt   180 cttcagaag aaagctaca aacttgcaag tgatggcttc aggaaagaca cctggactga    240
ctcaggaagc taatggggtt gcaattgata gacaaaacaa cactgatgta tttgacgaca   300
tgaaacagcg gttcctggcc ttcaagaagc ttaagtacat ggatgacttt gaacactaca   360
aaaatctggc agatgctcaa gctccaaagt ttctggtgat tgcttgtgca gactctagag   420
tttgtccttc tgctgtcctg ggattccaac cgggtgacgc attcactgtt cgtaacattg   480
caaatttagt acctccatat gagtctggac ctactgaaac caaagctgct ctagagttct   540
ctgtgaatac tcttaatgtg gaaaacatct tagtcattgg tcatagccgg tgtggaggaa   600
ttcaagcttt aatgaaaatg gaagacgaag gagattccag aagtttcata cacaactggg   660
tagttgtggg aaagaaggca aaggaaagca caaaagctgt tgcttcaaac ctccatttg   720 atcatcagtg ccaacattgt gaaaaggcat cgataaatca ttcattagaa aggctgcttg   780
ggtacccgtg gatagaagag aaagtgcggc aaggttcact gtctctccat ggtggatact   840
ataattttgt tgattgtacg ttcgagaaat ggacagtgga ttatgcagca gcagaggta    900 agaagaagga aggcagtgga atcgctgtta aagaccggtc agtttggtct tgacttacga   960
ctatctcaat cttcatagag tttttttca taatttatag agaaacatca accccttt    1020 ggttgggatt atcatgtgtt tgttccactt gtgtgttgaa gtcatttcc ttcttctgtc   1080 ttattgaggc agggactaat gtttgtttta tctttcagtt gtttcgttta aattccacat  1140
ttgtgcaatg aactggttgg tgtttcttta agatataatc attttgccga aaaaaaaaa   1200 aaaaaaaaa                                                          1209

<210> SEQ ID NO 4
<211> LENGTH: 906
<212> TYPE: DNA
<213> ORGANISM: Arabidopsis thaliana

<400> SEQUENCE: 4
atggcagcca ctcccacaca cttctctgtc tcccatgatc cttttcttc cacgtctctc    60 cttaatctcc aaactcaagc gatctttggt cccaatcaca gtttaaagac aacccagttg   120
agaattccag cttctttcag aagaaagct acaaacttgc aagtgatggc ttcaggaaag   180
acacctggac tgactcagga agctaatggg gttgcaattg atagacaaaa caacactgat   240
gtatttgacg acatgaaaca gcggttcctg gccttcaaga agcttaagta catggatgac   300
tttgaacact acaaaaatct ggcagatgct caagctccaa agtttctggt gattgcttgt   360
gcagactcta gagtttgtcc ttctgctgtc ctgggattcc aaccgggtga cgcattcact   420
gttcgtaaca ttgcaaattt agtacctcca tatgagtctg gacctactga aaccaaagct   480
gctctagagt tctctgtgaa tactcttaat gtggaaaaca tcttagtcat tggtcatagc   540
cggtgtggag gaattcaagc tttaatgaaa atggaagacg aaggagattc agaagtttc    600 atacacaact gggtagttgt gggaaagaag gcaaggaaa gcacaaaagc tgttgcttca   660
aacctccatt ttgatcatca gtgccaacat tgtgaaaagg catcgataaa tcattcatta   720
gaaaggctgc ttgggtaccc gtggatagaa gagaaagtgc ggcaaggttc actgtctctc   780
catggtggat actataattt tgttgattgt acgttcgaga aatggacagt ggattatgca   840
```
gcaagcagag gtaagaagaa ggaaggcagt ggaatcgctg ttaaagaccg gtcagtttgg    900
tcttga    906

<210> SEQ ID NO 5
<211> LENGTH: 301
<212> TYPE: PRT
<213> ORGANISM: Arabidopsis thaliana

<400> SEQUENCE: 5

Met Ala Ala Thr Pro Thr His Phe Ser Val Ser His Asp Pro Phe Ser
1               5                   10                  15

Ser Thr Ser Leu Leu Asn Leu Gln Thr Gln Ala Ile Phe Gly Pro Asn
            20                  25                  30

His Ser Leu Lys Thr Thr Gln Leu Arg Ile Pro Ala Ser Phe Arg Arg
        35                  40                  45

Lys Ala Thr Asn Leu Gln Val Met Ala Ser Gly Lys Thr Pro Gly Leu
    50                  55                  60

Thr Gln Glu Ala Asn Gly Val Ala Ile Asp Arg Gln Asn Asn Thr Asp
65                  70                  75                  80

Val Phe Asp Asp Met Lys Gln Arg Phe Leu Ala Phe Lys Lys Leu Lys
                85                  90                  95

Tyr Met Asp Asp Phe Glu His Tyr Lys Asn Leu Ala Asp Ala Gln Ala
            100                 105                 110

Pro Lys Phe Leu Val Ile Ala Cys Ala Asp Ser Arg Val Cys Pro Ser
        115                 120                 125

Ala Val Leu Gly Phe Gln Pro Gly Asp Ala Phe Thr Val Arg Asn Ile
130                 135                 140

Ala Asn Leu Val Pro Pro Tyr Glu Ser Gly Pro Thr Glu Thr Lys Ala
145                 150                 155                 160

Ala Leu Glu Phe Ser Val Asn Thr Leu Asn Val Glu Asn Ile Leu Val
                165                 170                 175

Ile Gly His Ser Arg Cys Gly Gly Ile Gln Ala Leu Met Lys Met Glu
            180                 185                 190

Asp Glu Gly Asp Ser Arg Ser Phe Ile His Asn Trp Val Val Gly
        195                 200                 205

Lys Lys Ala Lys Glu Ser Thr Lys Ala Val Ala Ser Asn Leu His Phe
    210                 215                 220

Asp His Gln Cys Gln His Cys Glu Lys Ala Ser Ile Asn His Ser Leu
225                 230                 235                 240

Glu Arg Leu Leu Gly Tyr Pro Trp Ile Glu Glu Lys Val Arg Gln Gly
                245                 250                 255

Ser Leu Ser Leu His Gly Gly Tyr Tyr Asn Phe Val Asp Cys Thr Phe
            260                 265                 270

Glu Lys Trp Thr Val Asp Tyr Ala Ala Ser Arg Gly Lys Lys Lys Glu
        275                 280                 285

Gly Ser Gly Ile Ala Val Lys Asp Arg Ser Val Trp Ser
    290                 295                 300

<210> SEQ ID NO 6
<211> LENGTH: 31
<212> TYPE: DNA
<213> ORGANISM: artificial sequence
<220> FEATURE:
<223> OTHER INFORMATION: primer oBCA5-1

<400> SEQUENCE: 6

<210> SEQ ID NO 7
<211> LENGTH: 27
<212> TYPE: DNA
<213> ORGANISM: artificial sequence
<220> FEATURE:
<223> OTHER INFORMATION: preimer oBCA5-2

<400> SEQUENCE: 7

| agcggccgcg tcaagaccaa actgacc | 27 |
|---|---|

<210> SEQ ID NO 8
<211> LENGTH: 10861
<212> TYPE: DNA
<213> ORGANISM: artificial sequence
<220> FEATURE:
<223> OTHER INFORMATION: vector pKR2559

<400> SEQUENCE: 8

| tgcggccgca ccatggcagc cactcccaca c | 31 |
|---|---|
| ggagatccaa gcttttgatc catgcccttc atttgccgct tattaattaa tttggtaaca | 60 |
| gtccgtacta atcagttact tatccttccc ccatcataat taatcttggt agtctcgaat | 120 |
| gccacaacac tgactagtct cttggatcat aagaaaaagc caaggaacaa agaagacaa | 180 |
| aacacaatga gagtatcctt tgcatagcaa tgtctaagtt cataaaattc aaacaaaaac | 240 |
| gcaatcacac acagtggaca tcacttatcc actagctgat caggatcgcc gcgtcaagaa | 300 |
| aaaaaaactg accccaaaa gccatgcaca acaacacgta ctcacaaagg tgtcaatcga | 360 |
| gcagcccaaa acattcacca actcaaccca tcatgagccc tcacatttgt tgtttctaac | 420 |
| ccaacctcaa actcgtattc tcttccgcca cctcattttt gtttatttca cacccgtca | 480 |
| aactgcatgc caccccgtgg ccaaatgtcc atgcatgtta acaagaccta tgactataaa | 540 |
| tagctgcaat ctcggcccag ttttcatca tcaagaacca gttcaatatc ctagtacacc | 600 |
| gtattaaaga atttaagata tactgcggcc gcaacatgac tatcgactca caatactaca | 660 |
| agtcgcgaga caaaaacgac acggcaccca aaatcgcggg aatccgatat gccccgctat | 720 |
| cgacaccatt actcaaccga tgtgagacct tctctctggt ctggcacatt ttcagcattc | 780 |
| ccactttcct cacaattttc atgctatgct gcgcaattcc actgctctgg ccatttgtga | 840 |
| ttgcgtatgt agtgtacgct gttaaagacg actccccgtc caacggagga gtggtcaagc | 900 |
| gatactcgcc tatttcaaga aacttcttca tctggaagct ctttggccgc tacttcccca | 960 |
| taactctgca caagacggtg gatctggagc ccacgcacac atactaccct ctggacgtcc | 1020 |
| aggagtatca cctgattgct gagagatact ggccgcagaa caagtacctc cgagcaatca | 1080 |
| tcaccaccat cgagtacttt ctgccccgcct tcatgaaacg gtctctttct atcaacgagc | 1140 |
| aggagcagcc tgccgagcga gatcctctcc tgtctcccgt ttctcccagc tctccgggtt | 1200 |
| ctcaacctga caagtggatt aaccacgaca gcagatatag ccgtggagaa tcatctggct | 1260 |
| ccaacggcca cgcctcgggc tccgaactta acggcaacgg caacaacggc accactaacc | 1320 |
| gacgaccttt gtcgtccgcc tctgctggct ccactgcatc tgattccacg cttcttaacg | 1380 |
| ggtccctcaa ctcctacgcc aaccagatca ttggcgaaaa cgaccacag ctgtcgccca | 1440 |
| caaaactcaa gcccactggc agaaaataca tcttcggcta ccacccccac ggcattatcg | 1500 |
| gcatgggagc ctttgtgga attgccaccg agggagctgg atggtccaag ctcttccgg | 1560 |
| gcatccctgt ttctccttat gactctcacca acaacttccg agtgcctctc tacagagagt | 1620 |
| acctcatgag tctgggagtc gcttctgtct ccaagaagtc ctgcaaggcc ctcctcaagc | 1680 |

-continued

```
gaaaccagtc tatctgcatt gtcgttggtg gagcacagga aagtcttctg gccagacccg   1740
gtgtcatgga cctggtgcta ctcaagcgaa agggttttgt tcgacttggt atggaggtcg   1800
gaaatgtcgc ccttgttccc atcatggcct ttggtgagaa cgacctctat gaccaggtta   1860
gcaacgacaa gtcgtccaag ctgtaccgat ccagcagtt tgtcaagaac ttccttggat    1920
tcacccttcc tttgatgcat gcccgaggcg tcttcaacta cgatgtcggt cttgtcccct   1980
acaggcgacc cgtcaacatt gtggttggtt cccccattga cttgccttat ctcccacacc   2040
ccaccgacga agaagtgtcc gaataccacg accgatacat cgccgagctg cagcgaatct   2100
acaacgagca caaggatgaa tatttcatcg attggaccga ggagggcaaa ggagccccag   2160
agttccgaat gattgagtaa gcggccgcaa gtatgaacta aaatgcatgt aggtgtaaga   2220
gctcatggag agcatggaat attgtatccg accatgtaac agtataataa ctgagctcca   2280
tctcacttct tctatgaata acaaaggat gttatgatat attaacactc tatctatgca    2340
ccttattgtt ctatgataaa tttcctctta ttattataaa tcatctgaat cgtgacggct   2400
tatggaatgc ttcaaatagt acaaaacaa atgtgtacta aagactttc taaacaattc     2460 taaccttagc attgtgaacg agacataagt gttaagaaga cataacaatt ataatggaag   2520
aagtttgtct ccatttatat attatatatt acccacttat gtattatatt aggatgttaa   2580
ggagacataa caattataaa gagagaagtt tgtatccatt tatatattat atactaccca   2640
tttatatatt atacttatcc acttatttaa tgtctttata aggtttgatc catgatattt   2700
ctaatatttt agttgatatg tatatgaaag ggtactattt gaactctctt actctgtata   2760
aaggttggat catccttaaa gtgggtctat ttaatttat tgcttcttac agataaaaaa    2820
aaaattatga gttggtttga taaaatattg aaggatttaa aataataata ataacatat    2880 aatatatgta tataaattta ttataatata acatttatct ataaaaagt aaatattgtc    2940 ataaatctat acaatcgttt agccttgctg gacgaatctc aattatttaa acgagagtaa   3000
acatatttga cttttggtt atttaacaaa ttattattta acactatatg aaattttttt    3060
ttttatcagc aaagaataaa attaaattaa gaaggacaat ggtgtcccaa tccttataca   3120
accaacttcc acaagaaagt caagtcagag acaacaaaaa aacaagcaaa ggaaatttt    3180 taatttgagt tgtcttgttt gctgcataat ttatgcagta aaacactaca cataaccctt   3240
ttagcagtag agcaatggtt gaccgtgtgc ttagcttctt ttattttatt tttttatcag   3300
caaagaataa ataaaataaa atgagacact tcagggatgt ttcaacaagc ttggcgcgcc   3360
gttctatagt gtcacctaaa tcgtatgtgt atgatacata aggttatgta ttaattgtag   3420
ccgcgttcta acgacaatat gtccatatgg tgcactctca gtacaatctg ctctgatgcc   3480
gcatagttaa gccagccccg cacccgcca acccgctg acgcgccctg acgggcttgt      3540
ctgctcccgg catccgctta cagacaagct gtgaccgtct ccgggagctg catgtgtcag   3600
aggttttcac cgtcatcacc gaaacgcgcg agacgaaagg gcctcgtgat acgcctattt   3660
ttataggtta atgtcatgac caaaatccct taacgtgagt tttcgttcca ctgagcgtca   3720
gaccccgtag aaaagatcaa aggatcttct tgagatcctt ttttctgcg cgtaatctgc    3780 tgcttgcaaa caaaaaaacc accgctacca gcggtggttt gtttgccgga tcaagagcta   3840
ccaactcttt ttccgaaggt aactggcttc agcagagcgc agataccaaa tactgtcctt   3900
ctagtgtagc cgtagttagg ccaccacttc aagaactctg tagcaccgcc tacatacctc   3960
gctctgctaa tcctgttacc agtggctgct gccagtggcg ataagtcgtg tcttaccggg   4020
```

```
ttggactcaa gacgatagtt accggataag gcgcagcggt cgggctgaac ggggggttcg    4080
tgcacacagc ccagcttgga gcgaacgacc tacaccgaac tgagatacct acagcgtgag    4140
cattgagaaa gcgccacgct tcccgaaggg agaaaggcgg acaggtatcc ggtaagcggc    4200
agggtcggaa caggagagcg cacgaggag cttccagggg gaaacgcctg gtatctttat     4260
agtcctgtcg ggtttcgcca cctctgactt gagcgtcgat ttttgtgatg ctcgtcaggg    4320
gggcggagcc tatggaaaaa cgccagcaac gcggccttt tacggttcct ggccttttgc     4380
tggccttttg ctcacatgtt ctttcctgcg ttatccctg attctgtgga taaccgtatt     4440
accgcctttg agtgagctga taccgctcgc cgcagccgaa cgaccgagcg cagcgagtca    4500
gtgagcgagg aagcggaaga gcgcccaata cgcaaaccgc ctctccccgc gcgttggccg    4560
attcattaat gcaggttgat cgattcgaca tcgatctagt aacatagatg acaccgcgcg    4620
cgataattta tcctagtttg cgcgctatat tttgttttct atcgcgtatt aaatgtataa    4680
ttgcgggact ctaatcataa aaacccatct cataaataac gtcatgcatt acatgttaat    4740
tattacatgc ttaacgtaat tcaacagaaa ttatatgata atcatcgcaa gaccggcaac    4800
aggattcaat cttaagaaac tttattgcca aatgtttgaa cgatctgctt cgacgcactc    4860
cttctttagg tacctcacta ttcctttgcc ctcggacgag tgctggggcg tcggtttcca    4920
ctatcggcga gtacttctac acagccatcg gtccagacgg ccgcgcttct gcgggcgatt    4980
tgtgtacgcc cgacagtccc ggctccggat cggacgattg cgtcgcatcg accctgcgcc    5040
caagctgcat catcgaaatt gccgtcaacc aagctctgat agagttggtc aagaccaatg    5100
cggagcatat acgcccggag ccgcggcgat cctgcaagct ccggatgcct ccgctcgaag    5160
tagcgcgtct gctgctccat acaagccaac cacggcctcc agaagaagat gttggcgacc    5220
tcgtattggg aatccccgaa catcgcctcg ctccagtcaa tgaccgctgt tatgcggcca    5280
ttgtccgtca ggacattgtt ggagccgaaa tccgcgtgca cgaggtgccg gacttcgggg    5340
cagtcctcgg cccaaagcat cagctcatcg agagcctgcg cgacgacgc actgacggtg     5400
tcgtccatca cagtttgcca gtgatacaca tggggatcag caatcgcgca tatgaaatca    5460
cgccatgtag tgtattgacc gattccttgc ggtccgaatg ggccgaaccc gctcgtctgg    5520
ctaagatcgg ccgcagcgat cgcatccatg gcctccgcga ccggctgcag aacagcgggc    5580
agttcggttt caggcaggtc ttgcaacgtg acaccctgtg cacggcggga gatgcaatag    5640
gtcaggctct cgctgaattc cccaatgtca agcacttccg gaatcgggag cgcggccgat    5700
gcaaagtgcc gataaacata acgatctttg tagaaaccat cggcgcagct atttacccgc    5760
aggacatatc cacgccctcc tacatcgaag ctgaaagcac gagattcttc gccctccgag    5820
agctgcatca ggtcggagac gctgtcgaac ttttcgatca gaaacttctc gacagacgtc    5880
gcggtgagtt caggcttttt catggtttaa taagaagaga aaagagttct tttgttatgg    5940
ctgaagtaat agagaaatga gctcgagcgt gtcctctcca aatgaaatga acttccttat    6000
atagaggaag ggtcttgcga aggatagtgg gattgtgcgt catcccttac gtcagtggag    6060
atgtcacatc aatccacttg ctttgaagac gtggttggaa cgtcttcttt ttccacgatg    6120
ctcctcgtgg gtgggggtcc atcttttggga ccactgtcgg cagaggcatc ttgaatgata   6180
gcctttcctt tatcgcaatg atggcatttg taggagccac cttcctttc tactgtcctt     6240
tcgatgaagt gacagatagc tgggcaatgg aatccgagga ggtttcccga aattatcctt    6300
tgttgaaaag tctcaatagc cctttggtct tctgagactg tatctttgac attttttggag   6360
tagaccagag tgtcgtgctc caccatgttg acgaagattt tcttcttgtc attgagtcgt    6420
```

```
aaaagactct gtatgaactg ttcgccagtc ttcacggcga gttctgttag atcctcgatt   6480
tgaatcttag actccatgca tggccttaga ttcagtagga actaccttt tagagactcc   6540 aatctctatt acttgccttg gtttatgaag caagccttga atcgtccata ctggaatagt   6600
acttctgatc ttgagaaata tgtctttctc tgtgttcttg atgcaattag tcctgaatct   6660
tttgactgca tctttaacct tcttgggaag gtatttgatc tcctggagat tgttactcgg   6720
gtagatcgtc ttgatgagac ctgctgcgta ggcctctcta accatctgtg ggtcagcatt   6780
ctttctgaaa ttgaagaggc taaccttctc attatcagtg gtgaacatag tgtcgtcacc   6840
ttcaccttcg aacttccttc ctagatcgta aagatagagg aaatcgtcca ttgtaatctc   6900
cggggcaaag gagatctctt tggggctgg atcactgctg ggccttttgg ttcctagcgt   6960
gagccagtgg gcttttgct ttggtgggct tgttagggcc ttagcaaagc tcttgggctt   7020
gagttgagct tctccttggg ggatgaagtt caacctgtct gtttgctgac ttgttgtgta   7080
cgcgtcagct gctgctcttg cctctgtaat agtggcaaat ttcttgtgtg caactccggg   7140
aacgccgttt gttgccgcct ttgtacaacc ccagtcatcg tatataccgg catgtggacc   7200
gttatacaca acgtagtagt tgatatgagg gtgttaata cccgattctg ctctgagagg   7260
agcaactgtg ctgttaagct cagatttttg tgggattgga attggatcga tctcgatccc   7320
gcgaaattaa tacgactcac tatagggaga ccacaacggt ttccctctag aaataatttt   7380
gtttaacttt aagaaggaga tatacccatg aaaagcctg aactcaccgc gacgtctgtc   7440
gagaagtttc tgatcgaaaa gttcgacagc gtctccgacc tgatgcagct ctcggagggc   7500
gaagaatctc gtgctttcag cttcgatgta ggagggcgtg gatatgtcct gcgggtaaat   7560
agctgcgccg atggtttcta caaagatcgt tatgtttatc ggcactttgc atcggccgcg   7620
ctcccgattc cggaagtgct tgacattggg gaattcagcg agagcctgac ctattgcatc   7680
tcccgccgtg cacagggtgt cacgttgcaa gacctgcctg aaaccgaact gcccgctgtt   7740
ctgcagccgg tcgcggaggc tatggatgcg atcgctgcgg ccgatcttag ccagacgagc   7800
gggttcggcc cattcggacc gcaaggaatc ggtcaataca ctacatggcg tgatttcata   7860
tgcgcgattg ctgatcccca tgtgtatcac tggcaaactg tgatggacga caccgtcagt   7920
gcgtccgtcg cgcaggctct cgatgagctg atgctttggg ccgaggactg ccccgaagtc   7980
cggcacctcg tgcacgcgga tttcggctcc aacaatgtcc tgacgacaa tggccgcata   8040 acagcggtca ttgactggag cgaggcgatg ttcggggatt cccaatacga ggtcgccaac   8100
atcttcttct ggaggccgtg gttggcttgt atggagcagc agacgcgcta cttcgagcgg   8160
aggcatccgg agcttgcagg atcgccgcgg ctccggcgt atatgctccg cattggtctt   8220
gaccaactct atcagagctt ggttgacggc aatttcgatg atgcagcttg gcgcagggt   8280 cgatgcgacg caatcgtccg atccggagcc gggactgtcg ggcgtacaca atcgcccgc   8340 agaagcgcgg ccgtctggac cgatggctgt gtagaagtac tcgccgatag tggaaaccga   8400
cgccccagca ctcgtccgag ggcaaaggaa tagtgaggta cagcttggat cgatccggct   8460
gctaacaaag cccgaaagga agctgagttg gctgctgcca ccgctgagca ataactagca   8520
taaccccttg gggcctctaa acgggtcttg aggggttttt tgctgaaagg aggaactata   8580
tccggatgat cgggcgcgcc gtcgacggat ccgtacgaga tccggccggc cagatcctgc   8640
aggccaactg cgtttgggc tccagattaa acgacgccgt ttcgttcctt tcgcttcacg   8700
gcttaacgat gtcgtttctg tctgtgccca aaaaataaag gcatttgtta tttgcaccag   8760
```

| | | | |
|---|---|---|---|
| atatttacta | agtgcaccct agtttgacaa gtaggcgata | attacaaata gatgcggtgc | 8820 |
| aaataataaa | ttttgaagga aataattaca | aagaacaga actatatttt actttatttt | 8880 |
| aaaaaactaa | aatgaaagaa caaaaaaagt | aaaaaataca aaaaatgtgc tttaaccact | 8940 |
| ttcattattt | gttacagaaa gtatgattct | actcaaattg atctgttgta tctggtgctg | 9000 |
| ccttgtcaca | ctggcgattt caatcccta | aagatatggt gcaaactgcg aagtgatcaa | 9060 |
| tatctgctcg | gttaatttag attaattaat | aatattcaac gtgatgtacc aaaaaaagac | 9120 |
| aattttttgc | tccattgaca aattaaacct | catcaaggta atttccaaac ctataagcaa | 9180 |
| aaaaatttca | cattaattgg cccgcaatcc | tattagtctt attatactag agtaggaaaa | 9240 |
| aaaacaatta | cacaacttgt cttattattc | tctatgctaa tgaatatttt tccttttgt | 9300 |
| tagaaatcag | tgtttcctaa tttattgagt | attaattcca ctcaccgcat atatttaccg | 9360 |
| ttgaataaga | aaattttaca cataattctt | tttaagataa ataattttt tatactagat | 9420 |
| cttatatgat | tacgtgaagc caagtgggtt | atactaatga tatataatgt ttgatagtaa | 9480 |
| tcagtttata | aaccaaatgc atggaaatgt | tacgtggaag cacgtaaatt aacaagcatt | 9540 |
| gaagcaaatg | cagccaccgc accaaaacca | ccccacttca cttccacgta ccatattcca | 9600 |
| tgcaactaca | acaccctaaa acttcaataa | atgccccac cttcacttca cttcacccat | 9660 |
| caatagcaag | cggccgcacc atggcagcca | ctcccacaca cttctctgtc tcccatgatc | 9720 |
| cttttttcttc | cacgtctctc cttaatctcc | aaactcaagc gatctttggt cccaatcaca | 9780 |
| gtttaaagac | aacccagttg agaattccag | cttctttcag aagaaaagct acaaacttgc | 9840 |
| aagtgatggc | ttcaggaaag acacctggac | tgactcagga agctaatggg gttgcaattg | 9900 |
| atagacaaaa | caacactgat gtatttgacg | acatgaaaca gcggttcctg gccttcaaga | 9960 |
| agcttaagta | catggatgac tttgaacact | acaaaaatct ggcagatgct caagctccaa | 10020 |
| agtttctggt | gattgcttgt gcagactcta | gagtttgtcc ttctgctgtc ctgggattcc | 10080 |
| aaccgggtga | cgcattcact gttcgtaaca | ttgcaaattt agtacctcca tatgagtctg | 10140 |
| gacctactga | aaccaaagct gctctagagt | tctctgtgaa tactcttaat gtggaaaaca | 10200 |
| tcttagtcat | tggtcatagc cggtgtggag | gaattcaagc tttaatgaaa atggaagacg | 10260 |
| aaggagattc | cagaagtttc atacacaact | gggtagttgt gggaaagaag gcaaaggaaa | 10320 |
| gcacaaaagc | tgttgcttca aacctccatt | ttgatcatca gtgccaacat tgtgaaaagg | 10380 |
| catcgataaa | tcattcatta gaaaggctgc | ttgggtaccc gtggatagaa gagaaagtgc | 10440 |
| ggcaaggttc | actgtctctc catggtggat | actataattt tgttgattgt acgttcgaga | 10500 |
| aatggacagt | ggattatgca gcaagcagag | gtaagaagaa ggaaggcagt ggaatcgctg | 10560 |
| ttaaagaccg | gtcagtttgg tcttgacgcg | gccgcgaagt taaaagcaat gttgtcactt | 10620 |
| gtcgtactaa | cacatgatgt gatagtttat | gctagctagc tataacataa gctgtctctg | 10680 |
| agtgtgttgt | atattaataa agatcatcac | tggtgaatgg tgatcgtgta cgtaccctac | 10740 |
| ttagtaggca | atggaagcac ttagagtgtg | ctttgtgcat ggccttgcct ctgttttgag | 10800 |
| acttttgtaa | tgttttcgag tttaaatctt | tgcctttgcg tacgtctaga gtcgacctgc | 10860 |
| a | | | 10861 |

<210> SEQ ID NO 9
<211> LENGTH: 780
<212> TYPE: DNA
<213> ORGANISM: Glycine max

<400> SEQUENCE: 9

```
atggctggag gatcatacga ggaagccatt gcagcgttga cgaagcttct cagcgagaaa    60
gccgacctgg gtggtgtcgc cgccgcaaag ataaaacagc tgacggcgga gctggatacc   120
gccaccgcaa acgggtcgac gccgtttaac ccggacgaga ggatccgaac cgggttcgcc   180
cacttcaaga acgagaaata ccagaagaac ccggaattat atggcgaact tgccaaaggc   240
cagagtccaa agtttatggt ttttgcttgc tcagactctc gagtttgccc atcccacatt   300
ctggatttca atccgggtga agcctttgtg gtccgaaata tcgccaacat ggttccacca   360
tatgacaaga ccaagtattc aggaaccggg gcggccattg aatatgcagt cttacattta   420
aaggtggaga atattgtggt cattgggcac agctgctgtg gaggtataaa gggcctaatg   480
tctatcccag atgatgggac cactgcaagt gaattcatag agcactgggt ccaaatttgc   540
actccagcaa agtccaaggt taaaacagaa gcaaacacat tagaattctc tgagcaatgt   600
accagctgcg agaaggaagc tgtgaatgta tcacttggga acctattgac atatcgattt   660
gtgagagatg cagttgtgaa gaaaactctt gccttgaaag gtgcacatta caatttcgtt   720
aagggcacat ttgagctgtg ggatctggac ttgaaaatct ctaactctgt atccgtttaa   780

<210> SEQ ID NO 10
<211> LENGTH: 30
<212> TYPE: DNA
<213> ORGANISM: artificial sequence
<220> FEATURE:
<223> OTHER INFORMATION: primer SA542

<400> SEQUENCE: 10
gcggccgcac catggctgga ggatcatacg                                       30

<210> SEQ ID NO 11
<211> LENGTH: 28
<212> TYPE: DNA
<213> ORGANISM: artificial sequence
<220> FEATURE:
<223> OTHER INFORMATION: primer SA539

<400> SEQUENCE: 11
gcggccgctt aaacggatac agagttag                                         28

<210> SEQ ID NO 12
<211> LENGTH: 259
<212> TYPE: PRT
<213> ORGANISM: Glycine max

<400> SEQUENCE: 12
```

Met Ala Gly Gly Ser Tyr Glu Glu Ala Ile Ala Ala Leu Thr Lys Leu
1               5                   10                  15

Leu Ser Glu Lys Ala Asp Leu Gly Gly Val Ala Ala Ala Lys Ile Lys
                20                  25                  30

Gln Leu Thr Ala Glu Leu Asp Thr Ala Thr Ala Asn Gly Ser Thr Pro
            35                  40                  45

Phe Asn Pro Asp Glu Arg Ile Arg Thr Gly Phe Ala His Phe Lys Asn
        50                  55                  60

Glu Lys Tyr Gln Lys Asn Pro Glu Leu Tyr Gly Glu Leu Ala Lys Gly
65                  70                  75                  80

Gln Ser Pro Lys Phe Met Val Phe Ala Cys Ser Asp Ser Arg Val Cys
                85                  90                  95

Pro Ser His Ile Leu Asp Phe Asn Pro Gly Glu Ala Phe Val Val Arg
            100                 105                 110

Asn Ile Ala Asn Met Val Pro Pro Tyr Asp Lys Thr Lys Tyr Ser Gly
         115                 120                 125

Thr Gly Ala Ala Ile Glu Tyr Ala Val Leu His Leu Lys Val Glu Asn
     130                 135                 140

Ile Val Val Ile Gly His Ser Cys Cys Gly Gly Ile Lys Gly Leu Met
145                 150                 155                 160

Ser Ile Pro Asp Asp Gly Thr Thr Ala Ser Glu Phe Ile Glu His Trp
             165                 170                 175

Val Gln Ile Cys Thr Pro Ala Lys Ser Lys Val Lys Thr Glu Ala Asn
             180                 185                 190

Thr Leu Glu Phe Ser Glu Gln Cys Thr Ser Cys Glu Lys Glu Ala Val
         195                 200                 205

Asn Val Ser Leu Gly Asn Leu Leu Thr Tyr Arg Phe Val Arg Asp Ala
210                 215                 220

Val Val Lys Lys Thr Leu Ala Leu Lys Gly Ala His Tyr Asn Phe Val
225                 230                 235                 240

Lys Gly Thr Phe Glu Leu Trp Asp Leu Asp Leu Lys Ile Ser Asn Ser
             245                 250                 255

Val Ser Val

<210> SEQ ID NO 13
<211> LENGTH: 10734
<212> TYPE: DNA
<213> ORGANISM: artificial sequence
<220> FEATURE:
<223> OTHER INFORMATION: pKR2495

<400> SEQUENCE: 13

| | | | | | |
|---|---|---|---|---|---|
| ggagatccaa | gcttttgatc | catgcccttc | atttgccgct | tattaattaa | tttggtaaca | 60 |
| gtccgtacta | atcagttact | tatccttccc | ccatcataat | taatcttggt | agtctcgaat | 120 |
| gccacaacac | tgactagtct | cttggatcat | aagaaaaagc | caaggaacaa | aagaagacaa | 180 |
| aacacaatga | gagtatcctt | tgcatagcaa | tgtctaagtt | cataaaattc | aaacaaaaac | 240 |
| gcaatcacac | acagtggaca | tcacttatcc | actagctgat | caggatcgcc | gcgtcaagaa | 300 |
| aaaaaaactg | gaccccaaaa | gccatgcaca | acaacacgta | ctcacaaagg | tgtcaatcga | 360 |
| gcagcccaaa | acattcacca | actcaaccca | tcatgagccc | tcacatttgt | tgtttctaac | 420 |
| ccaacctcaa | actcgtattc | tcttccgcca | cctcattttt | gtttatttca | acaccgtca | 480 |
| aactgcatgc | caccccgtgg | ccaaatgtcc | atgcatgtta | acaagaccta | tgactataaa | 540 |
| tagctgcaat | ctcggcccag | gttttcatca | tcaagaacca | gttcaatatc | ctagtacacc | 600 |
| gtattaaaga | atttaagata | tactgcggcc | gcaacatgac | tatcgactca | caatactaca | 660 |
| agtcgcgaga | caaaaacgac | acggcaccca | aaatcgcggg | aatccgatat | gccccgctat | 720 |
| cgacaccatt | actcaaccga | tgtgagacct | tctctctggt | ctggcacatt | ttcagcattc | 780 |
| ccactttcct | cacaattttc | atgctatgct | gcgcaattcc | actgctctgg | ccatttgtga | 840 |
| ttgcgtatgt | agtgtacgct | gttaaagacg | actccccgtc | caacggagga | gtggtcaagc | 900 |
| gatactcgcc | tatttcaaga | aacttcttca | tctggaagct | ctttggccgc | tacttcccca | 960 |
| taactctgca | caagacggtg | gatctggagc | ccacgcacac | atactaccct | ctggacgtcc | 1020 |
| aggagtatca | cctgattgct | gagagatact | ggccgcagaa | caagtacctc | cgagcaatca | 1080 |
| tcaccaccat | cgagtacttt | ctgccccgcct | tcatgaaacg | gtctctttct | atcaacgagc | 1140 |
| aggagcagcc | tgccgagcga | gatcctctcc | tgtctcccgt | ttctcccagc | tctccgggtt | 1200 |

```
ctcaacctga caagtggatt aaccacgaca gcagatatag ccgtggagaa tcatctggct    1260
ccaacggcca cgcctcgggc tccgaactta acggcaacgg caacaacggc accactaacc    1320
gacgaccttt gtcgtccgcc tctgctggct ccactgcatc tgattccacg cttcttaacg    1380
ggtccctcaa ctcctacgcc aaccagatca ttggcgaaaa cgaccacag ctgtcgccca     1440 caaaactcaa gcccactggc agaaaataca tcttcggcta ccaccccac ggcattatcg     1500 gcatgggagc ctttggtgga attgccaccg agggagctgg atggtccaag ctcttccgg    1560 gcatccctgt ttctcttatg actctcacca caaacttccg agtgcctctc tacagagagt    1620
acctcatgag tctgggagtc gcttctgtct ccaagaagtc ctgcaaggcc ctcctcaagc    1680
gaaaccagtc tatctgcatt gtcgttggtg gagcacagga aagtcttctg ccagacccg    1740 gtgtcatgga cctggtgcta ctcaagcgaa agggttttgt tcgacttggt atggaggtcg    1800
gaaatgtcgc ccttgttccc atcatggcct ttggtgagaa cgacctctat gaccaggtta    1860
gcaacgacaa gtcgtccaag ctgtaccgat tccagcagtt tgtcaagaac ttccttggat    1920
tcacccttcc tttgatgcat gcccgaggcg tcttcaacta cgatgtcggt cttgtcccct    1980
acaggcgacc cgtcaacatt gtggttggtt cccccattga cttgccttat ctcccacacc    2040
ccaccgacga agaagtgtcc gaataccacg accgatacat cgccgagctg cagcgaatct    2100
acaacgagca caaggatgaa tatttcatcg attggaccga ggagggcaaa ggagccccag    2160
agttccgaat gattgagtaa gcggccgcaa gtatgaacta aaatgcatgt aggtgtaaga    2220
gctcatggag agcatggaat attgtatccg accatgtaac agtataataa ctgagctcca    2280
tctcacttct tctatgaata aacaaaggat gttatgatat attaacactc tatctatgca    2340
ccttattgtt ctatgataaa tttcctctta ttattataaa tcatctgaat cgtgacggct    2400
tatggaatgc ttcaaatagt acaaaaacaa atgtgtacta aagactttc taaacaattc    2460 taaccttagc attgtgaacg agacataagt gttaagaaga cataacaatt ataatggaag    2520
aagtttgtct ccatttatat attatatatt acccacttat gtattatatt aggatgttaa    2580
ggagacataa caattataaa gagagaagtt tgtatccatt tatatattat atactaccca    2640
tttatatatt atacttatcc acttatttaa tgtctttata aggtttgatc catgatattt    2700
ctaatatttt agttgatatg tatatgaaag ggtactattt gaactctctt actctgtata    2760
aaggttggat catccttaaa gtgggtctat ttaatttat tgcttcttac agataaaaaa    2820
aaaattatga gttggtttga taaaatattg aaggatttaa ataataata ataacatat     2880 aatatatgta tataaattta ttataatata acatttatct ataaaaaagt aaatattgtc    2940
ataaatctat acaatcgttt agccttgctg gacgaatctc aattatttaa acgagagtaa    3000
acatatttga cttttttggtt atttaacaaa ttattattta acactatatg aaattttttt    3060
ttttatcagc aaagaataaa attaaattaa gaaggacaat ggtgtcccaa tccttataca    3120
accaacttcc acaagaaagt caagtcagag acaacaaaaa aacaagcaaa ggaaattttt    3180
taatttgagt tgtcttgttt gctgcataat ttatgcagta aaacactaca cataacccctt    3240 ttagcagtag agcaatggtt gaccgtgtgc ttagcttctt ttattttatt tttttatcag    3300
caaagaataa ataaaataaa atgagacact tcagggatgt ttcaacaagc ttggcgcgcc    3360
gttctatagt gtcacctaaa tcgtatgtgt atgatacata aggttatgta ttaattgtag    3420
ccgcgttcta acgacaatat gtccatatgg tgcactctca gtacaatctg ctctgatgcc    3480
gcatagttaa gccagccccg acacccgcca acacccgctg acgcgccctg acgggcttgt    3540
```

```
ctgctcccgg catccgctta cagacaagct gtgaccgtct ccgggagctg catgtgtcag    3600
aggttttcac cgtcatcacc gaaacgcgcg agacgaaagg cctcgtgat acgcctattt    3660
ttataggtta atgtcatgac caaaatccct taacgtgagt tttcgttcca ctgagcgtca    3720
gaccccgtag aaaagatcaa aggatcttct tgagatcctt ttttctgcg cgtaatctgc    3780
tgcttgcaaa caaaaaaacc accgctacca gcggtggttt gtttgccgga tcaagagcta    3840
ccaactcttt ttccgaaggt aactggcttc agcagagcgc agataccaaa tactgtcctt    3900
ctagtgtagc cgtagttagg ccaccacttc aagaactctg tagcaccgcc tacatacctc    3960
gctctgctaa tcctgttacc agtggctgct gccagtggcg ataagtcgtg tcttaccggg    4020
ttggactcaa gacgatagtt accggataag gcgcagcggt cgggctgaac ggggggttcg    4080
tgcacacagc ccagcttgga gcgaacgacc tacaccgaac tgagatacct acagcgtgag    4140
cattgagaaa gcgccacgct tcccgaaggg agaaaggcgg acaggtatcc ggtaagcggc    4200
agggtcggaa caggagagcg cacgagggag cttccagggg gaaacgcctg gtatctttat    4260
agtcctgtcg ggtttcgcca cctctgactt gagcgtcgat ttttgtgatg ctcgtcaggg    4320
gggcggagcc tatggaaaaa cgccagcaac gcggccttt tacggttcct ggccttttgc    4380
tggcctttg ctcacatgtt ctttcctgcg ttatcccctg attctgtgga taaccgtatt    4440
accgcctttg agtgagctga taccgctcgc cgcagccgaa cgaccgagcg cagcgagtca    4500
gtgagcgagg aagcggaaga gcgcccaata cgcaaaccgc ctctccccgc gcgttggccg    4560
attcattaat gcaggttgat cgattcgaca tcgatctagt aacatagatg acaccgcgcg    4620
cgataattta tcctagtttg cgcgctatat tttgttttct atcgcgtatt aaatgtataa    4680
ttgcgggact ctaatcataa aaacccatct cataaataac gtcatgcatt acatgttaat    4740
tattacatgc ttaacgtaat tcaacagaaa ttatatgata atcatcgcaa gaccggcaac    4800
aggattcaat cttaagaaac tttattgcca aatgtttgaa cgatctgctt cgacgcactc    4860
cttctttagg tacctcacta ttccctttgcc ctcggacgag tgctggggcg tcggtttcca    4920
ctatcggcga gtacttctac acagccatcg gtccagacgg ccgcgcttct gcgggcgatt    4980
tgtgtacgcc cgacagtccc ggctccggat cggacgattg cgtcgcatcg accctgcgcc    5040
caagctgcat catcgaaatt gccgtcaacc aagctctgat agagttggtc aagaccaatg    5100
cggagcatat acgcccggag ccgcggcgat cctgcaagct ccggatgcct ccgctcgaag    5160
tagcgcgtct gctgctccat acaagccaac cacggcctcc agaagaagat gttggcgacc    5220
tcgtattggg aatccccgaa catcgcctcg ctccagtcaa tgaccgctgt tatgcggcca    5280
ttgtccgtca ggacattgtt ggagccgaaa tccgcgtgca cgaggtgccg gacttcgggg    5340
cagtcctcgg cccaaagcat cagctcatcg agagcctgcg cgacggacgc actgacggtg    5400
tcgtccatca cagtttgcca gtgatacaca tggggatcag caatcgcgca tatgaaatca    5460
cgccatgtag tgtattgacc gattccttgc ggtccgaatg ggccgaaccc gctcgtctgg    5520
ctaagatcgg ccgcagcgat cgcatccatg gcctccgcga ccggctgcag aacagcgggc    5580
agttcggttt caggcaggtc ttgcaacgtg acaccctgtg cacggcggga gatgcaatag    5640
gtcaggctct cgctgaattc cccaatgtca agcacttccg gaatcgggag gcggccgat    5700
gcaaagtgcc gataaacata cgatctttg tagaaaccat cggcgcagct atttacccgc    5760
aggacatatc cacgccctcc tacatcgaag ctgaaagcac gagattcttc gccctccgag    5820
agctgcatca ggtcggagac gctgtcgaac ttttcgatca gaaacttctc gacagacgtc    5880
gcggtgagtt caggcttttt catggtttaa taagaagaga aaagagttct tttgttatgg    5940
```

```
ctgaagtaat agagaaatga gctcgagcgt gtcctctcca aatgaaatga acttccttat    6000
atagaggaag ggtcttgcga aggatagtgg gattgtgcgt catcccttac gtcagtggag    6060
atgtcacatc aatccacttg ctttgaagac gtggttggaa cgtcttcttt ttccacgatg    6120
ctcctcgtgg gtggggtcc atctttggga ccactgtcgg cagaggcatc ttgaatgata    6180
gcctttcctt tatcgcaatg atggcatttg taggagccac cttccttttc tactgtcctt    6240
tcgatgaagt gacagatagc tgggcaatgg aatccgagga ggtttcccga aattatcctt    6300
tgttgaaaag tctcaatagc cctttggtct tctgagactg tatctttgac attttttggag   6360 tagaccagag tgtcgtgctc caccatgttg acgaagattt tcttcttgtc attgagtcgt    6420
aaaagactct gtatgaactg ttcgccagtc ttcacggcga gttctgttag atcctcgatt    6480
tgaatcttag actccatgca tggccttaga ttcagtagga actacctttt tagagactcc    6540
aatctctatt acttgccttg gtttatgaag caagccttga atcgtccata ctggaatagt    6600
acttctgatc ttgagaaata tgtctttctc tgtgttcttg atgcaattag tcctgaatct    6660
tttgactgca tctttaacct tcttgggaag gtatttgatc tcctggagat tgttactcgg    6720
gtagatcgtc ttgatgagac ctgctgcgta ggcctctcta accatctgtg ggtcagcatt    6780
ctttctgaaa ttgaagaggc taaccttctc attatcagtg gtgaacatag tgtcgtcacc    6840
ttcaccttcg aacttccttc ctagatcgta aagatagagg aaatcgtcca ttgtaatctc    6900
cggggcaaag gagatctctt tggggctgg atcactgctg ggccttttgg ttcctagcgt     6960
gagccagtgg gctttttgct ttggtgggct tgttagggcc ttagcaaagc tcttgggctt    7020
gagttgagct tctcctttgg ggatgaagtt caacctgtct gtttgctgac ttgttgtgta    7080
cgcgtcagct gctgctcttg cctctgtaat agtggcaaat ttcttgtgtg caactccggg    7140
aacgccgttt gttgccgcct ttgtacaacc ccagtcatcg tatataccgg catgtggacc    7200
gttatacaca acgtagtagt tgatatgagg gtgttgaata cccgattctg ctctgagagg    7260
agcaactgtg ctgttaagct cagatttttg tgggattgga attggatcga tctcgatccc    7320
gcgaaattaa tacgactcac tatagggaga ccacaacggt ttccctctag aaataatttt    7380
gtttaacttt aagaaggaga tatacccatg aaaagcctg aactcaccgc gacgtctgtc    7440
gagaagtttc tgatcgaaaa gttcgacagc gtctccgacc tgatgcagct ctcggagggc    7500
gaagaatctc gtgctttcag cttcgatgta ggagggcgtg gatatgtcct gcgggtaaat    7560
agctgcgccg atggtttcta caaagatcgt tatgtttatc ggcactttgc atcggccgcg    7620
ctcccgattc cggaagtgct tgacattggg gaattcagcg agagcctgac ctattgcatc    7680
tcccgccgtg cacagggtgt cacgttgcaa gacctgcctg aaaccgaact gcccgctgtt    7740
ctgcagccgt cgcggaggc tatggatgcg atcgctgcgg ccgatcttag ccagacgagc    7800
gggttcggcc cattcggacc gcaaggaatc ggtcaataca ctacatggcg tgatttcata    7860
tgcgcgattg ctgatcccca tgtgtatcac tggcaaactg tgatggacga caccgtcagt    7920
gcgtccgtcg cgcaggctct cgatgagctg atgctttggg ccgaggactg ccccgaagtc    7980
cggcacctcg tgcacgcgga tttcggctcc aacaatgtcc tgacggacaa tggccgcata    8040
acagcggtca ttgactggag cgaggcgatg ttcgggatt cccaatacga ggtcgccaac    8100
atcttcttct ggaggccgtg gttggcttgt atggagcagc agacgcgcta cttcgagcgg    8160
aggcatccgg agcttgcagg atcgccgcgg ctccgggcgt atatgctccg cattggtctt    8220
gaccaactct atcagagctt ggttgacggc aatttcgatg atgcagcttg ggcgcagggt    8280
```

```
cgatgcgacg caatcgtccg atccggagcc gggactgtcg ggcgtacaca aatcgcccgc    8340
agaagcgcgg ccgtctggac cgatggctgt gtagaagtac tcgccgatag tggaaaccga    8400
cgccccagca ctcgtccgag ggcaaaggaa tagtgaggta cagcttggat cgatccggct    8460
gctaacaaag cccgaaagga agctgagttg gctgctgcca ccgctgagca ataactagca    8520
taaccccttg gggcctctaa acgggtcttg aggggttttt tgctgaaagg aggaactata    8580
tccggatgat cgggcgcgcc gtcgacggat ccgtacgaga tccggccggc cagatcctgc    8640
aggccaactg cgtttggggc tccagattaa acgacgccgt ttcgttcctt tcgcttcacg    8700
gcttaacgat gtcgtttctg tctgtgccca aaaataaag gcatttgtta tttgcaccag    8760
atatttacta agtgcaccct agtttgacaa gtaggcgata attacaaata gatgcggtgc    8820
aaataataaa ttttgaagga aataattaca aagaacaga acttatattt actttatttt    8880
aaaaaactaa aatgaaagaa caaaaaaagt aaaaaataca aaaaatgtgc tttaaccact    8940
ttcattattt gttacagaaa gtatgattct actcaaattg atctgttgta tctggtgctg    9000
ccttgtcaca ctggcgattt caatcccta aagatatggg gcaaactgcg aagtgatcaa    9060
tatctgctcg gttaatttag attaattaat aatattcaac gtgatgtacc aaaaaaagac    9120
aattttttgc tccattgaca aattaaacct catcaaggta atttccaaac ctataagcaa    9180
aaaaatttca cattaattgg cccgcaatcc tattagtctt attatactag agtaggaaaa    9240
aaaacaatta cacaacttgt cttattattc tctatgctaa tgaatatttt tcccttttgt    9300
tagaaatcag tgttctccta tttattgagt attaattcca ctcaccgcat atatttaccg    9360
ttgaataaga aaattttaca cataattctt tttaagataa ataattttt tatactagat    9420
cttatatgat tacgtgaagc caagtgggtt atactaatga tatataatgt ttgatagtaa    9480
tcagtttata aaccaaatgc atggaaatgt tacgtggaag cacgtaaatt aacaagcatt    9540
gaagcaaatg cagccaccgc accaaaacca ccccacttca cttccacgta ccatattcca    9600
tgcaactaca acaccctaaa acttcaataa atgcccccac cttcacttca cttcacccat    9660
caatagcaag cggccgcacc atggctggag gatcatacga ggaagccatt gcagcgttga    9720
cgaagcttct cagcgagaaa gccgacctgg gtggtgtcgc cgccgcaaag ataaaacagc    9780
tgacggcgga gctggatacc gccaccgcaa acgggtcgac gccgtttaac ccggacgaga    9840
ggatccgaac cgggttcgcc cacttcaaga acgagaaata ccagaagaac ccggaattat    9900
atggcgaact tgccaaaggc cagagtccaa agtttatggt ttttgcttgc tcagactctc    9960
gagtttgccc atcccacatt ctggatttca atccgggtga agccttgtg gtccgaaata   10020
tcgccaacat ggttccacca tatgacaaga ccaagtattc aggaaccggg gcggccattg   10080
aatatgcagt cttacattta aaggtggaga atattgtggt cattgggcac agctgctgtg   10140
gaggtataaa gggcctaatg tctatcccag atgatgggac cactgcaagt gaattcatag   10200
agcactgggt ccaaatttgc actccagcaa agtccaaggt taaaacagaa gcaaacacat   10260
tagaattctc tgagcaatgt accagctgcg agaaggaagc tgtgaatgta tcacttggga   10320
acctattgac atatcgattt gtgagagatg cagttgtgaa gaaaactctt gccttgaaag   10380
gtgcacatta caatttcgtt aaaggcacat ttgagctgtg ggatctggac ttgaaaaact   10440
ctaactctgt atccgtttaa gcggccgcga agttaaaagc aatgttgtca cttgtcgtac   10500
taacacatga tgtgatagtt tatgctagct agctataaca taagctgtct ctgagtgtgt   10560
tgtatattaa taaagatcat cactggtgaa tggtgatcgt gtacgtaccc tacttagtag   10620
gcaatggaag cacttagagt gtgctttgtg catggccttg cctctgtttt gagactttg   10680
```

```
taatgttttc gagtttaaat ctttgccttt gcgtacgtct agagtcgacc tgca          10734
```

<210> SEQ ID NO 14
<211> LENGTH: 960
<212> TYPE: DNA
<213> ORGANISM: Glycine max

<400> SEQUENCE: 14

```
atggtttggc caattaggtc cagaataagt tctcttctct gttctaaggc acctttagtt      60
ggttcataca tctatgactc atgtgggtgc ttacgctttt ctgctccaac cagctcctcc     120
ataacaaggc attggccaaa aattatggat tgggtacaaa tggaccgttg ccgtgcagca     180
gcatcgttac cttcgatcaa agagaaacaa ccagaaagtc atagtaatcg tgtcagactc     240
ggtcaagaaa tcaaaggtct tgatgaaggg aatatggctg aaattgatag ctatcaaaac     300
ttgtttggtt tgatgaaaca gaggtttctg agtttcaaga gccaaaaata tataaaagag     360
ttggagcatt tgaagctct tgctgaagct caatttccta gtttatggt gattgcttgt      420
gcagactcta gggtatgccc ctctaacata ttaggattcc aacctggaga agtctttatg     480
atacgtaaca ttgccaatct tgttcctgtg atgaagaatg gaccatcaga atgtaatgct     540
gctcttcagt ttgcagtaac tactcttcag gttgagaata tattagtcat tggtcatagt     600
agctgcgctg gaattgaagc tttgatgaat atgcaagaag atgcagaatc aagaaacttc     660
atacacaagt gggttgccaa tggaaaactt gccaaacaaa ggacaaaagc tgccacagct     720
catcttagct ttgatcagca atgcaaattc tgtgagaagg aatctattaa ccaatcatta     780
ttgaacttgc tcagctatcc ttggatacaa gatagagtga gaaaagagtt gctttctcta     840
catggaggat attataattt ctctaattgc tcttttgaga aatggaccct tgattttaaa     900
caatgcaatg ttgaagaagg aagcagttat gttgtcaaag aacaagaatt ctggtgctga     960
```

<210> SEQ ID NO 15
<211> LENGTH: 23
<212> TYPE: DNA
<213> ORGANISM: artificial sequence
<220> FEATURE:
<223> OTHER INFORMATION: primer oCA2-1

<400> SEQUENCE: 15

```
cagggcggcc gcaccatggt ttg                                              23
```

<210> SEQ ID NO 16
<211> LENGTH: 23
<212> TYPE: DNA
<213> ORGANISM: artificial sequence
<220> FEATURE:
<223> OTHER INFORMATION: primer oCA2-2

<400> SEQUENCE: 16

```
cagggcggcc gccaagcttc ctg                                              23
```

<210> SEQ ID NO 17
<211> LENGTH: 319
<212> TYPE: PRT
<213> ORGANISM: Glycine max

<400> SEQUENCE: 17

```
Met Val Trp Pro Ile Arg Ser Arg Ile Ser Ser Leu Leu Cys Ser Lys
1               5                   10                  15

Ala Pro Leu Val Gly Ser Tyr Ile Tyr Asp Ser Cys Gly Cys Leu Arg
```

```
                 20                  25                  30
Phe Ser Ala Pro Thr Ser Ser Ile Thr Arg His Trp Pro Lys Ile
             35                  40                  45
Met Asp Trp Val Gln Met Asp Arg Cys Arg Ala Ala Ala Ser Leu Pro
 50                  55                  60
Ser Ile Lys Glu Lys Gln Pro Glu Ser His Ser Asn Arg Val Arg Leu
 65                  70                  75                  80
Gly Gln Glu Ile Lys Gly Leu Asp Glu Gly Asn Met Ala Glu Ile Asp
                 85                  90                  95
Ser Tyr Gln Asn Leu Phe Gly Leu Met Lys Gln Arg Phe Leu Ser Phe
                100                 105                 110
Lys Ser Gln Lys Tyr Ile Lys Glu Leu Glu His Phe Glu Ala Leu Ala
            115                 120                 125
Glu Ala Gln Phe Pro Lys Phe Met Val Ile Ala Cys Ala Asp Ser Arg
            130                 135                 140
Val Cys Pro Ser Asn Ile Leu Gly Phe Gln Pro Gly Glu Val Phe Met
145                 150                 155                 160
Ile Arg Asn Ile Ala Asn Leu Val Pro Val Met Lys Asn Gly Pro Ser
                165                 170                 175
Glu Cys Asn Ala Ala Leu Gln Phe Ala Val Thr Thr Leu Gln Val Glu
            180                 185                 190
Asn Ile Leu Val Ile Gly His Ser Ser Cys Ala Gly Ile Glu Ala Leu
            195                 200                 205
Met Asn Met Gln Glu Asp Ala Glu Ser Arg Asn Phe Ile His Lys Trp
            210                 215                 220
Val Ala Asn Gly Lys Leu Ala Lys Gln Arg Thr Lys Ala Ala Thr Ala
225                 230                 235                 240
His Leu Ser Phe Asp Gln Gln Cys Lys Phe Cys Glu Lys Glu Ser Ile
                245                 250                 255
Asn Gln Ser Leu Leu Asn Leu Leu Ser Tyr Pro Trp Ile Gln Asp Arg
            260                 265                 270
Val Arg Lys Glu Leu Leu Ser Leu His Gly Gly Tyr Tyr Asn Phe Ser
            275                 280                 285
Asn Cys Ser Phe Glu Lys Trp Thr Leu Asp Phe Lys Gln Cys Asn Val
            290                 295                 300
Glu Glu Gly Ser Ser Tyr Val Val Lys Glu Gln Glu Phe Trp Cys
305                 310                 315

<210> SEQ ID NO 18
<211> LENGTH: 10937
<212> TYPE: DNA
<213> ORGANISM: artificial sequence
<220> FEATURE:
<223> OTHER INFORMATION: vector pKR2537

<400> SEQUENCE: 18
ggagatccaa gcttttgatc catgcccttc atttgccgct tattaattaa tttggtaaca    60
gtccgtacta atcagttact tatccttccc ccatcataat taatcttggt agtctcgaat   120
gccacaacac tgactagtct cttggatcat aagaaaaagc caaggaacaa agaagacaa   180 aacacaatga gagtatcctt tgcatagcaa tgtctaagtt cataaaattc aaacaaaaac   240
gcaatcacac acagtggaca tcacttatcc actagctgat caggatcgcc gcgtcaagaa   300
aaaaaaactg accccaaaaa gccatgcaca acaacacgta ctcacaaagg tgtcaatcga   360
gcagcccaaa acattcacca actcaaccca tcatgagccc tcacatttgt tgtttctaac   420
```

```
ccaacctcaa actcgtattc tcttccgcca cctcattttt gtttatttca acacccgtca    480
aactgcatgc caccccgtgg ccaaatgtcc atgcatgtta caagaccta tgactataaa    540 tagctgcaat ctcggcccag gttttcatca tcaagaacca gttcaatatc ctagtacacc   600
gtattaaaga atttaagata tactgcggcc gcaacatgac tatcgactca caatactaca   660
agtcgcgaga caaaaacgac acggcaccca aaatcgcggg aatccgatat gccccgctat   720
cgacaccatt actcaaccga tgtgagacct tctctctggt ctggcacatt ttcagcattc   780
ccactttcct cacaattttc atgctatgct gcgcaattcc actgtctgg ccatttgtga    840 ttgcgtatgt agtgtacgct gttaaagacg actccccgtc caacggagga gtggtcaagc   900
gatactcgcc tatttcaaga aacttcttca tctggaagct cttttggccgc tacttcccca   960 taactctgca caagacggtg gatctggagc ccacgcacac atactaccct ctggacgtcc   1020
aggagtatca cctgattgct gagagatact ggccgcagaa caagtacctc cgagcaatca   1080
tcaccaccat cgagtacttt ctgcccgcct tcatgaaacg gtctctttct atcaacgagc   1140
aggagcagcc tgccgagcga gatcctctcc tgtctcccgt ttctcccagc tctccgggtt   1200
ctcaacctga caagtggatt aaccacgaca gcagatatag ccgtggagaa tcatctggct   1260
ccaacggcca cgcctcgggc tccgaactta acggcaacgg caacaacggc accactaacc   1320
gacgaccttt gtcgtccgcc tctgctggct ccactgcatc tgattccacg cttcttaacg   1380
ggtccctcaa ctcctacgcc aaccagatca ttggcgaaaa cgacccacag ctgtcgccca   1440
caaaactcaa gcccactggc agaaaataca tcttcggcta ccaccccac ggcattatcg     1500 gcatgggagc ctttggtgga attgccaccg agggagctgg atggtccaag ctcttccgg    1560 gcatccctgt ttctcttatg actctcacca caacttccg agtgcctctc tacagagagt     1620
acctcatgag tctgggagtc gcttctgtct ccaagaagtc ctgcaaggcc ctcctcaagc   1680
gaaaccagtc tatctgcatt gtcgttggtg gagcacagga aagtcttctg gccagacccg   1740
gtgtcatgga cctggtgcta ctcaagcgaa agggttttgt tcgacttggt atggaggtcg   1800
gaaatgtcgc ccttgttccc atcatggcct ttggtgagaa cgacctctat gaccaggtta   1860
gcaacgacaa gtcgtccaag ctgtaccgat tccagcagtt tgtcaagaac ttccttggat   1920
tcacccttcc tttgatgcat gcccgaggcg tcttcaacta cgatgtcggt cttgtcccct   1980
acaggcgacc cgtcaacatt gtggttggtt cccccattga cttgccttat ctcccacacc   2040
ccaccgacga agaagtgtcc gaataccacg accgatacat cgccgagctg cagcgaatct    2100
acaacgagca caaggatgaa tatttcatcg attggaccga ggagggcaaa ggagccccag   2160
agttccgaat gattgagtaa gcggccgcaa gtatgaacta aaatgcatgt aggtgtaaga   2220
gctcatggag agcatggaat attgtatccg accatgtaac agtataataa ctgagctcca   2280
tctcacttct tctatgaata aacaaaggat gttatgatat attaacactc tatctatgca   2340
ccttattgtt ctatgataaa tttcctctta ttattataaa tcatctgaat cgtgacggct   2400
tatggaatgc ttcaaatagt acaaaaacaa atgtgtacta aagactttc taaacaattc    2460 taaccttagc attgtgaacg agacataagt gttaagaaga cataacaatt ataatggaag   2520
aagtttgtct ccatttatat attatatatt acccacttat gtattatatt aggatgttaa   2580
ggagacataa caattataaa gagagaagtt tgtatccatt tatatattat atactaccca   2640
tttatatatt atacttatcc acttatttaa tgtctttata aggtttgatc catgatattt   2700
ctaatatttt agttgatatg tatatgaaag ggtactattt gaactctctt actctgtata   2760
```

```
aaggttggat catccttaaa gtgggtctat ttaattttat tgcttcttac agataaaaaa    2820
aaaattatga gttggtttga taaaatattg aaggatttaa aataataata aataacatat    2880
aatatatgta tataaattta ttataatata acatttatct ataaaaaagt aaatattgtc    2940
ataaatctat acaatcgttt agccttgctg gacgaatctc aattatttaa acgagagtaa    3000
acatatttga cttttttggtt atttaacaaa ttattattta acactatatg aaattttttt    3060
ttttatcagc aaagaataaa attaaattaa gaaggacaat ggtgtcccaa tccttataca    3120
accaacttcc acaagaaagt caagtcagag acaacaaaaa aacaagcaaa ggaaattttt    3180
taatttgagt tgtcttgttt gctgcataat ttatgcagta aaacactaca cataacccctt   3240 ttagcagtag agcaatggtt gaccgtgtgc ttagcttctt ttatttattt ttttatcag     3300 caaagaataa ataaaataaa atgagacact tcagggatgt ttcaacaagc ttggcgcgcc    3360
gttctatagt gtcacctaaa tcgtatgtgt atgatacata aggttatgta ttaattgtag    3420
ccgcgttcta acgacaatat gtccatatgg tgcactctca gtacaatctg ctctgatgcc    3480
gcatagttaa gccagccccg acacccgcca acacccgctg acgcgccctg acgggcttgt    3540
ctgctcccgg catccgctta cagacaagct gtgaccgtct ccgggagctg catgtgtcag    3600
aggttttcac cgtcatcacc gaaacgcgcg agacgaaagg gcctcgtgat acgcctattt    3660
ttataggtta atgtcatgac caaaatccct taacgtgagt tttcgttcca ctgagcgtca    3720 gacccccgtag aaaagatcaa aggatcttct tgagatcctt ttttctgcg cgtaatctgc    3780 tgcttgcaaa caaaaaaacc accgctacca gcggtggttt gtttgccgga tcaagagcta    3840
ccaactcttt ttccgaaggt aactggcttc agcagagcgc agataccaaa tactgtcctt    3900
ctagtgtagc cgtagttagg ccaccacttc aagaactctg tagcaccgcc tacataccctc    3960 gctctgctaa tcctgttacc agtggctgct gccagtggcg ataagtcgtg tcttaccggg    4020
ttggactcaa gacgatagtt accggataag gcgcagcggt cgggctgaac ggggggttcg    4080
tgcacacagc ccagcttgga gcgaacgacc tacaccgaac tgagatacct acagcgtgag    4140
cattgagaaa gcgccacgct tcccgaaggg agaaaggcgg acaggtatcc ggtaagcggc    4200
agggtcggaa caggagagcg cacgagggag cttccagggg gaaacgcctg gtatctttat    4260
agtcctgtcg ggtttcgcca cctctgactt gagcgtcgat ttttgtgatg ctcgtcaggg    4320
gggcggagcc tatggaaaaa cgccagcaac gcggcctttt tacggttcct ggccttttgc    4380
tggccttttg ctcacatgtt ctttcctgcg ttatcccctg attctgtgga taaccgtatt    4440
accgcctttg agtgagctga taccgctcgc cgcagccgaa cgaccgagcg cagcgagtca    4500
gtgagcgagg aagcggaaga gcgcccaata cgcaaaccgc ctctccccgc gcgttggccg    4560
attcattaat gcaggttgat cgattcgaca tcgatctagt aacatagatg acaccgcgcg    4620
cgataattta tcctagtttg cgcgctatat tttgttttct atcgcgtatt aaatgtataa    4680
ttgcgggact ctaatcataa aaacccatct cataaataac gtcatgcatt acatgttaat    4740
tattacatgc ttaacgtaat tcaacagaaa ttatatgata atcatcgcaa gaccggcaac    4800
aggattcaat cttaagaaac tttattgcca aatgtttgaa cgatctgctt cgacgcactc    4860
cttctttagg tacctcacta ttcctttgcc ctcggacgag tgctggggcg tcggtttcca    4920
ctatcggcga gtacttctac acagccatcg gtccagacgg ccgcgcttct gcgggcgatt    4980
tgtgtacgcc cgacagtccc ggctccggat cggacgattg cgtcgcatcg accctgcgcc    5040
caagctgcat catcgaaatt gccgtcaacc aagctctgat agagttggtc aagaccaatg    5100
cggagcatat acgcccggag ccgcggcgat cctgcaagct ccggatgcct ccgctcgaag    5160
```

```
tagcgcgtct gctgctccat acaagccaac cacggcctcc agaagaagat gttggcgacc    5220
tcgtattggg aatccccgaa catcgcctcg ctccagtcaa tgaccgctgt tatgcggcca    5280
ttgtccgtca ggacattgtt ggagccgaaa tccgcgtgca cgaggtgccg gacttcgggg    5340
cagtcctcgg cccaaagcat cagctcatcg agagcctgcg cgacggacgc actgacggtg    5400
tcgtccatca cagtttgcca gtgatacaca tggggatcag caatcgcgca tatgaaatca    5460
cgccatgtag tgtattgacc gattccttgc ggtccgaatg ggccgaaccc gctcgtctgg    5520
ctaagatcgg ccgcagcgat cgcatccatg gcctccgcga ccggctgcag aacagcgggc    5580
agttcggttt caggcaggtc ttgcaacgtg acaccctgtg cacggcggga gatgcaatag    5640
gtcaggctct cgctgaattc cccaatgtca agcacttccg gaatcgggag cgcggccgat    5700
gcaaagtgcc gataaacata acgatctttg tagaaaccat cggcgcagct atttacccgc    5760
aggacatatc cacgccctcc tacatcgaag ctgaaagcac gagattcttc gccctccgag    5820
agctgcatca ggtcggagac gctgtcgaac ttttcgatca gaaacttctc gacagacgtc    5880
gcggtgagtt caggcttttt catggtttaa taagaagaga aaagagttct tttgttatgg    5940
ctgaagtaat agagaaatga gctcgagcgt gtcctctcca aatgaaatga acttccttat    6000
atagaggaag ggtcttgcga aggatagtgg gattgtgcgt catcccttac gtcagtggag    6060
atgtcacatc aatccacttg cttgaagac gtggttggaa cgtcttcttt ttccacgatg    6120
ctcctcgtgg gtgggggtcc atctttggga ccactgtcgg cagaggcatc ttgaatgata    6180
gcctttcctt tatcgcaatg atggcatttg taggagccac cttccttttc tactgtcctt    6240
tcgatgaagt gacagatagc tgggcaatgg aatccgagga ggtttcccga aattatcctt    6300
tgttgaaaag tctcaatagc cctttggtct tctgagactg tatctttgac atttttggag    6360
tagaccagag tgtcgtgctc caccatgttg acgaagattt tcttcttgtc attgagtcgt    6420
aaaagactct gtatgaactg ttcgccagtc ttcacggcga gttctgttag atcctcgatt    6480
tgaatcttag actccatgca tggccttaga ttcagtagga actacctttt tagagactcc    6540
aatctctatt acttgccttg gtttatgaag caagccttga atcgtccata ctggaatagt    6600
acttctgatc ttgagaaata tgtctttctc tgtgttcttg atgcaattag tcctgaatct    6660
tttgactgca tctttaacct tcttgggaag gtatttgatc tcctggagat tgttactcgg    6720
gtagatcgtc ttgatgagac ctgctgcgta ggcctctcta accatctgtg ggtcagcatt    6780
ctttctgaaa ttgaagaggc taaccttctc attatcagtg gtgaacatag tgtcgtcacc    6840
ttcaccttcg aacttccttc ctagatcgta aagatagagg aaatcgtcca ttgtaatctc    6900
cggggcaaag gagatctctt ttggggctgg atcactgctg ggccttttgg ttcctagcgt    6960
gagccagtgg gcttttgct ttggtgggct tgttagggcc ttagcaaagc tcttgggctt    7020
gagttgagct tctcctttgg ggatgaagtt caacctgtct gtttgctgac ttgttgtgta    7080
cgcgtcagct gctgctcttg cctctgtaat agtggcaaat ttcttgtgtg caactccggg    7140
aacgccgttt gttgccgcct ttgtacaacc ccagtcatcg tatataccgg catgtggacc    7200
gttatacaca acgtagtagt tgatatgagg gtgttgaata cccgattctg ctctgagagg    7260
agcaactgtg ctgttaagct cagatttttg tgggattgga attggatcga tctcgatccc    7320
gcgaaattaa tacgactcac tatagggaga ccacaacggt ttccctctag aaataatttt    7380
gtttaacttt aagaaggaga tatacccatg gaaaagcctg aactcaccgc gacgtctgtc    7440
gagaagtttc tgatcgaaaa gttcgacagc gtctccgacc tgatgcagct ctcggagggc    7500
```

```
gaagaatctc gtgctttcag cttcgatgta ggagggcgtg gatatgtcct gcgggtaaat    7560
agctgcgccg atggtttcta caaagatcgt tatgtttatc ggcactttgc atcggccgcg    7620
ctcccgattc cggaagtgct tgacattggg gaattcagcg agagcctgac ctattgcatc    7680
tcccgccgtg cacagggtgt cacgttgcaa gacctgcctg aaaccgaact gcccgctgtt    7740
ctgcagccgg tcgcggaggc tatggatgcg atcgctgcgg ccgatcttag ccagacgagc    7800
gggttcggcc cattcggacc gcaaggaatc ggtcaataca ctacatggcg tgatttcata    7860
tgcgcgattg ctgatcccca tgtgtatcac tggcaaactg tgatggacga caccgtcagt    7920
gcgtccgtcg cgcaggctct cgatgagctg atgctttggg ccgaggactg ccccgaagtc    7980
cggcacctcg tgcacgcgga tttcggctcc aacaatgtcc tgacggacaa tggccgcata    8040
acagcggtca ttgactggag cgaggcgatg ttcggggatt cccaatacga ggtcgccaac    8100
atcttcttct ggaggccgtg gttggcttgt atggagcagc agacgcgcta cttcgagcgg    8160
aggcatccgg agcttgcagg atcgccgcgg ctccgggcgt atatgctccg cattggtctt    8220
gaccaactct atcagagctt ggttgacggc aatttcgatg atgcagcttg ggcgcagggt    8280
cgatgcgacg caatcgtccg atccggagcc gggactgtcg gcgtacaca aatcgcccgc    8340 agaagcgcgc ccgtctggac cgatggctgt gtagaagtac tcgccgatag tggaaaccga    8400
cgccccagca ctcgtccgag ggcaaaggaa tagtgaggta cagcttggat cgatccggct    8460
gctaacaaag cccgaaagga agctgagttg gctgctgcca ccgctgagca ataactagca    8520 taacccttg gggcctctaa acgggtcttg aggggttttt tgctgaaagg aggaactata    8580
tccggatgat cgggcgcgcc gtcgacggat ccgtacgaga tccggccggc cagatcctgc    8640
aggccaactg cgtttgggc tccagattaa acgacgccgt ttcgttcctt tcgcttcacg    8700
gcttaacgat gtcgtttctg tctgtgccca aaaaataaag gcatttgtta tttgcaccag    8760
atatttacta agtgcaccct agtttgacaa gtaggcgata attacaaata gatgcggtgc    8820
aaataataaa ttttgaagga ataattaca aagaacaga acttatattt actttatttt    8880
aaaaaactaa aatgaaagaa caaaaaaagt aaaaaaataca aaaaatgtgc tttaaccact    8940
ttcattattt gttacagaaa gtatgattct actcaaattg atctgttgta tctggtgctg    9000
ccttgtcaca ctggcgattt caatccccta agatatggt gcaaactgcg aagtgatcaa    9060
tatctgctcg gttaatttag attaattaat aatattcaac gtgatgtacc aaaaaaagac    9120
aattttttgc tccattgaca aattaaacct catcaaggta atttccaaac ctataagcaa    9180
aaaaatttca cattaattgg cccgcaatcc tattagtctt attatactag agtaggaaaa    9240
aaaacaatta cacaacttgt cttattattc tctatgctaa tgaatatttt tcccttttgt    9300
tagaaatcag tgtttcctaa tttattgagt attaattcca ctcaccgcat atatttaccg    9360
ttgaataaga aaattttaca cataattctt tttaagataa ataattttt tatactagat    9420 cttatatgat tacgtgaagc caagtgggtt atactaatga tatataatgt ttgatagtaa    9480
tcagtttata aaccaaatgc atggaaatgt tacgtggaag cacgtaaatt aacaagcatt    9540
gaagcaaatg cagccaccgc accaaaacca ccccacttca cttccacgta ccatattcca    9600
tgcaactaca acaccctaaa acttcaataa atgcccccac cttcacttca cttcacccat    9660
caatagcaag cggccgcacc atggtttggc caattaggtc cagaataagt tctcttctct    9720
gttctaaggc acctttagtt ggttcataca tctatgactc atgtgggtgc ttacgctttt    9780
ctgctccaac cagctcctcc ataacaaggc attggcaaa aattatggat tgggtacaaa    9840
tggaccgttg ccgtgcagca gcatcgttac cttcgatcaa agagaaacaa ccagaaagtc    9900
```

```
atagtaatcg tgtcagactc ggtcaagaaa tcaaaggtct tgatgaaggg aatatggctg      9960
aaattgatag ctatcaaaac ttgtttggtt tgatgaaaca gaggtttctg agtttcaaga     10020
gccaaaaata tataaaagag ttggagcatt ttgaagctct tgctgaagct caatttccta     10080
agtttatggt gattgcttgt gcagactcta gggtatgccc ctctaacata ttaggattcc     10140
aacctggaga agtctttatg atacgtaaca ttgccaatct tgttcctgtg atgaagaatg     10200
gaccatcaga atgtaatgct gctcttcagt ttgcagtaac tactcttcag gttgagaata     10260
tattagtcat tggtcatagt agctgcgctg gaattgaagc tttgatgaat atgcaagaag     10320
atgcagaatc aagaaacttc atacacaagt gggttgccaa tggaaaactt gccaaacaaa     10380
ggacaaaagc tgccacagct catcttagct tgatcagca atgcaaattc tgtgagaagg      10440
aatctattaa ccaatcatta ttgaacttgc tcagctatcc ttggatacaa gatagagtga     10500 gaaagagtt gctttctcta catggaggat attataattt ctctaattgc tcttttgaga      10560
aatggaccct tgattttaaa caatgcaatg ttgaagaagg aagcagttat gttgtcaaag     10620
aacaagaatt ctggtgctga ctgttgctat accaggaagc ttggcggccg cgaagttaaa     10680
agcaatgttg tcacttgtcg tactaacaca tgatgtgata gtttatgcta gctagctata     10740
acataagctg tctctgagtg tgttgtatat taataaagat catcactggt gaatggtgat     10800
cgtgtacgta ccctacttag taggcaatgg aagcacttag agtgtgcttt gtgcatggcc     10860
ttgcctctgt tttgagactt ttgtaatgtt ttcgagttta aatctttgcc tttgcgtacg     10920
tctagagtcg acctgca                                                    10937
```

<210> SEQ ID NO 19
<211> LENGTH: 8641
<212> TYPE: DNA
<213> ORGANISM: artificial sequence
<220> FEATURE:
<223> OTHER INFORMATION: plasmid pKR1256

<400> SEQUENCE: 19

```
ggccgcaagt atgaactaaa atgcatgtag gtgtaagagc tcatggagag catggaatat       60
tgtatccgac catgtaacag tataataact gagctccatc tcacttcttc tatgaataaa      120
caaaggatgt tatgatatat taacactcta tctatgcacc ttattgttct atgtaaaatt      180
tcctcttatt attataaatc atctgaatcg tgacggctta tggaatgctt caaatagtac      240
aaaaacaaat gtgtactata agactttcta aacaattcta accttagcat tgtgaacgag      300
acataagtgt taagaagaca taacaattat aatggaagaa gtttgtctcc atttatatat      360
tatatattac ccacttatgt attatattag gatgttaagg agacataaca attataaaga      420
gagaagtttg tatccattta tatattatat actacccatt tatatattat acttatccac      480
ttatttaatg tctttataag gtttgatcca tgatatttct aatatttttag ttgatatgta    540 tatgaaaggg tactatttga actctcttac tctgtataaa ggttggatca tcctttaagt     600 gggtctatttt aattttattg cttcttacag ataaaaaaaa aattatgagt tggtttgata   660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa atttttttt ttatcagcaa agaataaaat    900
taaattaaga aggacaatgg tgtcccaatc cttatacaac caacttccac aagaaagtca    960
```

```
agtcagagac aacaaaaaaa caagcaaagg aaattttta atttgagttg tcttgtttgc      1020
tgcataattt atgcagtaaa acactacaca taaccctttt agcagtagag caatggttga      1080
ccgtgtgctt agcttctttt attttatttt tttatcagca aagaataaat aaaataaaat      1140
gagacacttc agggatgttt caacaagctt ggcgcgccgt tctatagtgt cacctaaatc      1200
gtatgtgtat gatacataag gttatgtatt aattgtagcc gcgttctaac gacaatatgt      1260
ccatatggtg cactctcagt acaatctgct ctgatgccgc atagttaagc cagccccgac      1320
acccgccaac acccgctgac gcgccctgac gggcttgtct gctcccggca tccgcttaca      1380
gacaagctgt gaccgtctcc gggagctgca tgtgtcagag gttttcaccg tcatcaccga      1440
aacgcgcgag acgaaagggc ctcgtgatac gcctattttt ataggttaat gtcatgacca      1500
aaatccctta acgtgagttt tcgttccact gagcgtcaga ccccgtagaa aagatcaaag      1560
gatcttcttg agatcctttt tttctgcgcg taatctgctg cttgcaaaca aaaaaaccac      1620
cgctaccagc ggtggtttgt ttgccggatc aagagctacc aactctttt ccgaaggtaa      1680 ctggcttcag cagagcgcag ataccaaata ctgtccttct agtgtagccg tagttaggcc      1740
accacttcaa gaactctgta gcaccgccta catacctcgc tctgctaatc ctgttaccag      1800
tggctgctgc cagtggcgat aagtcgtgtc ttaccgggtt ggactcaaga cgatagttac      1860
cggataaggc gcagcggtcg ggctgaacgg ggggttcgtg cacacagccc agcttggagc      1920
gaacgaccta caccgaactg agatacctac agcgtgagca ttgagaaagc gccacgcttc      1980
ccgaagggag aaaggcggac aggtatccgg taagcggcag ggtcggaaca ggagagcgca      2040
cgagggagct ccaggggga aacgcctggt atctttatag tcctgtcggg tttcgccacc      2100
tctgacttga gcgtcgattt ttgtgatgct cgtcaggggg gcggagccta tggaaaaacg      2160
ccagcaacgc ggccttttta cggttcctgg ccttttgctg gccttttgct cacatgttct      2220
ttcctgcgtt atcccctgat tctgtggata accgtattac cgcctttgag tgagctgata      2280
ccgctcgccg cagccgaacg accgagcgca gcgagtcagt gagcgaggaa gcggaagagc      2340
gcccaatacg caaaccgcct ctccccgcgc gttggccgat tcattaatgc aggttgatcg      2400
attcgacatc gatctagtaa catagatgac accgcgcgcg ataatttatc ctagtttgcg      2460
cgctatattt tgttttctat cgcgtattaa atgtataatt gcgggactct aatcataaaa      2520
acccatctca taaataacgt catgcattac atgttaatta ttacatgctt aacgtaattc      2580
aacagaaatt atatgataat catcgcaaga ccggcaacag gattcaatct taagaaactt      2640
tattgccaaa tgtttgaacg atctgcttcg acgcactcct tctttaggta cctcactatt      2700
cctttgccct cggacgagtg ctggggcgtc ggtttccact atcggcgagt acttctacac      2760
agccatcggt ccagacggcc gcgcttctgc gggcgatttg tgtacgcccg acagtcccgg      2820
ctccggatcg gacgattgcg tcgcatcgac cctgcgccca agctgcatca tcgaaattgc      2880
cgtcaaccaa gctctgatag agttggtcaa gaccaatgcg gagcatatac gcccggagcc      2940
gcggcgatcc tgcaagctcc ggatgcctcc gctcgaagta gcgcgtctgc tgctccatac      3000
aagccaacca cggcctccag aagaagatgt tggcgacctc gtattgggaa tccccgaaca      3060
tcgcctcgct ccagtcaatg accgctgtta tgcggccatt gtccgtcagg acattgttgg      3120
agccgaaatc cgcgtgcacg aggtgccgga cttcgggca gtcctcggcc caaagcatca      3180
gctcatcgag agcctgcgcg acggacgcac tgacggtgtc gtccatcaca gtttgccagt      3240
gatacacatg gggatcagca atcgcgcata tgaaatcacg ccatgtagtg tattgaccga      3300
ttccttgcgg tccgaatggg ccgaacccgc tcgtctggct aagatcggcc gcagcgatcg      3360
```

-continued

```
catccatggc ctccgcgacc ggctgcagaa cagcgggcag ttcggtttca ggcaggtctt    3420
gcaacgtgac accctgtgca cggcgggaga tgcaataggt caggctctcg ctgaattccc    3480
caatgtcaag cacttccgga atcgggagcg cggccgatgc aaagtgccga taaacataac    3540
gatctttgta gaaaccatcg gcgcagctat ttacccgcag acatatcca cgccctccta     3600 catcgaagct gaaagcacga gattcttcgc cctccgagag ctgcatcagg tcggagacgc    3660
tgtcgaactt ttcgatcaga aacttctcga cagacgtcgc ggtgagttca ggcttttca    3720 tggtttaata agaagagaaa agagttcttt tgttatggct gaagtaatag agaaatgagc    3780
tcgagcgtgt cctctccaaa tgaaatgaac ttccttatat agaggaaggg tcttgcgaag    3840
gatagtggga ttgtgcgtca tcccttacgt cagtggagat gtcacatcaa tccacttgct    3900
ttgaagacgg ggttggaacg tcttcttttt ccacgatgct cctcgtgggt ggggtccat     3960 ctttgggacc actgtcggca gaggcatctt gaatgatagc cttccttta tcgcaatgat     4020 ggcatttgta ggagccacct tccttttcta ctgtcctttc gatgaagtga cagatagctg    4080
ggcaatggaa tccgaggagg tttcccgaaa ttatcctttg ttgaaaagtc tcaatagccc    4140
tttggtcttc tgagactgta tcttgacat ttttggagta gaccagagtg tcgtgctcca     4200
ccatgttgac gaagattttc ttcttgtcat tgagtcgtaa aagactctgt atgaactgtt    4260
cgccagtctt cacggcgagt tctgttagat cctcgatttg aatcttagac tccatgcatg    4320
gccttagatt cagtaggaac tacctttta gagactccaa tctctattac ttgccttggt     4380
ttatgaagca agccttgaat cgtccatact ggaatagtac ttctgatctt gagaaatatg    4440
tctttctctg tgttcttgat gcaattagtc ctgaatcttt tgactgcatc tttaaccttc    4500
ttgggaaggt atttgatctc ctggagattg ttactcgggt agatcgtctt gatgagacct    4560
gctgcgtagg cctctctaac catctgtggg tcagcattct ttctgaaatt gaagaggcta    4620
accttctcat tatcagtggt gaacatagtg tcgtcacctt caccttcgaa cttccttcct    4680
agatcgtaaa gatagaggaa atcgtccatt gtaatctccg gggcaaagga gatctctttt    4740
ggggctggat cactgctggg cctttttggtt cctagcgtga gccagtgggc ttttgctt     4800 ggtgggcttg ttagggcctt agcaaagctc ttgggcttga gttgagcttc tcctttgggg    4860
atgaagttca acctgtctgt ttgctgactt gttgtgtacg cgtcagctgc tgctcttgcc    4920
tctgtaatag tggcaaattt cttgtgtgca actccgggaa cgccgtttgt tgccgccttt    4980
gtacaacccc agtcatcgta tataccggca tgtggaccgt tatacacaac gtagtagttg    5040
atatgagggt gttgaatacc cgattctgct ctgagaggag caactgtgct gttaagctca    5100 gattttgtg ggattggaat tggatcgatc tcgatcccgc gaaattaata cgactcacta     5160
tagggagacc acaacggttt ccctctagaa ataatttttgt ttaactttaa gaaggagata    5220
tacccatgga aaagcctgaa ctcaccgcga cgtctgtcga agtttctg atcgaaaagt      5280 tcgacagcgt ctccgacctg atgcagctct cggaggcga agaatctcgt gctttcagct     5340
tcgatgtagg agggcgtgga tatgtcctgc gggtaaatag ctgcgccgat ggtttctaca    5400
aagatcgtta tgtttatcgg cactttgcat cggccgcgct cccgattccg gaagtgcttg    5460
acattgggga attcagcgag agcctgacct attgcatctc ccgccgtgca cagggtgtca    5520
cgttgcaaga cctgcctgaa accgaactgc ccgctgttct gcagccggtc gcggaggcta    5580
tggatgcgat cgctgcggcc gatcttagcc agacagagcg gttcggccca ttcggaccgc    5640
aaggaatcgg tcaatacact acatggcgtg atttcatatg cgcgattgct gatccccatg    5700
```

```
tgtatcactg gcaaactgtg atggacgaca ccgtcagtgc gtccgtcgcg caggctctcg    5760
atgagctgat gctttgggcc gaggactgcc ccgaagtccg gcacctcgtg cacgcggatt    5820
tcggctccaa caatgtcctg acggacaatg ccgcataac  agcggtcatt gactggagcg    5880
aggcgatgtt cggggattcc caatacgagg tcgccaacat cttcttctgg aggccgtggt    5940
tggcttgtat ggagcagcag acgcgctact tcgagcggag gcatccggag cttgcaggat    6000
cgccgcggct ccgggcgtat atgctccgca ttggtcttga ccaactctat cagagcttgg    6060
ttgacggcaa tttcgatgat gcagcttggg cgcagggtcg atgcgacgca atcgtccgat    6120
ccggagccgg gactgtcggg cgtacacaaa tcgcccgcag aagcgcggcc gtctggaccg    6180
atggctgtgt agaagtactc gccgatagtg gaaaccgacg ccccagcact cgtccgaggg    6240
caaaggaata gtgaggtaca gcttggatcg atccggctgc taacaaagcc cgaaaggaag    6300
ctgagttggc tgctgccacc gctgagcaat aactagcata ccccttgggg cctctaaac    6360
gggtcttgag gggttttttg ctgaaaggag gaactatatc cggatgatcg ggcgcgccgt    6420
cgacggatcc gtacgagatc cggccggcca gatcctgcag gagatccaag cttttgatcc    6480
atgcccttca tttgccgctt attaattaat ttggtaacag tccgtactaa tcagttactt    6540
atccttcccc catcataatt aatcttggta gtctcgaatg ccacaacact gactagtctc    6600
ttggatcata agaaaaagcc aaggaacaaa agaagacaaa acacaatgag agtatccttt    6660
gcatagcaat gtctaagttc ataaaattca acaaaaacg  caatcacaca cagtggacat    6720
cacttatcca ctagctgatc aggatcgccg cgtcaagaaa aaaaaactgg accccaaaag    6780
ccatgcacaa caacacgtac tcacaaaggt gtcaatcgag cagcccaaaa cattcaccaa    6840
ctcaacccat catgagccct cacatttgtt gtttctaacc caacctcaaa ctcgtattct    6900
cttccgccac ctcattttg  tttatttcaa cacccgtcaa actgcatgcc accccgtggc    6960
caaatgtcca tgcatgttaa caagacctat gactataaat agctgcaatc tcggcccagg    7020
ttttcatcat caagaaccag ttcaatatcc tagtacaccg tattaaagaa tttaagatat    7080
actgcggccg caacatgact atcgactcac aatactacaa gtcgcgagac aaaaacgaca    7140
cggcacccaa aatcgcggga atccgatatg ccccgctatc gacaccatta ctcaaccgat    7200
gtgagacctt ctctctggtc tggcacattt tcagcattcc cactttcctc acaattttca    7260
tgctatgctg cgcaattcca ctgctctggc catttgtgat tgcgtatgta gtgtacgctg    7320
ttaaagacga ctccccgtcc aacggaggag tggtcaagcg atactcgcct atttcaagaa    7380
acttcttcat ctggaagctc tttgccgct  acttccccat aactctgcac aagacggtgg    7440
atctggagcc cacgcacaca tactaccctc tggacgtcca ggagtatcac ctgattgctg    7500
agagatactg gccgcagaac aagtacctcc gagcaatcat caccaccatc gagtactttc    7560
tgcccgcctt catgaaacgg tctctttcta tcaacgagca ggagcagcct gccgagcgag    7620
atcctctcct gtctcccgtt tctcccagct ctccgggttc tcaacctgac aagtggatta    7680
accacgacag cagatatagc cgtggagaat catctggctc caacgccac  gcctcgggct    7740
ccgaacttaa cggcaacggc aacaacggca ccactaaccg acgacctttg tcgtccgcct    7800
ctgctggctc cactgcatct gattccacgc ttcttaacgg gtcctcaac  tcctacgcca    7860
accagatcat tggcgaaaac gacccacagc tgtcgcccac aaaactcaag cccactggca    7920
gaaaatacat cttcggctac cacccccacg gcattatcgg catggagcc  tttggtggaa    7980
ttgccaccga gggagctgga tggtccaagc tcttttccggg catccctgtt tctcttatga    8040
ctctcaccaa caacttccga gtgcctctct acagagagta cctcatgagt ctgggagtcg    8100
```

```
cttctgtctc caagaagtcc tgcaaggccc tcctcaagcg aaaccagtct atctgcattg    8160
tcgttggtgg agcacaggaa agtcttctgg ccagacccgg tgtcatggac ctggtgctac    8220
tcaagcgaaa gggttttgtt cgacttggta tggaggtcgg aaatgtcgcc cttgttccca    8280
tcatggcctt tggtgagaac gacctctatg accaggttag caacgacaag tcgtccaagc    8340
tgtaccgatt ccagcagttt gtcaagaact tccttggatt caccettcct ttgatgcatg    8400 cccgaggcgt cttcaactac gatgtcggtc ttgtccccta caggcgaccc gtcaacattg    8460
tggttggttc ccccattgac ttgccttatc tcccacaccc caccgacgaa gaagtgtccg    8520
aataccacga ccgatacatc gccgagctgc agcgaatcta caacgagcac aaggatgaat    8580
atttcatcga ttggaccgag gagggcaaag gagccccaga gttccgaatg attgagtaag    8640
c                                                                   8641

<210> SEQ ID NO 20
<211> LENGTH: 7361
<212> TYPE: DNA
<213> ORGANISM: artificial sequence
<220> FEATURE:
<223> OTHER INFORMATION: vector pKR2609

<400> SEQUENCE: 20
ggccgcgaag ttaaaagcaa tgttgtcact tgtcgtacta acacatgatg tgatagttta      60
tgctagctag ctataacata agctgtctct gagtgtgttg tatattaata aagatcatca     120
ctggtgaatg gtgatcgtgt acgtacccta cttagtaggc aatggaagca cttagagtgt     180
gctttgtgca tggccttgcc tctgttttga gacttttgta atgttttcga gtttaaatct     240
ttgcctttgc gtacgtctag agtcgacggc gcgcccgatc atccggatat agttcctcct     300
ttcagcaaaa aaccccctcaa gacccgttta gaggccccaa ggggttatgc tagttattgc     360
tcagcggtgg cagcagccaa ctcagcttcc tttcgggctt tgttagcagc cggatcgatc     420
caagctgtac ctcactattc ctttgccctc ggacgagtgc tggggcgtcg gtttccacta     480
tcggcgagta cttctacaca gccatcggtc cagacggccg cgcttctgcg ggcgatttgt     540
gtacgcccga cagtcccggc tccggatcgg acgattgcgt cgcatcgacc ctgcgcccaa     600
gctgcatcat cgaaattgcc gtcaaccaag ctctgataga gttggtcaag accaatgcgg     660
agcatatacg cccggagccg cggcgatcct gcaagctccg gatgcctccg ctcgaagtag     720
cgcgtctgct gctccataca agccaaccac ggcctccaga agaagatgtt ggcgacctcg     780 tatgggaat ccccgaacat cgcctcgctc cagtcaatga ccgctgttat gcggccattg     840
tccgtcagga cattgttgga gccgaaatcc gcgtgcacga ggtgccggac ttcggggcag     900
tcctcggccc aaagcatcag ctcatcgaga gcctgcgcga cggacgcact gacggtgtcg     960
tccatcacag tttgccagtg atacacatgg ggatcagcaa tcgcgcatat gaaatcacgc    1020
catgtagtgt attgaccgat tccttgcggt ccgaatgggc cgaacccgct cgtctggcta    1080
agatcggccg cagcgatcgc atccatagcc tccgcgaccg gctgcagaac agcgggcagt    1140
tcggtttcag gcaggtcttg caacgtgaca ccctgtgcac ggcgggagat gcaataggtc    1200
aggctctcgc tgaattcccc aatgtcaagc acttccggaa tcgggagcgc ggccgatgca    1260
aagtgccgat aaacataacg atctttgtag aaaccatcgg cgcagctatt tacccgcagg    1320
acatatccac gccctcctac atcgaagctg aaagcacgag attcttcgcc ctccgagagc    1380
tgcatcaggt cggagacgct gtcgaacttt tcgatcagaa acttctcgac agacgtcgcg    1440
```

-continued

```
gtgagttcag gcttttccat gggtatatct ccttcttaaa gttaaacaaa attatttcta    1500
gagggaaacc gttgtggtct ccctatagtg agtcgtatta atttcgcggg atcgagatcg    1560
atccaattcc aatcccacaa aaatctgagc ttaacagcac agttgctcct ctcagagcag    1620
aatcgggtat tcaacaccct catatcaact actacgttgt gtataacggt ccacatgccg    1680
gtatatacga tgactggggt tgtacaaagg cggcaacaaa cggcgttccc ggagttgcac    1740
acaagaaatt tgccactatt acagaggcaa gagcagcagc tgacgcgtac acaacaagtc    1800
agcaaacaga caggttgaac ttcatcccca aaggagaagc tcaactcaag cccaagagct    1860
ttgctaaggc cctaacaagc ccaccaaagc aaaaagccca ctggctcacg ctaggaacca    1920
aaaggcccag cagtgatcca gccccaaaag agatctcctt tgccccggag attacaatgg    1980
acgatttcct ctatctttac gatctaggaa ggaagttcga aggtgaaggt gacgacacta    2040
tgttcaccac tgataatgag aaggttagcc tcttcaattt cagaaagaat gctgacccac    2100
agatggttag agaggcctac gcagcaggtc tcatcaagac gatctacccg agtaacaatc    2160
tccaggagat caaatacctt cccaagaagg ttaaagatgc agtcaaaaga ttcaggacta    2220
attgcatcaa gaacacagag aaagacatat ttctcaagat cagaagtact attccagtat    2280
ggacgattca aggcttgctt cataaaccaa ggcaagtaat agagattgga gtctctaaaa    2340
aggtagttcc tactgaatct aaggccatgc atggagtcta agattcaaat cgaggatcta    2400
acagaactcg ccgtgaagac tggcgaacag ttcatacaga gtcttttacg actcaatgac    2460
aagaagaaaa tcttcgtcaa catggtggag cacgacactc tggtctactc caaaaatgtc    2520
aaagatacag tctcagaaga ccaaagggct attgagactt ttcaacaaag gataatttcg    2580
ggaaacctcc tcggattcca ttgcccagct atctgtcact tcatcgaaag gacagtagaa    2640
aaggaaggtg gctcctacaa atgccatcat tgcgataaag gaaaggctat cattcaagat    2700
gcctctgccg acagtggtcc caaagatgga cccccaccca cgaggagcat cgtggaaaaa    2760
gaagacgttc caaccacgtc ttcaaagcaa gtggattgat gtgacatctc cactgacgta    2820
agggatgacg cacaatccca ctatccttcg caagacccct cctctatata aggaagttca    2880
tttcatttgg agaggacacg ctcgagctca tttctctatt acttcagcca taacaaaaga    2940
actcttttct cttcttatta aaccatgaaa aagcctgaac tcaccgcgac gtctgtcgag    3000
aagtttctga tcgaaaagtt cgacagcgtc tccgacctga tgcagctctc ggagggcgaa    3060
gaatctcgtg ctttcagctt cgatgtagga gggcgtggat atgtcctgcg ggtaaatagc    3120
tgcgccgatg gtttctacaa agatcgttat gtttatcggc actttgcatc ggccgcgctc    3180
ccgattccgg aagtgcttga cattggggaa ttcagcgaga gcctgaccta ttgcatctcc    3240
cgccgtgcac agggtgtcac gttgcaagac ctgcctgaaa ccgaactgcc cgctgttctg    3300
cagccggtcg cggaggccat ggatgcgatc gctgcggccg atcttagcca cgagcggg    3360 ttcggcccat tcggaccgca aggaatcggt caatacacta catggcgtga tttcatatgc    3420
gcgattgctg atccccatgt gtatcactgg caaactgtga tggacgacac cgtcagtgcg    3480
tccgtcgcgc aggctctcga tgagctgatg ctttgggccg aggactgccc cgaagtccgg    3540
cacctcgtgc acgcggattt cggctccaac aatgtcctga cggacaatgg ccgcataaca    3600
gcggtcattg actggagcga ggcgatgttc ggggattccc aatacgaggt cgccaacatc    3660
ttcttctgga ggccgtggtt ggcttgtatg gagcagcaga cgcgctactt cgagcggagg    3720
catccggagc ttgcaggatc gccgcggctc cgggcgtata tgctccgcat tggtcttgac    3780
caactctatc agagcttggt tgacggcaat ttcgatgatg cagcttgggc gcagggtcga    3840
```

```
tgcgacgcaa tcgtccgatc cggagccggg actgtcgggc gtacacaaat cgcccgcaga    3900
agcgcggccg tctggaccga tggctgtgta gaagtactcg ccgatagtgg aaaccgacgc    3960
cccagcactc gtccgagggc aaaggaatag tgaggtacct aaagaaggag tgcgtcgaag    4020
cagatcgttc aaacatttgg caataaagtt tcttaagatt gaatcctgtt gccggtcttg    4080
cgatgattat catataattt ctgttgaatt acgttaagca tgtaataatt aacatgtaat    4140
gcatgacgtt atttatgaga tgggttttta tgattagagt cccgcaatta tacatttaat    4200
acgcgataga aaacaaaata tagcgcgcaa actaggataa attatcgcgc gcggtgtcat    4260
ctatgttact agatcgatgt cgaatctgat caacctgcat taatgaatcg ccaacgcgc    4320 ggggagaggc ggtttgcgta ttgggcgctc ttccgcttcc tcgctcactg actcgctgcg    4380
ctcggtcgtt cggctgcggc gagcggtatc agctcactca aaggcggtaa tacgttatc    4440 cacagaatca ggggataacg caggaaagaa catgtgagca aaaggccagc aaaaggccag    4500
gaaccgtaaa aaggccgcgt tgctggcgtt tttccatagg ctccgccccc ctgacgagca    4560
tcacaaaaat cgacgctcaa gtcagaggtg gcgaaacccg acaggactat aaagatacca    4620
ggcgtttccc cctggaagct ccctcgtgcg ctctcctgtt ccgaccctgc cgcttaccgg    4680
atacctgtcc gcctttctcc cttcgggaag cgtggcgctt tctcaatgct cacgctgtag    4740
gtatctcagt tcggtgtagg tcgttcgctc caagctgggc tgtgtgcacg aaccccccgt    4800
tcagcccgac cgctgcgcct tatccggtaa ctatcgtctt gagtccaacc cggtaagaca    4860
cgacttatcg ccactggcag cagccactgg taacaggatt agcagagcga ggtatgtagg    4920
cggtgctaca gagttcttga agtggtggcc taactacggc tacactagaa ggacagtatt    4980
tggtatctgc gctctgctga agccagttac cttcggaaaa agagttggta gctcttgatc    5040
cggcaaacaa accaccgctg gtagcggtgg ttttttgtt tgcaagcagc agattacgcg    5100
cagaaaaaaa ggatctcaag aagatccttt gatcttttct acggggtctg acgctcagtg    5160
gaacgaaaac tcacgttaag ggattttggt catgacatta acctataaaa ataggcgtat    5220
cacgaggccc tttcgtctcg cgcgtttcgg tgatgacggt gaaaacctct gacacatgca    5280
gctcccggag acgtcacag cttgtctgta agcggatgcc gggagcagac aagcccgtca    5340
gggcgcgtca gcgggtgttg gcgggtgtcg ggctggctt aactatgcgg catcagagca    5400
gattgtactg agagtgcacc atatggacat attgtcgtta aacgcggct acaattaata    5460 cataaccta tgtatcatac acatacgatt taggtgacac tatagaacgg cgcgccaagc    5520
ttggatcctc tagacctgca ggccaactgc gtttggggct ccagattaaa cgacgccgtt    5580
tcgttccttt cgcttcacgg cttaacgatg tcgtttctgt ctgtgcccaa aaataaagg    5640 catttgttat ttgcaccaga tatttactaa gtgcacccta gtttgacaag taggcgataa    5700
ttacaaatag atgcggtgca aataataaat tttgaaggaa ataattacaa agaacagaa    5760 cttatattta ctttatttta aaaactaaa atgaagaac aaaaaagta aaaatacaa    5820 aaaatgtgct ttaaccactt tcattatttg ttacagaaag tatgattcta ctcaaattga    5880
tctgttgtat ctggtgctgc cttgtcacac tggcgatttc aatcccctaa agatatggtg    5940
caaactgcga agtgatcaat atctgctcgg ttaatttaga ttaattaata atattcaacg    6000
tgatgtacca aaaaaagaca atttttgct ccattgacaa attaaacctc atcaaggtaa    6060
tttccaaacc tataagcaaa aaatttcac attaattggc ccgcaatcct attagtctta    6120
ttatactaga gtaggaaaaa aaacaattac acaacttgtc ttattattct ctatgctaat    6180
```

| gaatatttttt ccctttgtt agaaatcagt gtttcctaat ttattgagta ttaattccac | 6240 |
| tcaccgcata tatttaccgt tgaataagaa aattttacac ataattcttt ttaagataaa | 6300 |
| taatttttt atactagatc ttatatgatt acgtgaagcc aagtgggtta tactaatgat | 6360 |
| atataatgtt tgatagtaat cagtttataa accaaatgca tggaaatgtt acgtggaagc | 6420 |
| acgtaaatta acaagcattg aagcaaatgc agccaccgca ccaaaaccac cccacttcac | 6480 |
| ttccacgtac catattccat gcaactacaa caccctaaaa cttcaataaa tgccccacc | 6540 |
| ttcacttcac ttcacccatc aatagcaagc ggccgcacca tggctggagg atcatacgag | 6600 |
| gaagccattg cagcgttgac gaagcttctc agcgagaaag ccgacctggg tggtgtcgcc | 6660 |
| gccgcaaaga taaaacagct gacggcggag ctggataccg ccaccgcaaa cgggtcgacg | 6720 |
| ccgtttaacc cggacgagag gatccgaacc gggttcgccc acttcaagaa cgagaaatac | 6780 |
| cagaagaacc cggaattata tggcgaactt gccaaaggcc agagtccaaa gtttatggtt | 6840 |
| tttgcttgct cagactctcg agtttgccca tcccacattc tggatttcaa tccgggtgaa | 6900 |
| gcctttgtgg tccgaaatat cgccaacatg gttccaccat atgacaagac caagtattca | 6960 |
| ggaaccgggg cggccattga atatgcagtc ttacatttaa aggtggagaa tattgtggtc | 7020 |
| attgggcaca gctgctgtgg aggtataaag ggcctaatgt ctatcccaga tgatgggacc | 7080 |
| actgcaagtg aattcataga gcactgggtc caaatttgca ctccagcaaa gtccaaggtt | 7140 |
| aaaacagaag caaacacatt agaattctct gagcaatgta ccagctgcga gaaggaagct | 7200 |
| gtgaatgtat cacttgggaa cctattgaca tatcgatttg tgagagatgc agttgtgaag | 7260 |
| aaaactcttg ccttgaaagg tgcacattac aatttcgtta aaggcacatt tgagctgtgg | 7320 |
| gatctggact tgaaaaactc taactctgta tccgtttaag c | 7361 |

<210> SEQ ID NO 21
<211> LENGTH: 12572
<212> TYPE: DNA
<213> ORGANISM: artificial sequence
<220> FEATURE:
<223> OTHER INFORMATION: vector pKR2749

<400> SEQUENCE: 21

| gtacgtctag agtcgacggc gcgcccgatc atccggatat agttcctcct ttcagcaaaa | 60 |
| aaccctcaa gacccgttta gaggccccaa ggggttatgc tagttattgc tcagcggtgg | 120 |
| cagcagccaa ctcagcttcc tttcgggctt tgttagcagc cggatcgatc caagctgtac | 180 |
| ctcactattc ctttgccctc ggacgagtgc tggggcgtcg gtttccacta tcggcgagta | 240 |
| cttctacaca gccatcggtc cagacggccg cgcttctgcg ggcgatttgt gtacgcccga | 300 |
| cagtcccggc tccggatcgg acgattgcgt cgcatcgacc ctgcgcccaa gctgcatcat | 360 |
| cgaaattgcc gtcaaccaag ctctgataga gttggtcaag accaatgcgg agcatatacg | 420 |
| cccggagccg cggcgatcct gcaagctccg gatgcctccg ctcgaagtag cgcgtctgct | 480 |
| gctccataca agccaaccac ggcctccaga agaagatgtt ggcgacctcg tattgggaat | 540 |
| ccccgaacat cgcctcgctc cagtcaatga ccgctgttat gcggccattg tccgtcagga | 600 |
| cattgttgga gccgaaatcc gcgtgcacga ggtgccggac ttcggggcag tcctcggccc | 660 |
| aaagcatcag ctcatcgaga gcctgcgcga cggacgcact gacggtgtcg tccatcacag | 720 |
| tttgccagtg atacacatgg ggatcagcaa tcgcgcatat gaaatcacgc catgtagtgt | 780 |
| attgaccgat tccttgcggt ccgaatgggc cgaacccgct cgtctggcta agatcggccg | 840 |
| cagcgatcgc atccatagcc tccgcgaccg gctgcagaac agcgggcagt tcggtttcag | 900 |

```
gcaggtcttg caacgtgaca ccctgtgcac ggcgggagat gcaataggtc aggctctcgc    960
tgaattcccc aatgtcaagc acttccggaa tcgggagcgc ggccgatgca aagtgccgat   1020
aaacataacg atctttgtag aaaccatcgg cgcagctatt tacccgcagg acatatccac   1080
gccctcctac atcgaagctg aaagcacgag attcttcgcc ctccgagagc tgcatcaggt   1140
cggagacgct gtcgaacttt tcgatcagaa acttctcgac agacgtcgcg gtgagttcag   1200
gcttttccat gggtatatct ccttcttaaa gttaaacaaa attatttcta gagggaaacc   1260
gttgtggtct ccctatagtg agtcgtatta atttcgcggg atcgagatcg atccaattcc   1320
aatcccacaa aaatctgagc ttaacagcac agttgctcct ctcagagcag aatcgggtat   1380
tcaacaccct catatcaact actacgttgt gtataacggt ccacatgccg gtatatacga   1440
tgactggggt tgtacaaagg cggcaacaaa cggcgttccc ggagttgcac aagaaaatt   1500 tgccactatt acagaggcaa gagcagcagc tgacgcgtac acaacaagtc agcaaacaga   1560
caggttgaac ttcatcccca aggagaagc tcaactcaag cccaagagct ttgctaaggc   1620
cctaacaagc ccaccaaagc aaaaagccca ctggctcacg ctaggaacca aaaggcccag   1680
cagtgatcca gccccaaaag agatctcctt tgccccggag attacaatgg acgatttcct   1740
ctatctttac gatctaggaa ggaagttcga aggtgaaggt gacgacacta tgttcaccac   1800
tgataatgag aaggttagcc tcttcaattt cagaaagaat gctgacccac agatggttag   1860
agaggcctac gcagcaggtc tcatcaagac gatctacccg agtaacaatc tccaggagat   1920
caaataccct cccaagaagg ttaaagatgc agtcaaaaga ttcaggacta attgcatcaa   1980
gaacacagag aaagacatat ttctcaagat cagaagtact attccagtat ggacgattca   2040
aggcttgctt cataaaccaa ggcaagtaat agagattgga gtctctaaaa aggtagttcc   2100
tactgaatct aaggccatgc atggagtcta agattcaaat cgaggatcta acagaactcg   2160
ccgtgaagac tggcgaacag ttcatacaga gtcttttacg actcaatgac aagaagaaaa   2220
tcttcgtcaa catggtggag cacgacactc tggtctactc caaaaatgtc aaagatacag   2280
tctcagaaga ccaaagggct attgagactt ttcaacaaag gataatttcg ggaaacctcc   2340
tcggattcca ttgcccagct atctgtcact tcatcgaaag gacagtagaa aaggaaggtg   2400
gctcctacaa atgccatcat tgcgataaag gaaaggctat cattcaagat gcctctgccg   2460
acagtggtcc caaagatgga cccccaccca cgaggagcat cgtggaaaaa gaagacgttc   2520
caaccacgtc ttcaaagcaa gtggattgat gtgacatctc cactgacgta agggatgacg   2580
cacaatccca ctatccttcg caagacccct cctctatata aggaagttca tttcatttgg   2640
agaggacacg ctcgagctca tttctctatt acttcagcca taacaaaaga actcttttct   2700
cttcttatta aaccatgaaa aagcctgaac tcaccgcgac gtctgtcgag aagtttctga   2760
tcgaaaagtt cgacagcgtc tccgacctga tgcagctctc ggagggcgaa gaatctcgtg   2820
ctttcagctt cgatgtagga gggcgtggat atgtcctgcg ggtaaatagc tgcgccgatg   2880
gtttctacaa agatcgttat gtttatcggc actttgcatc ggccgcgctc ccgattccgg   2940
aagtgcttga cattggggaa ttcagcgaga gcctgaccta ttgcatctcc cgccgtgcac   3000
agggtgtcac gttgcaagac ctgcctgaaa ccgaactgcc cgctgttctg cagccggtcg   3060
cggaggccat ggatgcgatc gctgcggccg atcttagcca cgagcggg ttcggcccat   3120 tcggaccgca aggaatcggt caatacacta catggcgtga tttcatatgc gcgattgctg   3180
atccccatgt gtatcactgg caaactgtga tggacgacac cgtcagtgcg tccgtcgcgc   3240
```

```
aggctctcga tgagctgatg ctttgggccg aggactgccc cgaagtccgg cacctcgtgc    3300
acgcggattt cggctccaac aatgtcctga cggacaatgg ccgcataaca gcggtcattg    3360
actggagcga ggcgatgttc ggggattccc aatacgaggt cgccaacatc ttcttctgga    3420
ggccgtggtt ggcttgtatg gagcagcaga cgcgctactt cgagcggagg catccggagc    3480
ttgcaggatc gccgcggctc cgggcgtata tgctccgcat tggtcttgac caactctatc    3540
agagcttggt tgacggcaat ttcgatgatg cagcttgggc gcagggtcga tgcgacgcaa    3600
tcgtccgatc cggagccggg actgtcgggc gtacacaaat cgcccgcaga agcgcggccg    3660
tctggaccga tggctgtgta gaagtactcg ccgatagtgg aaaccgacgc cccagcactc    3720
gtccgagggc aaaggaatag tgaggtacct aaagaaggag tgcgtcgaag cagatcgttc    3780
aaacatttgg caataaagtt tcttaagatt gaatcctgtt gccggtcttg cgatgattat    3840
catataattt ctgttgaatt acgttaagca tgtaataatt aacatgtaat gcatgacgtt    3900
atttatgaga tgggttttta tgattagagt cccgcaatta tacatttaat acgcgataga    3960
aaacaaaata tagcgcgcaa actaggataa attatcgcgc gcggtgtcat ctatgttact    4020
agatcgatgt cgaatctgat caacctgcat taatgaatcg gccaacgcgc ggggagaggc    4080
ggtttgcgta ttgggcgctc ttccgcttcc tcgctcactg actcgctgcg ctcggtcgtt    4140
cggctgcggc gagcggtatc agctcactca aaggcggtaa tacggttatc cacagaatca    4200
ggggataacg caggaaagaa catgtgagca aaaggccagc aaaaggccag gaaccgtaaa    4260
aaggccgcgt tgctggcgtt tttccatagg ctccgccccc ctgacgagca tcacaaaaat    4320
cgacgctcaa gtcagaggtg gcgaaacccg acaggactat aaagatacca ggcgtttccc    4380
cctggaagct ccctcgtgcg ctctcctgtt ccgaccctgc cgcttaccgg atacctgtcc    4440
gcctttctcc cttcgggaag cgtggcgctt tctcaatgct cacgctgtag gtatctcagt    4500
tcggtgtagg tcgttcgctc caagctgggc tgtgtgcacg aaccccccgt tcagcccgac    4560
cgctgcgcct tatccggtaa ctatcgtctt gagtccaacc cggtaagaca cgacttatcg    4620
ccactggcag cagccactgg taacaggatt agcagagcga ggtatgtagg cggtgctaca    4680
gagttcttga agtggtggcc taactacggc tacactagaa ggacagtatt tggtatctgc    4740
gctctgctga agccagttac cttcggaaaa agagttggta gctcttgatc cggcaaacaa    4800
accaccgctg gtagcggtgg tttttttgtt tgcaagcagc agattacgcg cagaaaaaaa    4860
ggatctcaag aagatccttt gatcttttct acggggtctg acgctcagtg gaacgaaaac    4920
tcacgttaag ggattttggt catgacatta acctataaaa ataggcgtat cacgaggccc    4980
tttcgtctcg cgcgtttcgg tgatgacggt gaaaacctct gacacatgca gctcccggag    5040
acggtcacag cttgtctgta agcggatgcc gggagcagac aagcccgtca gggcgcgtca    5100
gcgggtgttg gcgggtgtcg gggctggctt aactatgcgg catcagagca gattgtactg    5160
agagtgcacc atatggacat attgtcgtta gaacgcggct acaattaata cataaccttt    5220
tgtatcatac acatacgatt taggtgacac tatagaacgg cgcgccaagc ttggatcctc    5280
tagacctgca ggccaactgc gtttgggctc cagattaaaa cgacgccgtt tcgttccttt    5340
cgcttcacgg cttaacgatg tcgtttctgt ctgtgcccaa aaaataaagg catttgttat    5400
ttgcaccaga tatttactaa gtgcacccta gtttgacaag taggcgataa ttacaaatag    5460
atgcggtgca ataataaat tttgaaggaa ataattacaa agaacagaa cttatattta    5520 ctttatttta aaaactaaa atgaaagaac aaaaaagta aaaatacaa aaatgtgct    5580 ttaaccactt tcattatttg ttacagaaag tatgattcta ctcaaattga tctgttgtat    5640
```

```
ctggtgctgc cttgtcacac tggcgatttc aatcccctaa agatatggtg caaactgcga    5700
agtgatcaat atctgctcgg ttaatttaga ttaattaata atattcaacg tgatgtacca    5760
aaaaaagaca attttttgct ccattgacaa attaaacctc atcaaggtaa tttccaaacc    5820
tataagcaaa aaaatttcac attaattggc ccgcaatcct attagtctta ttatactaga    5880
gtaggaaaaa aaacaattac acaacttgtc ttattattct ctatgctaat gaatattttt    5940
cccttttgtt agaaatcagt gtttcctaat ttattgagta ttaattccac tcaccgcata    6000
tatttaccgt tgaataagaa aattttacac ataattcttt ttaagataaa tattttttt    6060 atactagatc ttatatgatt acgtgaagcc aagtgggtta tactaatgat atataatgtt    6120
tgatagtaat cagtttataa accaaatgca tggaaatgtt acgtggaagc acgtaaatta    6180
acaagcattg aagcaaatgc agccaccgca ccaaaaccac cccacttcac ttccacgtac    6240
catattccat gcaactacaa caccctaaaa cttcaataaa tgcccccacc ttcacttcac    6300
ttcacccatc aatagcaagc ggccgcacca tggctggagg atcatacgag gaagccattg    6360
cagcgttgac gaagcttctc agcgagaaag ccgacctggg tggtgtcgcc gccgcaaaga    6420
taaaacagct gacggcggag ctggataccg ccaccgcaaa cgggtcgacg ccgtttaacc    6480
cggacgagag gatccgaacc gggttcgccc acttcaagaa cgagaaatac cagaagaacc    6540
cggaattata tggcgaactt gccaaaggcc agagtccaaa gtttatggtt tttgcttgct    6600
cagactctcg agtttgccca tcccacattc tggatttcaa tccgggtgaa gcctttgtgg    6660
tccgaaatat cgccaacatg gttccaccat atgacaagac caagtattca ggaaccgggg    6720
cggccattga atatgcagtc ttacatttaa aggtggagaa tattgtggtc attgggcaca    6780
gctgctgtgg aggtataaag ggcctaatgt ctatcccaga tgatgggacc actgcaagtg    6840
aattcataga gcactgggtc caaatttgca ctccagcaaa gtccaaggtt aaaacagaag    6900
caaacacatt agaattctct gagcaatgta ccagctgcga aaggaagct gtgaatgtat    6960 cacttgggaa cctattgaca tatcgatttg tgagagatgc agttgtgaag aaaactcttg    7020
ccttgaaagg tgcacattac aatttcgtta aaggcacatt tgagctgtgg gatctggact    7080
tgaaaaactc taactctgta tccgtttaag cggccgcgaa gttaaaagca atgttgtcac    7140
ttgtcgtact aacacatgat gtgatagttt atgctagcta gctataacat aagctgtctc    7200
tgagtgtgtt gtatattaat aaagatcatc actggtgaat ggtgatcgtg tacgtaccct    7260
acttagtagg caatggaagc acttagagtg tgctttgtgc atggccttgc ctctgttttg    7320 agactttgt aatgttttcg agtttaaatc tttgcctttg cgtacccatc tgcaggtaaa    7380
ttgcagctga aggacagtga agggtgaatt tatccattta aaccattttc ttttttaacac    7440 atttcttatg gtaatctctt ctcactacac tataaaaatg gcttctcaat cccatttct    7500 acatcatccc attctattga gttttgttta tttgctttca cttttttttt tatctgcctc    7560
ttcccttaat ttgcttgact tcttcttcac attttgcttt gttttctcct ccggcttccg    7620
gtatttcaaa ttcaagatga gcaagttgaa atttataaat agaaatacag atattattta    7680
caacgtcaaa tctttggtat tttcaatatt tgaatggggt aaatttgtca tatagtcatc    7740
atcactgact acttatctaa cctatttaat ttggagcata ttctttataa ggtccctctc    7800
acggccaatg tctaattatt gatatacagc tcttgttttc tagtgctgct tataatatta    7860
tctacacata tatatggtac tgcacactac tactatatag tagtaagtaa actagcaaca    7920
gccggggcca aactccaata actaggcatt ggggtttagt tggtaatata aatataacat    7980
```

```
caaaaagtct ttgcttgtga cgaacatcac aatgcaccca ccattgatgc cacgacagac   8040
attgttaatt ttttttttaa ttttaaaaa agaagcaatt ccaatagttc tatattacaa    8100
tctcacgtga tccaagcaca acgtttcatt ttttgtacat gctcgatata taaataatat   8160
ttcattttat agtaaaatat aatgacattt tcgaatataa ttttgaaat ttcatttcc     8220 aaatgaaata ctaatattaa tattaatgag attaccacaa atcatgttat gaatgaaata   8280
aagagttttg gcattctaac tttctttgaa tagaacaaaa tgtatacaac actctccata   8340
tatacacgat ttattcaggg atcatataca ttctctcatg attaacatag tctgctttct   8400
tcacgtctaa gcagataatt tttggtccac aagataaaat tatcattagt cgttttaatt   8460
aattccttga gcatcaagca ctaaaataat taaacttctc cattaccaaa aaaaaagat    8520 aggtgattca gtaacatgta gtactagtac tactgatttt tttttctctt tgattttaat   8580
gaatggttcg tatcgagcat cgagaaatcc atttattagg tgtgtaatgt aatagtagta   8640
tttccttgat tttcagtaat aagatggatt cttacattta tatctgtttg acagaaaatg   8700
ttgtcaatgc atttcttggg cacaaagttt tttgaaacat gaattaattt tttcaaaata   8760
tttatgacat caaattgacc ctaaaataag tgataaagct ttaacgtgga atgacattaa   8820
tttttccatg ataaataaaa cacttaaaac attttaatat taatattata atcagttaca   8880
actatgttca attaatgcaa taacttttaa ataaatatta aaatattttt tttctgttct   8940
ccaataaaga gatcttgttg cacggaaaaa gtcacattct tatttagtaa aaattataa    9000 ttattgtttg aaaaatatca ttttcactgc agaaatttg atccagctct acagatcata    9060
cttttattgt acaataatac aataaaaata ttcatctgca ggaaatatca ttttcattgt   9120
acaataatat aaagataaat ataccagca aagaaaaag aaactgatgt ggcacaatgt     9180
attcactgaa agaatgcata ttgtatttca cctttcaagc agcactaaga atatacttct   9240
tttattatac ttgtgcattt actcaaccac cctcggtgga gtaagaaaga agatagataa   9300 aagtttttt tgacatttgg tgaatctctt aattaaaaaa ataaataat ccatttcctt     9360 tatttaattt ctttttttccc atctgtgaaa ttccaattct gcttcgcgct cctgtctata  9420
aattgactta gccaccacct cagtttccat tcattcactt cttctcttta taccccccct   9480
ctcttttttg cgttcattct gttttcgtaa gtactgttgt ttttctcttc tatttctttt   9540
tttgtttgtg ttgttttttt ttcttcctta tcgttgttct gcctctcctc tgtttcggtg   9600
ctctgttcac cacttccacg tgagaatgat cttccttctt tgcatgttca ttctctcgtg   9660
accactggat cagactccat gttctgatcc agggtctctc tctaacgcct gtactttcat   9720
ccatgaccac cttaaaaaca acatgggggt ggtgctgtta cactaactct gtttctgggg   9780
tgctgtcttt gttcaatttt actcagaaaa tatcttttct tggattctat tcggtgtgtg   9840
ggaacatgat cctgtcggtc ggttgttttt aggttaatcc ttaactggtt acaaggatct   9900
aacgcttgaa tgcatgtcct gagttaaaga aacaaaagaa gaacacacct agtacagcct   9960
ggcctcgaac caagaacttc tttgttggtt tctcattatt actaaaataa aataaagtat   10020
acgttttctt ttttctttgg gatgaacggt tcagacttat gagaagttta agctaatcct   10080
gtagtggagt gttcaattta ttttaaactt taaagcaata gctcaagcac taaacttctt   10140
tttcaagttc aaccactttg gtagcttgct aattgctgct attgttctaa ttaattaatg   10200
taattattgt ttaaaaaaga aaagttggtg acactggaat aaaaaagtgt actatctggc   10260
aattattctt ctgcagcaat gtttgaggtt gaaatcttag tagaacaaag tagaagatct   10320
ggtatttata ttttttgtag acagatggtg ggggtgggtg gtaggccttg aaatccaata   10380
```

-continued

```
tagttttgta gaataatttt attatttttt tttttttgctc acttgtttgt ggtattgatt    10440
ttgtgatgac tcaagattaa tgatttacct tcattttttt catggtgaca tattatgtat    10500
attcttgatc tgtttcttac acttcttttt cgttgttgta gctgttgaag tctgcggccg    10560
catgaagagg tctccagcat cttccttgtc atcatctact tcctctgttg ggtttgaagc    10620
tcccattgaa aaagaaggc ctaagcatcc aaggaggaat aatttgaagt cacaaaaatg     10680
caagcagaac caaaccacca ctggtggcag aagaagctct atctatagag gagttacaag    10740
gcataggtgg acagggaggt ttgaagctca cctatgggat aagagctctt ggaacaacat    10800
tcagagcaag aagggtcgac aagtttattt gggggcatat gatactgaag aatctgcagc    10860
ccgtacctat gaccttgcag cccttaaata ctggggaaaa gatgcaaccc tgaatttccc    10920
gatagaaact tataccaagg agctcgagga aatggacaag gtttcaagag aagaatattt    10980
ggcttctttg cggcgccaaa gcagtggctt ttctagaggc ctgtctaagt accgtggggt    11040
tgctaggcat catcataatg gtcgctggga agcacgaatt ggaagagtat gcggaaacaa    11100
gtacctctac ttggggacat ataaaactca agaggaggca gcagtggcat atgacatggc    11160
agcaatagag taccgtggag tcaatgcagt gaccaatttt gacataagca actacatgga    11220
caaaataaag aagaaaaatg accaaaccca acaacaacaa acagaagcac aaacggaaac    11280
agttcctaac tcctctgact ctgaagaagt agaagtagaa caacagacaa caacaataac    11340
cacaccaccc ccatctgaaa atctgcacat gccaccacag cagcaccaag ttcaatacac    11400
cccccatgtc tctccaaggg aagaagaatc atcatcactg atcacaatta tggaccatgt    11460
gcttgagcag gatctgccat ggagcttcat gtacactggc ttgtctcagt ttcaagatcc    11520
aaacttggct ttctgcaaag gtgatgatga cttggtgggc atgtttgata gtgcagggtt    11580
tgaggaagac attgattttc tgttcagcac tcaacctggt gatgagactg agagtgatgt    11640
caacaatatg agcgcagttt tggatagtgt tgagtgtgga gacacaaatg gggctggtgg    11700
aagcatgatg catgtggata acaagcagaa gatagtatca tttgcttctt caccatcatc    11760
tacaactaca gtttcttgtg actatgctct agatctatga gcggccgcat ttcgcaccaa    11820
atcaatgaaa gtaataatga aaagtctgaa taagaatact taggcttaga tgcctttgtt    11880
acttgtgtaa aataacttga gtcatgtacc tttggcggaa acagaataaa taaaaggtga    11940
aattccaatg ctctatgtat aagttagtaa tacttaatgt gttctacggt tgtttcaata    12000
tcatcaaact ctaattgaaa ctttagaacc acaaatctca atcttttctt aatgaaatga    12060
aaaatcttaa ttgtaccatg tttatgttaa acaccttaca attaattggt tggagaggag    12120
gaccaaccga tgggacaaca ttgggagaaa gagattcaat ggagatttgg ataggagaac    12180
aacattcttt ttcacttcaa tacaagatga gtgcaacact aaggatatgt atgagacttt    12240
cagaagctac gacaacatag atgagtgagg tggtgattcc tagcaagaaa gacattagag    12300
gaagccaaaa tcgaacaagg aagacatcaa gggcaagaga caggaccatc catctcagga    12360
aaaggagctt tgggatagtc cgagaagttg tacaagaaat ttttttggagg gtgagtgatg    12420
cattgctggt gactttaact caatcaaaat tgagaaagaa agaaaaggga gggggctcac    12480
atgtgaatag aagggaaacg ggagaatttt acagttttga tctaatgggc atcccagcta    12540
gtggtaacat attccaccatg tttaaccttc ac                                  12572
```

<210> SEQ ID NO 22
<211> LENGTH: 12521
<212> TYPE: DNA

<213> ORGANISM: artificial sequence
<220> FEATURE:
<223> OTHER INFORMATION: pKR2748

<400> SEQUENCE: 22

```
gtacgtctag agtcgacggc gcgcccgatc atccggatat agttcctcct ttcagcaaaa        60
aaccccctcaa gacccgttta gaggccccaa ggggttatgc tagttattgc tcagcggtgg      120
cagcagccaa ctcagcttcc tttcgggctt tgttagcagc cggatcgatc caagctgtac      180
ctcactattc ctttgccctc ggacgagtgc tgggcgtcg gtttccacta tcggcgagta       240
cttctacaca gccatcggtc cagacggccg cgcttctgcg ggcgatttgt gtacgcccga      300
cagtcccggc tccggatcgg acgattgcgt cgcatcgacc ctgcgcccaa gctgcatcat      360
cgaaattgcc gtcaaccaag ctctgataga gttggtcaag accaatgcgg agcatatacg      420
cccggagccg cggcgatcct gcaagctccg gatgcctccg ctcgaagtag cgcgtctgct      480
gctccataca agccaaccac ggcctccaga agaagatgtt ggcgacctcg tattgggaat      540
ccccgaacat cgcctcgctc cagtcaatga ccgctgttat gcggccattg tccgtcagga      600
cattgttgga gccgaaatcc gcgtgcacga ggtgccggac ttcggggcag tcctcggccc      660
aaagcatcag ctcatcgaga gcctgcgcga cggacgcact gacggtgtcg tccatcacag      720
tttgccagtg atacacatgg ggatcagcaa tcgcgcatat gaaatcacgc catgtagtgt      780
attgaccgat tccttgcggt ccgaatgggc cgaacccgct cgtctggcta agatcggccg      840
cagcgatcgc atccatagcc tccgcgaccg gctgcagaac agcgggcagt tcggtttcag      900
gcaggtcttg caacgtgaca ccctgtgcac ggcgggagag caataggtc aggctctcgc       960
tgaattcccc aatgtcaagc acttccggaa tcgggagcgc ggccgatgca aagtgccgat     1020
aaacataacg atctttgtag aaaccatcgg cgcagctatt tacccgcagg acatatccac     1080
gccctcctac atcgaagctg aaagcacgag attcttcgcc ctccgagagc tgcatcaggt     1140
cggagacgct gtcgaacttt tcgatcagaa acttctcgac agacgtcgcg gtgagttcag     1200
gcttttccat gggtatatct ccttcttaaa gttaaacaaa attatttcta gagggaaacc     1260
gttgtggtct ccctatagtg agtcgtatta atttcgcggg atcgagatcg atccaattcc     1320
aatcccacaa aaatctgagc ttaacagcac agttgctcct ctcagagcag aatcgggtat     1380
tcaacaccct catatcaact actacgttgt gtataacggt ccacatgccg gtatatacga     1440
tgactggggt tgtacaaagg cggcaacaaa cggcgttccc ggagttgcac acaagaaatt     1500
tgccactatt acagaggcaa gagcagcagc tgacgcgtac acaacaagtc agcaaacaga     1560
caggttgaac ttcatcccca aggagaagc tcaactcaag cccaagagct tgctaaggc      1620
cctaacaagc ccaccaaagc aaaaagccca ctggctcacg ctaggaacca aaaggcccag     1680
cagtgatcca gccccaaaag agatctcctt tgccccggag attacaatgg acgatttcct     1740
ctatctttac gatctaggaa ggaagttcga aggtgaaggt gacgacacta tgttcaccac     1800
tgataatgag aaggttagcc tcttcaattt cagaaagaat gctgacccac agatgggttag    1860
agaggcctac gcagcaggtc tcatcaagac gatctacccg agtaacaatc tccaggagat     1920
caaatacctt cccaagaagg ttaaagatgc agtcaaaaga ttcaggacta attgcatcaa     1980
gaacacagag aaagacatat ttctcaagat cagaagtact attccagtat ggacgattca     2040
aggcttgctt cataaaccaa ggcaagtaat agagattgga gtctctaaaa aggtagttcc     2100
tactgaatct aaggccatgc atggagtcta agattcaaat cgaggatcta acagaactcg     2160
ccgtgaagac tggcgaacag ttcatacaga gtcttttacg actcaatgac aagaagaaaa     2220
```

```
tcttcgtcaa catggtggag cacgacactc tggtctactc caaaaatgtc aaagatacag    2280
tctcagaaga ccaaagggct attgagactt ttcaacaaag gataatttcg ggaaacctcc    2340
tcggattcca ttgcccagct atctgtcact tcatcgaaag gacagtagaa aaggaaggtg    2400
gctcctacaa atgccatcat tgcgataaag gaaaggctat cattcaagat gcctctgccg    2460
acagtggtcc caaagatgga cccccaccca cgaggagcat cgtggaaaaa gaagacgttc    2520
caaccacgtc ttcaaagcaa gtggattgat gtgacatctc cactgacgta agggatgacg    2580
cacaatccca ctatccttcg caagacccct cctctatata aggaagttca tttcatttgg    2640
agaggacacg ctcgagctca tttctctatt acttcagcca taacaaaaga actctttttct   2700
cttcttatta aaccatgaaa aagcctgaac tcaccgcgac gtctgtcgag aagtttctga    2760
tcgaaaagtt cgacagcgtc tccgacctga tgcagctctc ggagggcgaa gaatctcgtg    2820
ctttcagctt cgatgtagga gggcgtggat atgtcctgcg ggtaaatagc tgcgccgatg    2880
gtttctacaa agatcgttat gtttatcggc actttgcatc ggccgcgctc ccgattccgg    2940
aagtgcttga cattggggaa ttcagcgaga gcctgaccta ttgcatctcc cgccgtgcac    3000
agggtgtcac gttgcaagac ctgcctgaaa ccgaactgcc cgctgttctg cagccggtcg    3060
cggaggccat ggatgcgatc gctgcggccg atcttagcca cgagcgggg ttcggcccat    3120
tcggaccgca aggaatcggt caatacacta catggcgtga tttcatatgc gcgattgctg    3180
atccccatgt gtatcactgg caaactgtga tggacgacac cgtcagtgcg tccgtcgcgc    3240
aggctctcga tgagctgatg ctttgggccg aggactgccc cgaagtccgg cacctcgtgc    3300
acgcggattt cggctccaac aatgtcctga cggacaatgg ccgcataaca gcggtcattg    3360
actggagcga ggcgatgttc ggggattccc aatacgaggt cgccaacatc ttcttctgga    3420
ggccgtggtt ggcttgtatg gagcagcaga cgcgctactt cgagcggagg catccggagc    3480
ttgcaggatc gccgcggctc cgggcgtata tgctccgcat tggtcttgac caactctatc    3540
agagcttggt tgacggcaat ttcgatgatg cagcttgggc gcagggtcga tgcgacgcaa    3600
tcgtccgatc cggagccggg actgtcgggc gtacacaaat cgcccgcaga agcgcggccg    3660
tctggaccga tggctgtgta aagtactcg ccgatagtgg aaaccgacgc cccagcactc    3720
gtccgagggc aaaggaatag tgaggtacct aaagaaggag tgcgtcgaag cagatcgttc    3780
aaacatttgg caataaagtt tcttaagatt gaatcctgtt gccggtcttg cgatgattat    3840
catataattt ctgttgaatt acgttaagca tgtaataatt aacatgtaat gcatgacgtt    3900
atttatgaga tgggttttta tgattagagt cccgcaatta tacatttaat acgcgataga    3960
aaacaaaata tagcgcgcaa actaggataa attatcgcgc gcggtgtcat ctatgttact    4020
agatcgatgt cgaatctgat caacctgcat taatgaatcg gccaacgcgc ggggagaggc    4080
ggtttgcgta ttgggcgctc ttccgcttcc tcgctcactg actcgctgcg ctcggtcgtt    4140
cggctgcggc gagcggtatc agctcactca aaggcggtaa tacggttatc cacagaatca    4200
ggggataacg caggaaagaa catgtgagca aaaggccagc aaaaggccag gaaccgtaaa    4260
aaggccgcgt tgctggcgtt tttccatagg ctccgccccc ctgacgagca tcacaaaaat    4320
cgacgctcaa gtcagaggtg gcgaaacccg acaggactat aaagatacca ggcgtttccc    4380
cctggaagct ccctcgtgcg ctctcctgtt ccgaccctgc cgcttaccgg atacctgtcc    4440
gcctttctcc cttcgggaag cgtggcgctt tctcaatgct cacgctgtag gtatctcagt    4500
tcggtgtagg tcgttcgctc caagctgggc tgtgtgcacg aaccccccgt tcagcccgac    4560
```

```
cgctgcgcct tatccggtaa ctatcgtctt gagtccaacc cggtaagaca cgacttatcg    4620
ccactggcag cagccactgg taacaggatt agcagagcga ggtatgtagg cggtgctaca    4680
gagttcttga agtggtggcc taactacggc tacactagaa ggacagtatt tggtatctgc    4740
gctctgctga agccagttac cttcggaaaa agagttggta gctcttgatc cggcaaacaa    4800
accaccgctg gtagcggtgg ttttttttgtt tgcaagcagc agattacgcg cagaaaaaaa    4860
ggatctcaag aagatccttt gatcttttct acggggtctg acgctcagtg gaacgaaaac    4920
tcacgttaag ggattttggt catgacatta acctataaaa ataggcgtat cacgaggccc    4980
tttcgtctcg cgcgtttcgg tgatgacggt gaaaacctct gacacatgca gctcccggag    5040
acggtcacag cttgtctgta agcggatgcc gggagcagac aagcccgtca gggcgcgtca    5100
gcgggtgttg gcgggtgtcg gggctggctt aactatgcgg catcagagca gattgtactg    5160
agagtgcacc atatggacat attgtcgtta gaacgcggct acaattaata cataacctta    5220
tgtatcatac acatacgatt taggtgacac tatagaacgg cgcgccaagc ttggatcctc    5280
tagacctgca ggccaactgc gtttgggct ccagattaaa cgacgccgtt tcgttccttt    5340
cgcttcacgg cttaacgatg tcgtttctgt ctgtgcccaa aaaataaagg catttgttat    5400
ttgcaccaga tatttactaa gtgcacccta gtttgacaag taggcgataa ttacaaatag    5460
atgcggtgca aataataaat tttgaaggaa ataattacaa agaacagaa cttatattta    5520 cttttatttta aaaactaaa atgaaagaac aaaaaaagta aaaatacaa aaatgtgct     5580 ttaaccactt tcattatttg ttacagaaag tatgattcta ctcaaattga tctgttgtat    5640
ctggtgctgc cttgtcacac tggcgatttc aatcccctaa agatatggtg caaactgcga    5700
agtgatcaat atctgctcgg ttaatttaga ttaattaata atattcaacg tgatgtacca    5760
aaaaaagaca attttttgct ccattgacaa attaaacctc atcaaggtaa tttccaaacc    5820
tataagcaaa aaaatttcac attaattggc ccgcaatcct attagtctta ttatactaga    5880
gtaggaaaaa aaacaattac acaacttgtc ttattattct ctatgctaat gaatattttt    5940
cccttttgtt agaaatcagt gtttcctaat ttattgagta ttaattccac tcaccgcata    6000
tatttaccgt tgaataagaa aattttacac ataattcttt ttaagataaa taatttttt    6060 atactagatc ttatatgatt acgtgaagcc aagtgggtta tactaatgat atataatgtt    6120
tgatagtaat cagtttataa accaaatgca tggaaatgtt acgtggaagc acgtaaatta    6180
acaagcattg aagcaaatgc agccaccgca ccaaaaccac cccacttcac ttccacgtac    6240
catattccat gcaactacaa caccctaaaa cttcaataaa tgcccccacc ttcacttcac    6300
ttcacccatc aatagcaagc ggccgcacca tggctggagg atcatacgag gaagccattg    6360
cagcgttgac gaagcttctc agcgagaaag ccgacctggg tggtgtcgcc gccgcaaaga    6420
taaaacagct gacggcggag ctggataccg ccaccgcaaa cgggtcgacg ccgtttaacc    6480
cggacgagag gatccgaacc gggttcgccc acttcaagaa cgagaaatac cagaagaacc    6540
cggaattata tggcgaactt gccaaaggcc agagtccaaa gtttatggtt tttgcttgct    6600
cagactctcg agtttgccca tcccacattc tggatttcaa tccgggtgaa gcctttgtgg    6660
tccgaaatat cgccaacatg gttccaccat atgacaagac caagtattca ggaaccgggg    6720
cggccattga atatgcagtc ttcatttaa aggtggagaa tattgtggtc attgggcaca    6780
gctgctgtgg aggtataaag ggcctaatgt ctatcccaga tgatgggacc actgcaagtg    6840 aattcatagac gcactgggtc caaatttgca ctccagcaaa gtccaaggtt aaaacagaag    6900
caaacacatt agaattctct gagcaatgta ccagctgcga gaaggaagct gtgaatgtat    6960
```

```
cacttgggaa cctattgaca tatcgatttg tgagagatgc agttgtgaag aaaactcttg   7020
ccttgaaagg tgcacattac aatttcgtta aaggcacatt tgagctgtgg gatctggact   7080
tgaaaaactc taactctgta tccgtttaag cggccgcgaa gttaaaagca atgttgtcac   7140
ttgtcgtact aacacatgat gtgatagttt atgctagcta gctataacat aagctgtctc   7200
tgagtgtgtt gtatattaat aaagatcatc actggtgaat ggtgatcgtg tacgtaccct   7260
acttagtagg caatggaagc acttagagtg tgctttgtgc atggccttgc ctctgttttg   7320
agacttttgt aatgttttcg agtttaaatc tttgcctttg cgtacccatc tgcaggtaaa   7380
ttgcagctga aggacagtga agggtgaatt tatccattta aaccattttc tttttaacac   7440
atttcttatg gtaatctctt ctcactacac tataaaaatg gcttctcaat cccatttcct   7500
acatcatccc attctattga gttttgttta tttgctttca cttttttttt tatctgcctc   7560
ttcccttaat ttgcttgact tcttcttcac attttgcttt gttttctcct ccggcttccg   7620
gtatttcaaa ttcaagatga gcaagttgaa atttataaat agaaatacag atattattta   7680
caacgtcaaa tctttggtat tttcaatatt tgaatggggt aaatttgtca tatagtcatc   7740
atcactgact acttatctaa cctatttaat ttggagcata ttctttataa ggtccctctc   7800
acggccaatg tctaattatt gatatacagc tcttgttttc tagtgctgct tataatatta   7860
tctacacata tatatggtac tgcacactac tactatatag tagtaagtaa actagcaaca   7920
gccggggcca aactccaata actaggcatt ggggtttagt tggtaatata aatataacat   7980 caaaagtct ttgcttgtga cgaacatcac aatgcaccca ccattgatgc cacgacagac   8040
attgttaatt ttttttttaa ttttttaaaaa agaagcaatt ccaatagttc tatattacaa   8100
tctcacgtga tccaagcaca acgtttcatt ttttgtacat gctcgatata taaataaat   8160 ttcattttat agtaaaatat aatgacattt tcgaatataa ttttgaaat ttcattttcc   8220 aaatgaaata ctaatattaa tattaatgag attaccacaa atcatgttat gaatgaaata   8280
aagagttttg gcattctaac tttctttgaa tagaacaaaa tgtatacaac actctccata   8340
tatacacgat ttattcaggg atcatataca ttctctcatg attaacatag tctgctttct   8400
tcacgtctaa gcagataatt tttggtccac aagataaaat tatcattagt cgttttaatt   8460
aattccttga gcatcaagca ctaaaataat taaacttctc cattaccaaa aaaaaaagat   8520
aggtgattca gtaacatgta gtactagtac tactgatttt ttttttcttt tgattttaat   8580
gaatggttcg tatcgagcat cgagaaatcc atttattagg tgtgtaatgt aatagtagta   8640
tttccttgat tttcagtaat aagatggatt cttacattta tatctgtttg acagaaaatg   8700
ttgtcaatgc atttcttggg cacaaagttt tttgaaacat gaattaattt tttcaaaata   8760
tttatgacat caaattgacc ctaaaataag tgataaagct ttaacgtgga atgacattaa   8820 ttttccatg ataaataaaa cacttaaaac atttaatat taatattata atcagttaca   8880
actatgttca attaatgcaa taacttttaa ataaatatta aaatatttt tttctgttct   8940 ccaataaaga gatcttgttg cacggaaaaa gtcacattct tatttagtaa aaaattataa   9000
ttattgtttg aaaaatatca ttttcactgc agaaaatttg atccagctct acagatcata   9060
cttttattgt acaataatac aataaaaata ttcatctgca ggaaatatca ttttcattgt   9120
acaataatat aaagataaat atataccaga aaagaaaaag aaactgatgt ggcacaatgt   9180
attcactgaa agaatgcata ttgtatttca cctttcaagc agcactaaga atatacttct   9240
tttattatac ttgtgcattt actcaaccac cctcggtgga gtaagaaaga agatagataa   9300
```

```
aagttttttt tgacatttgg tgaatctctt aattaaaaaa ataaaataat ccatttcctt      9360
tatttaattt cttttttccc atctgtgaaa ttccaattct gcttcgcgct cctgtctata      9420
aattgactta gccaccacct cagtttccat tcattcactt cttctcttta tacccccct      9480 ctcttttttg cgttcattct gttttcgtaa gtactgttgt ttttctcttc tatttctttt      9540
tttgtttgtg ttgttttttt ttcttcctta tcgttgttct gcctctcctc tgtttcggtg      9600
ctctgttcac cacttccacg tgagaatgat cttccttctt tgcatgttca ttctctcgtg      9660
accactggat cagactccat gttctgatcc agggtctctc tctaacgcct gtactttcat      9720
ccatgaccac cttaaaaaca acatgggggt ggtgctgtta cactaactct gtttctgggg      9780
tgctgtcttt gttcaatttt actcagaaaa tatctttct tggattctat tcggtgtgtg      9840
ggaacatgat cctgtcggtc ggttgttttt aggttaatcc ttaactggtt acaaggatct      9900
aacgcttgaa tgcatgtcct gagttaaaga aacaaaagaa gaacacacct agtacagcct      9960
ggcctcgaac caagaacttc tttgttggtt tctcattatt actaaaataa aataaagtat      10020
acgttttctt ttttctttgg gatgaacggt tcagacttat gagaagttta agctaatcct      10080
gtagtggagt gttcaattta ttttaaactt taaagcaata gctcaagcac taaacttctt      10140
tttcaagttc aaccactttg gtagcttgct aattgctgct attgttctaa ttaattaatg      10200
taattattgt ttaaaaaga aaagttggtg acactggaat aaaaaagtgt actatctggc      10260
aattattctt ctgcagcaat gtttgaggtt gaaatcttag tagaacaaag tagaagatct      10320
ggtatttata ttttttgtag acagatggtg ggggtgggtg gtaggccttg aaatccaata      10380
tagttttgta gaataatttt attatttttt tttttgctc acttgtttgt ggtattgatt      10440
ttgtgatgac tcaagattaa tgatttacct tcatttttt catggtgaca tattatgtat      10500
attcttgatc tgtttcttac acttctttt cgttgttgta gctgttgaag tctgcggccg      10560
catggagaga tctcaacggc agtctcctcc gccaccgtcg ccgtcctcct cctcgtcctc      10620 cgtccgcg acaccgtcc tcgtccctcc cggaaagagg cggagggcgg cgacggccaa      10680
ggccggcgcc gagcctaata agaggatccg caaggacccc gccgccgccg ccgcggggaa      10740
gaggagctcc gtctacaggg gagtcaccag gcacaggtgg acgggcaggt tcgaggcgca      10800
tctctgggac aagcactgcc tcgccgcgct ccacaacaag aagaaaggca ggcaagtcta      10860
cctgggggcg tatgacagcg aggaggcagc tgctcgtgcc tatgacctcg cagctctcaa      10920
gtactggggt cctgagactc tgctcaactt ccctgtggag gattactcca gcgagatgcc      10980
ggagatggag gccgtgtccc gggaggagta cctggcctcc ctccgccgca ggagcagcgg      11040
cttctccagg ggcgtctcca agtacagagg cgtcgccagg catcaccaca acgggaggtg      11100
ggaggcacgg attgggcgag tctttgggaa caagtacctc tacttgggaa catttgacac      11160
tcaagaagag gcagccaagg cctatgacct tgcggccatt gaataccgtg gcgtcaatgc      11220
tgtaaccaac ttcgacatca gctgctacct ggaccacccg ctgttcctgg cacagctcca      11280
acaggtgcca caggtggtgc cggcactcaa ccaagaacct caacctgatc agagcgaaac      11340
cggaactaca gagcaagagc cggagtcaag cgaagccaag acaccggatg gcagtgcaga      11400
acccgatgag aacgcggttc ctgacgcacac cgcggagccc ctcaccacag tcgacgcacag      11460 catcgaagag ggcttgtgga gcccttgcat ggattacgag ctagacacca tgtcgagacc      11520
aaactttggc agctcaatca atctgagcga gtggttcgct gacgcagact tcgactgcaa      11580
catcggatgc tgttcgatg ggtgttctgc ggctgacgaa ggaagcaagg atggtgtagg      11640
tctggcagat ttcagtctgt ttgaggcagg tgatgtccag ctgaaggatg ttctttcgga      11700
```

```
tatggaagag gggatacaac ctccagcgat gatcagtgtg tgcaactaag cggccgcatt   11760
tcgcaccaaa tcaatgaaag taataatgaa aagtctgaat aagaatactt aggcttagat   11820
gcctttgtta ctcgtgtaaa ataacttgag tcatgtacct ttggcggaaa cagaataaat   11880
aaaaggtgaa attccaatgc tctatgtata agttagtaat acttaatgtg ttctacggtt   11940
gtttcaatat catcaaactc taattgaaac tttagaacca caaatctcaa tcttttctta   12000
atgaaatgaa aaatcttaat tgtaccatgt ttatgttaaa caccttacaa ttaattggtt   12060
ggagaggagg accaaccgat gggacaacat gggagaaag agattcaatg gagatttgga    12120
taggagaaca acattctttt tcacttcaat acaagatgag tgcaacacta aggatatgta   12180
tgagactttc agaagctacg acaacataga tgagtgaggt ggtgattcct agcaagaaag   12240
acattagagg aagccaaaat cgaacaagga agacatcaag gcaagagac aggaccatcc     12300 atctcaggaa aaggagcttt gggatagtcc gagaagttgt acaagaaatt ttttggaggg   12360
tgagtgatgc attgctggtg actttaactc aatcaaaatt gagaaagaaa gaaaaggag    12420 ggggctcaca tgtgaataga agggaaacgg gagaatttta cagttttgat ctaatgggca   12480
tcccagctag tggtaacata ttcaccatgt ttaaccttca c                       12521

<210> SEQ ID NO 23
<211> LENGTH: 1736
<212> TYPE: DNA
<213> ORGANISM: artificial sequence
<220> FEATURE:
<223> OTHER INFORMATION: hairpin Gas123hp

<400> SEQUENCE: 23
gcggccgctc tagaccacct aacatcacca ccgttgttgc caatgtcacc accgagcaat     60
tacccaaggc tcgtggagga agtgggcgtg ccttcgtgac cttcttgct ggaaacggtg     120 attatgtaaa gggtgttgtg ggtttggcca aaggactgag aaaggccaaa agcatgtacc    180
ctttggtggt tgctgtgtta ccagatgttc ctgaagaaca tcgtgcgatt ctcaaatccc    240
aaggttgcat tgtcagggag attgaacctg tgtaccctcc tgagaaccag acccagttcg    300
ggatccatat tacgtcatca actattccaa gctacgtatt tgggagtttg tggagttcag    360
caagatgata tacctagacg gtgatataca agtgtttgac aatattgacc acttgtttga    420
cttgcctgat aactactttt atgcggtgat ggactgtttt tgtgagccca cttggggcca    480
cactctgcag tcatgaccta ttgaaaacgg tgcaagtcac cactcccacc tcgttcgctg    540
aacaagattt cttgaacatg tacttcaagg acatttacag gccaatccct ttaaattaca    600
atcttgtcct cgccatgctg tggcgccacc cggaaaacgt taaattagac caagtcaagg    660
ttgttcacta ttgcgcagcg gggtccaagc catggagata tacggggaag gaagagaata   720
tgcagaggga ggacataaag atgctggtga agaaatggtg ggatatctac aatgatgctt    780
cgcttgacta caagccattg atgaatgcaa gtgaagctcc agcagcggat ggtgttgaca    840
ttgaacaatt cgtgcaggct ctatcagagg ttggtcatgt tcaatatgtc accgaattct    900
atgtcctccc tctgcatatt ctcttccttc ccgtatatc tccatggctt ggaccccgct     960
gcgcaatagt gaacaacctt gacttggtct aatttaacgt tttccgggtg cgccacagc    1020 atggcgagga caagattgta atttaaaggg attggcttgt aaatgtcctt gaagtacatg   1080
ttcaagaaat cttgttcagc gaacgaggtg ggagtggtga cttgcaccgt tttcaatagg   1140
tcatgaaagc ttacacaaac atgccagcat tgaaatagag aggaggcttg gcccaaagt    1200
```

```
gagtgggcca ctgaacctta tgagggcact gctggcagta tccgatttga tactgcagag   1260
tgtggcccca agtgggctca caaaaacagt ccatcaccgc ataaaagtag ttatcaggca   1320
agtcaaacaa gtggtcaata ttgtcaaaca cttgtatatc accgtctagg tatatcatct   1380
tgctgaactc cacaaactcc caaatacgta gcttggaata gttgatgacg taatatgtcg   1440
accgaactgg gtctggttct caggagggta cacaggttca atctccctga caatgcaacc   1500
ttgggatttg agaatctcac gatgttcttc aggaacatct ggtaacacag caaccaccaa   1560
agggtacatg cttttggcct ttctcagtcc tttggccaaa cccacgacac cctttacgta   1620
atcaccgttc ccagcaagaa aggtcacgaa ggcacgccca cttcctccac gagccttggg   1680
taattgctcg gtggtgacat tggcaacaac ggtggtgatg ttaggtgggc ggccgc       1736

<210> SEQ ID NO 24
<211> LENGTH: 16111
<212> TYPE: DNA
<213> ORGANISM: artificial sequence
<220> FEATURE:
<223> OTHER INFORMATION: vector PHP70086

<400> SEQUENCE: 24
ctgctgccag tggcgataag tcgtgtctta ccgggttgga ctcaagacga tagttaccgg     60
ataaggcgca gcggtcgggc tgaacggggg gttcgtgcac acagcccagc ttggagcgaa    120
cgacctacac cgaactgaga tacctacagc gtgagctatg agaaagcgcc acgcttcccg    180
aagggagaaa ggcggacagg tatccggtaa gcggcagggt cggaacagga gagcgcacga    240
gggagcttcc aggggggaaac gcctggtatc tttatagtcc tgtcgggttt cgccacctct    300
gacttgagcg tcgatttttg tgatgctcgt caggggggcg gagcctatgg aaaaacgcca    360
gcaacgcggc cttttttacgg ttcctggcct tttgctggcc ttttgctcac atgttctttc    420
ctgcgttatc ccctgattct gtggataacc gtattaccgc ctttgagtga gctgataccg    480
ctcgccgcag ccgaacgacc gagcgcagcg agtcagtgag cgaggaagcg gaagagcgcc    540
caatacgcaa accgcctctc cccgcgcgtt ggccgattca ttaatgcagg ttgatcagat    600
ctcgatcccg cgaaattaat acgactcact atagggagac cacaacggtt tccctctaga    660
aataattttg tttaacttta agaaggagat atacccatgg aaaagcctga actcaccgcg    720
acgtctgtcg agaagtttct gatcgaaaag ttcgacagcg tctccgacct gatgcagctc    780
tcggagggcg aagaatctcg tgctttcagc ttcgatgtag gagggcgtgg atatgtcctg    840
cgggtaaata gctgcgccga tggtttctac aaagatcgtt atgtttatcg gcactttgca    900
tcggccgcgc tcccgattcc ggaagtgctt gacattgggg aattcagcga gagcctgacc    960
tattgcatct cccgccgtgc acagggtgtc acgttgcaag acctgcctga aaccgaactg   1020
cccgctgttc tgcagccggt cgcggaggct atggatgcga tcgctgcggc cgatcttagc   1080
cagacgagcg ggttcggccc attcggaccg caaggaatcg gtcaatacac tacatggcgt   1140
gatttcatat gcgcgattgc tgatccccat gtgtatcact ggcaaactgt gatggacgac   1200
accgtcagtg cgtccgtcgc gcaggctctc gatgagctga tgctttgggc cgaggactgc   1260
cccgaagtcc ggcacctcgt gcacgcggat ttcggctcca acaatgtcct gacggacaat   1320
ggccgcataa cagcggtcat tgactggagc gaggcgatgt tcgggattc ccaatacgag   1380 gtcgccaaca tcttcttctg gaggccgtgg ttggcttgta tggagcagca gacgcgctac   1440
ttcgagcgga ggcatccgga gcttgcagga tcgccgcggc tccgggcgta tatgctccgc   1500
attggtcttg accaactcta tcagagcttg gttgacggca atttcgatga tgcagcttgg   1560
```

```
gcgcagggtc gatgcgacgc aatcgtccga tccggagccg ggactgtcgg gcgtacacaa   1620
atcgcccgca gaagcgcggc cgtctggacc gatggctgtg tagaagtact cgccgatagt   1680
ggaaaccgac gccccagcac tcgtccgagg gcaaaggaat agtgaggtac agcttggatc   1740
gatccggctg ctaacaaagc ccgaaaggaa gctgagttgg ctgctgccac cgctgagcaa   1800
taactagcat aaccccttgg ggcctctaaa cgggtcttga ggggtttttt gctgaaagga   1860
ggaactatat ccgatgatc gtcgaggcct cacgtgttaa cagaagttcc tattccgaag   1920
ttcctattct ctagaaagta taggaacttc caccacacaa cacaatggcg gccaccgctt   1980
ccagaaccac ccgattctct tcttcctctt cacaccccac cttccccaaa cgcattacta   2040
gatccaccct ccctctctct catcaaaccc tcaccaaacc caaccacgct ctcaaaatca   2100
aatgttccat ctccaaaccc cccacggcgg cgcccttcac caaggaagcg ccgaccacgg   2160
agcccttcgt gtcacggttc gcctccggcg aacctcgcaa gggcgcggac atccttgtgg   2220
aggcgctgga gaggcagggc gtgacgacgg tgttcgcgta ccccggcggt gcgtcgatgg   2280
agatccacca ggcgctcacg cgctccgccg ccatccgcaa cgtgctcccg cgccacgagc   2340
agggcggcgt cttcgccgcc gaaggctacg cgcgttcctc cggcctcccc ggcgtctgca   2400
ttgccacctc cggccccggc gccaccaacc tcgtgagcgg cctcgccgac gctttaatgg   2460
acagcgtccc agtcgtcgcc atcaccggcc aggtcagccg ccggatgatc ggcaccgacg   2520
ccttccaaga aaccccgatc gtggaggtga gcagatccat cacgaagcac aactacctca   2580
tcctcgacgt cgacgacatc ccccgcgtcg tcgccgaggc tttcttcgtc gccacctccg   2640
gccgccccgg tccggtcctc atcgacattc ccaaagacgt tcagcagcaa ctcgccgtgc   2700
ctaattggga cgagcccgtt aacctccccg gttacctcgc caggctgccc aggcccccg    2760 ccgaggccca attggaacac attgtcagac tcatcatgga ggcccaaaag cccgttctct   2820
acgtcggcgg tggcagtttg aattccagtg ctgaattgag gcgctttgtt gaactcactg   2880
gtattcccgt tgctagcact ttaatgggtc ttggaacttt tcctattggt gatgaatatt   2940
cccttcagat gctgggtatg catggtactg tttatgctaa ctatgctgtt gacaatagtg   3000
atttgttgct tgcctttggg gtaaggtttg atgaccgtgt tactgggaag cttgaggctt   3060
ttgctagtag ggctaagatt gttcacattg atattgattc tgccgagatt gggaagaaca   3120
agcaggcgca cgtgtcggtt tgcgcggatt tgaagttggc cttgaaggga attaatatga   3180
ttttggagga gaaaggagtg gagggtaagt ttgatcttgg aggttggaga gaagagatta   3240
atgtgcagaa acacaagttt ccattgggtt acaagacatt ccaggacgcg atttctccgc   3300
agcatgctat cgaggttctt gatgagttga ctaatggaga tgctattgtt agtactgggg   3360
ttgggcagca tcaaatgtgg gctgcgcagt tttacaagta caagagaccg aggcagtggt   3420
tgacctcagg gggtcttgga gccatgggtt ttggattgcc tgcggctatt ggtgctgctg   3480
ttgctaaccc tggggctgtt gtggttgaca ttgatgggga tggtagtttc atcatgaatg   3540
ttcaggagtt ggccactata agagtggaga atctcccagt taagatattg ttgttgaaca   3600
atcagcattt gggtatggtg gttcagtggg aggataggtt ctacaagtcc aatagagctc   3660
acacctatct tggagatccg tctagcgaga gcgagatatt cccaaacatg ctcaagtttg   3720
ctgatgcttg tgggataccg gcagcgcgag tgacgaagaa ggaagagctt agagcggcaa   3780
ttcagagaat gttggacacc cctggcccct accttcttga tgtcattgtg ccccatcagg   3840
agcatgtgtt gccgatgatt cccagtaatg gatccttcaa ggatgtgata actgagggtg   3900
```

```
atggtagaac gaggtactga ctagctagtc agttaaccta gacttgtcca tcttctggat    3960
tggccaactt aattaatgta tgaaataaaa ggatgcacac atagtgacat gctaatcact    4020
ataatgtggg catcaaagtt gtgtgttatg tgtaattact agttatctga ataaaagaga    4080
aagagatcat ccatatttct tatcctaaat gaatgtcacg tgtctttata attctttgat    4140
gaaccagatg catttcatta accaaatcca tatacatata aatattaatc atatataatt    4200
aatatcaatt gggttagcaa aacaaatcta gtctaggtgt gttttgcccc caagcttatc    4260
gataccgtcg gcgcggggta cgttagctga ttaagtcagc atgcgcggcc ggcgtatgaa    4320
ctaaaatgca tgtaggtgta agagctcatg gagagcatgg aatattgtat ccgaccatgt    4380
aacagtataa taactgagct ccatctcact tcttctatga ataaacaaag gatgttatga    4440
tatattaaca ctctatctat gcaccttatt gttctatgat aaatttcctc ttattattat    4500
aaatcatctg aatcgtgacg gcttatggaa tgcttcaaat agtacaaaaa caaatgtgta    4560
ctataagact ttctaaacaa ttctaacctt agcattgtga acgagacata agtgttaaga    4620
agacataaca attataatgg aagaagtttg tctccattta tatattatat attacccact    4680
tatgtattat attaggatgt taaggagaca taacaattat aaagagagaa gtttgtatcc    4740
atttatatat tatatactac ccatttatat attatactta tccacttatt taatgtcttt    4800
ataaggtttg atccatgata tttctaatat tttagttgat atgtatatga aaaggtacta    4860
tttgaactct cttactctgt ataaaggttg gatcatcctt aaagtgggtc tatttaattt    4920
tattgcttct tacagataaa aaaaaaatta tgagttggtt tgataaaata ttgaaggatt    4980
taaaataata ataataaca tataatatat gtatataaat ttattataat ataacattta    5040
tctataaaaa agtaaatatt gtcataaatc tatacaatcg tttagccttg ctggaacgaa    5100
tctcaattat ttaaacgaga gtaaacatat ttgactttt ggttatttaa caaattatta    5160
tttaacacta tatgaaattt tttttttat cagcaaagaa taaaattaaa ttaagaagga    5220
caatggtgtc ccaatcctta tacaaccaac ttccacaaga aagtcaagtc agagacaaca    5280
aaaaaacaag caaaggaaat ttttaattt gagttgtctt gtttgctgca taatttatgc    5340
agtaaaacac tacacataac ccttttagca gtagagcaat ggttgaccgt gtgcttagct    5400
tctttattt tattttttta tcagcaaaga ataaataaaa taaaatgaga cacttcaggg    5460
atgtttcaac aggtacgatc catgcccttc atttgccgca tattaattaa tttggtaaca    5520
gtccgtacta atcagttact tatccttccc ccatcataat taatcttggt agtctcgaat    5580
gccacaacac tgactagtct cttggatcat aagaaaagc caaggaacaa aagaagacaa    5640
aacacaatga gagtatcctt tgcatagcaa tgtctaagtt cataaaattc aaacaaaaac    5700
gcaatcacac acagtggaca tcacttatcc actagctgat caggatcgcc gcgtcaagaa    5760
aaaaaaactg gaccccaaaa gccatgcaca acaacacgta ctcacaaagg tgtcaatcga    5820
gcagcccaaa acattcacca actcaaccca tcatgagccc tcacatttgt tgtttctaac    5880
ccaacctcaa actcgtattc tcttccgcca cctcattttt gtttatttca acacccgtca    5940
aactgcatgc caccccgtgg ccaaatgtcc atgcatgtta acaagaccta tgactataaa    6000
tagctgcaat ctcggcccag gttttcatca tcaagaacca gttcaatatc ctagtacacc    6060
gtattaaaga atttaagata tactgcggcc gcatgactat cgactcacaa tactacaagt    6120
cgcgagacaa aaacgacacg gcacccaaaa tcgcgggaat ccgatatgcc ccgctatcga    6180
caccattact caaccgatgt gagacctcct ctctggtctg gcacattttc agcattccca    6240
cttccctcac aattttcatg ctatgctgcg caattccact gctctggcca tttgtgattg    6300
```

```
cgtatgtagt gtacgctgtt aaagacgact ccccgtccaa cggaggagtg gtcaagcgat    6360
actcgcctat ttcaagaaac ttcttcatct ggaagctctt tggccgctac ttccccataa    6420
ctctgcacaa gacggtggat ctggagccca cgcacacata ctaccctctg gacgtccagg    6480
agtatcacct gattgctgag agatactggc cgcagaacaa gtacctccga gcaatcatca    6540
ccaccatcga gtactttctg cccgccttca tgaaacggtc tctttctatc aacgagcagg    6600
agcagcctgc cgagcgagat cctctcctgt ctcccgtttc tcccagctct ccgggttctc    6660
aacctgacaa gtggattaac cacgacagca gatatagccg tggagaatca tctggctcca    6720
acggccacgc ctcgggctcc gaacttaacg gcaacggcaa caacggcacc actaaccgac    6780
gacctttgtc gtccgcctct gctggctcca ctgcatctga ttccacgctt cttaacgggt    6840
ccctcaactc ctacgccaac cagatcattg gcgaaaacga cccacagctg tcgcccacaa    6900
aactcaagcc cactggcaga aaatacatct tcggctacca cccccacggc attatcggca    6960
tgggagcctt tggtggaatt gccaccgagg gagctggatg gtccaagctc tttccgggca    7020
tccctgtttc tcttatgact ctcaccaaca acttccgagt gcctctctac agagagtacc    7080
tcatgagtct gggagtcgct tctgtctcca gaagtcctg caaggccctc ctcaagcgaa    7140
accagtctat ctgcattgtc gttggtggag cacaggaaag tcttctggcc agaccggtg    7200 tcatggacct ggtgctactc aagcgaaagg gttttgttcg acttggtatg gaggtcggaa    7260
atgtcgccct tgttcccatc atggccttg gtgagaacga cctctatgac caggttagca    7320
acgacaagtc gtccaagctg taccgattcc agcagtttgt caagaacttc cttggattca    7380
cccttccttt gatgcatgcc cgaggcgtct tcaactacga tgtcggtctt gtcccctaca    7440
ggcgacccgt caacattgtg gttggttccc ccattgactt gccttatctc ccacacccca    7500
ccgacgaaga agtgtccgaa taccacgacc gatacatcgc cgagctgcag cgaatctaca    7560
acgagcacaa ggatgaatat ttcatcgatt ggaccgagga gggcaaagga gccccagagt    7620
tccgaatgat tgagtaagcg gccgcaagta tgaactaaaa tgcatgtagg tgtaagagct    7680
catggagagc atggaatatt gtatccgacc atgtaacagt ataataactg agctccatct    7740
cacttcttct atgaataaac aaaggatgtt atgatatatt aacactctat ctatgcacct    7800
tattgttcta tgataaattt cctcttatta ttataaatca tctgaatcgt gacggcttat    7860
ggaatgcttc aaatagtaca aaaacaaatg tgtactataa gactttctaa acaattctaa    7920
ccttagcatt gtgaacgaga cataagtgtt aagaagacat aacaattata atggaagaag    7980
tttgtctcca tttatatatt atatattacc cacttatgta ttatattagg atgttaagga    8040
gacataacaa ttataaagag agaagtttgt atccatttat atattatata ctacccattt    8100
atatattata cttatccact tatttaatgt ctttataagg tttgatccat gatatttcta    8160
atattttagt tgatatgtat atgaaaaggt actatttgaa ctctcttact ctgtataaag    8220
gttggatcat ccttaaagtg ggtctatta attttattgc ttcttacaga taaaaaaaaa    8280
attatgagtt ggtttgataa aatattgaag gatttaaaat aataataaat aacatataat    8340
atatgtatat aaatttatta taatataaca tttatctata aaaagtaaa tattgtcata    8400 aatctataca atcgtttagc cttgctggaa cgaatctcaa ttatttaaac gagagtaaac    8460
atatttgact ttttggttat ttaacaaatt attatttaac actatatgaa attttttttt    8520
ttatcagcaa agaataaaat taaattaaga aggacaatgg tgtcccaatc cttatacaac    8580
caacttccac aagaaagtca agtcagagac aacaaaaaaa caagcaaagg aaattttta    8640
```

-continued

```
atttgagttg tcttgtttgc tgcataattt atgcagtaaa acactacaca taacccttttt    8700 agcagtagag caatggttga ccgtgtgctt agcttctttt attttatttt tttatcagca    8760
aagaataaat aaaataaaat gagacacttc agggatgttt caacgtactt tctagacgta    8820
cccatcactt aagtggcgcg ccgtcgacgg atccgtaccc ggggatcctc tagacgtacg    8880
aaaccaactg cgtttggggc tccagattaa acgacgccgt ttcgttcctt tcgcttcacg    8940
gcttaacgat gtcgtttctg tctgtgccca aaaataaag gcatttgtta tttgcaccag    9000
atatttacta agtgcaccct aatttgacaa gtaggcgata attacaaata gatgcggtgc    9060
aaataataaa ttttgaagga aataattaca aagaacaga acttatattt actttatttt    9120
aaaaaactaa aatgaaagaa caaaaaaagt aaaaaataca aaaaatgtgc tttaaccact    9180
ttcattattt gttacagaaa gtatgattct actcaaattg atctgttgta tctggtgctg    9240
ccttgtcaca ctggcgattt caatccccta agatatggt gcaaactgcg aagtgatcaa    9300
tatctgctcg gttaatttag attaattaat aatattcaac gtgatgtacc aaaaaaagac    9360
aattttttgc tccattgtca aattaaacct catcaaggta atttccaaac ctataagcaa    9420
aaaaatttca cattaattgg cccgcaatcc tattagtctt attatactag agtaggaaaa    9480
aaaacaatta cacaacttgt cttattattc tctatgctaa tgaatatttt tccctttgt    9540 tagaaatcag tgtttcctaa tttattgagt attaattcca ctcaccgcat atatttaccg    9600
ttgaataaga aaattttaca cataattctt tttaagataa ataatttttt tatactagat    9660
cttatatgat tacgtgaagc caagtgggtt atactaatga tatataatgt ttgatagtaa    9720
tcagtttata aaccaaatgc atggaaatgt tacgtggaag cacgtaaatt aacaagcatt    9780
gaagcaaatg cagccaccgc accaaaacca ccccacttca cttccacgta ccatattcca    9840
tgcaactaca acaccctaaa acttcaataa atgccccac cttcacttca cttcaccat    9900 caatagcaag cggccgcacc atggctggag gatcatacga ggaagccatt gcagcgttga    9960
cgaagcttct cagcgagaaa gccgacctgg gtggtgtcgc cgccgcaaag ataaaacagc    10020
tgacggcgga gctggatacc gccaccgcaa acgggtcgac gccgtttaac ccggacgaga    10080
ggatccgaac cgggttcgcc cacttcaaga acgagaaata ccagaagaac ccggaattat    10140
atggcgaact tgccaaaggc cagagtccaa agtttatggt ttttgcttgc tcagactctc    10200
gagtttgccc atcccacatt ctggatttca atccgggtga agcctttgtg gtccgaaata    10260
tcgccaacat ggttccacca tatgacaaga ccaagtattc aggaaccggg gcggccattg    10320
aatatgcagt cttacattta aaggtggaga atattgtggt cattgggcac agctgctgtg    10380
gaggtataaa gggcctaatg tctatcccag atgatgggac cactgcaagt gaattcatag    10440
agcactgggg ccaaatttgc actccagcaa agtccaaggt taaaacagaa gcaaacacat    10500
tagaattctc tgagcaatgt accagctgcg agaaggaagc tgtgaatgta tcacttggga    10560
acctattgac atatcgattt gtgagagatg cagttgtgaa gaaaactctt gccttgaaag    10620
gtgcacatta caatttcgtt aagggcacat ttgagctgtg ggatctggac ttgaaaatct    10680
ctaactctgt atccgtttaa gcggccgcga agttaaaagc aatgttgtca cttgtacgta    10740
ctaacacatg atgtgatagt ttatgctagc tagctataac ataagctgtc tctgagtgtg    10800
ttgtatatta ataaagatca tcactggtga atggtgatcg tgtacgtacc ctacttagta    10860
ggcaatggaa gcacttagag tgtgctttgt gcatggcctt gcctctgttt tgagactttt    10920
gtaatgtttt cgagtttaaa tctttgcctt tgcgtacgag tcgacctgca ggtcgactcg    10980
tacgtcctcg aagagaaggg ttaataacac acttttttaa cattttaac acaaattta    11040
```

```
gttatttaaa aatttattaa aaaatttaaa ataagaagag gaactcttta aataaatcta  11100
acttacaaaa tttatgattt ttaataagtt ttcaccaata aaaaatgtca taaaaatatg  11160
ttaaaaagta tattatcaat attctcttta tgataaataa aaagaaaaaa aaaataaaag  11220
ttaagtgaaa atgagattga agtgactttt ggtgtgtata aatatatcaa ccccgccaac  11280
aatttattta atccaaatat attgaagtat attattccat agcctttatt tatttatata  11340
tttattatat aaaagcttta tttgttctag gttgttcatg aaatattttt ttggttttat  11400
ctccgttgta agaaaatcat gtgctttgtg tcgccactca ctattgcagc ttttcatgc   11460
attggtcaga ttgacggttg attgtatttt tgttttttat ggttttgtgt tatgacttaa  11520
gtcttcatct ctttatctct tcatcaggtt tgatggttac ctaatatggt ccatgggtac  11580
atgcatggta aaattaggtg gccaactttg ttgtgaacga tagaatttt ttttatatta   11640
agtaaactat ttttatatta tgaaataata ataaaaaaaa tattttatca ttattaacaa  11700
aatcatatta gttaatttgt taactctata ataaagaaa tactgtaaca ttcacattac   11760
atggtaacat ctttccaccc tttcatttgt tttttgtttg atgactttt tcttgttta    11820
aatttatttc tcttcttta aatttggaat acattatcat catatataaa ctaaatact    11880
aaaaacagga ttacacaaat gataaataat aacacaaata tttataaatc tagctgcaat  11940
atatttaaac tagctatatc gatattgtaa aataaaacta gctgcattga tactgataaa  12000
aaaatatcat gtgctttctg gactgatgat gcagtatact tttgacattg cctttatttt  12060
attttttcaga aaagctttct tagttctggg ttcttcatta tttgtttccc atctccattg  12120
tgaattgaat catttgcttc gtgtcacaaa tacatttagc taggtacatg cattggtcag  12180
attcacggtt tattatgtca tgacttaagt tcatggtagt acattacctg ccacgcatgc  12240
attatattgg ttagatttga taggcaaatt tggttgtcaa caatataaat ataaataatg  12300
tttttatatt acgaaataac agtgatcaaa acaaacagtt ttatctttat taacaagatt  12360
ttgttttttgt ttgatgacgt ttttaatgt ttacgctttc ccccttcttt tgaatttaga  12420
acactttatc atcataaaat caaatactaa aaaaattaca tatttcataa ataataacac  12480
aaatatttt aaaaaatctt aaataataat gaacaatatt acatattatc acgaaaattc   12540
attaataaaa atattatata aataaaatgt aatagtagtt atatgtagga aaaaagtact  12600
gcacgcataa tatatacaaa aaagattaaa atgaactatt ataaataata acactaaatt  12660
aatggtgaat catatcaaaa taatgaaaaa gtaaataaaa tttgtaatta acttctatat  12720
gtattacaca cacaaataat aaataatagt aaaaaaaatt atgataaata tttaccatct  12780
cataaagata tttaaaataa tgataaaaat atagattatt ttttatgcaa ctagctagcc  12840
aaaaagagaa cacgggtata tataaaaga gtaccttaa attctactgt acttccttta    12900
ttcctgacgt ttttatatca agtggacata cgtgaagatt ttaattatca gtctaaatat  12960
ttcattagca cttaatactt ttctgttta ttcctatcct ataagtagtc ccgattctcc   13020
caacattgct tattcacaca actaactaag aaagtcttcc atagccccc aagcggccgc  13080
tctagaccac ctaacatcac caccgttgtt gccaatgtca ccaccgagca attacccaag  13140
gctcgtggag gaagtgggcg tgccttcgtg acctttcttg ctggaaacgg tgattatgta  13200
aagggtgttg tgggtttggc caaaggactg agaaaggcca aaagcatgta ccctttggtg  13260
gttgctgtgt taccagatgt tcctgaagaa catcgtgcga ttctcaaatc ccaaggttgc  13320
attgtcaggg agattgaacc tgtgtaccct cctgagaacc agacccagtt cgggatccat  13380
```

```
attacgtcat caactattcc aagctacgta tttgggagtt tgtggagttc agcaagatga    13440
tatacctaga cggtgatata caagtgtttg acaatattga ccacttgttt gacttgcctg    13500
ataactactt ttatgcggtg atggactgtt tttgtgagcc cacttggggc cacactctgc    13560
agtcatgacc tattgaaaac ggtgcaagtc accactccca cctcgttcgc tgaacaagat    13620
ttcttgaaca tgtacttcaa ggacatttac aggccaatcc ctttaaatta caatcttgtc    13680
ctcgccatgc tgtggcgcca cccggaaaac gttaaattag accaagtcaa ggttgttcac    13740
tattgcgcag cggggtccaa gccatggaga tatacgggga aggaagagaa tatgcagagg    13800
gaggacataa agatgctggt gaagaaatgg tgggatatct acaatgatgc ttcgcttgac    13860
tacaagccat tgatgaatgc aagtgaagct ccagcagcgg atggtgttga cattgaacaa    13920
ttcgtgcagg ctctatcaga ggttggtcat gttcaatatg tcaccgaatt ctatgtcctc    13980
cctctgcata ttctcttcct tccccgtata tctccatggc ttggaccccg ctgcgcaata    14040
gtgaacaacc ttgacttggt ctaatttaac gttttccggg tggcgccaca gcatggcgag    14100
gacaagattg taatttaaag ggattggctt gtaaatgtcc ttgaagtaca tgttcaagaa    14160
atcttgttca gcgaacgagg tgggagtggt gacttgcacc gttttcaata ggtcatgaaa    14220
gcttacacaa acatgccagc attgaaatag agaggaggct gggcccaaa gtgagtgggc     14280 cactgaacct tatgagggca ctgctggcag tatccgattt gatactgcag agtgtggccc    14340
caagtgggct cacaaaaaca gtccatcacc gcataaaagt agttatcagg caagtcaaac    14400
aagtggtcaa tattgtcaaa cacttgtata tcaccgtcta ggtatatcat cttgctgaac    14460
tccacaaact cccaaatacg tagcttggaa tagttgatga cgtaatatgt cgaccgaact    14520
gggtctggtt ctcaggaggg tacacaggtt caatctccct gacaatgcaa ccttgggatt    14580
tgagaatctc acgatgttct tcaggaacat ctggtaacac agcaaccacc aaagggtaca    14640
tgcttttggc ctttctcagt cctttggcca aacccacgac acccttacg taatcaccgt     14700 tcccagcaag aaaggtcacg aaggcacgcc cacttcctcc acgagccttg ggtaattgct    14760
cggtggtgac attggcaaca acggtggtga tgttaggtgg gcggccgcga cacaagtgtg    14820
agagtactaa ataaatgctt tggttgtacg aaatcattac actaaataaa ataatcaaag    14880
cttatatatg ccttccgcta aggccgaatg caaagaaatt ggttctttct cgttatcttt    14940
tgccactttt actagtacgt attaattact acttaatcat ctttgtttac ggctcattat    15000
atccggtcta ggccaaggcc gcgaagttaa aagcaatgtt gtcacttgta cgtactaaca    15060
catgatgtga tagtttatgc tagctagcta aacataagc tgtctctgag tgtgttgtat      15120
attaataaag atcatcactg gtgaatggtg atcgtgtacg taccctactt agtaggcaat    15180
ggaagcactt agagtgtgct ttgtgcatgg ccttgcctct gttttgagac ttttgtaatg    15240
ttttcgagtt taaatctttg cctttgcgta cgtgggcgga tcccctgcag gagatccaag    15300
cttggcgcgc cggaattaat taggtaattt cacgcgccgg atccttaatt aagtctagag    15360
tcgactgttt aattctagtg gccggcctct gcctgcgttc tgctgtggaa gttcctattc    15420
cgaagttcct attctccaga aagtatagga acttcacatg ctgcctcgtg caagtcacga    15480
tctcgagttc tatagtgtca cctaaatcgt atgtgtatga tacataaggt tatgtattaa    15540
ttgtagccgc gttctaacga caatatgtcc atatggtgca ctctcagtac aatctgctct    15600
gatgccgcat agttaagcca gccccgacac ccgccaacac ccgctgacgc gccctgacgg    15660
gcttgtctgc tcccggcatc cgcttacaga caagctgtga ccgtccggg gagctgcatg     15720 tgtcagaggt tttcaccgtc atcaccgaaa cgcgcgagac gaaagggcct cgtgatacgc    15780
```

```
ctattttat aggttaatgt catgaccaaa atcccttaac gtgagttttc gttccactga    15840
gcgtcagacc ccgtagaaaa gatcaaagga tcttcttgag atccttttt tctgcgcgta    15900 atctgctgct tgcaaacaaa aaaaccaccg ctaccagcgg tggtttgttt gccggatcaa    15960
gagctaccaa ctcttttcc gaaggtaact ggcttcagca gagcgcagat accaaatact    16020
gttcttctag tgtagccgta gttaggccac cacttcaaga actctgtagc accgcctaca    16080
tacctcgctc tgctaatcct gttaccagtg g                                   16111
```

<210> SEQ ID NO 25
<211> LENGTH: 1239
<212> TYPE: DNA
<213> ORGANISM: Glycine max

<400> SEQUENCE: 25

```
atgaagaggt ctccagcatc ttcttgttca tcatctactt cctctgttgg gtttgaagct      60
cccattgaaa aagaaggcc taagcatcca aggaggaata atttgaagtc acaaaaatgc     120
aagcagaacc aaaccaccac tggtggcaga agaagctcta tctatagagg agttacaagg    180
cataggtgga cagggaggtt tgaagctcac ctatgggata gagctcttg gaacaacatt     240 cagagcaaga agggtcgaca gtttatttg ggggcatatg atactgaaga atctgcagcc    300
cgtacctatg accttgcagc ccttaaatac tggggaaaag atgcaaccct gaatttcccg    360
atagaaactt ataccaagga gctcgaggaa atggacaagg tttcaagaga gaatatttg     420 gcttcttgc ggcgccaaag cagtggcttt tctagaggcc tgtctaagta ccgtgggtt      480 gctaggcatc atcataatgg tcgctgggaa gcacgaattg gaagagtatg cggaaacaag    540
tacctctact tggggacata taaaactcaa gaggaggcag cagtggcata tgacatggca    600
gcaatagagt accgtggagt caatgcagtg accaattttg acataagcaa ctacatggac    660
aaaataaaga agaaaatga ccaaacccaa caacaacaaa cagaagcaca aacggaaaca    720
gttcctaact cctctgactc tgaagaagta gaagtagaac aacagacaac aacaataacc    780
acaccacccc catctgaaaa tctgcacatg ccaccacagc agcaccaagt tcaatacacc    840
ccccatgtct ctccaaggga agaagaatca tcatcactga tcacaattat ggaccatgtg    900
cttgagcagg atctgccatg gagcttcatg tacactggct tgtctcagtt tcaagatcca    960
aacttggctt tctgcaaagg tgatgatgac ttggtgggca tgtttgatag tgcagggttt    1020
gaggaagaca ttgatttct gttcagcact caacctggtg atgagactga gagtgatgtc    1080
aacaatatga gcgcagtttt ggatagtgtt gagtgtggag acacaaatgg ggctggtgga    1140
agcatgatgc atgtggataa caagcagaag atagtatcat ttgcttcttc accatcatct    1200
acaactacag tttcttgtga ctatgctcta gatctatga                           1239
```

<210> SEQ ID NO 26
<211> LENGTH: 412
<212> TYPE: PRT
<213> ORGANISM: Glycine max

<400> SEQUENCE: 26

```
Met Lys Arg Ser Pro Ala Ser Ser Cys Ser Ser Ser Thr Ser Ser Val
1               5                   10                  15

Gly Phe Glu Ala Pro Ile Glu Lys Arg Arg Pro Lys His Pro Arg Arg
            20                  25                  30

Asn Asn Leu Lys Ser Gln Lys Cys Lys Gln Asn Gln Thr Thr Thr Gly
        35                  40                  45
```

```
Gly Arg Arg Ser Ser Ile Tyr Arg Gly Val Thr Arg His Arg Trp Thr
 50                  55                  60

Gly Arg Phe Glu Ala His Leu Trp Asp Lys Ser Trp Asn Asn Ile
 65                  70                  75                  80

Gln Ser Lys Lys Gly Arg Gln Val Tyr Leu Gly Ala Tyr Asp Thr Glu
                 85                  90                  95

Glu Ser Ala Ala Arg Thr Tyr Asp Leu Ala Ala Leu Lys Tyr Trp Gly
            100                 105                 110

Lys Asp Ala Thr Leu Asn Phe Pro Ile Glu Thr Tyr Thr Lys Glu Leu
        115                 120                 125

Glu Glu Met Asp Lys Val Ser Arg Glu Glu Tyr Leu Ala Ser Leu Arg
    130                 135                 140

Arg Gln Ser Ser Gly Phe Ser Arg Gly Leu Ser Lys Tyr Arg Gly Val
145                 150                 155                 160

Ala Arg His His His Asn Gly Arg Trp Glu Ala Arg Ile Gly Arg Val
                165                 170                 175

Cys Gly Asn Lys Tyr Leu Tyr Leu Gly Thr Tyr Lys Thr Gln Glu Glu
            180                 185                 190

Ala Ala Val Ala Tyr Asp Met Ala Ala Ile Glu Tyr Arg Gly Val Asn
        195                 200                 205

Ala Val Thr Asn Phe Asp Ile Ser Asn Tyr Met Asp Lys Ile Lys Lys
    210                 215                 220

Lys Asn Asp Gln Thr Gln Gln Gln Thr Glu Ala Gln Thr Glu Thr
225                 230                 235                 240

Val Pro Asn Ser Ser Asp Ser Glu Glu Val Glu Gln Gln Thr
                245                 250                 255

Thr Thr Ile Thr Thr Pro Pro Ser Glu Asn Leu His Met Pro Pro
                260                 265                 270

Gln Gln His Gln Val Gln Tyr Thr Pro His Val Ser Pro Arg Glu Glu
            275                 280                 285

Glu Ser Ser Ser Leu Ile Thr Ile Met Asp His Val Leu Glu Gln Asp
    290                 295                 300

Leu Pro Trp Ser Phe Met Tyr Thr Gly Leu Ser Gln Phe Gln Asp Pro
305                 310                 315                 320

Asn Leu Ala Phe Cys Lys Gly Asp Asp Asp Leu Val Gly Met Phe Asp
                325                 330                 335

Ser Ala Gly Phe Glu Glu Asp Ile Asp Phe Leu Phe Ser Thr Gln Pro
            340                 345                 350

Gly Asp Glu Thr Glu Ser Asp Val Asn Asn Met Ser Ala Val Leu Asp
        355                 360                 365

Ser Val Glu Cys Gly Asp Thr Asn Gly Ala Gly Gly Ser Met Met His
    370                 375                 380

Val Asp Asn Lys Gln Lys Ile Val Ser Phe Ala Ser Ser Pro Ser Ser
385                 390                 395                 400

Thr Thr Thr Val Ser Cys Asp Tyr Ala Leu Asp Leu
                405                 410
```

<210> SEQ ID NO 27
<211> LENGTH: 1185
<212> TYPE: DNA
<213> ORGANISM: Glycine max

<400> SEQUENCE: 27
atgtttcctg tgtcttcacc atccatccgt cactcactgc ttgggcaatc tctaaccacc    60

```
accaccaccc cgcagcacca aaccctatgc cacaaactta accctgaaag agaaccaact    120
actacagtca cagaaaacca aaaaacact gtgttgtgtg tgtgtcaaaa aaaaaaccct    180
aagctaatga tgatggatca gcgacagcga gagaagctgc ttcacaaaac cgaggcctgt    240
gctttcgtgg caggtgttgt tccggagctt tcccttgtca ccgttccagg gaacaacacc    300
aacaacgtta acaacaacaa caacgttgtt tctcattctc aatctaacgg gtcgggtcgg    360
atccaggaaa acaaccacca ccttggactc gttgctgctg tcacctccgc cttcggtacc    420
gttcaaagga gaaaaggat ggcgagacaa agaagatcca ctaaacccac ttcgttgatg    480
aaccatctca acaaccataa gcacaacaag cctcgttctc ttccttctcc cagtgcatcc    540
tcctcgtacg tgccactctc ctccgcaact ctccagcccg cacgtgaaat cgatcaaaga    600
aggttgagat cctttttcca gaaggagtta aagaacagtg atgttagctc ccttaggaga    660
atgatattgc caagaaagc agcagaggct ttccttccag ctcttgaatc caagaagga    720 attgtaatca gcatggatga tatagatggt cttcatgtat ggagtttcaa gtacaggttt    780
tggcctaaca caacagtcg gatgtatgta cttgaaaata ctggagattt tgtcaacaca    840
catggccttc gctttggaga ttccattatg gtttaccaag atagtgaaaa caacaattat    900
gttattcagg ccaaaaaggc ttctgatcaa gatgaattta tggaagaaac tagtgatacc    960
atcaatgata tcttccttaa tgattatgag gtgaacaaac ctggttgctt caatgtaact   1020
aatcctgcag tgaatgatac aggcatgtca ttcatatatg agactacctt ctcaaatgac   1080
tcccctcttg atttttggg tggatcaatg accaattttt caaggattgg gccagttgaa   1140
acctttggct ctgttgagaa tttgtcactt gatgacttct attaa                  1185
```

<210> SEQ ID NO 28
<211> LENGTH: 394
<212> TYPE: PRT
<213> ORGANISM: Glycine Max

<400> SEQUENCE: 28

```
Met Phe Pro Val Ser Ser Pro Ser Ile Arg His Ser Leu Leu Gly Gln
1               5                   10                  15

Ser Leu Thr Thr Thr Thr Pro Gln His Gln Thr Leu Cys His Lys
            20                  25                  30

Leu Asn Pro Glu Arg Glu Pro Thr Thr Thr Val Thr Glu Asn Gln Lys
        35                  40                  45

Asn Thr Val Leu Cys Val Cys Gln Lys Lys Asn Pro Lys Leu Met Met
    50                  55                  60

Met Asp Gln Arg Gln Arg Glu Lys Leu Leu His Lys Thr Glu Ala Cys
65                  70                  75                  80

Ala Phe Val Ala Gly Val Val Pro Glu Leu Ser Leu Val Thr Val Pro
                85                  90                  95

Gly Asn Asn Thr Asn Asn Val Asn Asn Asn Asn Val Val Ser His
            100                 105                 110

Ser Gln Ser Asn Gly Ser Gly Arg Ile Gln Glu Asn Asn His His Leu
        115                 120                 125

Gly Leu Val Ala Ala Val Thr Ser Ala Phe Gly Thr Val Gln Arg Lys
    130                 135                 140

Lys Arg Met Ala Arg Gln Arg Arg Ser Thr Lys Pro Thr Ser Leu Met
145                 150                 155                 160

Asn His Leu Asn Asn His Lys His Asn Lys Pro Arg Ser Leu Pro Ser
                165                 170                 175
```

```
Pro Ser Ala Ser Ser Tyr Val Pro Leu Ser Ser Ala Thr Leu Gln
            180                 185                 190

Pro Ala Arg Glu Ile Asp Gln Arg Arg Leu Arg Phe Leu Phe Gln Lys
        195                 200                 205

Glu Leu Lys Asn Ser Asp Val Ser Ser Leu Arg Arg Met Ile Leu Pro
210                 215                 220

Lys Lys Ala Ala Glu Ala Phe Leu Pro Ala Leu Glu Ser Lys Glu Gly
225                 230                 235                 240

Ile Val Ile Ser Met Asp Asp Ile Asp Gly Leu His Val Trp Ser Phe
                245                 250                 255

Lys Tyr Arg Phe Trp Pro Asn Asn Asn Ser Arg Met Tyr Val Leu Glu
                260                 265                 270

Asn Thr Gly Asp Phe Val Asn Thr His Gly Leu Arg Phe Gly Asp Ser
            275                 280                 285

Ile Met Val Tyr Gln Asp Ser Glu Asn Asn Asn Tyr Val Ile Gln Ala
        290                 295                 300

Lys Lys Ala Ser Asp Gln Asp Glu Phe Met Glu Glu Thr Ser Asp Thr
305                 310                 315                 320

Ile Asn Asp Ile Phe Leu Asn Asp Tyr Glu Val Asn Lys Pro Gly Cys
                325                 330                 335

Phe Asn Val Thr Asn Pro Ala Val Asn Asp Thr Gly Met Ser Phe Ile
            340                 345                 350

Tyr Glu Thr Thr Phe Ser Asn Asp Ser Pro Leu Asp Phe Leu Gly Gly
        355                 360                 365

Ser Met Thr Asn Phe Ser Arg Ile Gly Pro Val Glu Thr Phe Gly Ser
370                 375                 380

Val Glu Asn Leu Ser Leu Asp Asp Phe Tyr
385                 390

<210> SEQ ID NO 29
<211> LENGTH: 999
<212> TYPE: DNA
<213> ORGANISM: Glycine max

<400> SEQUENCE: 29
atgatgatgg atcagcgaca gcgagagaag ctgcttcaca aaaccgaggc ctgtgctttc      60
gtggcaggtg ttgttccgga gctttccctt gtcaccgttc agggaacaa caccaacaac     120 gttaacaaca caacaacgt tgtttctcat tctcaatcta acgggtcggg tcggatccag     180
gaaaacaacc accaccttgg actcgttgct gctgtcacct ccgccttcgg taccgttcaa     240
aggaagaaaa ggatggcgag acaaagaaga tccactaaac ccacttcgtt gatgaaccat     300
ctcaacaacc ataagcacaa caagcctcgt tctcttcctt ctcccagtgc atcctcctcg     360
tacgtgccac tctcctccgc aactctccag cccgcacgtg aaatcgatca agaaggttg     420 agattccttt tccagaagga gttaaagaac agtgatgtta gctcccttag agaatgata     480 ttgccaaaga aagcagcaga ggctttcctt ccagctcttg aatccaaaga aggaattgta     540
atcagcatgg atgatataga tggtcttcat gtatggagtt tcaagtacag gttttggcct     600
aacaacaaca gtcggatgta tgtacttgaa atactggaa attttgtcaa cacacatggc     660
cttcgctttg gagattccat tatggtttac caagatagtg aaaacaacaa ttatgttatt     720
caggccaaaa aggcttctga tcaagatgaa tttatggaag aaactagtga taccatcaat     780
gatatcttcc ttaatgatta tgaggtgaac aaacctggtt gcttcaatgt aactaatcct     840
```

```
gcagtgaatg atacaggcat gtcattcata tatgagacta ccttctcaaa tgactcccct    900
cttgattttt tgggtggatc aatgaccaat ttttcaagga ttgggccagt tgaaaccttt    960
ggctctgttg agaatttgtc acttgatgac ttctattaa                           999
```

<210> SEQ ID NO 30
<211> LENGTH: 332
<212> TYPE: PRT
<213> ORGANISM: Glycine max

<400> SEQUENCE: 30

```
Met Met Met Asp Gln Arg Gln Arg Glu Lys Leu Leu His Lys Thr Glu
1               5                   10                  15

Ala Cys Ala Phe Val Ala Gly Val Val Pro Glu Leu Ser Leu Val Thr
            20                  25                  30

Val Pro Gly Asn Asn Thr Asn Asn Val Asn Asn Asn Asn Asn Val Val
        35                  40                  45

Ser His Ser Gln Ser Asn Gly Ser Gly Arg Ile Gln Glu Asn Asn His
    50                  55                  60

His Leu Gly Leu Val Ala Ala Val Thr Ser Ala Phe Gly Thr Val Gln
65                  70                  75                  80

Arg Lys Lys Arg Met Ala Arg Gln Arg Arg Ser Thr Lys Pro Thr Ser
                85                  90                  95

Leu Met Asn His Leu Asn Asn His Lys His Asn Lys Pro Arg Ser Leu
            100                 105                 110

Pro Ser Pro Ser Ala Ser Ser Ser Tyr Val Pro Leu Ser Ser Ala Thr
        115                 120                 125

Leu Gln Pro Ala Arg Glu Ile Asp Gln Arg Arg Leu Arg Phe Leu Phe
    130                 135                 140

Gln Lys Glu Leu Lys Asn Ser Asp Val Ser Ser Leu Arg Arg Met Ile
145                 150                 155                 160

Leu Pro Lys Lys Ala Ala Glu Ala Phe Leu Pro Ala Leu Glu Ser Lys
                165                 170                 175

Glu Gly Ile Val Ile Ser Met Asp Asp Ile Asp Gly Leu His Val Trp
            180                 185                 190

Ser Phe Lys Tyr Arg Phe Trp Pro Asn Asn Asn Ser Arg Met Tyr Val
        195                 200                 205

Leu Glu Asn Thr Gly Asp Phe Val Asn Thr His Gly Leu Arg Phe Gly
    210                 215                 220

Asp Ser Ile Met Val Tyr Gln Asp Ser Glu Asn Asn Asn Tyr Val Ile
225                 230                 235                 240

Gln Ala Lys Lys Ala Ser Asp Gln Asp Glu Phe Met Glu Glu Thr Ser
                245                 250                 255

Asp Thr Ile Asn Asp Ile Phe Leu Asn Asp Tyr Glu Val Asn Lys Pro
            260                 265                 270

Gly Cys Phe Asn Val Thr Asn Pro Ala Val Asn Asp Thr Gly Met Ser
        275                 280                 285

Phe Ile Tyr Glu Thr Thr Phe Ser Asn Asp Ser Pro Leu Asp Phe Leu
    290                 295                 300

Gly Gly Ser Met Thr Asn Phe Ser Arg Ile Gly Pro Val Glu Thr Phe
305                 310                 315                 320

Gly Ser Val Glu Asn Leu Ser Leu Asp Asp Phe Tyr
                325                 330
```

<210> SEQ ID NO 31

<211> LENGTH: 1515
<212> TYPE: DNA
<213> ORGANISM: Glycine max

<400> SEQUENCE: 31

```
atggcgattt ccgatgagcc tgaaagtgta gccactgctc tcaaccactc ttccctgcgc      60
cgccgtccct ccgccacctc caccgccggc ctcttcaatt cgcctgagac aaccaccgac     120
agttccggtg atgacttggc caaggattct ggttccgacg actccatcaa caacgacgac     180
gccgccgtca attcccaaca gcaaaacgaa aaacaagaca ctgatttctc cgtcctcaaa     240
ttcgcctacc gtccttccgt ccccgctcac cgcaaagtga aggaaagtcc gctcagctcc     300
gacactattt tccgtcagag tcacgcgggc ctcttcaacc tttgtatagt agtccttgtt     360
gctgtgaata gccgactcat cattgagaat ttaatgaagt atggttggtt gatcaaatct     420
ggcttttggt ttagtgcaaa gtcattgaga gactggcccc ttttcatgtg ttgtctttct     480
cttgtggtat ttcctttcgc tgcctttatg gtggagaagt tggcacaacg gaagtgtata     540
cccgaaccag ttgttgttgt acttcatata atcattacct caacttcgct tttctatcca     600
gttttagtta ttctcaagtg tgattctgct tttgtatcag gtgtcacgtt aatgctgttt     660
tcttgtgttg tatggttaaa attggtgtct tttgcacata caaactatga tatgagagca     720
cttaccaaat tagttgaaaa gggagaagca ctgctcgata ctctgaacat ggagtatcct     780
tacaacgtaa ccttcaagag cttggcatat ttcctgcttg cccctacatt atgttaccag     840
ccaagctatc ctcgcacacc ttatattcga aagggttggt tgtttcgcca acttgtcaag     900
ctgatagtat ttacaggagt tatgggtattt ataatagaac aatatattaa tcccatagta     960
caaaattcac agcatcctct caagggaaac cttctttacg ccaccgagag agttctgaag    1020
cttttctgttc caaatttata tgtgtggctc tgcatgttct attgcttttt ccacctttgg    1080
ttaaatatcg tggcagagct tcttcgattt ggtgatcgtg aattctacaa ggattggtgg    1140
aatgccaaaa ctgtcgaaga ttattggagg atgtggaata tgcctgttca caaatggatg    1200
atccgccacc tatatttttcc atgtttaagg cacggtctac caaaggctgc tgctcttttta    1260
atttccttcc tggtttctgc tttattccat gagctgtgca ttgctgttcc ttgccacatg    1320
ttcaagttgt gggctttcgg tggaattatg tttcaggttc ctttggtctt gatcactaat    1380
tatctgcaaa ataaattcaa aaactcaatg gttggaaata tgattttttg gttcatattc    1440
agtatcgttg gtcaacctat gtgtgtactg ctatactacc atgacttgat gaataggaaa    1500
ggcaaacttg actga                                                     1515
```

<210> SEQ ID NO 32
<211> LENGTH: 504
<212> TYPE: PRT
<213> ORGANISM: Glycine max

<400> SEQUENCE: 32

Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Asn Asp Ala Ala Val Asn
    50                  55                  60

Ser Gln Gln Gln Asn Glu Lys Gln Asp Thr Asp Phe Ser Val Leu Lys

-continued

```
                65                  70                  75                  80
        Phe Ala Tyr Arg Pro Ser Val Pro Ala His Arg Lys Val Lys Glu Ser
                        85                  90                  95

Pro Leu Ser Ser Asp Thr Ile Phe Arg Gln Ser His Ala Gly Leu Phe
                        100                 105                 110

Asn Leu Cys Ile Val Val Leu Ala Val Asn Ser Arg Leu Ile Ile
                        115                 120                 125

Glu Asn Leu Met Lys Tyr Gly Trp Leu Ile Lys Ser Gly Phe Trp Phe
                130                 135                 140

Ser Ala Lys Ser Leu Arg Asp Trp Pro Leu Phe Met Cys Cys Leu Ser
        145                 150                 155                 160

Leu Val Val Phe Pro Phe Ala Ala Phe Met Val Glu Lys Leu Ala Gln
                        165                 170                 175

Arg Lys Cys Ile Pro Glu Pro Val Val Val Leu His Ile Ile Ile
                        180                 185                 190

Thr Ser Thr Ser Leu Phe Tyr Pro Val Leu Val Ile Leu Lys Cys Asp
                        195                 200                 205

Ser Ala Phe Val Ser Gly Val Thr Leu Met Leu Phe Ser Cys Val Val
                210                 215                 220

Trp Leu Lys Leu Val Ser Phe Ala His Thr Asn Tyr Asp Met Arg Ala
        225                 230                 235                 240

Leu Thr Lys Leu Val Glu Lys Gly Glu Ala Leu Leu Asp Thr Leu Asn
                        245                 250                 255

Met Glu Tyr Pro Tyr Asn Val Thr Phe Lys Ser Leu Ala Tyr Phe Leu
                        260                 265                 270

Leu Ala Pro Thr Leu Cys Tyr Gln Pro Ser Tyr Pro Arg Thr Pro Tyr
                        275                 280                 285

Ile Arg Lys Gly Trp Leu Phe Arg Gln Leu Val Lys Leu Ile Val Phe
                        290                 295                 300

Thr Gly Val Met Gly Phe Ile Ile Glu Gln Tyr Ile Asn Pro Ile Val
        305                 310                 315                 320

Gln Asn Ser Gln His Pro Leu Lys Gly Asn Leu Leu Tyr Ala Thr Glu
                        325                 330                 335

Arg Val Leu Lys Leu Ser Val Pro Asn Leu Tyr Val Trp Leu Cys Met
                        340                 345                 350

Phe Tyr Cys Phe Phe His Leu Trp Leu Asn Ile Val Ala Glu Leu Leu
                355                 360                 365

Arg Phe Gly Asp Arg Glu Phe Tyr Lys Asp Trp Trp Asn Ala Lys Thr
                370                 375                 380

Val Glu Asp Tyr Trp Arg Met Trp Asn Met Pro Val His Lys Trp Met
        385                 390                 395                 400

Ile Arg His Leu Tyr Phe Pro Cys Leu Arg His Gly Leu Pro Lys Ala
                        405                 410                 415

Ala Ala Leu Leu Ile Ser Phe Leu Val Ser Ala Leu Phe His Glu Leu
                        420                 425                 430

Cys Ile Ala Val Pro Cys His Met Phe Lys Leu Trp Ala Phe Gly Gly
                        435                 440                 445

Ile Met Phe Gln Val Pro Leu Val Leu Ile Thr Asn Tyr Leu Gln Asn
                        450                 455                 460

Lys Phe Lys Asn Ser Met Val Gly Asn Met Ile Phe Trp Phe Ile Phe
        465                 470                 475                 480

Ser Ile Val Gly Gln Pro Met Cys Val Leu Leu Tyr Tyr His Asp Leu
                        485                 490                 495
```

Met Asn Arg Lys Gly Lys Leu Asp
            500

<210> SEQ ID NO 33
<211> LENGTH: 1545
<212> TYPE: DNA
<213> ORGANISM: Yarrowia lipolytica

<400> SEQUENCE: 33

```
atgactatcg actcacaata ctacaagtcg cgagacaaaa acgacacggc acccaaaatc     60
gcgggaatcc gatatgcccc gctatcgaca ccattactca accgatgtga gaccttctct    120
ctggtctggc acatttcag cattcccact ttcctcacaa ttttcatgct atgctgcgca    180
attccactgc tctggccatt tgtgattgcg tatgtagtgt acgctgttaa agacgactcc    240
ccgtccaacg gaggagtggt caagcgatac tcgcctattt caagaaactt cttcatctgg    300
aagctctttg ccgctactt cccataact ctgcacaaga cggtggatct ggagcccacg    360
cacacatact accctctgga cgtccaggag tatcacctga ttgctgagag atactggccg    420
cagaacaagt acctccgagc aatcatcacc accatcgagt actttctgcc cgccttcatg    480
aaacggtctc tttctatcaa cgagcaggag cagcctgccg agcgagatcc tctcctgtct    540
cccgtttctc ccagctctcc gggttctcaa cctgacaagt ggattaacca cgacagcaga    600
tatagccgtg gagaatcatc tggctccaac ggccacgcct cgggctccga acttaacggc    660
aacggcaaca acggcaccac taaccgacga cctttgtcgt ccgcctctgc tggctccact    720
gcatctgatt ccacgcttct taacgggtcc ctcaactcct acgccaacca gatcattggc    780
gaaaacgacc cacagctgtc gcccacaaaa ctcaagccca ctggcagaaa atacatcttc    840
ggctaccacc ccacggcat tatcggcatg ggagcctttg gtggaattgc caccgaggga    900
gctggatggt ccaagctctt tccgggcatc cctgtttctc ttatgactct caccaacaac    960
ttccgagtgc ctctctacag agagtaccttc atgagtctgg gagtcgcttc tgtctccaag   1020
aagtcctgca aggccctcct caagcgaaac cagtctatct gcattgtcgt tggtggagca   1080
caggaaagtc ttctggccag acccggtgtc atggacctgg tgctactcaa gcgaaagggt   1140
tttgttcgac ttggtatgga ggtcggaaat gtcgcccttg ttcccatcat ggcctttggt   1200
gagaacgacc tctatgacca ggttagcaac gacaagtcgt ccaagctgta ccgattccag   1260
cagtttgtca agaacttcct tggattcacc cttcctttga tgcatgcccg aggcgtcttc   1320
aactacgatg tcggtcttgt ccctacagg cgacccgtca acattgtggt tggttccccc   1380
attgacttgc cttatctccc acaccccacc gacgaagaag tgtccgaata ccacgaccga   1440
tacatcgccg agctgcagcg aatctacaac gagcacaagg atgaatattt catcgattgg   1500
accgaggagg gcaaaggagc cccagagttc cgaatgattg agtaa             1545
```

<210> SEQ ID NO 34
<211> LENGTH: 514
<212> TYPE: PRT
<213> ORGANISM: Yarrowia lipolytica

<400> SEQUENCE: 34

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile

```
                35                  40                  45
Pro Thr Phe Leu Thr Ile Phe Met Leu Cys Cys Ala Ile Pro Leu Leu
 50                  55                  60

Trp Pro Phe Val Ile Ala Tyr Val Val Tyr Ala Val Lys Asp Asp Ser
 65                  70                  75                  80

Pro Ser Asn Gly Gly Val Val Lys Arg Tyr Ser Pro Ile Ser Arg Asn
                 85                  90                  95

Phe Phe Ile Trp Lys Leu Phe Gly Arg Tyr Phe Pro Ile Thr Leu His
                100                 105                 110

Lys Thr Val Asp Leu Glu Pro Thr His Thr Tyr Tyr Pro Leu Asp Val
                115                 120                 125

Gln Glu Tyr His Leu Ile Ala Glu Arg Tyr Trp Pro Gln Asn Lys Tyr
                130                 135                 140

Leu Arg Ala Ile Ile Thr Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
                180                 185                 190

Lys Trp Ile Asn His Asp Ser Arg Tyr Ser Arg Gly Glu Ser Ser Gly
                195                 200                 205

Ser Asn Gly His Ala Ser Gly Ser Glu Leu Asn Gly Asn Gly Asn Asn
210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
                260                 265                 270

Pro Thr Gly Arg Lys Tyr Ile Phe Gly Tyr His Pro His Gly Ile Ile
                275                 280                 285

Gly Met Gly Ala Phe Gly Gly Ile Ala Thr Glu Gly Ala Gly Trp Ser
290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
                340                 345                 350

Ile Cys Ile Val Val Gly Gly Ala Gln Glu Ser Leu Leu Ala Arg Pro
                355                 360                 365

Gly Val Met Asp Leu Val Leu Leu Lys Arg Lys Gly Phe Val Arg Leu
                370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
                420                 425                 430

Leu Met His Ala Arg Gly Val Phe Asn Tyr Asp Val Gly Leu Val Pro
                435                 440                 445

Tyr Arg Arg Pro Val Asn Ile Val Val Gly Ser Pro Ile Asp Leu Pro
450                 455                 460
```

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
            485                 490                 495

Phe Ile Asp Trp Thr Glu Glu Gly Lys Gly Ala Pro Glu Phe Arg Met
        500                 505                 510

Ile Glu

<210> SEQ ID NO 35
<211> LENGTH: 837
<212> TYPE: DNA
<213> ORGANISM: Zea mays

<400> SEQUENCE: 35
atggactcca gcagcttcct ccctgccgcc ggcgcggaga tggctcggc ggcgggcggc      60 gccaacaatg gcggcgctgc tcagcagcat gcggcgccgg cgatccgcga gcaggaccgg    120
ctgatgccga tcgcgaacgt gatccgcatc atgcggcgcg tgctgccggc gcacgccaag    180
atctcggacg acgccaagga gacgatccag gagtgcgtgt cggagtacat cagcttcatc    240 acggggagg ccaacgagcg gtgccagcgg gagcagcgca agaccatcac cgccgaggac     300
gtgctgtggg ccatgagccg cctcggcttc gacgactacg tcgagccgct cggcgcctac    360
ctccaccgct accgcgagtt cgaggcgac gcgcgcggcg tcgggctcgt cccgggggcc     420
gccccatcgc gcggcggcga ccaccacccg cactccatgt cgccagcggc gatgctcaag    480
tcccgcgggc cagtctccgg agccgccatg ctaccgcacc accaccacca ccacgacatg    540
cagatgcacg ccgccatgta cggggaacg gccgtgcccc cgccggccgg gcctcctcac     600
cacggcgggt tcctcatgcc acacccacag ggtagtagcc actacctgcc ttacgcgtac    660
gagcccacgt acggcggtga gcacgccatg gctgcatact atggaggcgc cgcgtacgcg    720
cccggcaacg gcgggagcgg cgacggcagt ggcagtggcg gcgtggcgg gagcgcgtcg     780 cacacaccgc agggcagcgg cggcttggag cacccgcacc cgttcgcgta caagtag        837

<210> SEQ ID NO 36
<211> LENGTH: 278
<212> TYPE: PRT
<213> ORGANISM: Zea mays

<400> SEQUENCE: 36

Met Asp Ser Ser Ser Phe Leu Pro Ala Ala Gly Ala Glu Asn Gly Ser
1               5                   10                  15

Ala Ala Gly Gly Ala Asn Asn Gly Gly Ala Ala Gln Gln His Ala Ala
            20                  25                  30

Pro Ala Ile Arg Glu Gln Asp Arg Leu Met Pro Ile Ala Asn Val Ile
        35                  40                  45

Arg Ile Met Arg Arg Val Leu Pro Ala His Ala Lys Ile Ser Asp Asp
    50                  55                  60

Ala Lys Glu Thr Ile Gln Glu Cys Val Ser Glu Tyr Ile Ser Phe Ile
65                  70                  75                  80

Thr Gly Glu Ala Asn Glu Arg Cys Gln Arg Glu Gln Arg Lys Thr Ile
            85                  90                  95

Thr Ala Glu Asp Val Leu Trp Ala Met Ser Arg Leu Gly Phe Asp Asp
            100                 105                 110

Tyr Val Glu Pro Leu Gly Ala Tyr Leu His Arg Tyr Arg Glu Phe Glu
        115                 120                 125

```
Gly Asp Ala Arg Gly Val Gly Leu Val Pro Gly Ala Ala Pro Ser Arg
    130                 135                 140
Gly Gly Asp His His Pro His Ser Met Ser Pro Ala Ala Met Leu Lys
145                 150                 155                 160
Ser Arg Gly Pro Val Ser Gly Ala Ala Met Leu Pro His His His
                165                 170                 175
His His Asp Met Gln Met His Ala Ala Met Tyr Gly Gly Thr Ala Val
            180                 185                 190
Pro Pro Pro Ala Gly Pro Pro His His Gly Gly Phe Leu Met Pro His
        195                 200                 205
Pro Gln Gly Ser Ser His Tyr Leu Pro Tyr Ala Tyr Glu Pro Thr Tyr
    210                 215                 220
Gly Gly Glu His Ala Met Ala Ala Tyr Tyr Gly Gly Ala Ala Tyr Ala
225                 230                 235                 240
Pro Gly Asn Gly Gly Ser Gly Asp Gly Ser Gly Ser Gly Gly Gly
                245                 250                 255
Gly Ser Ala Ser His Thr Pro Gln Gly Ser Gly Gly Leu Glu His Pro
            260                 265                 270
His Pro Phe Ala Tyr Lys
        275
```

<210> SEQ ID NO 37
<211> LENGTH: 1188
<212> TYPE: DNA
<213> ORGANISM: Zea mays

<400> SEQUENCE: 37

```
atggagagat ctcaacggca gtctcctccg ccaccgtcgc cgtcctcctc ctcgtcctcc    60
gtctccgcgg acaccgtcct cgtccctccc ggaaagaggc ggagggcggc gacggccaag   120
gccggcgccg agcctaataa gaggatccgc aaggaccccg ccgccgccgc cgcggggaag   180
aggagctccg tctacagggg agtcaccagg cacaggtgga cgggcaggtt cgaggcgcat   240
ctctgggaca gcactgcct cgccgcgctc cacaacaaga agaaaggcag gcaagtctac   300
ctgggggcgt atgacagcga ggaggcagct gctcgtgcct atgacctcgc agctctcaag   360
tactggggtc ctgagactct gctcaacttc cctgtggagg attactccag cgagatgccg   420
gagatggagg ccgtgtcccg ggaggagtac ctggcctccc tccgccgcag gagcagcggc   480
ttctccaggg gcgtctccaa gtacagaggc gtcgccaggc atcaccacaa cgggaggtgg   540
gaggcacgga ttgggcgagt ctttgggaac aagtacctct acttgggaac atttgacact   600
caagaagagg cagccaaggc ctatgacctt gcggccattg aataccgtgg cgtcaatgct   660
gtaaccaact cgacatcag ctgctacctg gaccacccgc tgttcctggc acagctccaa   720
caggagccac aggtggtgcc ggcactcaac caagaacctc aacctgatca gagcgaaacc   780
ggaactacag agcaagagcc ggagtcaagc gaagccaaga caccggatgg cagtgcagaa   840
cccgatgaga acgcggtgcc tgacgacacc gcggagcccc tcaccacagt cgacgacagc   900
atcgaagagg gcttgtggag cccttgcatg gattacgagc tagacaccat gtcgagacca   960
aactttggca gctcaatcaa tctgagcgag tggttcgctg acgcagactt cgactgcaac  1020
atcggatgcc tgttcgatgg gtgttctgcg gctgacgaag gaagcaagga tggtgtaggt  1080
ctggcagatt tcagtctgtt tgaggcaggt gatgtccagc tgaaggatgt tctttcggat  1140
atggaagagg ggatacaacc tccagcgatg atcagtgtgt gcaactaa                1188
```

-continued

```
<210> SEQ ID NO 38
<211> LENGTH: 395
<212> TYPE: PRT
<213> ORGANISM: Zea mays

<400> SEQUENCE: 38
```

| | | | | | | | | | | | | | | |
|---|---|---|---|---|---|---|---|---|---|---|---|---|---|---|
| Met<br>1 | Glu | Arg | Ser | Gln<br>5 | Arg | Gln | Ser | Pro | Pro<br>10 | Pro | Ser | Pro | Ser<br>15 | Ser |
| Ser | Ser | Ser | Ser<br>20 | Val | Ser | Ala | Asp | Thr<br>25 | Val | Leu | Val | Pro | Pro<br>30 | Gly | Lys |
| Arg | Arg | Arg<br>35 | Ala | Ala | Thr | Ala | Lys<br>40 | Ala | Gly | Ala | Glu | Pro<br>45 | Asn | Lys | Arg |
| Ile | Arg<br>50 | Lys | Asp | Pro | Ala | Ala<br>55 | Ala | Ala | Ala | Gly | Lys<br>60 | Arg | Ser | Ser | Val |
| Tyr<br>65 | Arg | Gly | Val | Thr | Arg<br>70 | His | Arg | Trp | Thr | Gly<br>75 | Arg | Phe | Glu | Ala | His<br>80 |
| Leu | Trp | Asp | Lys | His<br>85 | Cys | Leu | Ala | Ala | Leu<br>90 | His | Asn | Lys | Lys | Lys<br>95 | Gly |
| Arg | Gln | Val | Tyr<br>100 | Leu | Gly | Ala | Tyr | Asp<br>105 | Ser | Glu | Ala | Ala | Ala<br>110 | Arg |
| Ala | Tyr | Asp<br>115 | Leu | Ala | Ala | Leu | Lys<br>120 | Tyr | Trp | Gly | Pro | Glu<br>125 | Thr | Leu | Leu |
| Asn | Phe<br>130 | Pro | Val | Glu | Asp | Tyr<br>135 | Ser | Ser | Glu | Met | Pro<br>140 | Glu | Met | Glu | Ala |
| Val<br>145 | Ser | Arg | Glu | Glu | Tyr<br>150 | Leu | Ala | Ser | Leu | Arg<br>155 | Arg | Arg | Ser | Ser | Gly<br>160 |
| Phe | Ser | Arg | Gly | Val<br>165 | Ser | Lys | Tyr | Arg | Gly<br>170 | Val | Ala | Arg | His | His<br>175 | His |
| Asn | Gly | Arg | Trp<br>180 | Glu | Ala | Arg | Ile | Gly<br>185 | Arg | Val | Phe | Gly | Asn<br>190 | Lys | Tyr |
| Leu | Tyr | Leu<br>195 | Gly | Thr | Phe | Asp | Thr<br>200 | Gln | Glu | Glu | Ala | Ala<br>205 | Lys | Ala | Tyr |
| Asp | Leu<br>210 | Ala | Ala | Ile | Glu | Tyr<br>215 | Arg | Gly | Val | Asn | Ala<br>220 | Val | Thr | Asn | Phe |
| Asp<br>225 | Ile | Ser | Cys | Tyr | Leu<br>230 | Asp | His | Pro | Leu | Phe<br>235 | Leu | Ala | Gln | Leu | Gln<br>240 |
| Gln | Glu | Pro | Gln | Val<br>245 | Val | Pro | Ala | Leu | Asn<br>250 | Gln | Glu | Pro | Gln | Pro<br>255 | Asp |
| Gln | Ser | Glu | Thr<br>260 | Gly | Thr | Thr | Glu | Gln<br>265 | Glu | Pro | Glu | Ser | Ser<br>270 | Glu | Ala |
| Lys | Thr | Pro<br>275 | Asp | Gly | Ser | Ala | Glu<br>280 | Pro | Asp | Glu | Asn | Ala<br>285 | Val | Pro | Asp |
| Asp | Thr<br>290 | Ala | Glu | Pro | Leu | Thr<br>295 | Thr | Val | Asp | Asp | Ser<br>300 | Ile | Glu | Glu | Gly |
| Leu<br>305 | Trp | Ser | Pro | Cys | Met<br>310 | Asp | Tyr | Glu | Leu | Asp<br>315 | Thr | Met | Ser | Arg | Pro<br>320 |
| Asn | Phe | Gly | Ser | Ser<br>325 | Ile | Asn | Leu | Ser | Glu<br>330 | Trp | Phe | Ala | Asp | Ala<br>335 | Asp |
| Phe | Asp | Cys | Asn<br>340 | Ile | Gly | Cys | Leu | Phe<br>345 | Asp | Gly | Cys | Ser | Ala<br>350 | Ala | Asp |
| Glu | Gly | Ser<br>355 | Lys | Asp | Gly | Val | Gly<br>360 | Leu | Ala | Asp | Phe | Ser<br>365 | Leu | Phe | Glu |

```
Ala Gly Asp Val Gln Leu Lys Asp Val Leu Ser Asp Met Glu Glu Gly
    370                 375                 380

Ile Gln Pro Pro Ala Met Ile Ser Val Cys Asn
385                 390                 395

<210> SEQ ID NO 39
<211> LENGTH: 11879
<212> TYPE: DNA
<213> ORGANISM: artificial sequence
<220> FEATURE:
<223> OTHER INFORMATION: vector PHP29252
<220> FEATURE:
<221> NAME/KEY: misc_feature
<222> LOCATION: (8799)..(8799)
<223> OTHER INFORMATION: n is a, c, g, or t

<400> SEQUENCE: 39
gtacgcaggt aagtttctgc ttctaccttt gatatatata taataattat cattaattag     60
tagtaatata atatttcaaa tattttttc  aaaataaaag aatgtagtat atagcaattg    120
cttttctgta gtttataagt gtgtatattt taatttataa cttttctaat atatgaccaa    180
aacatggtga tgtgcaggtc ctgcaggtta aatcagctca gaaagggagg ttcaattttt    240
tagcagcacg gtccagagca ccgcttgttg gcattgatcg agcaagaccc ttaacaccgt    300
tcttgaagta tggaatcgct tctcttgcat tggctgcaat aactgctaca gagtctgaag    360
gagttacaaa gaaacttctt cctaaaatca tatttctatc accatcccca tcactggcag    420
ctccaaaatc aggtccattt tcagcataca gaatgtcgac aagatccttc gcatatgtta    480
gattaggatc aggatggcca tgtccaaaat cttccaaagg gattccattt gaaattgaat    540
ccagactagc accgagttta tcaacgaaga tgggtttagc ataagcacca gtaactgcat    600
gcatggcatc aaatataaac ctaaaatctg gacgtgaaag aagacctctg attagctgaa    660
aatcaaatac tgtctccaat agctccagat agtcagaaac tgggtctatt acttccacac    720
tgaagcttcc aaaatttgta accccaactt ttgataaatc ttaaatcagc tcacctaggc    780
tacttccccg tatatctcca tggcttggac cccgctgcgc aatagtgaac aaccttgact    840
tggtctaatt taacgttttc cgggtggcgc cacagcatgg cgaggacaag attgtaattt    900
aaagggattg gcttgtaaat gtccttgaag tacatgttca agaaatcttg ttcagcgaac    960
gaggtgggag tggtgacttg caccgttttc aataggtcat gataggtggc gatgttgggt   1020
tcgaacacga acatgccagc gttgaagtaa agagaagggg gctgacccaa ttcggtgggc   1080
caccgcacct tctccgggca ttgctggcag taacccacct tgtactgagg ggtgtgactc   1140
catgtcttct cgcagaaaca atccatcaca gcgtaaaagt taccatcagg taggtcaaat   1200
aggtggtcta tgttctcata tacctcaatg tctccgtcca agtatatcat cttgctgtac   1260
tccacaaact cccatatacg gagcttggag tagttgatga cctgcagtta cttcccagtg   1320
aacctccaag gcttagaccc agcagcacag taatgaacca cttgaacttt atcaagttca   1380
acattttcag ggtgacgcca caacatggcc agcacaaggt tgtacatgtt cggtattggc   1440
ttgtacttgt ccttgaagta catgttgaga aagtcctgct cagcaaaaga agtgggcttg   1500
gtgagttgga cagtttggag aagatcacgg taggtgtcga gattaggctc ataaacaaac   1560
atgccagcat tgaaatatag aggaggtttg gaaccaaagt gagagggcca ttgaaccttA   1620
tcagggcact gttggcagta cccaatctgg aactgagggg tgtggctcca agtcttctcg   1680
cagaaacaat ccatcaccgc atagaaataa ttatcaggca gatcaaacaa gtggtctatg   1740
tttccaaata cttggatgtc accgtctagg tatatcgtct tcttgtactc cacgaactcc   1800
```

```
caaatacgta gcttggagta attgatgacc tcgagtcact tcccagtgta cctccaaggc    1860
ttagacccag cagcacagta gtgaaccact ttaactttgt caagctcaac gttctcaggg    1920
tgacgccaca gcatggccag cacaagattg tagacattag gaattggcct atatttgtcc    1980
ttgaagtaca tgttcaaaaa atcctgttca gcaaaggaag tgggctgggt gacttggact    2040
gtttgaagga ggtcacggta agtagccaaa ttgggctcat acacaaacat gccagcattg    2100
aaatagagag gaggtttggg cccaaagtga gtgggccact gaaccttatg ggggcactgc    2160
tggcagtaac cgatctgata ttgtttagtg tggccccaag ttggctcaca gaaacagtcc    2220
atcaccgcat agaagtagtt atcaggcaag tcaaacaagt ggtcaatgtt gtcaaaaact    2280
tggatatcac cgtctaggta tatcatcttg ctgtactcca caaactccca aatacgtagc    2340
ttggaatagt tgatgactta gtcgacggcg cgcccgatca tccggatata gttcctcctt    2400
tcagcaaaaa accccctcaag acccgtttag aggcccaag gggttatgct agttattgct    2460
cagcggtggc agcagccaac tcagcttcct ttcgggcttt gttagcagcc ggatcgatcc    2520
aagctgtacc tcactattcc tttgcccctcg acgagtgct ggggcgtcgg tttccactat    2580
cggcgagtac ttctacacag ccatcggtcc agacggccgc gcttctgcgg gcgatttgtg    2640
tacgcccgac agtcccggct ccggatcgga cgattgcgtc gcatcgaccc tgcgcccaag    2700
ctgcatcatc gaaattgccg tcaaccaagc tctgatagag ttggtcaaga ccaatgcgga    2760
gcatatacgc ccggagccgc ggcgatcctg caagctccgg atgcctccgc tcgaagtagc    2820
gcgtctgctg ctccatacaa gccaaccacg gcctccagaa aagatgttg gcgacctcgt    2880 attgggaatc cccgaacatc gcctcgctcc agtcaatgac cgctgttatg cggccattgt    2940
ccgtcaggac attgttggag ccgaaatccg cgtgcacgag gtgccggact cggggcagt    3000 cctcggccca aagcatcagc tcatcgagag cctgcgcgac ggacgcactg acggtgtcgt    3060
ccatcacagt ttgccagtga tacacatggg gatcagcaat cgcgcatatg aaatcacgcc    3120
atgtagtgta ttgaccgatt ccttgcggtc cgaatgggcc gaacccgctc gtctggctaa    3180
gatcggccgc agcgatcgca tccatagcct ccgcgaccgg ctgcagaaca gcgggcagtt    3240
cggtttcagg caggtcttgc aacgtgacac cctgtgcacg gcgggagatg caataggtca    3300
ggctctcgct gaattcccca atgtcaagca cttccggaat cgggagcgcg gccgatgcaa    3360
agtgccgata aacataacga tctttgtaga aaccatcggc gcagctattt acccgcagga    3420
catatccacg ccctcctaca tcgaagctga aagcacgaga ttcttcgccc tccgagagct    3480
gcatcaggtc ggagacgctg tcgaactttt cgatcagaaa cttctcgaca gacgtcgcgg    3540
tgagttcagg cttttccatg ggtatatctc cttcttaaag ttaaacaaaa ttatttctag    3600
agggaaaccg ttgtggtctc cctatagtga gtcgtattaa tttcgcggga tcgagatcga    3660
tccaattcca atcccacaaa aatctgagct taacagcaca gttgctcctc tcagagcaga    3720
atcgggtatt caacccctc atatcaacta ctacgttgtg tataacgtc cacatgccgg    3780 tatatacgat gactggggtt gtacaaaggc ggcaacaaac ggcgttccg gagttgcaca    3840 caagaaattt gccactatta cagaggcaag agcagcagct gacgcgtaca caacaagtca    3900
gcaaacagac aggttgaact tcatcccaa aggagaagct caactcaagc ccagagctt    3960 tgctaaggcc ctaacaagcc caccaaagca aaaagcccac tggctcacgc taggaaccaa    4020
aaggcccagc agtgatccag ccccaaaaga gatctccttt gccccggaga ttacaatgga    4080
cgatttcctc tatctttacg atctaggaag gaagttcgaa ggtgaaggtg acgacactat    4140
gttcaccact gataatgaga aggttagcct cttcaatttc agaaagaatg ctgacccaca    4200
```

```
gatggttaga gaggcctacg cagcaggtct catcaagacg atctacccga gtaacaatct    4260
ccaggagatc aaataccttc caagaaggt taaagatgca gtcaaaagat tcaggactaa    4320
ttgcatcaag aacacagaga agacatatt tctcaagatc agaagtacta ttccagtatg    4380
gacgattcaa ggcttgcttc ataaaccaag gcaagtaata gagattggag tctctaaaaa    4440
ggtagttcct actgaatcta aggccatgca tggagtctaa gattcaaatc gaggatctaa    4500
cagaactcgc cgtgaagact ggcgaacagt tcatacagag tcttttacga ctcaatgaca    4560
agaagaaaat cttcgtcaac atggtggagc acgacactct ggtctactcc aaaaatgtca    4620
aagatacagt ctcagaagac caaagggcta ttgagacttt tcaacaaagg ataatttcgg    4680
gaaacctcct cggattccat tgcccagcta tctgtcactt catcgaaagg acagtagaaa    4740
aggaaggtgg ctcctacaaa tgccatcatt gcgataaagg aaaggctatc attcaagatg    4800
cctctgccga cagtggtccc aaagatggac ccccacccac gaggagcatc gtggaaaaag    4860
aagacgttcc aaccacgtct tcaaagcaag tggattgatg tgacatctcc actgacgtaa    4920
gggatgacgc acaatcccac tatccttcgc aagacccttc ctctatataa ggaagttcat    4980
ttcatttgga gaggacacgc tcgagctcat ttctctatta cttcagccat aacaaaagaa    5040
ctcttttctc ttcttattaa accatgaaaa agcctgaact caccgcgacg tctgtcgaga    5100
agtttctgat cgaaaagttc gacagcgtct ccgacctgat gcagctctcg gagggcgaag    5160
aatctcgtgc tttcagcttc gatgtaggag ggcgtggata tgtcctgcgg gtaaatagct    5220
gcgccgatgg tttctacaaa gatcgttatg tttatcggca ctttgcatcg gccgcgctcc    5280
cgattccgga agtgcttgac attggggaat tcagcgagag cctgacctat tgcatctccc    5340
gccgtgcaca gggtgtcacg ttgcaagacc tgcctgaaac cgaactgccc gctgttctgc    5400
agccggtcgc ggaggccatg gatgcgatcg ctgcggccga tcttagccag acgagcgggt    5460
tcggcccatt cggaccgcaa ggaatcggtc aatacactac atggcgtgat ttcatatgcg    5520
cgattgctga tccccatgtg tatcactggc aaactgtgat ggacgacacc gtcagtgcgt    5580
ccgtcgcgca ggctctcgat gagctgatgc tttgggccga ggactgcccc gaagtccggc    5640
acctcgtgca cgcggatttc ggctccaaca atgtcctgac ggacaatggc cgcataacag    5700
cggtcattga ctggagcgag gcgatgttcg gggattccca atacgaggtc gccaacatct    5760
tcttctggag gccgtggttg gcttgtatgg agcagcagac gcgctacttc gagcggaggc    5820
atccggagct tgcaggatcg ccgcggctcc gggcgtatat gctccgcatt ggtcttgacc    5880
aactctatca gagcttggtt gacggcaatt tcgatgatgc agcttgggcg cagggtcgat    5940
gcgacgcaat cgtccgatcc ggagccggga ctgtcgggcg tacacaaatc gcccgcagaa    6000
gcgcggccgt ctggaccgat ggctgtgtag aagtactcgc cgatagtgga aaccgacgcc    6060
ccagcactcg tccgagggca aggaatagt gaggtaccta agaaggagt gcgtcgaagc    6120
agatcgttca acatttggc aataaagttt cttaagattg aatcctgttg ccggtcttgc    6180
gatgattatc atataatttc tgttgaatta cgttaagcat gtaataatta acatgtaatg    6240
catgacgtta tttatgagat gggtttttat gattagagtc ccgcaattat acatttaata    6300
cgcgatagaa acaaaatat agcgcgcaaa ctaggataaa ttatcgcgcg cggtgtcatc    6360
tatgttacta gatcgatgtc gaatctgatc aacctgcatt aatgaatcgg ccaacgcgcg    6420
gggagaggcg gtttgcgtat tgggcgctct tccgcttcct cgctcactga ctcgctgcgc    6480
tcggtcgttc ggctgcggcg agcggtatca gctcactcaa aggcggtaat acggttatcc    6540
acagaatcag gggataacgc aggaaagaac atgtgagcaa aaggccagca aaaggccagg    6600
```

```
aaccgtaaaa aggccgcgtt gctggcgttt ttccataggc tccgcccccc tgacgagcat    6660
cacaaaaatc gacgctcaag tcagaggtgg cgaaacccga caggactata aagataccag    6720
gcgtttcccc ctggaagctc cctcgtgcgc tctcctgttc cgaccctgcc gcttaccgga    6780
tacctgtccg cctttctccc ttcgggaagc gtggcgcttt ctcaatgctc acgctgtagg    6840
tatctcagtt cggtgtaggt cgttcgctcc aagctgggct gtgtgcacga accccccgtt    6900
cagcccgacc gctgcgcctt atccggtaac tatcgtcttg agtccaaccc ggtaagacac    6960
gacttatcgc cactggcagc agccactggt aacaggatta gcagagcgag gtatgtaggc    7020
ggtgctacag agttcttgaa gtggtggcct aactacggct acactagaag gacagtattt    7080
ggtatctgcg ctctgctgaa gccagttacc ttcggaaaaa gagttggtag ctcttgatcc    7140
ggcaaacaaa ccaccgctgg tagcggtggt ttttttgttt gcaagcagca gattacgcgc    7200
agaaaaaaag gatctcaaga gatcctttga tcttttcta cggggtctga cgctcagtgg    7260
aacgaaaact cacgttaagg gattttggtc atgacattaa cctataaaaa taggcgtatc    7320
acgaggccct ttcgtctcgc gcgtttcggt gatgacggtg aaaacctctg acacatgcag    7380
ctcccggaga cggtcacagc ttgtctgtaa gcggatgccg ggagcagaca agcccgtcag    7440
ggcgcgtcag cgggtgttgg cgggtgtcgg gctggcttaa ctatgcggc atcagagcag    7500 attgtactga gagtgcacca tatggacata ttgtcgttag aacgcggcta caattaatac    7560
ataaccttat gtatcataca catacgattt aggtgacact atagaacggc gcgccaagct    7620
tggatcctcg aagagaaggg ttaataacac attttttaac attttttaaca caaattttag    7680 ttatttaaaa atttattaaa aaatttaaaa taagaagagg aactctttaa ataaatctaa    7740
cttacaaaat ttatgatttt taataagttt tcaccaataa aaaatgtcat aaaaatatgt    7800
taaaaagtat attatcaata ttctctttat gataaataaa aagaaaaaaa aaataaaagt    7860
taagtgaaaa tgagattgaa gtgactttag gtgtgtataa atatatcaac cccgccaaca    7920
atttatttaa tccaaatata ttgaagtata ttattccata gcctttattt atttatatat    7980
ttattatata aaagctttat ttgttctagg ttgttcatga atatttttt tggttttatc    8040 tccgttgtaa gaaaatcatg tgctttgtgt cgccactcac tattgcagct ttttcatgca    8100
ttggtcagat tgacggttga ttgtattttt gttttttatg gttttgtgtt atgacttaag    8160
tcttcatctc tttatctctt catcaggttt gatggttacc taatatggtc catgggtaca    8220
tgcatggtta aattaggtgg ccaactttgt tgtgaacgat agaatttttt ttatattaag    8280
taaactattt ttatattatg aaataataat aaaaaaaata ttttatcatt attaacaaaa    8340
tcatattagt taatttgtta actctataat aaaagaaata ctgtaacatt cacattacat    8400
ggtaacatct ttccacccct tcatttgttt tttgtttgat gactttttt cttgttaaa     8460 tttatttccc ttcttttaaa tttggaatac attatcatca tatataaact aaaatactaa    8520
aaacaggatt acacaaatga taaataataa cacaaatatt tataaatcta gctgcaatat    8580
atttaaacta gctatatcga tattgtaaaa taaaactagc tgcattgata ctgataaaaa    8640
aatatcatgt gctttctgga ctgatgatgc agtatacttt tgacattgcc tttattttat    8700
ttttcagaaa agctttctta gttctgggtt cttcattatt tgtttcccat ctccattgtg    8760
aattgaatca tttgcttcgt gtcacaaata caatttagnt aggtacatgc attggtcaga    8820
ttcacggttt attatgtcat gacttaagtt catggtagta cattacctgc cacgcatgca    8880
ttatattggt tagatttgat aggcaaattt ggttgtcaac aatataaata taataatgt    8940 ttttatatta cgaaataaca gtgatcaaaa caaacagttt tatctttatt aacaagattt    9000
```

```
tgttttgtt tgatgacgtt ttttaatgtt tacgctttcc cccttctttt gaatttagaa    9060
cactttatca tcataaaatc aaatactaaa aaaattacat atttcataaa taataacaca    9120
aatattttta aaaatctga aataataatg aacaatatta catattatca cgaaaattca     9180
ttaataaaaa tattatataa ataaaatgta atagtagtta tatgtaggaa aaaagtactg    9240
cacgcataat atatacaaaa agattaaaat gaactattat aaataataac actaaattaa    9300
tggtgaatca tatcaaaata atgaaaaagt aaataaaatt tgtaattaac ttctatatgt    9360
attacacaca caaataataa ataatagtaa aaaaaattat gataaatatt taccatctca    9420
taagatattt aaaataatga taaaaatata gattattttt tatgcaacta gctagccaaa    9480
aagagaacac gggtatatat aaaaagagta cctttaaatt ctactgtact tcctttattc    9540
ctgacgtttt tatatcaagt ggacatacgt gaagatttta attatcagtc taaatatttc    9600
attagcactt aatactttc tgttttattc ctatcctata agtagtcccg attctcccaa     9660
cattgcttat tcacacaact aactaagaaa gtcttccata gcccccaag cggccgctag     9720 tcgactaagt catcaactat tccaagctac gtatttggga gtttgtggag tacagcaaga    9780
tgatatacct agacggtgat atccaagttt ttgacaacat tgaccacttg tttgacttgc    9840
ctgataacta cttctatgcg gtgatggact gtttctgtga gccaacttgg ggccacacta    9900
aacaatatca gatcggttac tgccagcagt gccccataa ggttcagtgg cccactcact      9960
ttgggcccaa acctcctctc tatttcaatg ctggcatgtt tgtgtatgag cccaatttgg   10020
ctacttaccg tgacctcctt caaacagtcc aagtcaccca gcccacttcc tttgctgaac   10080
aggatttttt gaacatgtac ttcaaggaca aatataggcc aattcctaat gtctacaatc   10140
ttgtgctggc catgctgtgg cgtcaccctg agaacgttga gcttgacaaa gttaaagtgg   10200
ttcactactg tgctgctggg tctaagcctt ggaggtacac tgggaagtga ctcgaggtca   10260
tcaattactc caagctacgt atttgggagt cgtggagta caagaagacg atatacctag     10320
acggtgacat ccaagtattt ggaaacatag accacttgtt tgatctgcct gataattatt   10380
tctatgcggt gatggattgt ttctgcgaga agacttggag ccacacccct cagttccaga   10440
ttgggtactg ccaacagtgc cctgataagg ttcaatggcc ctctcacttt ggttccaaac   10500
ctcctctata tttcaatgct ggcatgtttg tttatgagcc taatctcgac acctaccgtg   10560
atcttctcca aactgtccaa ctcaccaagc ccacttcttt tgctgagcag acttttctca   10620
acatgtactt caaggacaag tacaagccaa taccgaacat gtacaacctt gtgctggcca   10680
tgttgtggcg tcaccctgaa aatgttgaac ttgataaagt tcaagtggtt cattactgtg   10740
ctgctgggtc taagccttgg aggttcactg ggaagtaact gcaggtcatc aactactcca   10800
agctccgtat atgggagttt gtggagtaca gcaagatgat atacttggac ggagacattg   10860
aggtatatga gaacatagac cacctatttg acctacctga tggtaacttt tacgctgtga   10920
tggattgttt ctgcgagaag acatggagtc acacccctca gtacaaggtg ggttactgcc   10980
agcaatgccc ggagaaggtg cggtggccca ccgaattggg tcagcccct tctctttact    11040 tcaacgctgg catgttcgtg ttcgaaccca acatcgccac ctatcatgac ctattgaaaa   11100
cggtgcaagt caccactccc acctcgttcg ctgaacaaga tttcttgaac atgtacttca   11160
aggacattta caagccaatc cctttaaatt acaatcttgt cctcgccatg ctgtggcgcc   11220
acccggaaaa cgttaaatta gaccaagtca aggttgttca ctattgcgca gcggggtcca   11280
agccatggag atatacgggg aagtagccta ggtgagctga tttaagattt atcaaaagtt   11340
ggggttacaa atttggaag cttcagtgtg gaagtaatag acccagtttc tgactatctg    11400
```

```
gagctattgg agacagtatt tgattttcag ctaatcagag gtcttctttc acgtccagat    11460
tttaggttta tatttgatgc catgcatgca gttactggtg cttatgctaa acccatcttc    11520
gttgataaac tcggtgctag tctggattca atttcaaatg gaatcccttt ggaagatttt    11580
ggacatggcc atcctgatcc taatctaaca tatgcgaagg atcttgtcga cattctgtat    11640
gctgaaaatg gacctgattt tggagctgcc agtgatgggg atggtgatag aaatatgatt    11700
ttaggaagaa gtttctttgt aactccttca gactctgtag cagttattgc agccaatgca    11760
agagaagcga ttccatactt caagaacggt gttaagggtc ttgctcgatc aatgccaaca    11820
agcggtgctc tggaccgtgc tgctaaaaaa ttgaacctcc ctttctgagc tgatttaac    11879

<210> SEQ ID NO 40
<211> LENGTH: 3984
<212> TYPE: DNA
<213> ORGANISM: artificial sequence
<220> FEATURE:
<223> OTHER INFORMATION: ASCI fragment of vector 29252 (PHP19031A)

<400> SEQUENCE: 40
cgcgccaagc ttggatccta gaactagaaa cgtgatgcca cttgttattg aagtcgatta      60
cagcatctat tctgttttac tatttataac tttgccattt ctgactttg aaaactatct     120 ctggatttcg gtatcgcttt gtgaagatcg agcaaaagag acgttttgtg gacgcaatgg     180
tccaaatccg ttctacatga acaaattggt cacaatttcc actaaaagta aataaatggc     240
aagttaaaaa aggaatatgc attttactga ttgcctaggt gagctccaag agaagttgaa     300
tctacacgtc taccaaccgc taaaaaaaga aaaacattga tatgtaacct gattccatta     360
gcttttgact tcttcaacag attctctact tagatttcta acagaaatat tattactagc     420 acatcattt cagtctcact acagcaaaaa atccaacggc acaatacaga caacaggaga     480
tatcagacta cagagataga tagatgctac tgcatgtagt aagttaaata aaggaaaat     540 aaaatgtctt gctaccaaaa ctactacaga ctatgatgct caccacaggc caaatcctgc     600
aactaggaca gcattatctt atatatattg tacaaaacaa gcatcaagga catttggtc     660 taggcaatca gtacctcgtt ctaccatcac cctcagttat cacatccttg aaggatccat     720
tactgggaat catcggcaac acatgctcct gatggggcac aatgacatca agaaggtagg     780
ggccaggggt gtccaacatt ctctgaattg ccgctctaag ctcttccttc ttcgtcactc     840
gcgctgccgg tatcccacaa gcatcagcaa acttgagcat gtttgggaat atctcgctct     900
cgctagacga atctccaaga taggtgtgag ctctattgga cttgtagaac ctatcctcca     960
actgaaccac catacccaaa tgctgattgt tcaacaacaa tatcttaact gggagattct    1020
ccactcttat agtggccaac tcctgaacat tcatgatgaa actaccatcc ccatcaatgt    1080
caaccacaac agccccaggg ttagcaacag cagcaccaat agccgcaggc aatccaaaac    1140
ccatggctcc aagaccccct gaggtcaacc actgcctcgg tctcttgtac ttgtaaaact    1200
gcgcagccca catttgatgc tgcccaaccc cagtactaac aatagcatct ccattagtca    1260
actcatcaag aacctcgata gcatgctgcg gagaaatcgc gtcctggaat gtcttgtaac    1320
ccaatggaaa cttgtgtttc tgcacattaa tctcttctct ccaacctcca agatcaaact    1380
taccctccac tccttttctcc tccaaaatca tattaattcc cttcaaggcc aacttcaaat    1440
ccgcgcaaac cgacacgtgc gcctgcttgt tctcccaat ctcggcagaa tcaatatcaa    1500
tgtgaacaat cttagcccta ctagcaaaag cctcaagctt cccagtaaca cggtcatcaa    1560
accttacccc aaaggcaagc aacaaatcac tattgtcaac agcatagtta gcataaacag    1620
```

```
taccatgcat acccagcatc tgaagggaat attcatcacc aataggaaaa gttccaagac    1680
ccattaaagt gctagcaacg ggaataccag tgagttcaac aaagcgcctc aattcagcac    1740
tggaattcaa actgccaccg ccgacgtaga gaacgggctt ttgggcctcc atgatgagtc    1800
tgacaatgtg ttccaattgg gcctcggcgg ggggcctggg cagccggcg aggtaaccgg     1860 ggaggttaac gggctcgtcc caattaggca cggcgagttg ctgctgaacg tctttgggaa    1920
tgtcgatgag gaccggaccg gggcggccgg aggtggcgac gaagaaagcc tcggcgacga    1980
cgcgggggat gtcgtcgacg tcgaggatga ggtagttgtg cttcgtgatg gatctgctca    2040
cctccacgat cggggtttct tggaaggcgt cggtgccgat catccggcgg gcgacctggc    2100
cggtgatggc gacgactggg acgctgtcca ttaaagcgtc ggcgaggccg ctcacgaggt    2160
tggtggcgcc ggggccggag gtggcaatgc agacgccggg gaggccgag gaacgcgcgt     2220 agccttcggc ggcgaagacg ccgccctgct cgtggcgcgg gagcacgttg cggatggcgg    2280
cggagcgcgt gagcgcctgg tggatctcca tcgacgcacc gccggggtac gcgaacaccg    2340
tcgtcacgcc ctgcctctcc agcgcctcca caaggatgtc cgcgcccttg cgaggttcgc    2400
cggaggcgaa ccgtgacacg aagggctccg tggtcggcgc ttccttggtg aagggcgccg    2460
ccgtgggggg tttggagatg gaacatttga ttttgagagc gtggttgggt ttggtgaggg    2520
tttgatgaga gagagggagg gtggatctag taatgcgttt ggggaaggtg gggtgtgaag    2580
aggaagaaga gaatcgggtg gttctggaag cggtggccgc cattgtgttg tgtggcatgg    2640
ttatacttca aaaactgcac aacaagccta gagttagtac ctaaacagta aatttacaac    2700
agagagcaaa gacacatgca aaaatttcag ccataaaaaa agttataata gaatttaaag    2760
caaaagtttc attttttaaa catatataca aacaaactgg atttgaagga agggattaat    2820 tccccctgctc aaagtttgaa ttcctattgt gacctatact cgaataaaat tgaagcctaa    2880
ggaatgtatg agaaacaaga aaacaaaaca aaactacaga caaacaagta caattacaaa    2940
attcgctaaa attctgtaat caccaaaccc catctcagtc agcacaaggc caaggttta     3000 ttttgaaata aaaaaaagt gattttattt ctcataagct aaaagaaaga aaggcaatta     3060
tgaaatgatt tcgactagat ctgaaagtcc aacgcgtatt ccgcagatat taagaaaga    3120 gtagagtttc acatggatcc tagatggacc cagttgagga aaaagcaagg caaagcaaac    3180
cagaagtgca agatccgaaa ttgaaccacg gaatctagga tttggtagag ggagaagaaa    3240
agtaccttga gaggtagaag agaagagaag agcagagaga tatatgaacg agtgtgtctt    3300
ggtctcaact ctgaagcgat acgagtttag aggggagcat tgagttccaa tttatagga     3360 aaccgggtgg caggggtgag ttaatgacgg aaaagcccct aagtaacgag attggattgt    3420
gggttagatt caaccgtttg catccgcggc ttagattggg gaagtcagag tgaatctcaa    3480
ccgttgactg agttgaaaat tgaatgtagc aaccaattga gccaacccca gcctttgccc    3540
tttgattttg atttgtttgt tgcatacttt ttatttgtct tctggttctg actctcttc     3600 tctcgtttca atgccaggtt gcctactccc acaccactca caagaagatt ctactgttag    3660
tattaaatat tttttaatgt attaaatgat gaatgctttt gtaaacagaa caagactatg    3720
tctaataagt gtcttgcaac attttttaag aaattaaaaa aatatatttt attatcaaaa    3780
tcaaatgtat gaaaaatcat gaataatata attttataca tttttttaaa aaatctttta    3840
atttcttaat taatatcttaaa aaataatga ttaatattta acccaaaata attagtatga    3900
ttggtaagga agatatccat gttatgtttg gatgtgagtt tgatctagag caaagcttac    3960
tagagtcgac cgatccgtcg acgg                                           3984
```

```
<210> SEQ ID NO 41
<211> LENGTH: 64
<212> TYPE: PRT
<213> ORGANISM: artificial sequence
<220> FEATURE:
<223> OTHER INFORMATION: Conserved sequence motif
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (54)..(57)
<223> OTHER INFORMATION: Xaa can be any naturally occurring amino acid
<220> FEATURE:
<221> NAME/KEY: misc_feature
<222> LOCATION: (61)..(63)
<223> OTHER INFORMATION: Xaa can be any naturally occurring amino acid

<400> SEQUENCE: 41

Arg Glu Gln Asp Xaa Xaa Met Pro Xaa Ala Asn Val Xaa Arg Ile Met
1               5                   10                  15

Arg Xaa Xaa Leu Pro Xaa Xaa Ala Lys Ile Ser Asp Asp Ala Lys Glu
            20                  25                  30

Xaa Ile Gln Glu Cys Val Ser Glu Xaa Ile Ser Phe Xaa Thr Xaa Glu
        35                  40                  45

Ala Asn Xaa Arg Cys Xaa Xaa Xaa Xaa Arg Lys Thr Xaa Xaa Xaa Glu
    50                  55                  60
```